United States Patent
Thomas et al.

(10) Patent No.: US 8,592,463 B2
(45) Date of Patent: Nov. 26, 2013

(54) HEDGEHOG PATHWAY ANTAGONISTS AND THERAPEUTIC APPLICATIONS THEREOF

(75) Inventors: Russell John Thomas, Siena (IT); Gal.la Pericot Mohr, Siena (IT); Giacomo Minetto, Siena (OA); Annette Cornelia Bakker, Siena (IT); Pietro Ferruzzi, Siena (IT)

(73) Assignee: Siena Biotech S.p.A., Siena (IT)

( * ) Notice: Subject to any disclaimer, the term of this patent is extended or adjusted under 35 U.S.C. 154(b) by 310 days.

(21) Appl. No.: 12/747,562

(22) PCT Filed: Dec. 10, 2008

(86) PCT No.: PCT/EP2008/010470
§ 371 (c)(1),
(2), (4) Date: Jul. 26, 2010

(87) PCT Pub. No.: WO2009/074300
PCT Pub. Date: Jun. 18, 2009

(65) Prior Publication Data
US 2010/0286114 A1    Nov. 11, 2010

(30) Foreign Application Priority Data

Dec. 13, 2007 (EP) .................................. 07024218

(51) Int. Cl.
*A61K 31/41*    (2006.01)
(52) U.S. Cl.
USPC .......................................... 514/361; 548/100
(58) Field of Classification Search
None
See application file for complete search history.

(56) References Cited

FOREIGN PATENT DOCUMENTS

| EP | 1 391 457 | 2/2004 |
|---|---|---|
| WO | 00/26192 | 5/2000 |
| WO | 03/032984 | 4/2003 |
| WO | 03/075921 | 9/2003 |

OTHER PUBLICATIONS

U.S. Appl. No. 13/377,290, filed Dec. 2011, Russell et al.*
Kubota et al., The interaction of 2-phenylbenzimidazole compounds with DNA: The influence of terminal substituents, Nucleic Acid Research, Supplement No. 2, 193-194, 2002.*
Abouzid et al., Synthesis and antihypertensive activity of new benzimidazole, benzoxazole and benzothiazole derivativs, STN DN 142:430234, XP-002483077, 2002.*
Zips et al., In vivo, 2005, 19, 1-8.*
Sikora, Current Science 2001, 81(5), 549-554.*
Kubota, Y. et al., "The interatcion of 2-phenylbenzimidazole compounds with DNA: the influences of terminal substituents" Nucleic Acids Research Supplement, vol. 2, 2002, pp. 193-194.
Abouzid, K. et al., "Synthesis and antihypertensive activity of novel benzimidazole, benzoxazole and benzothiazole derivatives" Bulletin of the Faculty of Pharmacy (Cairo University), 40(1), Abstract, Jul. 13, 2002.

* cited by examiner

*Primary Examiner* — Sreeni Padmanabhan
*Assistant Examiner* — Svetlana M Ivanova
(74) *Attorney, Agent, or Firm* — Lucas & Mercanti, LLP

(57) ABSTRACT

Heterocyclic compounds that modulate the hedgehog signaling pathway, pharmaceutical composition thereof and their therapeutic applications.

5 Claims, No Drawings

HEDGEHOG PATHWAY ANTAGONISTS AND THERAPEUTIC APPLICATIONS THEREOF

This application is a U.S. national stage of PCT/EP2008/010470 filed on Dec. 10, 2008, which claims priority to and the benefit of European Application No. 07024218.5 filed on Dec. 13, 2007, the contents of which are incorporated herein by reference.

FIELD OF THE INVENTION

The present invention relates to organic compounds, pharmaceutical compositions thereof and their use for therapy and/or prophylaxis in a mammal, in particular to heterocyclic compounds that modulate the hedgehog signaling pathway.

BACKGROUND OF THE INVENTION

Autoproteolysis of a 45 kDa Human Shh precursor protein gives a 20 kDa N-terminal fragment that is responsible for normal hedgehog signalling and a 25 kDa C-terminal fragment involved in autoprocessing activity in which the N-terminal fragment is conjugated to cholesterol (Lee et al. Science 266 1528-1537 (1994) and Bumcrot et al. Mol. Cell. Biol. 15 2294-2303 (1995)).

Normally functioning Hedgehog (Hh) signaling specifies embryonic pattern by directing cellular differentiation and proliferation, which was first reported in Drosophilia melanogaster (Nusslein-Vollhard et al. Roux. Arch. Dev. Biol. 193: 267-282 (1984)). Cellular responses to the secreted Hh polypeptide are mediated by two integral membrane proteins, Patched (Ptc) and Smoothened (Smo). Hh binds to the twelve transmembrane protein Ptc and hence reverses the Ptc-mediated suppression of the seven transmembrane protein Smo. This Smo activation then triggers a series of intracellular events, culminating in the stabilization of the transcription factor Cubitus interruptus (Ci) and the expression of Ci-dependent genes. These events are recapitulated during mammalian development and tumourigenesis through multiple protein homologues, including three distinct Hh family members [Sonic (Shh), Indian (Ihh), and Desert (Dhh)], two Ptc proteins (Ptch1 and Ptch2), and three Ci-like transcription factors (Gli1, Gli2, and Gli3). However, there is a single vertebrate homologue of Smo, which is implicated in all forms of Hh signaling by genetic analyses in *Drosophila*, mice, and zebrafish (Chen et al. PNAS 99(22): 14071-14076 (2002)).

Smo initiates a signal cascade causing the activation of Gli transcription factors and their subsequent nuclear translocation resulting in the control of transcription of target genes. Through a negative feedback loop, Gli influences transcription of Ptc and Hip1 (hedgehog-interacting protein 1 (Hip1)) which inhibit the Hh pathway. The loss of control over the activation of the Hh pathway has been associated with an increasing range of cancers including those affecting the brain such as medulloblastoma (Romer and Curran, Cancer Res 65(12) 4975-4978 (2005)) and glioblastoma (Bar et al. Stem Cells 25(10):2524-33 (2007)); prostate cancer (Sanchez et al. PNAS 101(34) 12561-12566 (2004)); pancreatic cancer (Thayer et al. Nature 423 851-856 (2003)); non-small cell lung carcinoma (Yuan et al. Oncogene 26 1046-1055 (2007); small-cell lung cancer (Watkins et al. Nature 422 313-317 (2003)); breast cancer (Kubo et al. Cancer Res 64 6071-6074 (2004)); various digestive tract tumours (Berman et al. Nature 425 846-851 (2003)) and (Lees et al. Gastroenterology 129(5) 1696-1710 (2006)); basal cell carcinoma (Williams et al. PNAS 100(8) 4616-4621 (2003)); malignant melanoma (Pons and Quintanilla Clin Trans Oncol. 8(7) 466-474 (2006)); squamous cell carcinomas (Xuan et al. Mod Pathol. 19(8) 1139-47 (2006)); B-cell malignancies such as multiple myeloma and lymphomas (Dierks et al. Nat. Med. 13(8) 944-951 (2007); Peacock et al. PNAS 104(10) 4048-4053 (2007)); mesenchymal cancers such as chondrosarcoma (Tiet et al. Am. J. Pathol. 168(1) 321-330 (2006)), clear cell sarcoma of the kidney (Cutcliffe et al. Clin Cancer Res. 11(22): 7986-94 (2005)) and rhabdomyosarcoma (Tostar et al. J. Pathol. 208(1) 17-25 (2006)); chronic myeloid leukaemia (Sengupta et al. Leukemia 21(5) 949-955 (2007)); endometrial carcinoma (Feng et al. Clin. Cancer Res. 13(5) 1389-1398 (2007); hepatocellular carcinomas (Huang et al. Carcinogenesis 27(7) 133401340 (2006)); ovarian tumours (Chen et al. Cancer Sci. 98(1) 68-76 (2007)).

It has also been found that Hh signaling regulates the expression of the ABC transporter proteins multi-drug resistance protein-1 (MDR1, ABCB1, P-glycoprotein) and (BCRP, ABCG2), and that targeted knockdown of MDR1 and BCRP expression by small interfering RNA partially reverses Hh-induced chemoresistance. This would suggest that the Hh pathway may be a target to overcome MDR and increase chemotherapeutic response (Sims-Mourtada et al Oncogene 26(38) 5674-5679 (2007)). The blockade of sonic hedgehog signal pathway was found to enhance the antiproliferative effect of EGFR inhibitors in pancreatic cancer cells (Hu et al. Acta Pharmacol Sin. 28(8) 1224-30 (2007)) and prostate cancer cells (Mimeault et al. Int. J. Cancer 118(4) 1022-31 (2006)).

The hedgehog pathway has also been associated to tumour regrowth after chemoradiotherapy and as a potential target to improve radiation response (Sims-Mourtada et al. Clin. Cancer Res. 12(21) 6565-6572 (2006)) and cyclopamine, a hedgehog pathway antagonist, increases the cytotoxic effects of paclitaxel and radiation in Hh expressing pancreatic cancer cells (Shafaee et al. Cancer Chemother. Pharmacol. 58(6) 765-70 (2006)).

It has also been reported that the inhibition of the Hedgehog signalling pathway may be of use for the treatment of a range of diseases related to inflammation, epithelial cell hyperplasia, fibrosis of tissue or immune disorders (Lamb et al. EP1183040). Inhibition of sonic hedgehog signaling has been reported to reduce chronic rejection and prolong allograft survival in a rat orthotopic small bowel transplantation model. Although acute graft rejection can be controlled by immunosuppressive agents, chronic rejection, which is characterized by arteriosclerosis in the donor organ vessels, is a major hurdle to long-term allograft survival. Graft survival in a rat orthotopic small bowel transplantation model was significantly prolonged after anti-Shh antibody treatment compared with the immunoglobulin G control (116 vs. 77.5 days). Collagen deposition and vascular occlusion in the mesentery were markedly reduced in recipients of the anti-Shh antibody (Chen et al. Transplantation 83(10) 1351-1357 (2007); Lamb et al. EP1183040B1).

It has also been reported that sFRP-1 is the downstream target gene of Hh signaling and that elevated expression of secreted frizzled related protein-1 (sFRP-1) following activation of the Hh pathway provides the molecular link for the inhibitory effect on Wnt signaling (He et al. J. Biol. Chem. 281(47)35598-35602 (2006)). Thus the modulation of Wnt signaling by antagonising Hh pathway through sFRP-1 could provide a method for the treatment of a range of diseases such as osteoporosis (Ai et al. Mol. Cell. Biol. 25(12) 4946-4955 (2005)) among others (Luo et al. Laboratory Investigation, 87, 97-103-(2007)).

Various inhibitors of the Hh pathway have been investigated, including the natural product cyclopamine, which is believed to act by binding to the heptahelical region of Smo. Additionally a number of synthetic small molecule antagonists of the Smo receptor have been reported in recent years: for a review see Kiselyov Anti-Cancer Agents in Medicinal Chemistry 6 445-449 (2006)

PRIOR ART

Lubisch et al. disclose a series of 2-phenyl-benzimidazoles as PARP inhibitors for useful for the cure of various diseases including cancer (WO2000026192) and in the field of cosmetics (WO2001082877). A recurring feature is the presence of a carbamoyl moiety at the 4-position of the benzimidazole ring.

Arienti et al. (WO2003032984) and Ameriks et al. (WO2004093873 and US2004214857) disclose a series of 2-phenyl-benzimidazole derivatives as checkpoint kinase 2 inhibitors for the cure of cancer, further characterised in that the 5-position of the benzimidazole ring is always substituted with either a carboxylate, a carbamoyl or a sulphamoyl group.

Ohemeng et al. (WO9911627 and U.S. Pat. No. 5,942,532) disclose a series of 5-carboxylmidamides-2-phenyl-benzimidazoles compounds as antibacterial agents.

Mjalli et al. (WO2003075921) describe the pharmaceutical applications of a series of 2-phenyl-benzimidazole derivatives.

Alekshun et al. (WO2004041209 and WO2006076009) disclose a series of 2-phenyl-benzimidazolol derivatives with antibiotic activity.

Khaled et al.[1] (Bulletin of the Faculty of Pharmacy (Cairo University), 40(1), 7-13, (2002)) describe the synthesis and antihypertensive activity of 2-phenyl-benzimidazoles derivatives whereas the DNA binding properties of some others are described by Kobuta et al. (Nucleic Acids Research Supplement, 2(Twenty-ninth Symposium on Nucleic Acids Chemistry), 193-194 (2002) and Nucleic Acids Symposium Series, 35(Twenty-third Symposium on Nucleic Acids Chemistry, 1996), 151-152 (1996)).

Guicherit et al. (WO2006050506), Beachy et al. (WO2003088970) and Rubin et al. (WO2003011219) disclose Aryl- and alkyl-amido/ureido derivatives of 2-phenyl-benzimidazole as Hedgehog pathway antagonists for the cure of various forms of cancer.

DETAILED DESCRIPTION OF THE INVENTION

This invention provides compounds of formula I

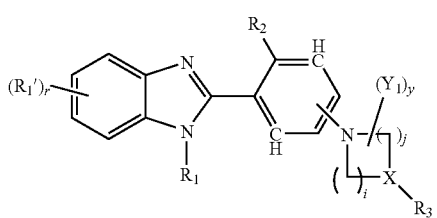

(I)

Wherein, as valence and stability permit $R_1$ is H; linear, branched or cyclic ($C_1$-$C_4$) alkyl group optionally substituted with one or more halogen, a branched or linear ($C_1$-$C_4$)alkoxy or a mono- or di-linear branched or cyclic ($C_1$-$C_6$)alkylamino group r equals nil, 1, 2 or 3;

$R_1'$ represent, independently from one another when r>1, halogen linear, branched or cyclic ($C_1$-$C_4$) alkoxy group; linear, branched or cyclic ($C_1$-$C_4$)alkyl optionally substituted with a linear or branched ($C_1$-$C_4$) alkoxy, alkylamino, or dialkylamino group;

$R_2$ can be H, Cl, F or Br

X can be either N or CH i and j may be 1, 2 or 3, the sum i+j may not exceed 5, and when X is N then i and j cannot be 1

$R_3$ may be H; linear, branched or cyclic ($C_1$-$C_6$)alkyl, oxaalkyl, alkylcarbonyl, alkylsulphonyl, oxaalkylcarbonyl, alkoxycarbonyl, alkylaminocarbonyl, oxaalkenyl, alkenylcarbonyl, oxaalkenylcarbonyl, alkenyloxycarbonyl, alkenylaminocarbonyl, alkylidene, alkyloxyimino, hydroxy, alkoxy, alkenyloxy group optionally substituted with carbamoyl or one or more fluorine atoms; Ar; Ar-aminocarbonyl; a linear or branched ($C_1$-$C_4$)alkyl, alkylamino, azaalkyl, oxaalkyl, alkylcarbonyl, alkoxycarbonyl or alkylaminocarbonyl group substituted with one or two Ar and optionally substituted with one or more fluorine atoms;

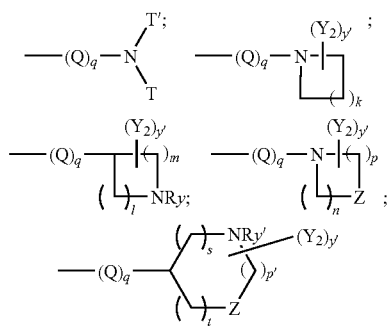

Q is such that no direct bond is formed between two nitrogen atoms or between a nitrogen atom and an oxygen atom and may be carbonyl; aminocarbonyl; carbonylamino, imine; $SO_2$; linear or branched ($C_1$-$C_6$)alkyl optionally substituted with one or more fluorine atoms wherein one methylene group may be replaced by O, NRx, carbonyl or $SO_2$ or wherein two subsequent methylene groups may be replaced with a carbonylamino, aminocarbonyl, sulphonylamino, aminosulphonyl group;

Ar is a 5 to 10 membered aromatic or heteroaromatic ring optionally substituted with one or more groups independently selected from halogen, hydroxy, mercapto, amino, cyano, nitro, carbamoyl, sulphamoyl, trihalomethyl, trihalomethoxy, linear, branched or cyclic (C1-C4) alkyl, hydroxyalkyl, mono- or di-alkylamino, alkoxy, alkylcarbonyl, alkoxycarbonyl, alkylcarbonylamino, oxaalkyl, azaalkyl, and such that two of these substituents may form a 5- to 8-membered ring with a fused junction to Ar.

Rx may be H or a linear, branched or cyclic ($C_1$-$C_4$)alkyl, dihaloakyl or trihaloalkyl;

q may be zero or 1 k may be 1, 2, 3 or 4 l, m, n, p, p' and s may independently be 1, 2 or 3 t may be zero, 1 or 2 the sums l+m, n+p or p'+s+t cannot exceed 5

T and T' represent, independently from one another, hydrogen; a linear, branched or cyclic ($C_1$-$C_6$)alkyl, azaalkyl, oxaalkyl, alkenyl, azaalkenyl, oxaalkenyl, chain optionally substituted with halogen, amino, cyano, hydroxy, oxo, linear, branched or cyclic ($C_1$-$C_3$)alkylcarbonyl, alkoxycarbonyl, alkylcarbonylamino, alkylaminocarbonyl, carbamoyl, guanidino, alkenylcarbonyl, oxaalkenylcarbonyl, alkenyloxycarbonyl, alkenylaminocarbonyl Z may be O, S, $SO_2$, SO, or NRy'

Ry and Ry' independently represent H; linear, branched or cyclic $(C_1-C_6)$alkyl, alkylcarbonyl, alkoxycarbonyl or alkylaminocarbonyl group optionally substituted with one or more fluorine atoms y and y' may independently be nil, 1, 2 or 3

$Y_1$ and $Y_2$ independently represent halogen; hydroxy; amino; cyano; nitro; oxo; linear, or branched $(C_1-C_6)$alkyl, dihaloalkyl, azaalkyl, oxaalkyl, alkylcarbonyl, oxaalkylcarbonyl, alkoxycarbonyl, alkylaminocarbonyl, alkylcarbonylamino, alkenyl, oxaalkenyl, azaalkenyl, alkenylcarbonyl, oxaalkenylcarbonyl, alkenyloxycarbonyl, alkenylaminocarbonyl, alkylamino, mercaptoalkyl, alkoxy, alkylthio group optionally substituted with one or more fluorine atoms; wherein two $Y_2$ groups may form a 5- to 8-membered ring with spiro or fused junction.

And with the exclusion of 2-[4-(4-methyl-piperazin-1-yl)-phenyl]-1H-benzoimidazole; 2-[4-(4-pyridin-2-yl-piperazin-1-yl)-phenyl]-1H-benzoimidazole A preferred group of compounds is that of formula Ia

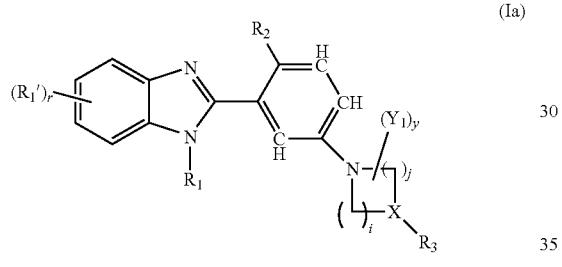

(Ia)

A particular embodiment of formula Ia groups those compounds wherein

X is N $R_3$ is linear, branched or cyclic $(C_1-C_6)$alkyl, oxaalkyl, alkylcarbonyl, alkylsulphonyl, oxaalkylarbonyl, alkoxycarbonyl, alkylaminocarbonyl, oxaalkenyl, alkenylcarbonyl, oxaalkenylcarbonyl, alkenyloxycarbonyl or alkenylaminocarbonyl group optionally substituted with carbamoyl or one or more fluorine atoms; Ar; Ar-aminocarbonyl; a linear or branched $(C_1-C_4)$ alkyl, alkylamino, azaalkyl, oxaalkyl, alkylcarbonyl, alkoxycarbonyl or alkylaminocarbonyl group substituted with one or two Ar and optionally substituted with one or more fluorine atoms;

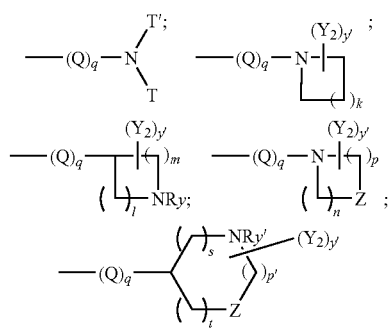

Q is such that no direct bond is formed between two nitrogen atoms or between a nitrogen atom and an oxygen atom and may be carbonyl; aminocarbonyl; carbonylamino, imine; $SO_2$; linear or branched $(C_1-C_6)$alkyl optionally substituted with one or more fluorines wherein one methylene group may be replaced by O, NRx, carbonyl or $SO_2$ or wherein two subsequent methylene groups may be replaced with a carbonylamino, aminocarbonyl, sulphonylamino, aminosulphonyl group;

In a second particular embodiment of formula Ia, X is CH. Under a preferred aspect of this embodiment, q is zero and $R_3$ is selected from

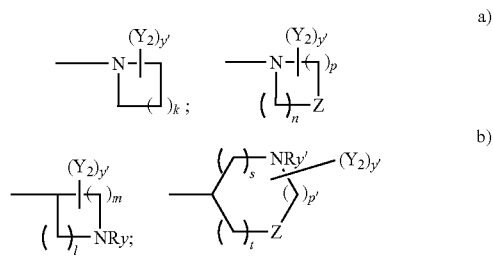

a)

b)

Another preferred embodiment falling under formula Ia, hereafter referred to as $G_1$, groups those compounds for which q is 1 and $R_3$ is

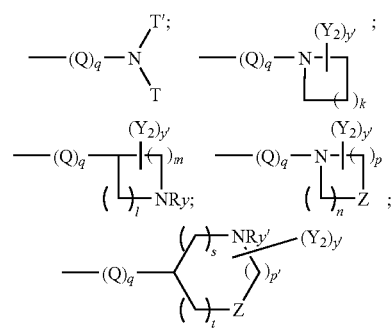

Within $G_1$, those compounds in which Q is carbonyl; linear, branched or cyclic $(C_1-C_6)$alkyl, $(C_1-C_5)$alkylcarbonyl or carbonyl$(C_1-C_5)$alkyl optionally substituted with one or more fluorine atoms constitute a preferred embodiment.

The pharmacological activity of a representative group of compounds of formula I was demonstrated using the two in vitro assays described below. According to a further aspect, the invention is therefore directed to a method of treating cancer or osteoporosis which comprises administering to a subject, preferably a human subject in need thereof, an effective amount of a compound of formula I. Types of cancer that may be treated using such method not limitedly include non-small cell lung carcinoma; small-cell lung cancer; breast cancer; ovarian tumours; digestive tract tumours; brain cancers such as medulloblastoma and glioblastoma; prostate cancer; pancreatic cancer; basal cell carcinoma; malignant melanoma; squamous cell carcinomas; multiple myeloma; lymphomas; mesenchymal cancers such as chondrosarcoma, clear cell sarcoma of the kidney and rhabdomyosarcoma; chronic myeloid leukaemia; endometrial carcinoma; hepatocellular carcinomas.

In general, the compounds of formula I can be used to treat any disease, condition or dysfunction that may benefit from the inhibition of the Hedgehog pathway by binding of the compounds to the Smo receptor, and not limitedly including osteoporosis and cancers selected from non-small cell lung carcinoma; small-cell lung cancer; breast cancer; ovarian tumours; digestive tract tumours; brain cancers such as medulloblastoma and glioblastoma; prostate cancer; pancreatic cancer; basal cell carcinoma; malignant melanoma; squamous cell carcinomas; multiple myeloma; lymphomas; mesenchymal cancers such as chondrosarcoma, clear cell sarcoma of the kidney and rhabdomyosarcoma; chronic myeloid leukaemia; endometrial carcinoma; hepatocellular carcinomas.

The dosage of the compounds for use in therapy may vary depending upon, for example, the administration route, the nature and severity of the disease. In general, an acceptable pharmacological effect in humans may be obtained with daily dosages ranging from 0.01 to 200 mg/kg.

In yet a further aspect, the invention refers to a pharmaceutical composition containing one or more compounds of formula I, in association with pharmaceutically acceptable carriers and excipients. The pharmaceutical compositions can be in the form of solid, semi-solid or liquid preparations, preferably in form of solutions, suspensions, powders, granules, tablets, capsules, syrups, suppositories, aerosols or controlled delivery systems. The compositions can be administered by a variety of routes, including oral, transdermal, subcutaneous, intravenous, intramuscular, rectal and intranasal, and are preferably formulated in unit dosage form. Oral unit dosage forms may contain from about 1 mg to about 1000 mg of the compound of the invention.

For those compounds which can be in the form of free bases, this invention also includes their acid addition salts, preferably salts with pharmaceutically acceptable acids. The invention also includes separated isomers and diastereomers of compounds I, or mixtures thereof (e.g. racemic mixtures). The principles and methods for the preparation of pharmaceutical compositions are described for example in Remington's Pharmaceutical Science, Mack Publishing Company, Easton (PA).

The compounds of formula I, their optical isomers or diastereomers can be purified or separated according to well-known procedures, not limitedly including chromatography with a chiral matrix and fractional crystallisation.

Compounds Synthesis and Experimental Procedures

The compounds of the present invention can be prepared using various synthetic routes, including those described by methods A-Z below, starting from commercially available compounds.

Method A

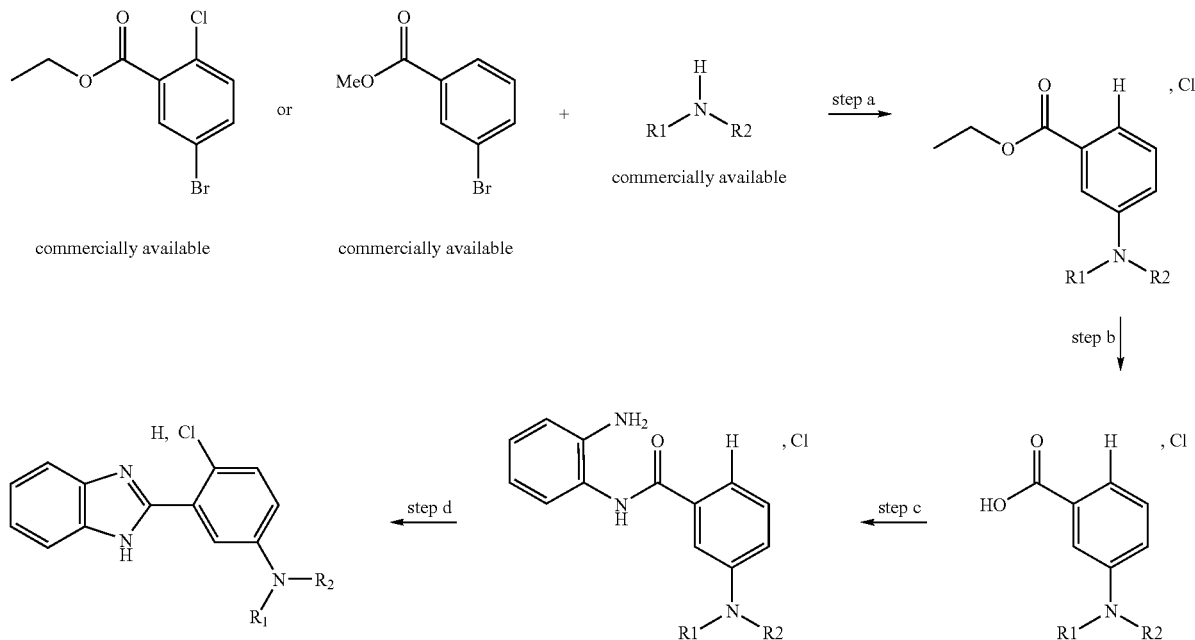

Method B

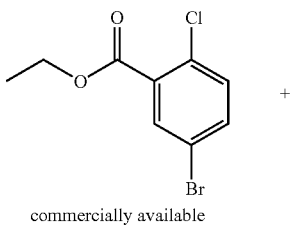

commercially available

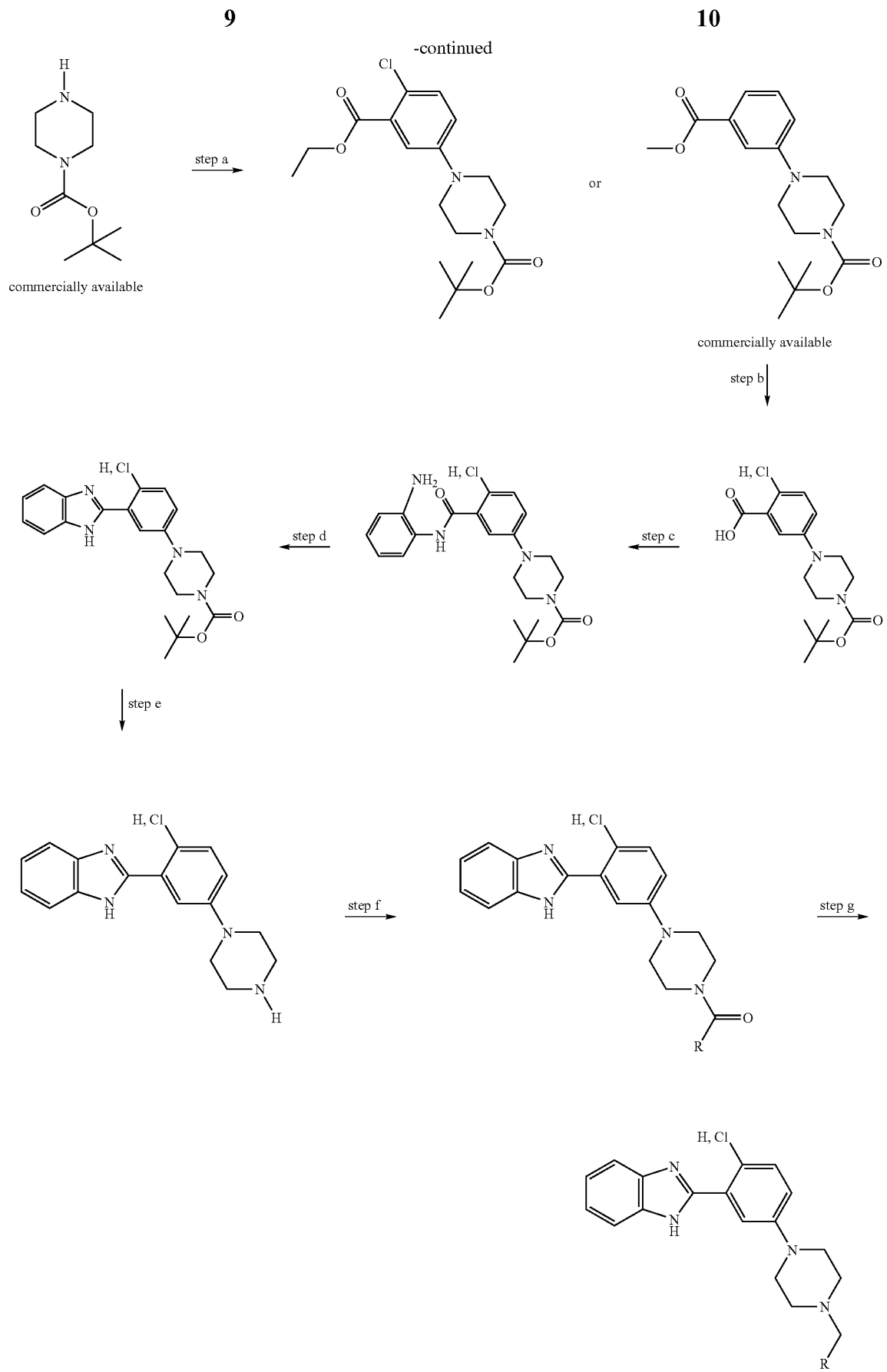

Method C
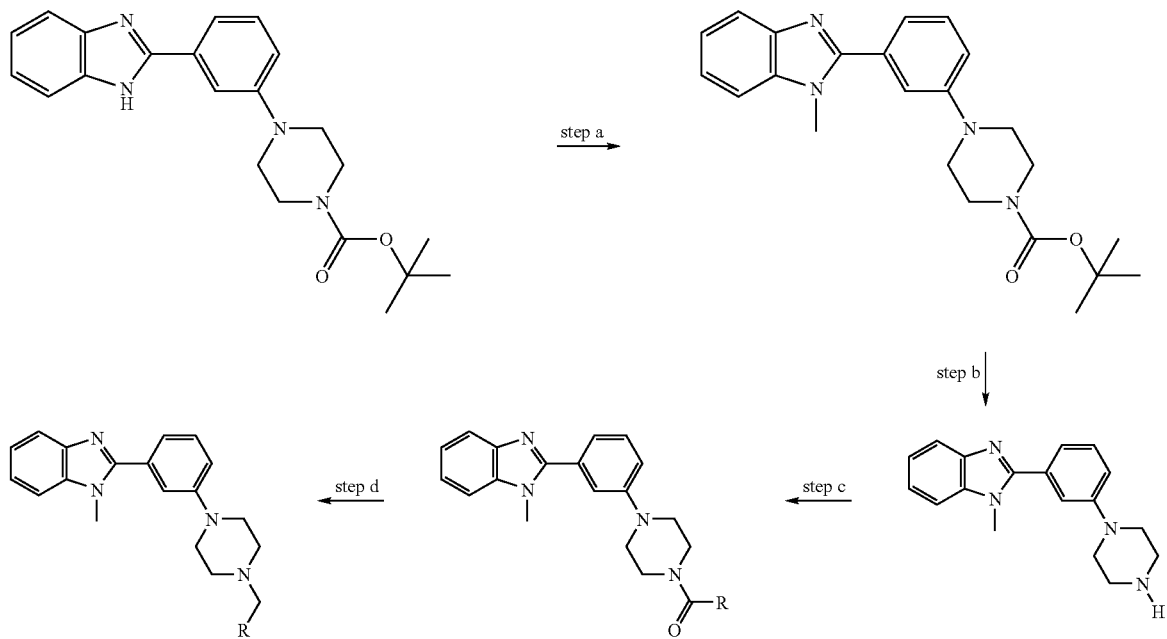
Methods D, E
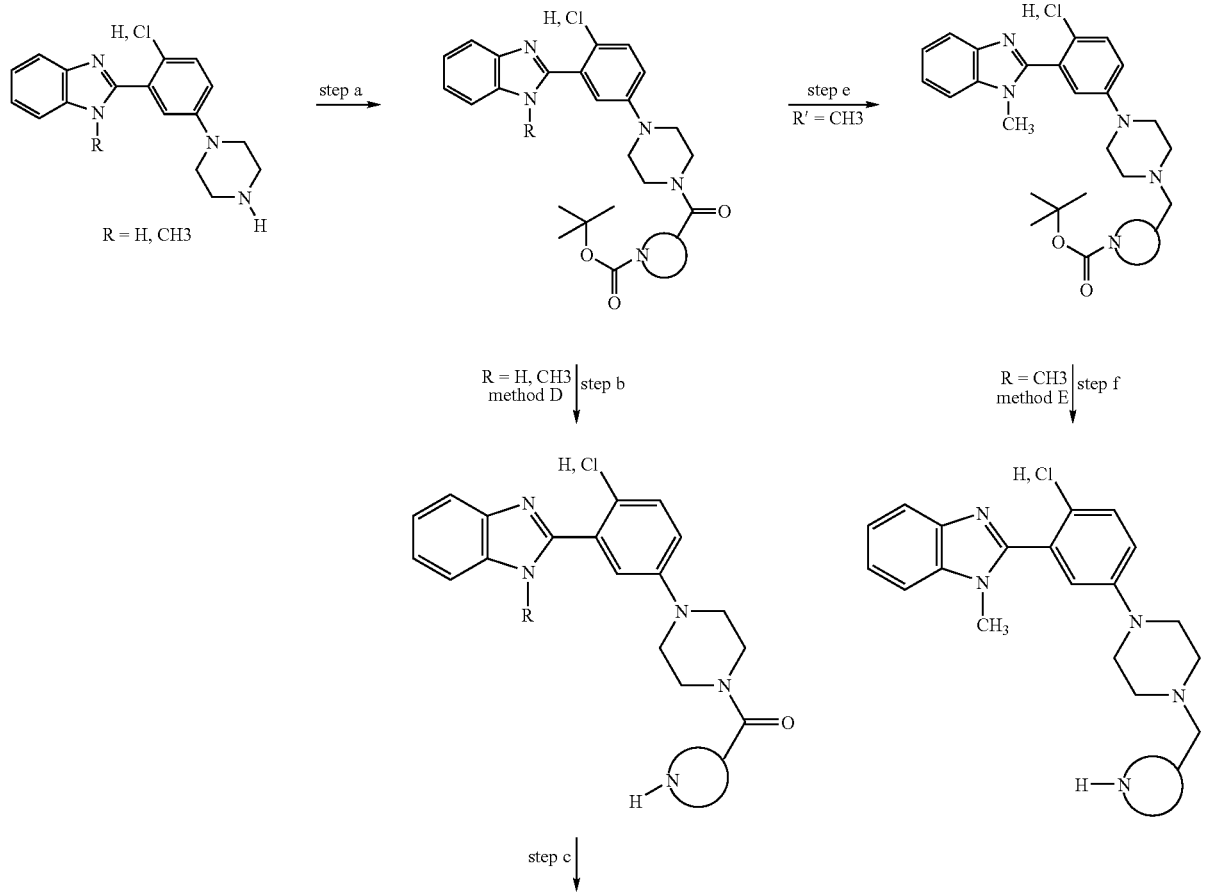

-continued
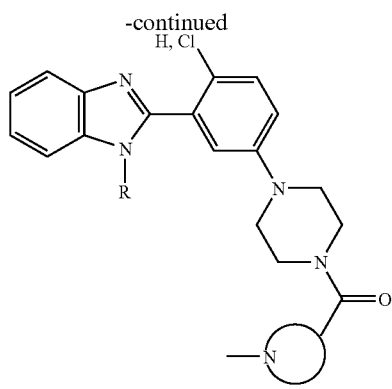
step d ↓
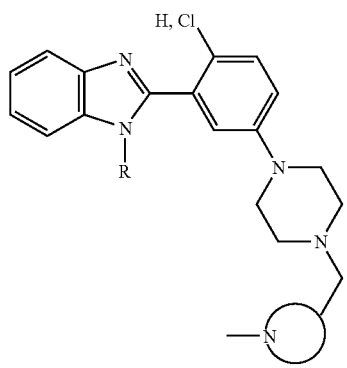
Method F
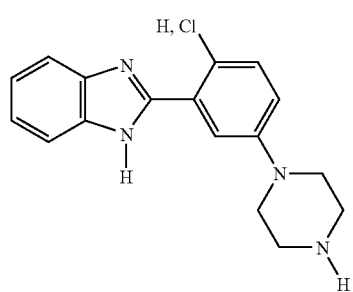
step a →
-continued
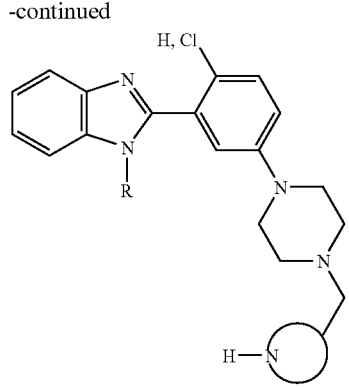
step b →
Methods G, H
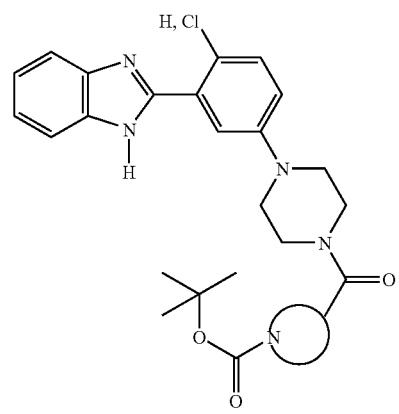
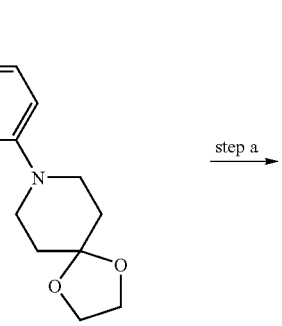
step a →

15
-continued
16
-continued
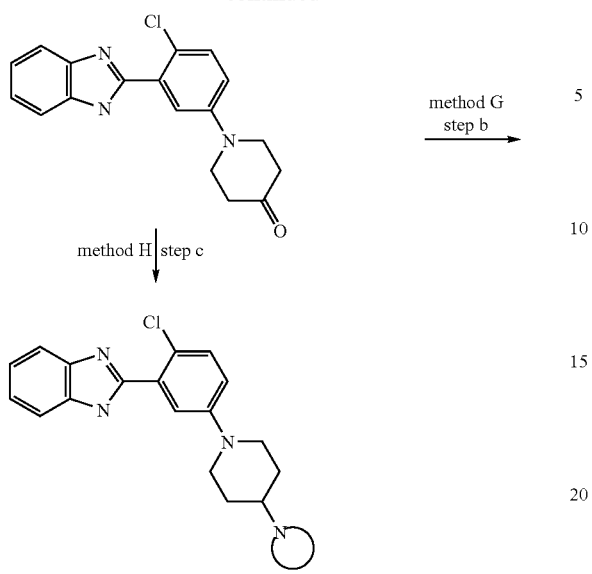
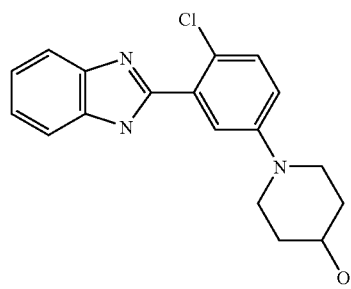
Methods I, J, K
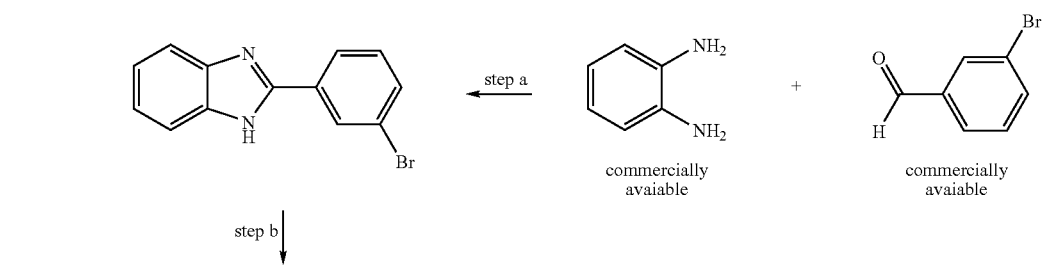
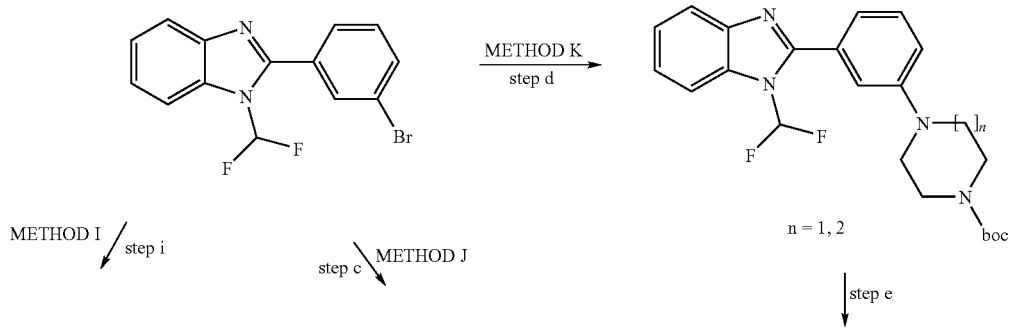
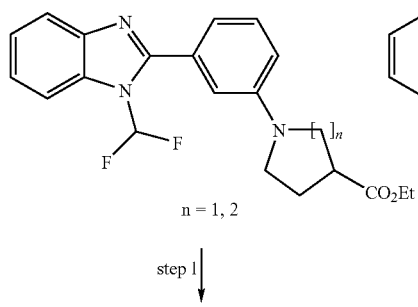
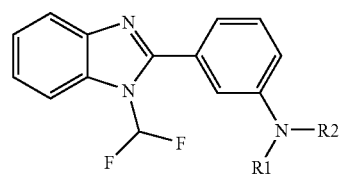
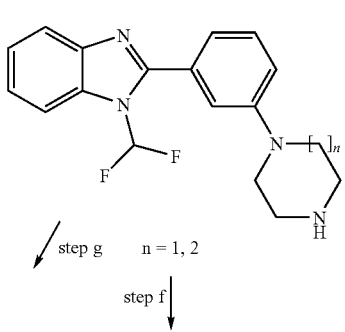

17
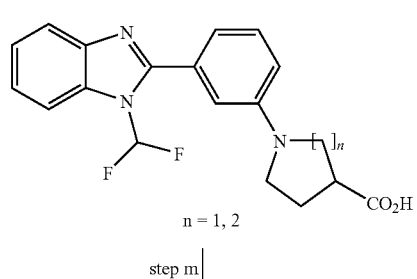
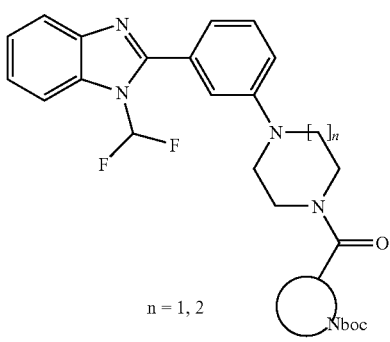
-continued
18
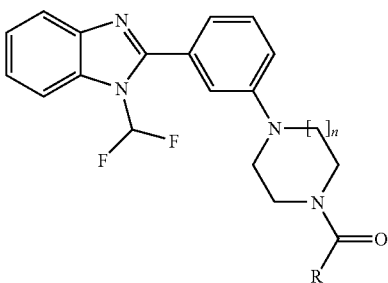
step m
step h
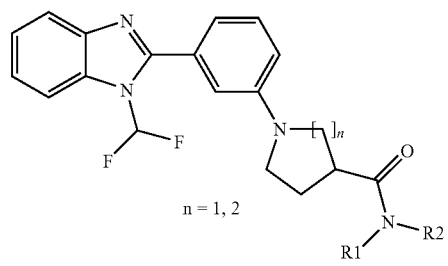
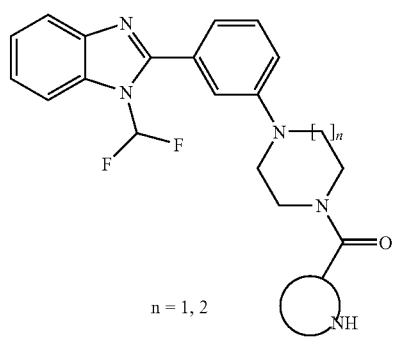
Methods L, M
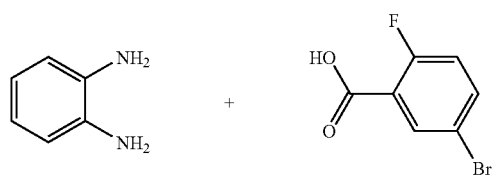
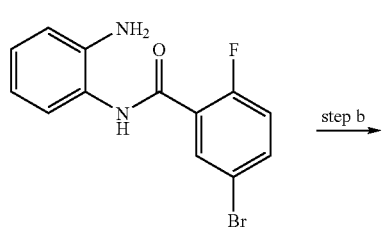
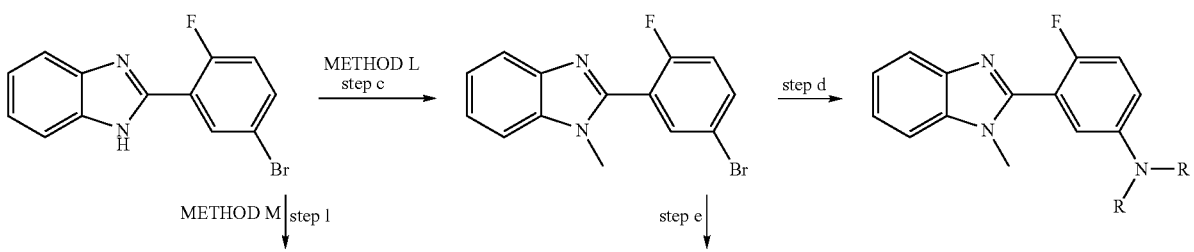

-continued
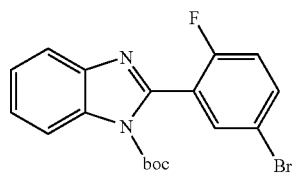 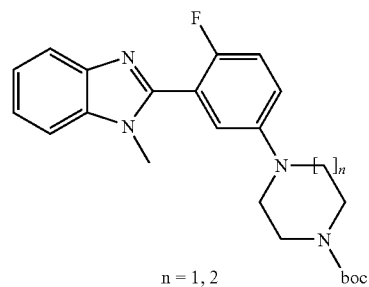
step m |      step f |
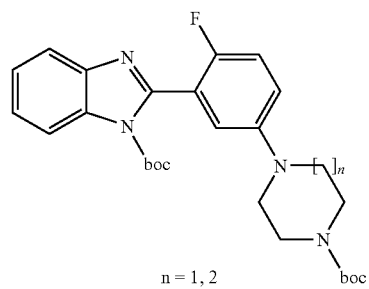 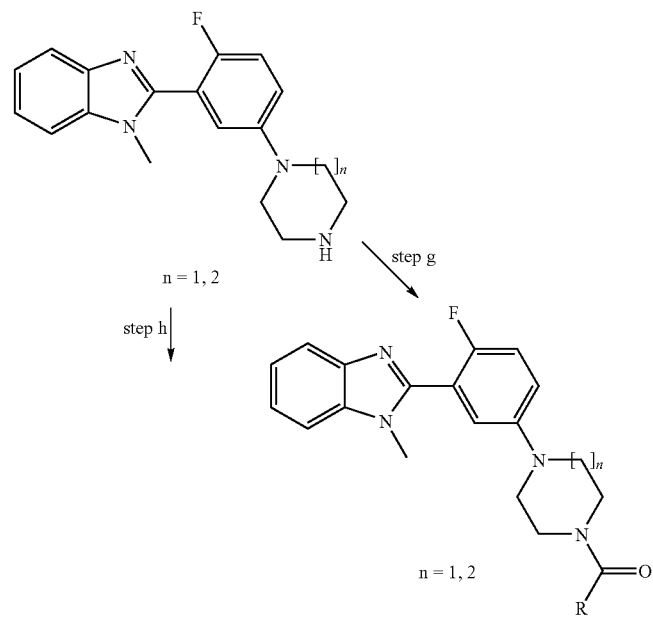
step n |      step h |
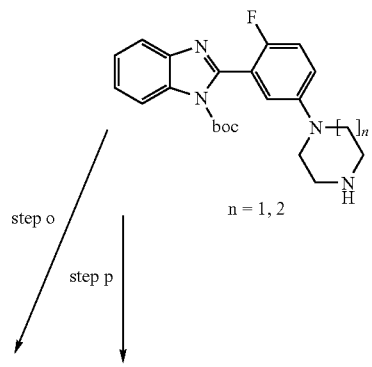 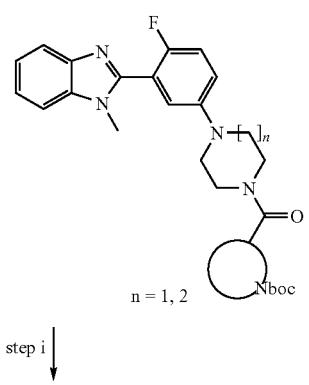
step o / step p |      step i |

-continued
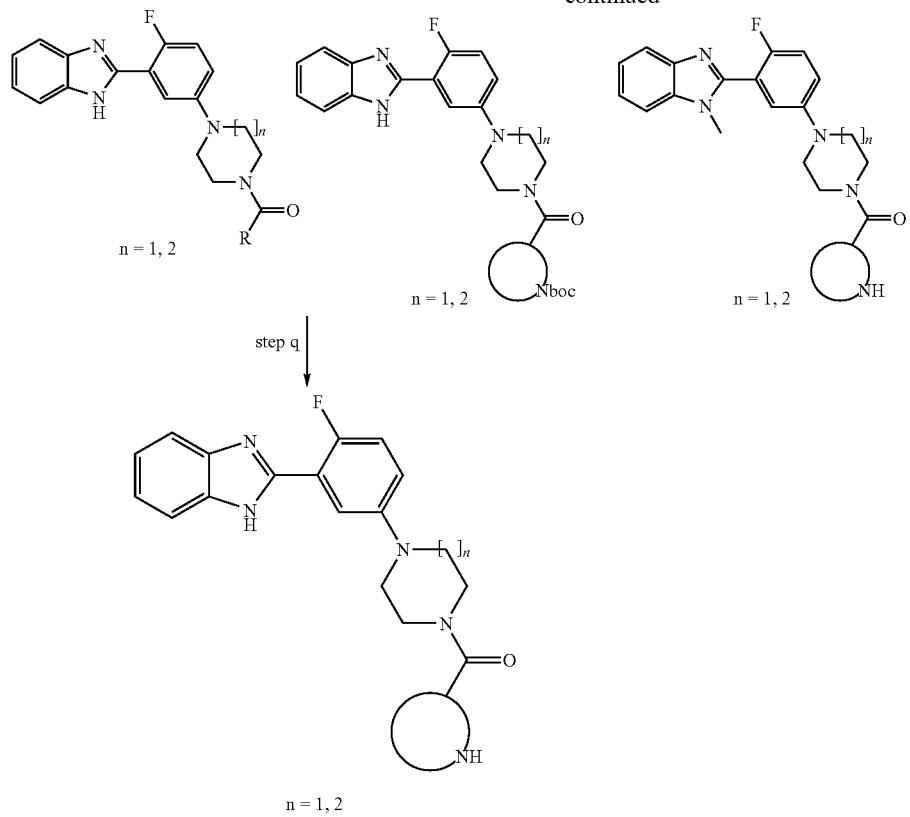
Method N
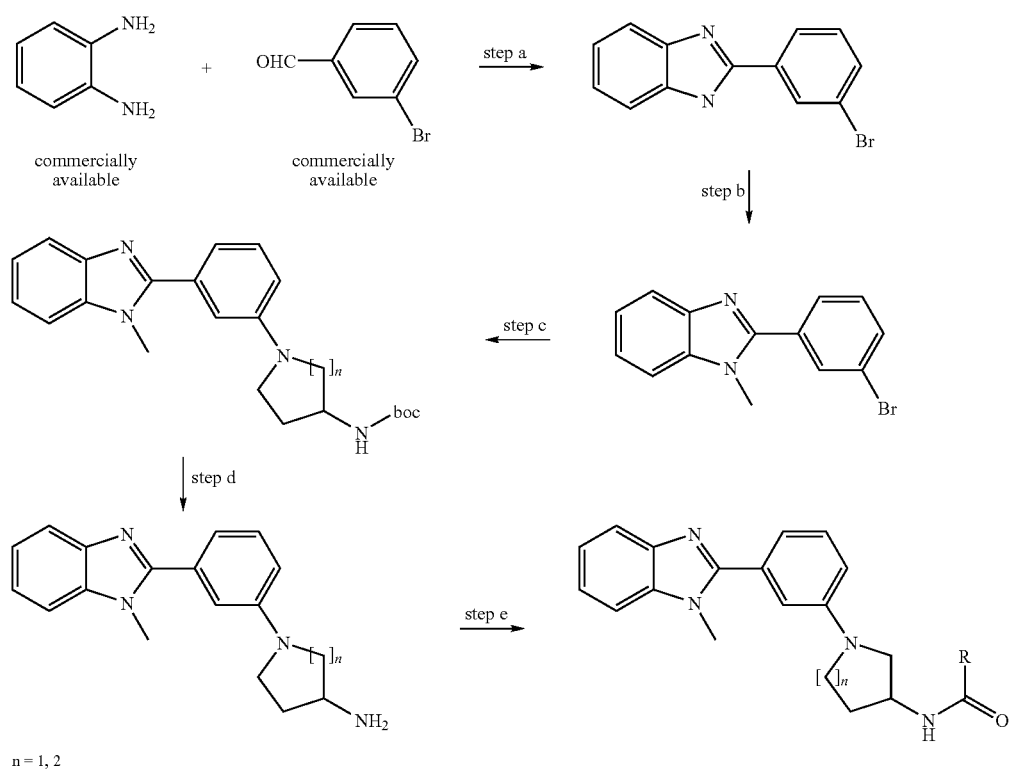

-continued
METHOD N
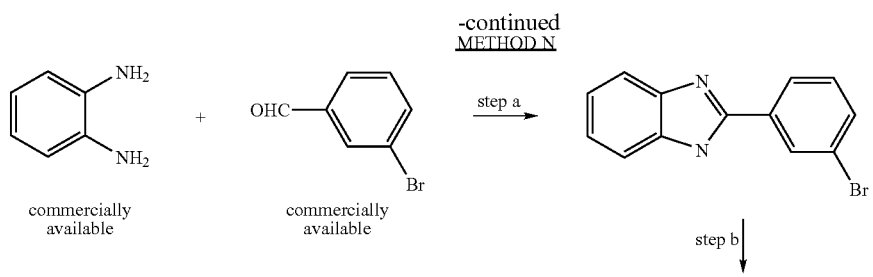
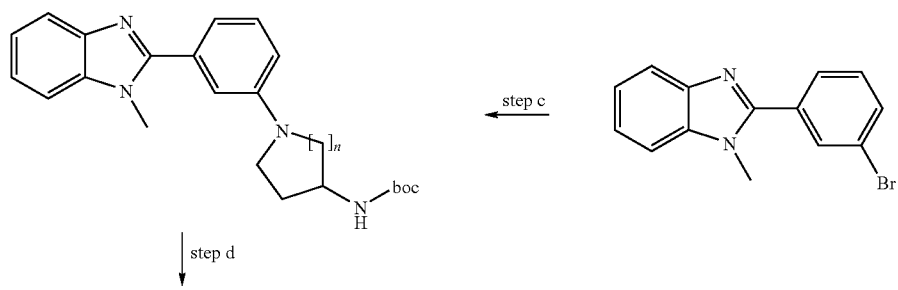
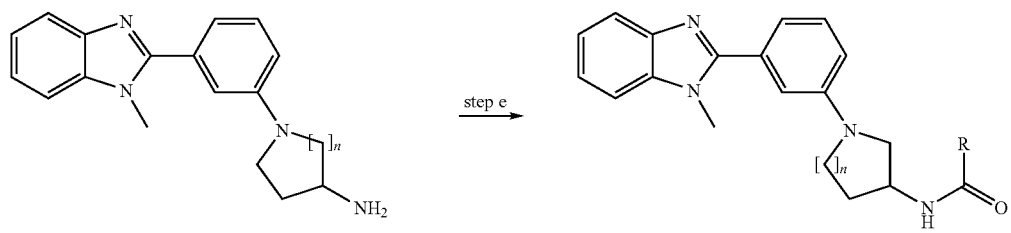
n = 1, 2
Methods O, OA
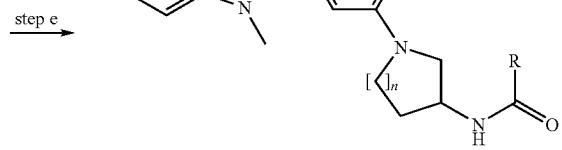
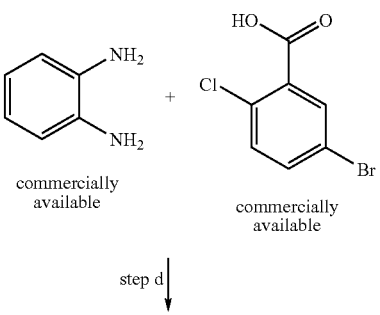

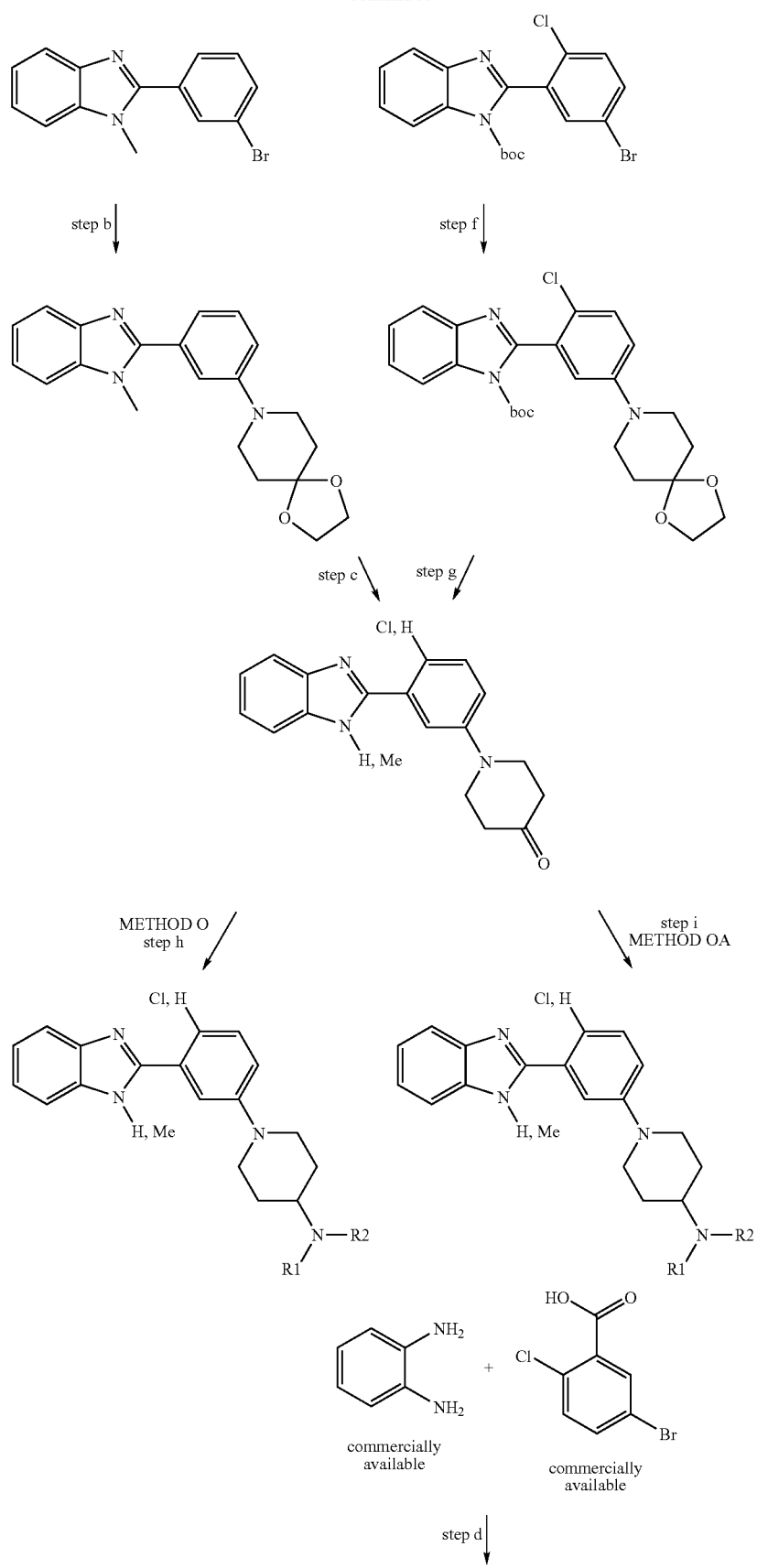

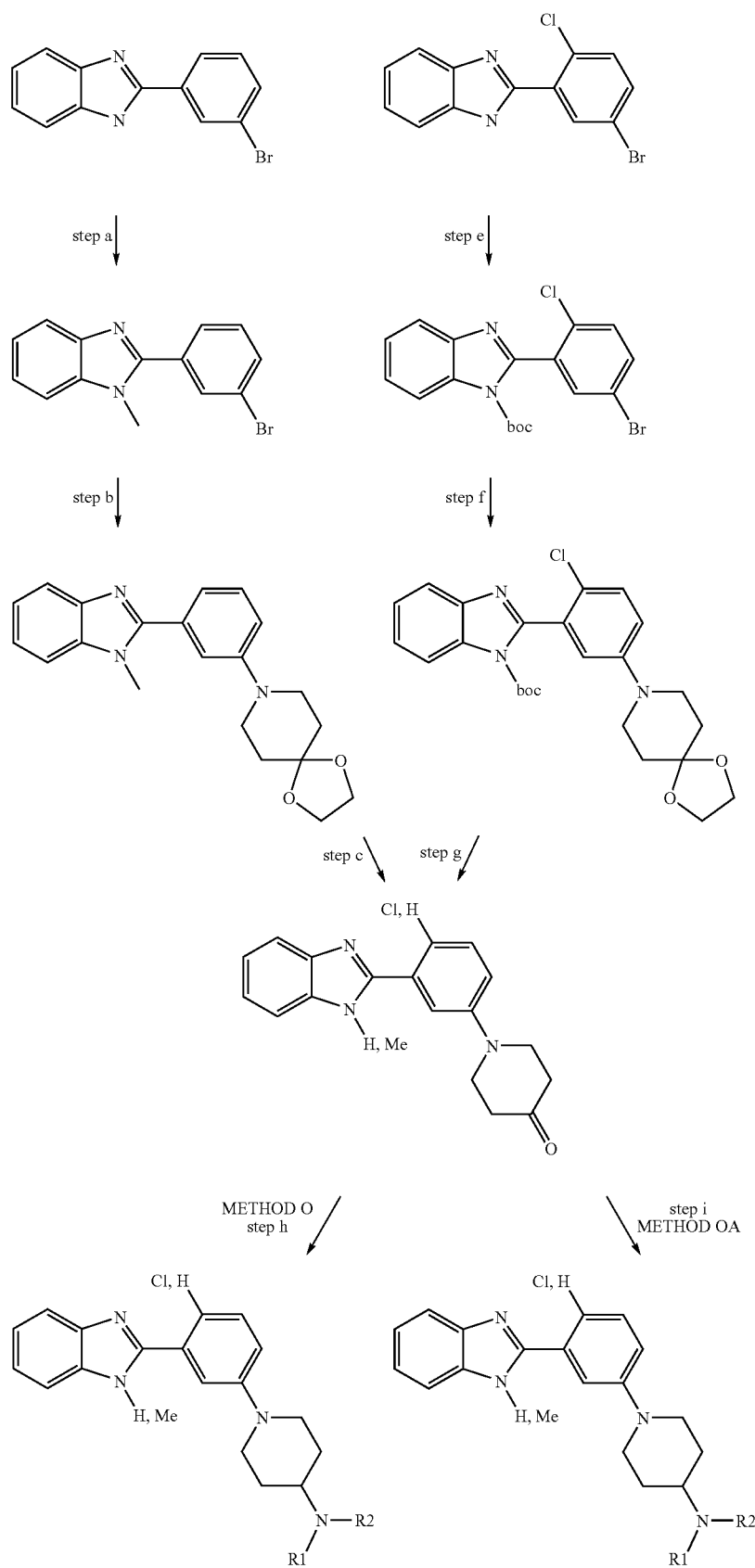

Method P
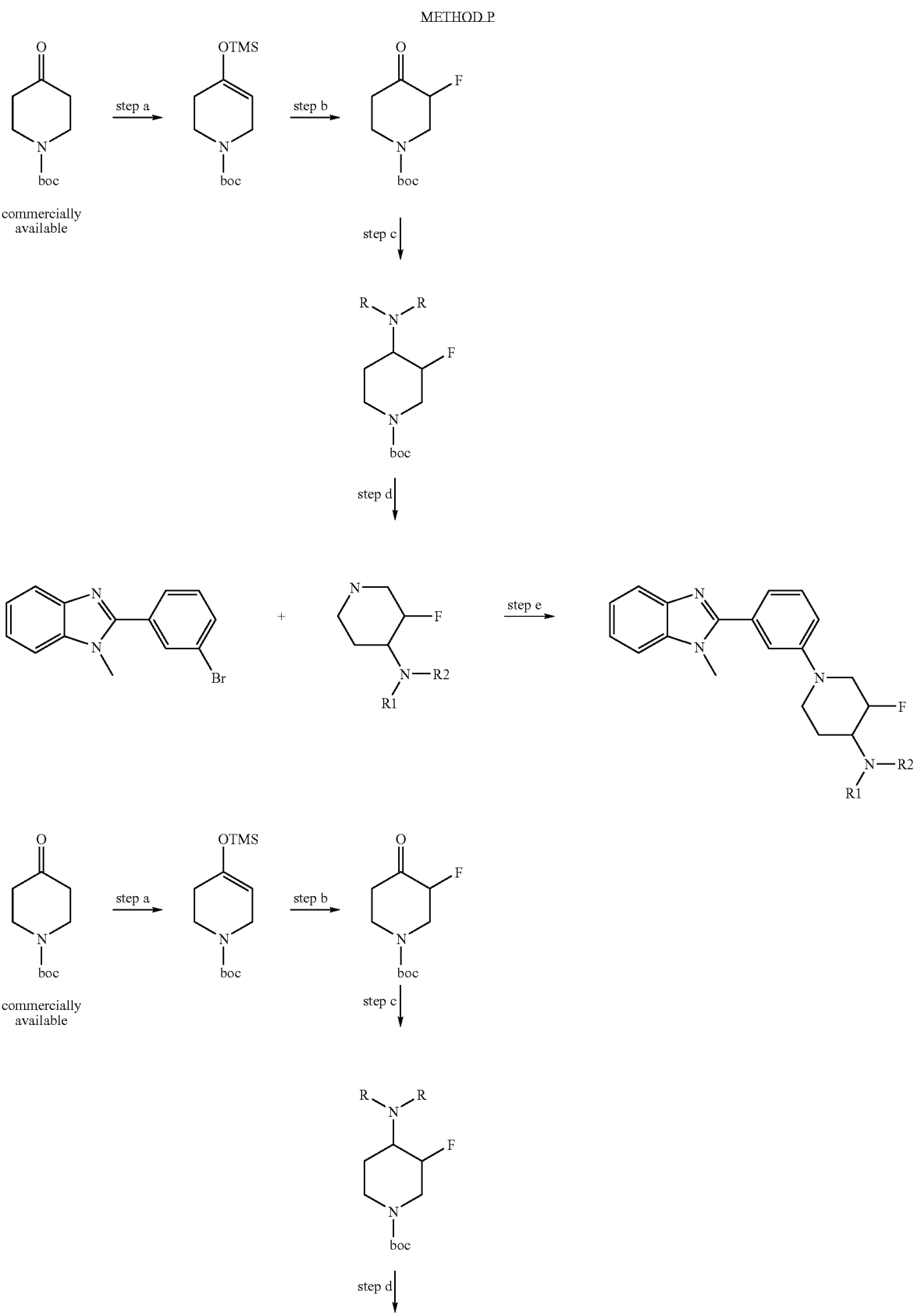

31
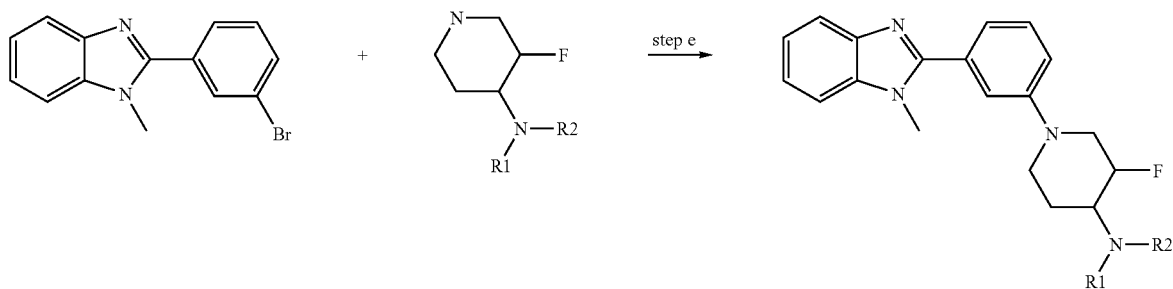
Method Q
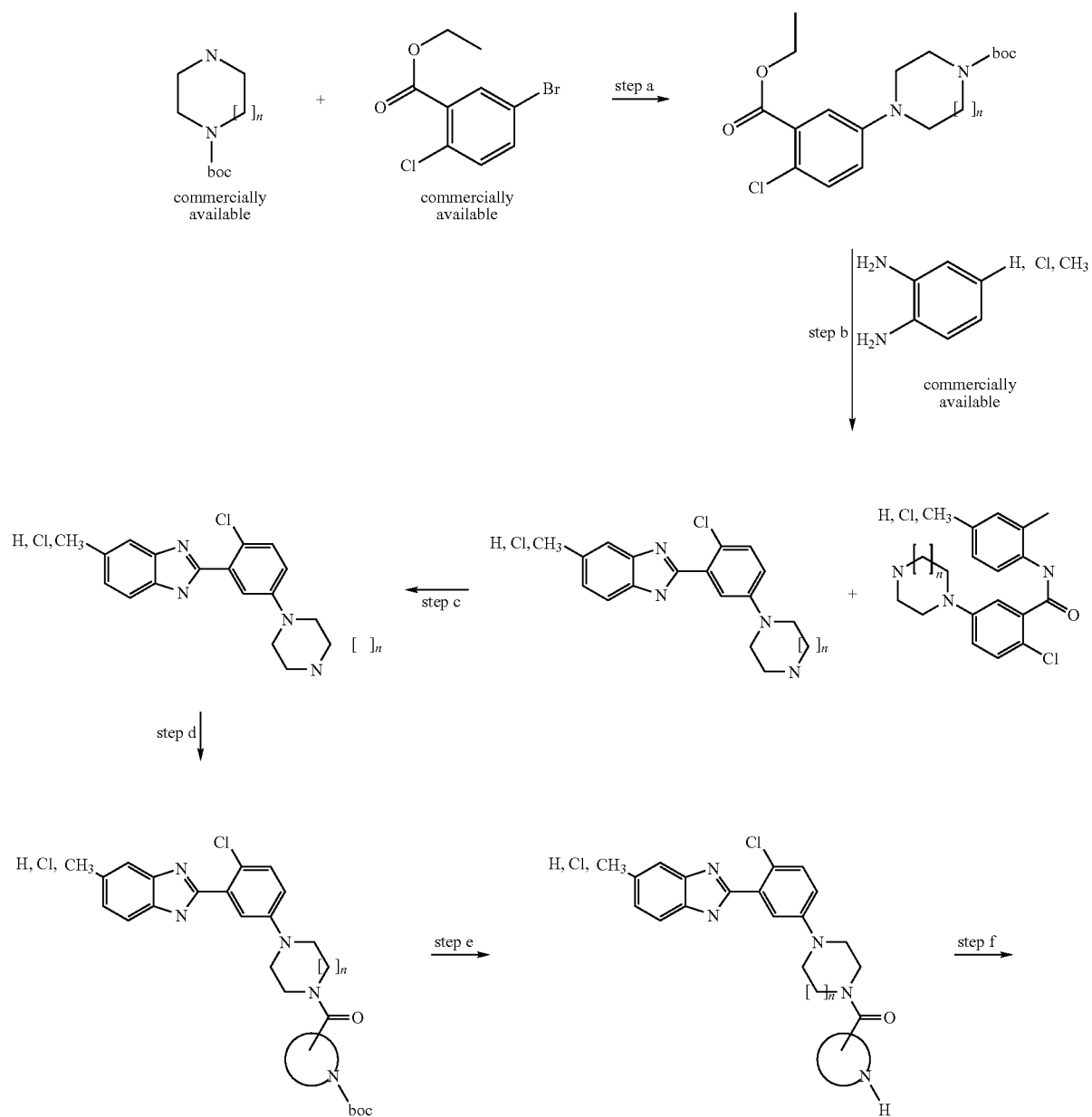

-continued
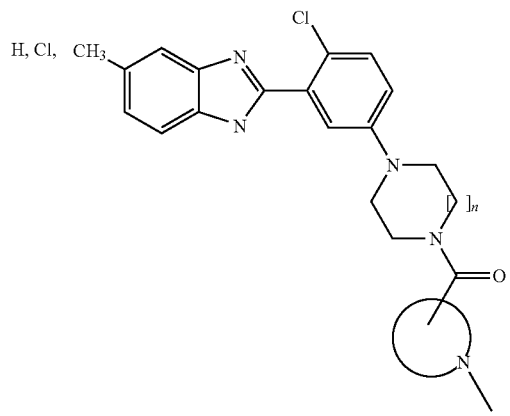
n = 1, 2
Methods R, S, T
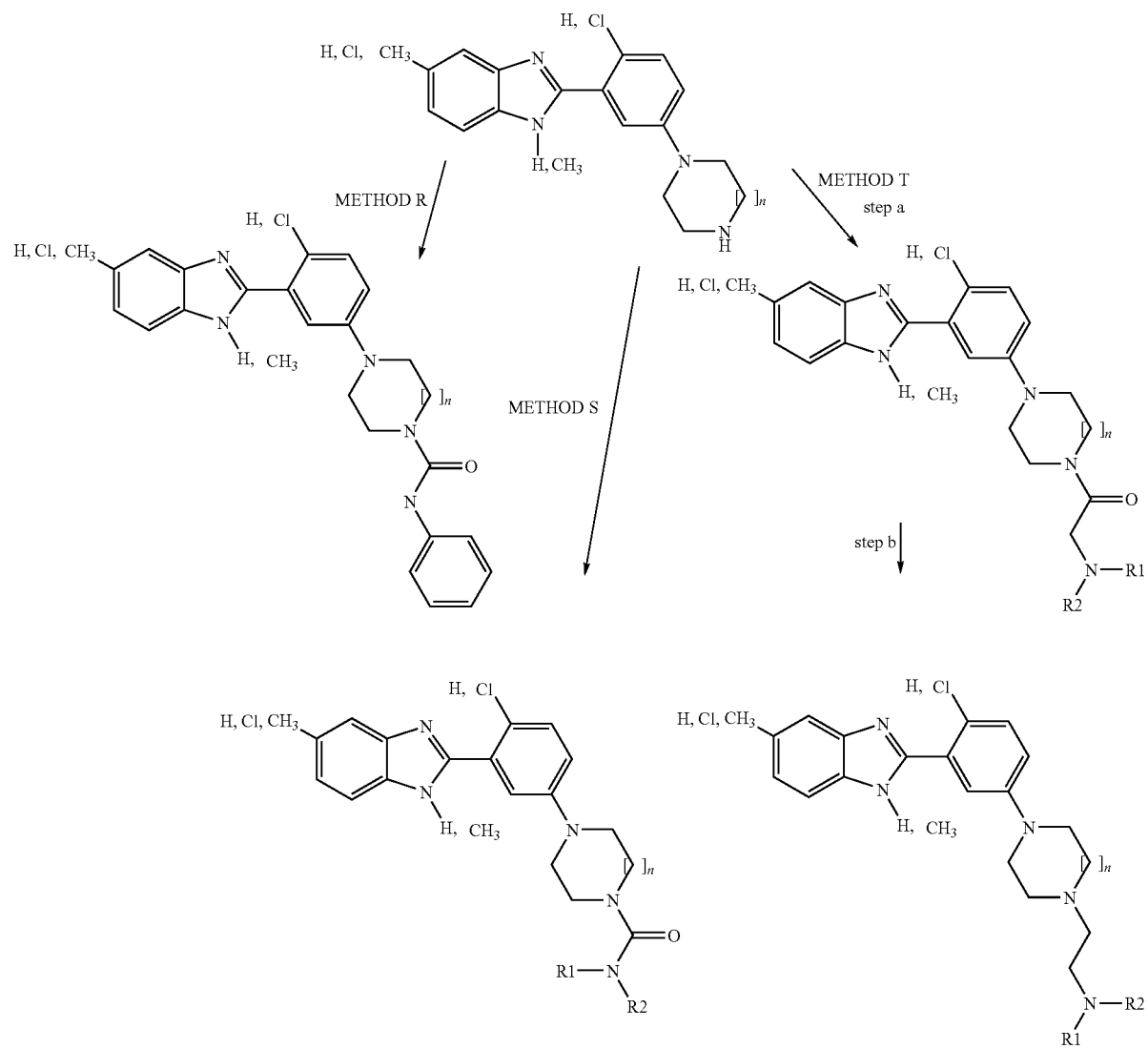

Methods U, V, W, Ab
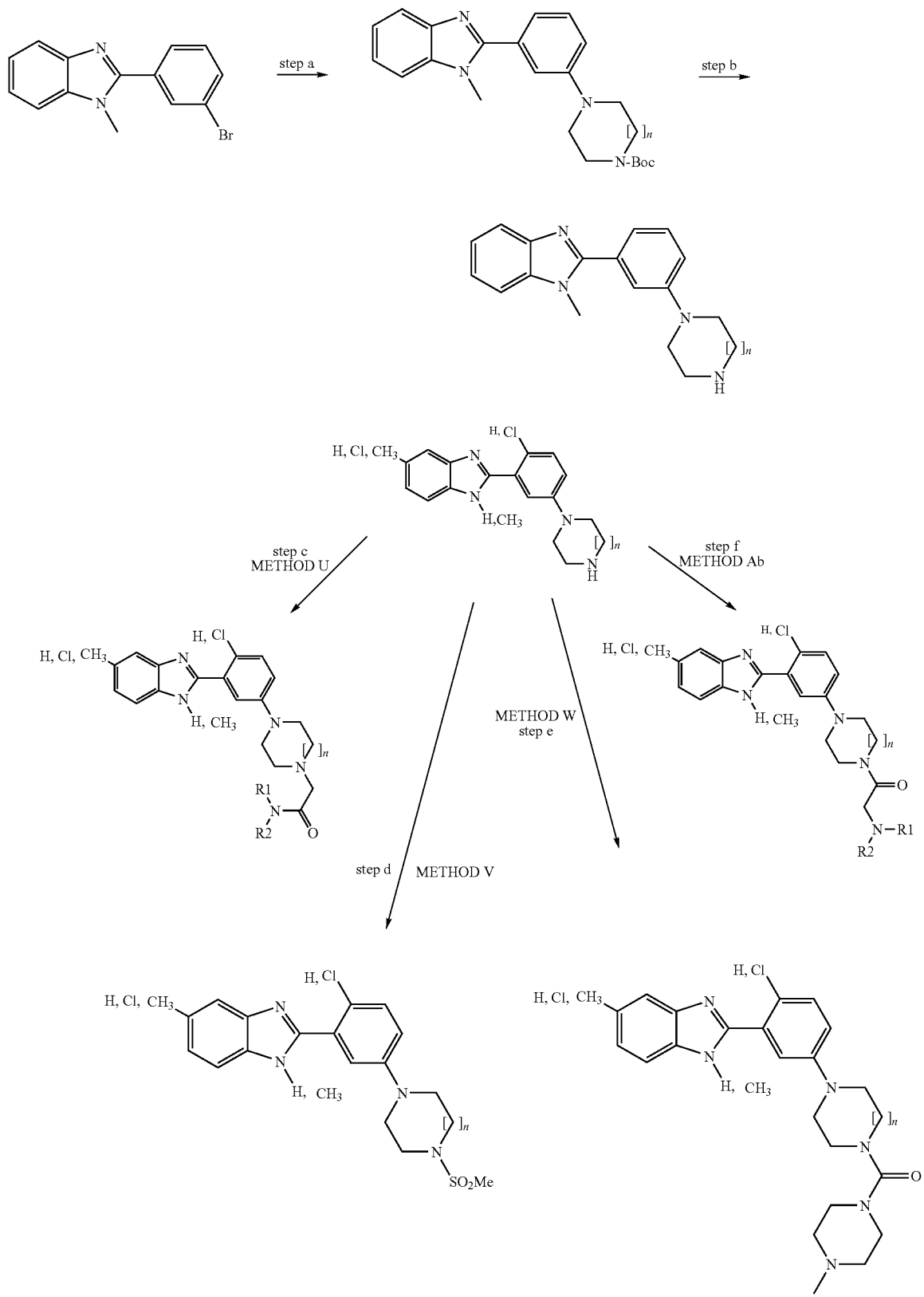
n = 1, 2

Method X
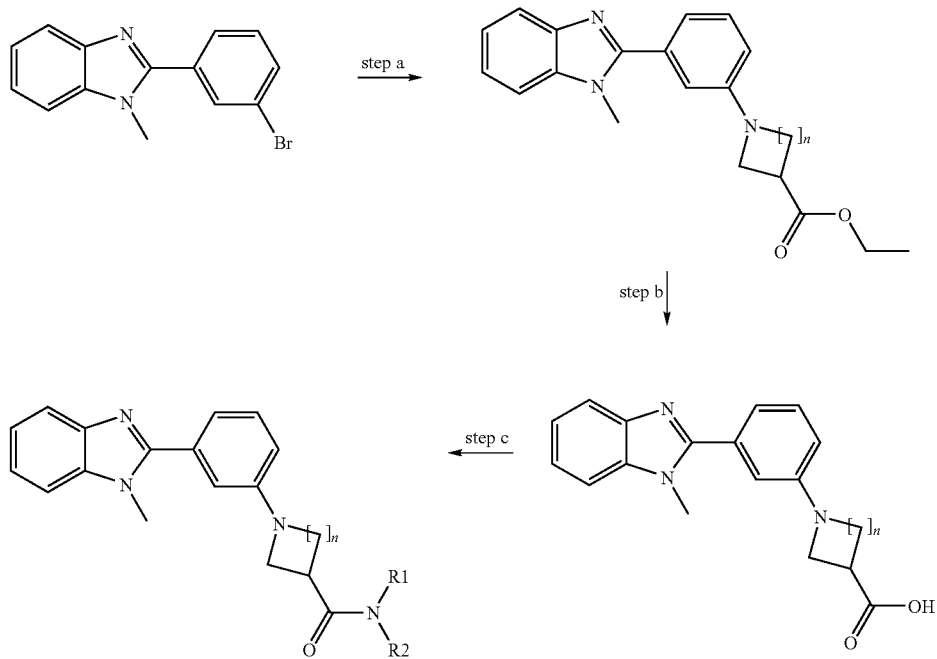
n = 1, 2, 3
Methods Y, Z
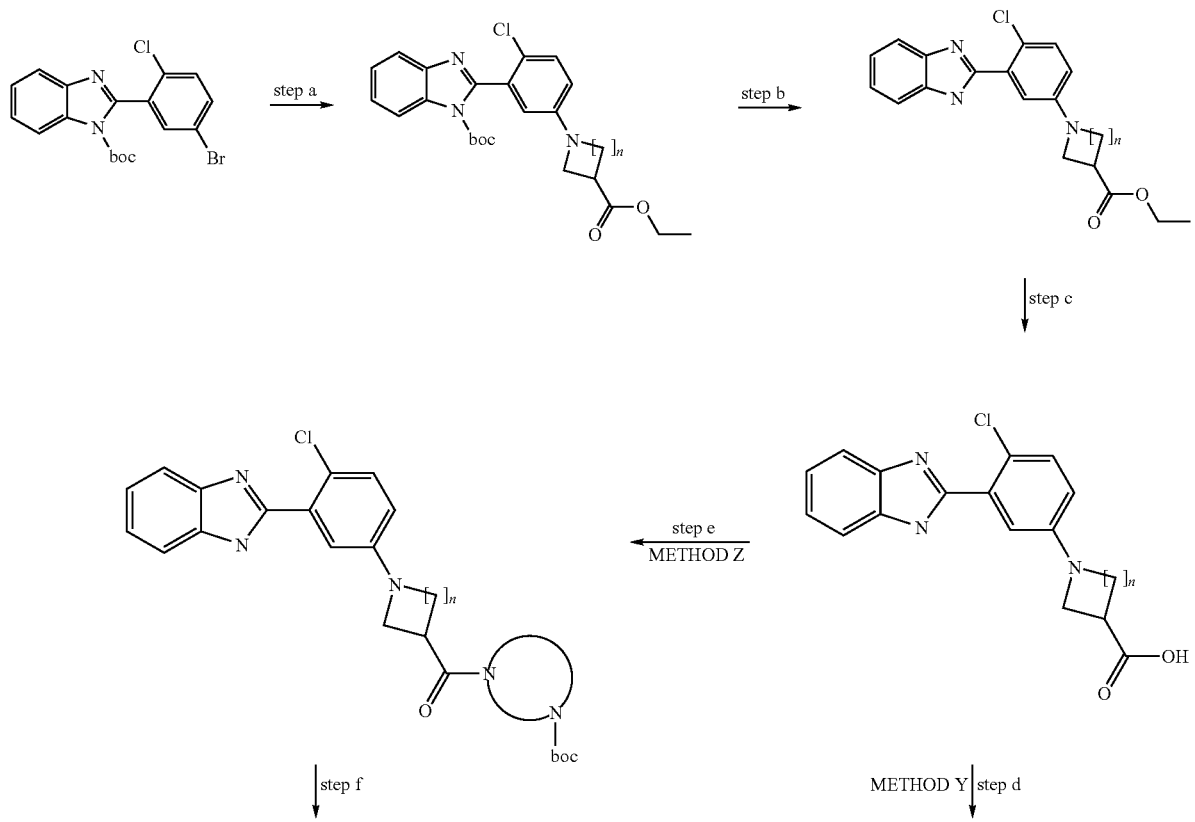

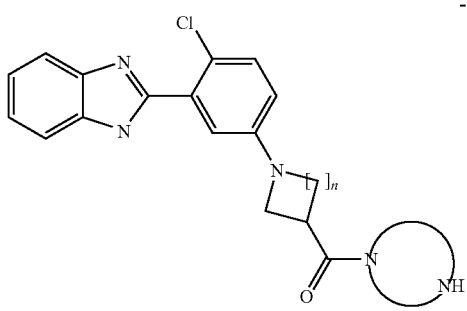

n = 1, 2, 3

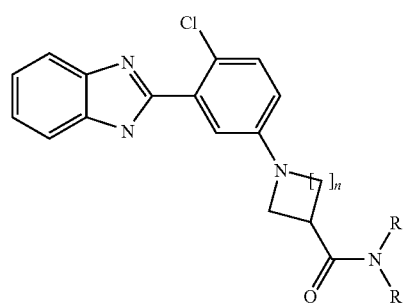

Materials and Methods

All reagents and solvents were obtained commercially. Air and moisture sensitive liquid solutions were transferred via syringe. The course of reactions was followed by thin-layer chromatography (TLC) and/or liquid chromatography-mass spectrometry (LC-MS).

All nuclear magnetic resonance spectra were recorded using a Varian Mercury Plus 400 MHz spectrometer equipped with a PFG ATB Broadband probe.

The 10 minute methods were run using a Waters 2795 separation module equipped with a Waters Micromass ZQ (ES ionisation) and Waters PDA 2996, using a Waters XTerra MS $C_{18}$ 3.5 µm 2.1×50 mm column.

Preparative HLPC was run using a Waters 2767 system with a binary Gradient Module Waters 2525 pump and coupled to a Waters Micromass ZQ (ES) or Waters 2487 DAD, using a Supelco Discovery HS C18 5.0 µm 10×21.2 mm column.

Gradients were run using 0.1% formic acid/water and 0.1% formic acid/acetonitrile with gradient 5/95 to 95/5 in the run time indicated.

Purifications were performed with a silica gel cartridges isolute flash Si, with purities above 95%.

All TLC analyses were performed on silica gel (Merck 60 F254) and spots revealed by UV visualisation at 254 nm and $KMnO_4$ or ninhydrin stain.

Microwaves: Personal Chemistry, Emrys Optimizer, microwave reactor, Absorption set to normal pre stir time 10 s.

Example 1

(2-[4-{3-(1H-Benzoimidazol-2-yl)-4-chloro-phenyl]-piperazin-1-yl}-ethyl)-dimethyl-amine 2-Chloro-5-[4-(2-dimethylamino-ethyl)-piperazin-1-yl]-benzoic acid ethyl ester Method A—Step a Ethyl 5-bromo-2-chlorobenzoate (0.80 g, 3.04 mmol), rac-2,2'-bis(diphenylphosphino)-1,1'-binaphthyl (BINAP) (0.19 g, 0.30 mmol), tris(dibenzylideneacetone)dipalladium ($Pd_2(dba)_3$) (0.28 g, 0.30 mmol) and cesium carbonate ($Cs_2CO_3$) (1.39 g, 4.26 mmol) were placed in a Schlenk tube and purged by repeated nitrogen/vacuum cycles for 30 minutes. Dry toluene (6 mL) and 1-(2-dimethylaminoethyl)piperazine (0.55 mL, 3.65 mmol) were then added. The reaction mixture was stirred for 10 min at room temperature, heated at 85° C. overnight and then cooled to room temperature. The solution was diluted with EtOAc (30 mL), the insoluble material was filtered off and the filtrate was washed with saturated brine (15 mL). The organic phase was dried over $Na_2SO_4$, filtered and concentrated under reduced pressure to obtain a residue that was purified by flash chromatography (eluent gradient: EtOAc, EtOAc:MeOH/1:1, EtOAc:MeOH:NH3 in MeOH (2M)/1:1:0.2) to afford 0.30 g of the title compound (30%).

$^1$H-NMR (400 MHz, DMSO): δ 1.28 (3H, t), 2.12 (6H, s), 2.32-2.42 (4H, m), 2.47-2.51 (4H, m), 3.11-3.14 (4H, m), 4.27 (2H, q), 7.06-7.09 (1H, m), 7.18-7.19 (1H, m), 7.30-7.32 (1H, m).

2-Chloro-5-[4-(2-dimethylamino-ethyl)-piperazin-1-yl]-benzoic acid

Method A—Step b

A solution of 2-chloro-5-[4-(2-dimethylamino-ethyl)-piperazin-1-yl]-benzoic acid ethyl ester (0.46 g, 1.36 mmol) in EtOH (6 mL) and NaOH 10% (2 mL) was heated at reflux overnight, then the reaction mixture was cooled to room temperature and the organic solvent concentrated by evaporation under reduced pressure. The resulting solution was neutralized by dropwise addition of 1N HCl and the water was then evaporated under reduced pressure. The resulting residue was dissolved in EtOH (10 mL), the insoluble material was filtered off and the filtrate concentrated under reduced pressure at room temperature, to obtain 0.24 g of the title compound (58%) without additional purification.

$^1$H-NMR (400 MHz, DMSO): δ 2.27 (6H, s), 2.46-2.55 (8H, m), 3.04-3.06 (4H, m), 7.76-7.79 (1H, m), 6.92-6.93 (1H, m), 7.07-7.09 (1H, m).

N-(2-Amino-phenyl)-2-chloro-5-[4-(2-dimethylamino-ethyl)-piperazin-1-yl]-benzamide Method A—Step c To a solution of 2-chloro-5-[4-(2-dimethylaminoethyl)-piperazin-1-yl]-benzoic acid (0.40 g, 1.29 mmol) in dry DMF (5 mL) was added 1-(3-dimethylaminopropyl)-3-ethylcarbodiimide hydrochloride (EDC) (0.25 g, 1.29 mmol), followed by 1-hydroxybenzotriazole hydrate (1-HOBt) (0.11 g, 0.77 mmol) and dimethyl-pyridin-4-yl-amine (DMAP) (0.08 g, 0.64 mmol). After 3 h stirring at room temperature, 1,2-phenylenediamine (0.21 g, 1.93 mmol) was added, and the resulting mixture was stirred at room temperature overnight. The solution was evaporated under reduced pressure, then diluted with dichlomethane (20 mL) and washed with saturated $Na_2CO_3$ solution (2×5 mL). The organic layer was dried over $Na_2SO_4$, filtered and evaporated under reduced pressure. The resulting solid was purified by flash chromatography (eluent:dichloromethane:MeOH:NH3 in MeOH (2M)/9:0.5:0.5) to obtain 0.18 g (35%) of the title compound.

¹H-NMR (400 MHz, DMSO): δ 2.13 (6H, m), 2.35-2.41 (4H, m), 2.48-2.53 (4H, m), 3.14-3.18 (4H, m), 4.91 (2H, br s), 6.54-6.59 (1H, m), 6.73-6.75 (1H, m), 6.92-7.00 (2H, m), 7.11-7.12 (1H, m), 7.23-7.25 (1H, m), 7.28-7.33 (1H, m), 9.62 (1H, br s).

(2-{4-[3-(1H-Benzoimidazol-2-yl)-4-chloro-phenyl]-piperazin-1-yl}-ethyl)-dimethyl-amine Method A—Step d A solution of N-(2-amino-phenyl)-2-chloro-5-[4-(2-dimethylamino-ethyl)-piperazin-1-yl]-benzamide (0.35 g, 0.87 mmol) in acetic acid (15 mL) was heated for 7 h at 85° C., then solvent was removed under reduced pressure and the residue triturated with Et₂O to obtain 0.25 g (75%) of the title compound as a solid without further purification.

¹H-NMR (400 MHz, DMSO): δ 2.12 (6H, s), 2.33-2.42 (4H, m), 2.49-2.57 (4H, m), 3.16-3.19 (4H, m), 7.07 (1H, dd), 7.18-7.23 (2H, m), 7.33 (1H, d), 7.38-7.41 (1H, m), 7.52 (1H, d), 7.65-7.67 (1H, m), 12.60 (1H, s). m/z 384 (M+H)⁺, retention time=0.68.

Example 2

4-[3-(1H-Benzoimidazol-2-yl)-phenyl]-piperazine-1-carboxylic acid tert-butyl ester 4-(3-Carboxy-phenyl)-piperazine-1-carboxylic acid tert-butyl ester Method B—Step b A solution of 4-(3-ethoxycarbonyl-phenyl)-piperazine-1-carboxylic acid tert-butyl ester (5.00 g, 14.95 mmol) in EtOH (50 mL) and NaOH 10% (20 mL) was refluxed for 3 h, then the reaction mixture was cooled to room temperature and the organic solvent evaporated under reduced pressure. The resulting solution was neutralized by the dropwise addition of 1N HCl and the aqueous solution was extracted with EtOAc (3×50 mL) The combined organic layers were dried over Na₂SO₄, filtered, and concentrated under reduced pressure to obtain 3.90 g of the title compound (85%) without further purification.

¹H-NMR (400 MHz, DMSO): δ 1.40 (9H, s), 3.15-3.18 (4H, m), 3.47-3.49 (4H, m), 7.27-7.29 (1H, m), 7.32-7.37 (1H, m), 7.42-7.44 (1H, m), 7.54 (1H, br s).

4-[3-(2-Amino-phenylcarbamoyl)-phenyl]-piperazine-1-carboxylic acid tert-butyl ester Method B—Step c A solution of 4-(3-carboxy-phenyl)-piperazine-1-carboxylic acid tert-butyl ester (5.80 g, 18.95 mmol) and 1,1-carbonyldiimidazole (CDI) (3.07 g, 18.95 mmol) in acetonitrile (120 mL) was stirred for 3 h at room temperature, then 1,2-phenylenediamine (2.25 g, 20.85 mmol) was added. The resulting suspension was refluxed for 3 h, then cooled to room temperature and the solvent removed under reduced pressure. The resulting residue was diluted with dichlomethane (200 mL), washed with water (3×40 mL) and the organic layer dried over Na₂SO₄, filtered and evaporated under reduced pressure. The crude product was recrystallized from EtOAc to obtain 2.99 g (40%) of the title compound.

¹H-NMR (400 MHz, DMSO): δ 1.40 (9H, m), 3.15-3.17 (4H, m), 3.45-3.47 (4H, m), 4.85 (2H, br s), 6.56-6.60 (1H, m), 6.75-6.77 (1H, m), 6.93-6.97 (1H, m), 7.11-7.14 (2H, m), 7.30-7.34 (1H, m), 7.38-7.40 (1H, m), 7.51 (1H, br s), 9.60 (1H, br s).

4-[3-(1H-Benzoimidazol-2-yl)-phenyl]-piperazine-1-carboxylic acid tert-butyl ester Method B—Step d A solution of 4-[3-(2-amino-phenylcarbamoyl)-phenyl]-piperazine-1-carboxylic acid tert-butyl ester (1.20 g, 3.03 mmol) in acetic acid (12 mL) was heated overnight at 55° C., then the solvent was removed under reduced pressure. The solid obtained was triturated with Et₂O to afford the title compound as a white solid (0.90 g, 79%) without further purification.

¹H-NMR (400 MHz, DMSO): δ 1.41 (9H, m), 3.19-3.21 (4H, m), 3.48-3.50 (4H, m), 7.05-7.08 (1H, m), 7.17-7.18 (2H, m), 7.35-7.40 (1H, m), 7.51-7.73 (4H, m), 12.80 (1H, br s). m/z 379 (M+H)⁺; retention time=2.58.

Example 3

2-(3-piperazin-1-yl-phenyl)-1H-benzoimidazole dihydrochloride 2-(3-piperazin-1-yl-phenyl)-1H-benzoimidazole dihydrochloride Method B—Step e To a solution of 4-[3-(1H-benzoimidazol-2-yl)-phenyl]-piperazine-1-carboxylic acid tert-butyl ester (1.80 g, 4.76 mmol) in MeOH (2 mL), 2M HCl in Et₂O (8 mL) was added and the resulting mixture was stirred for 6 h at room temperature.

The solvent was then removed under reduced pressure, and the resulting salt triturated with Et₂O to obtain 1.66 g (100%) of the title compound as dihydrochloride salt.

¹H-NMR (400 MHz, CD₃OD): δ 3.34-3.37 (4H, m), 3.54-3.57 (4H, m), 7.34-7.37 (1H, m), 7.52-7.58 (4H, m), 7.74-7.77 (3H, m). m/z 279 (M+H)⁺; retention time=0.26.

Example 4

{4-[3-(1H-Benzoimidazol-2-yl)-phenyl]-piperazin-1-yl}-(1-methyl-piperidin-4-yl)-methanone {4-[3-(1H-Benzoimidazol-2-yl)-phenyl]-piperazin-1-yl}-(1-methylpiperidin-4-yl)-methanone Method B—Step f To a solution of 1-methylpiperidine-4-carboxylic acid hydrochloride (0.13 g, 0.72 mmol) and N,N-diisopropylethylamine (DIPEA) (0.16 mL, 0.72 mmol) in acetonitrile (8 mL), was added CDI (0.12 g, 0.72 mmol) and the resulting suspension was stirred at room temperature for 5 h. 2-(3-piperazin-1-yl-phenyl)-1H-benzoimidazole dihydrochloride (0.20 g, 0.57 mmol) was then added and the resulting solution was heated at 65° C. overnight. The solution was then cooled to room temperature and the solvent was removed. The crude product was re-dissolved in dichloromethane (15 mL) and saturated NaHCO₃ solution (6 mL) was added with stirring. The precipitate obtained was then filtered, washed with water (3 mL) and diethyl ether (5 mL) and dried under reduced pressure to afford 0.20 g (87%) of the title compound.

¹H-NMR (400 MHz, CD₃OD): δ 1.80-1.84 (4H, m), 2.19-2.26 (2H, m), 2.35 (3H, s), 2.79-2.83 (1H, m), 2.99-3.02 (2H, m), 3.28-3.33 (4H, m), 3.78-3.79 (4H, m), 7.10-7.15 (1H, m), 7.24-7.27 (2H, m), 7.40-7.44 (1H, m), 7.55-7.59 (3H, m), 7.73-7.74 (1H, m). m/z 404 (M+H)⁺; retention time=1.10.

Example 5

2-{3-[4-(1-Methyl-piperidin-4-ylmethyl)-piperazin-1-yl]-phenyl}-1H-benzoimidazole formate

2-{3-[4-(1-Methyl-piperidin-4-ylmethyl)-piperazin-1-yl]-phenyl}-1H-benzoimidazole Method B—Step g To a solution of {4-[3-(1H-benzoimidazol-2-yl)-phenyl]-piperazin-1-yl}-(1-methyl-piperidin-4-yl)-methanone (0.12 g, 0.35 mmol) in dry THF (4 mL) boran-methyl sulfide complex in THF (($CH_3$)$_2$S.BH$_3$) (0.07 mL, 0.74 mmol) was added and the resulting suspension was heated at 60° C. overnight. The reaction was then cooled to room temperature, the solvent removed under reduced pressure and 1N HCl (3 mL) was added to the residue before heating at 100° C. for 5 h. The reaction was then cooled to room temperature, neutralized with 10% NaOH and extracted with dichloromethane (3×10 mL) The combined organic layers were dried over Na$_2$SO$_4$, filtered, and concentrated under reduced pressure to afford a residue that was purified by Preparative HPLC, to obtain 0.08 g (69%) of the title compound.

$^1$H-NMR (400 MHz, CD$_3$OD): δ 1.55-1.61 (2H, m), 2.01-2.06 (3H, m), 2.63-2.81 (5H, m), 2.94-3.00 (2H, m), 3.09-3.11 (4H, m), 3.43-3.48 (6H, m), 7.08-7.11 (1H, m), 7.26-7.28 (2H, m), 7.38-7.42 (1H, m), 7.57-7.63 (3H, m), 7.70-7.71 (1H, m), 8.36 (3H, s). m/z 390 (M+H)$^+$; retention time=0.21.

Example 6

4-[3-(1-Methyl-1H-benzoimidazol-2-yl)-phenyl]-piperazine-1-carboxylic acid tert-butyl ester

4-[3-(1-Methyl-1H-benzoimidazol-2-yl)-phenyl]-piperazine-1-carboxylic acid tert-butyl ester Method C—Step a.

A mixture of 4-[3-(1H-benzoimidazol-2-yl)-phenyl]-piperazine-1-carboxylic acid tert-butyl ester (0.83 g, 2.20 mmol) (obtained as described in method B) and NaH 60% oil (0.11 g, 4.39 mmol) in THF (10 mL) was stirred at room temperature for 1 h. Methyl iodide (0.27 mL, 4.39 mmol) was added and the resulting solution was stirred overnight. Water (15 mL) was added to the reaction solution, then the suspension was neutralized with 1N HCl and extracted with EtOAc (3×40 mL) The combined organic layers were dried (Na$_2$SO$_4$), filtered, and concentrated under reduced pressure. The residue was triturated with Et$_2$O and the solid obtained filtered, to give 0.76 g (88%) of the title compound.

$^1$H-NMR (400 MHz, DMSO): δ 1.40 (9H, m), 3.18-3.20 (4H, m), 3.45-3.48 (4H, m), 3.85 (3H, br s), 7.14-7.15 (1H, m), 7.22-7.29 (3H, m), 7.33 (1H, br s), 7.39-7.42 (1H, m), 7.60-7.62 (1H, m), 7.65-7.67 (1H, m). m/z 393 (M+H)$^+$; retention time=2.56.

Example 7

1-Methyl-2-(3-piperazin-1-yl-phenyl)-1H-benzoimidazole dihydrochloride

1-Methyl-2-(3-piperazin-1-yl-phenyl)-1H-benzoimidazole dihydrochloride

Method C—Step b

To a solution of 4-[3-(1-methyl-1H-benzoimidazol-2-yl)-phenyl]-piperazine-1-carboxylic acid tert-butyl ester (1.30 g, 3.32 mmol) in MeOH (4 mL) was added 2M HCl in Et$_2$O (9 mL) and the resulting solution was stirred for 6 h at room temperature.

The solvent was then removed under reduced pressure, and the resulting salt triturated with Et$_2$O to obtain 1.21 g (100%) of the title compound as dihydrochloride salt.

$^1$H-NMR (400 MHz, CD$_3$OD): δ 3.42-3.44 (m, 4H), 3.60-3.63 (m, 4H), 4.13 (s, 3H), 7.41-7.48 (m, 2H), 7.53-7.55 (m, 1H), 7.65-7.73 (m, 3H), 7.85-7.88 (m, 1H), 7.97-7.99 (m, 1H). m/z 293 (M+H)$^+$; retention time=0.30.

Example 8

Cyclopropyl-{4-[3-(1-methyl-1H-benzoimidazol-2-yl)-phenyl]-piperazin-1-yl}-methanone

Cyclopropyl-{4-[3-(1-methyl-1H-benzoimidazol-2-yl)-phenyl]-piperazin-1-yl}-methanone Method C—Step c To a solution of cyclopropanecarboxylic acid (0.06 g, 0.68 mmol) in acetonitrile (8 mL) was added CDI (0.11 g, 0.68 mmol) and the resulting suspension was stirred at room temperature for 5 h. 1-Methyl-2-(3-piperazin-1-yl-phenyl)-1H-benzoimidazole dihydrochloride (0.20 g, 0.55 mmol) was added and the resulting solution heated at 65° C. overnight. The reaction was then cooled to room temperature, the solvent removed under reduced pressure. The crude product was redissolved in dichloromethane (15 mL) and washed with saturated NaHCO$_3$ solution (2×3 mL) The organic layer was dried over Na$_2$SO$_4$, filtered and concentrated under reduced pressure. The residue was purified by flash chromatography (eluent: cyclohexane:EtOAc, gradient from 100% cyclohexane to 100% ethyl acetate) to afford 0.17 g (85%) of the title compound.

$^1$H-NMR (400 MHz, CD$_3$OD): δ 0.82-0.84 (2H, m), 0.89-0.91 (2H, m), 1.99-2.00 (1H, m), 3.24-3.28 (2H, m), 3.29-3.35 (2H, m), 3.67-3.78 (2H, m), 3.85 (3H, br s), 3.89-3.95 (2H, m), 7.16-7.22 (1H, m), 7.28-7.35 (3H, m), 7.44 (1H, t), 7.51-7.53 (1H, m), 7.66-7.68 (1H, m). m/z 361 (M+H)$^+$; retention time=1.75.

Example 9

2-{3-[4-Cyclopropylmethyl-piperazin-1-yl]-phenyl}-1-methyl-1H-benzoimidazole formate

2-{3-[4-Cyclopropylmethyl-piperazin-1-yl]-phenyl}-1-methyl-1H-benzoimidazole Method C—Step d To a solution of cyclopropyl-{4-[3-(1-methyl-1H-benzoimidazol-2-yl)-phenyl]-piperazin-1-yl}-methanone (0.17 g, 0.47 mmol) in dry THF (3.50 mL) was added (CH$_3$)$_2$S.BH$_3$ in THF (0.11 mL, 1.18 mmol) and the resulting suspension was heated at 65° C. overnight. The reaction solution was then cooled to room temperature, solvent was removed under reduced pressure and 1N HCl (3 mL) was added to the residue before heating at 100° C. for 6 h. The reaction was cooled to room temperature, then made basic by the dropwise addition of 15% NaOH and extracted with EtOAc (3×10 mL) The combined organic layers were dried over Na$_2$SO$_4$, filtered and concentrated under reduced pressure to afford a residue that was purified by Preparative HPLC, to obtain 0.05 g (32%) of the title compound.

$^1$H-NMR (400 MHz, CD$_3$OD): δ 0.42-0.46 (2H, m), 0.74-0.78 (2H, m), 1.14-1.17 (1H, m), 3.06-3.08 (2H, m), 3.47 (4H, br s), 3.57 (4H, br s), 3.86 (3H, s), 7.21-7.38 (5H, m), 7.47-7.55 (2H, m), 7.68-7.70 (1H, m), 8.33 (2H, s). m/z 347 (M+H)$^+$; retention time=0.65.

Example 10

3-{4-[3-(1-Methyl-1H-benzoimidazol-2-yl)-phenyl]-piperazine-1-carbonyl}-morpholine-4-carboxylic acid tert-butyl ester 3-{4-[3-(1-Methyl-1H-benzoimidazol-2-yl)-phenyl]-piperazine-1-carbonyl}-morpholine-4-carboxylic acid tert-butyl ester Method D, E—Step a To a solution of morpholine-3,4-dicarboxylic acid-4-tert-butyl ester (0.16 g, 0.71 mmol) in acetonitrile (8 mL) was added CDI (0.16 g, 0.71 mmol) and the resulting suspension was stirred at room temperature overnight. 1-Methyl-2-(3-piperazin-1-yl-phenyl)-1H-benzoimidazole dihydrochloride (0.20 g, 0.55 mmol) (obtained as described in method C) and DIPEA (0.19 mL, 1.10 mmol) were added and the resulting solution heated at 65° C. overnight. The reaction was then cooled to room temperature, the solvent removed, the crude product was dissolved with dichloromethane (15 mL) and washed with saturated NaHCO$_3$ solution (2×3 mL) The organic layer was dried over Na$_2$SO$_4$, filtered and concentrated under reduced pressure. The residue was purified by flash chromatography (eluent: gradient from cyclohexane to cyclohexane:EtOAc 2:1) to afford 0.11 g (40%) of the title compound.

$^1$H-NMR (400 MHz, CD$_3$OD): δ 1.44 (9H, br s), 3.30-3.89 (16H, br m), 4.02-4.18 (2H, m), 7.20-7.26 (2H, m), 7.30-7.37 (3H, m), 7.47 (1H, t), 7.55-7.57 (1H, m), 7.67-7.68 (1H, m). m/z 506 (M+H)$^+$; retention time=2.24.

Example 11

{4-[3-(1-Methyl-1H-benzoimidazol-2-yl)-phenyl]-piperazin-1-yl}-morpholin-3-yl-methanone hydrochloride {4-[1-(1-Methyl-1H-benzoimidazol-2-yl)-phenyl]-piperazin-1-yl}-morpholin-3-yl-methanone Method D—Step b A solution of 3-{4-[3-(1-methyl-1H-benzoimidazol-2-yl)-phenyl]-piperazine-1-carbonyl}-morpholine-4-carboxylic acid tert-butyl ester (0.15 g, 0.30 mmol) in 2M HCl in Et$_2$O (3 mL) was stirred at room temperature overnight.

The precipitate was filtered, washed with diethyl ether and the solid solved in water (15 mL) and washed with dichloromethane (2×3 mL). The organic layer was then dried over Na$_2$SO$_4$, filtered and concentrated under reduced pressure, to afford 0.09 g (79%) of the title compound.

$^1$H-NMR (400 MHz, CD$_3$OD): δ 2.81 (2H, d), 3.12-3.25 (7H, m), 3.54-3.65 (4H, m), 3.72 (3H, br s), 3.77-3.89 (2H, m), 7.04-7.10 (2H, m), 7.16-7.24 (3H, m), 7.32 (1H, t), 7.38-7.40 (1H, d), 7.56-7.58 (1H, d). m/z 406 (M+H)$^+$; retention time=0.52.

Example 12

{4-[3-(1-Methyl-1H-benzoimidazol-2-yl)-phenyl]-piperazin-1-yl}-(4-methyl-morpholin-3-yl)-methanone {4-[1-(1-Methyl-1H-benzoimidazol-2-yl)-phenyl]-piperazin-1-yl}-(4-methyl-morpholin-3-yl)-methanone Method D—Step c To a suspension of {4-[3-(1-Methyl-1H-benzoimidazol-2-yl)-phenyl]-piperazin-1-yl}-morpholin-3-yl-methanone (0.08 g, 0.20 mmol) and sodium triacetoxyborohydride (NaB(OAc)$_3$H) (0.17 g, 0.79 mmol) in dichloroethane (2 mL) formaldehyde 37% (0.64 mL, 7.90 mmol) was added. The reaction mixture was stirred at room temperature overnight, quenched with saturated Na$_2$CO$_3$ solution (3 mL) and then extracted with dichloromethane (4×2 mL). The combined organic layers were dried over Na$_2$SO$_4$, filtered, and concentrated under reduced pressure to obtain a yellow oil (0.08 g, 97%).

$^1$H-NMR (MHz, CD$_3$OD): δ 2.24 (3H, s), 2.33-2.39 (1H, m), 2.78-2.82 (1H, m), 3.25-3.28 (2H, m), 3.30-3.32 (2H, m), 3.34-3.37 (1H, m), 3.47-3.52 (1H, m), 3.62-3.68 (1H, m), 3.76-3.85 (4H, m), 3.87 (3H, s), 3.94-3.96 (2H, m), 7.18-7.24 (2H, m), 7.28-7.36 (3H, m), 7.44-7.48 (1H, m), 7.53-7.55 (1H, m), 7.66-7.69 (1H, m). m/z 420 (M+H)$^+$; retention time=1.12.

Example 13

1-Methyl-2-{3-[4-(4-methyl-morpholin-3-ylmethyl)-piperazin-1-yl]-phenyl}-1H-benzoimidazole formate 1-Methyl-2-{3-[4-(4-methyl-morpholin-3-ylmethyl)-piperazin-1-yl]-phenyl}-1H-benzoimidazole Method D—Step d To a solution of {4-[3-(1-Methyl-1H-benzoimidazol-2-yl)-phenyl]-piperazin-1-yl}-(4-methyl-morpholin-3-yl)-methanone (0.06 g, 0.16 mmol) in dry THF (2 mL) at room temperature under a nitrogen atmosphere was added lithium aluminium hydride (LiAlH$_4$) (0.02 g, 0.47 mmol). The reaction was heated at reflux for 2 h and other LiAlH$_4$ (0.01 g, 0.24 mmol). After 30 min the solution was cooled to room temperature, quenched with 10% NaOH (3 mL) and then extracted with dichloromethane (3×3 mL) The combined organic layers were dried over Na$_2$SO$_4$, filtered, and concentrated under reduced pressure. The crude was then purified by Preparative HPLC to obtain 0.03 g (41%) of the title compound.

$^1$H-NMR (MHz, CD$_3$OD): δ 2.49-2.54 (1H, m), 2.66-2.77 (4H, m), 2.88-2.94 (1H, m), 2.96 (3H, s), 3.09-3.16 (1H, s), 3.57-3.63 (1H, m), 3.29-3.43 (6H, m), 3.78-3.86 (1H, m), 3.88 (3H, s), 3.92-3.97 (1H, m), 4.01-4.05 (1H, m), 7.16-7.18 (2H, m), 7.31-7.39 (3H, m), 7.38-7.46 (1H, m), 7.55-7.58 (1H, m), 7.67-7.70 (1H, m), 8.28 (2H, s). m/z 406 (M+H)$^+$; retention time=0.92.

Example 14

3-{4-[3-(1-Methyl-1H-benzoimidazol-2-yl)-phenyl]-piperazin-1-ylmethyl}-morpholine-4-carboxylic acid tert-butyl ester formate 3-{4-[3-(1-Methyl-1H-benzoimidazol-2-yl)-phenyl]-piperazin-1-ylmethyl}-morpholine-4-carboxylic acid tert-butyl ester Method E—Step e To a solution of 3-{4-[3-(1-methyl-1H-benzoimidazol-2-yl)-phenyl]-piperazine-1-carbonyl}-morpholine-4-carboxylic acid tert-butyl ester (0.21 g, 0.42 mmol) in dry THF (3 mL) at room temperature under a nitrogen atmosphere was added lithium aluminium hydride (LiAlH$_4$) (0.05 g, 1.27 mmol). The reaction was heated at reflux for 2 h. The solution was then cooled to room temperature, quenched with 15% NaOH and then extracted with dichloromethane (3×10 mL). The combined organic layers were dried over Na$_2$SO$_4$, filtered, and concentrated under reduced pressure. The crude was then purified by Preparative HPLC to obtain 0.09 g (43%) of the title compound.

$^1$H-NMR (400 MHz, CD$_3$OD): δ 1.48 (9H, s), 3.02-3.25 (6H, m), 3.39-3.46 (6H, m), 3.55-3.59 (1H, m), 3.76-3.90 (6H, m), 4.15-4.35 (1H, m), 7.20-7.24 (2H, m), 7.64-7.41 (3H, m), 7.45-7.49 (1H, m), 7.58-7.60 (1H, m), 7.69-7.71 (1H, m). m/z 492 (M+H)$^+$; retention time=1.45.

Example 15

1-Methyl-2-[3-(4-morpholin-3-ylmethyl-piperazin-1-yl)-phenyl]-1H-benzoimidazole

1-Methyl-2-[3-(4-morpholin-3-ylmethyl-piperazin-1-yl)-phenyl]-1H-benzoimidazole

Method E—Step f

To a solution of 3-{4-[3-(1-methyl-1H-benzoimidazol-2-yl)-phenyl]-piperazin-1-ylmethyl}-morpholine-4-carboxylic acid tert-butyl ester (0.07 g, 0.15 mmol) in dichloromethane (1 mL) was added 2M HCl in Et$_2$O (3 mL) and the resulting solution was stirred for 7 h at room temperature.

The resulting precipitate was filtered off, washed with diethyl ether and then purified by Prep-HPLC. The fractions were basified with K$_2$CO$_3$ to avoid an eventual formylation and then the solvent was removed under reduced pressure. The crude was then recovered with dichloromethane (15 mL) and the organic layer was washed with water (3×4 mL), dried over Na$_2$SO$_4$, filtered and concentrated under reduced pressure, to afford 0.02 g (37%) of the title compound.

$^1$H-NMR (400 MHz, DMSO): δ 2.11-2.24 (2H, m), 2.48-2.58 (3H, m), 2.71-2.76 (2H, m), 2.83-2.89 (1H, m), 2.98-3.06 (1H, m), 3.19-3.24 (4H, m), 3.28-3.38 (2H, m), 3.62-3.71 (2H, m), 3.86 (3H, s), 7.08-7.12 (1H, m), 7.17-7.30 (4H, m), 7.35-7.40 (1H, m), 7.58-7.67 (2H, m). m/z 392 (M+H)$^+$; retention time=0.77.

Example 16

(2-{4-[3-(1H-Benzoimidazol-2-yl)-phenyl]-piperazin-1-yl}-2-oxo-ethyl)-carbamic acid tert-butyl ester (2-{4-[3-(1H-Benzoimidazol-2-yl)-phenyl]-piperazin-1-yl}-2-oxo-ethyl)-carbamic acid tert-butyl ester Method F—Step a To a solution of N-(tert-butoxycarbonyl)-glycine (0.13 g, 0.74 mmol) in acetonitrile (8 mL) was added CDI (0.12 g, 0.68 mmol) and the resulting suspension was stirred at room temperature overnight. 2-(3-piperazin-1-yl-phenyl)-1H-benzoimidazole dihydrochloride (0.20 g, 0.57 mmol) (obtained as described in method B) and DIPEA (0.20 mL, 1.14 mmol) were then added and the resulting solution was heated at 65° C. overnight. The reaction was then cooled to room temperature, solvent removed, the crude recovered with dichloromethane (15 mL) and washed with saturated NaHCO$_3$ solution (2×3 mL). The organic layer was dried over Na$_2$SO$_4$, filtered and concentrated under reduced pressure. The residue was purified by flash chromatography (eluent: cyclohexane:EtOAc/2:1) to afford 0.14 g (56%) of the title compound.

$^1$H-NMR (400 MHz, CD3OD): δ 1.46 (9H, s), 3.29-3.36 (4H, m), 3.69-3.71 (2H, m), 3.67-3.80 (2H, m), 4.00 (2H, s), 7.13-7.16 (1H, m), 7.24-7.27 (2H, m), 7.42 (1H, t), 7.56-7.62 (3H, m), 7.73-7.74 (1H, m). m/z 436 (M+H)$^+$; retention time=2.13.

Example 17

2-{4-[3-(1H-benzoimidazol-2-yl)-phenyl]-piperazin-1-yl]-ethylamine

2-{4-[3-(1H-benzoimidazol-2-yl)-phenyl]-piperazin-1-yl]-ethylamine

Method F—Step b

To a solution of (2-{4-[3-(1H-benzoimidazol-2-yl)-phenyl]-piperazin-1-yl}-2-oxo-ethyl)-carbamic acid tert-butyl ester (0.12 g, 0.28 mmol) in dry THF (3.50 mL) (CH$_3$)$_2$S.BH$_3$ in THF (0.06 mL, 0.69 mmol) was added and the resulting suspension was heated at 65° C. overnight. The reaction was then cooled to room temperature, the solvent removed under reduced pressure and 1N HCl (3 mL) was added to the residue before heating at 100° C. for 6 h. The reaction was cooled to room temperature, then made basic by the dropwise addition of 15% NaOH and the white solid obtained was filtered and washed with water and diethyl ether, to obtain 0.06 g (73%) of the title compound.

$^1$H-NMR (400 MHz, CD$_3$OD): δ 2.60-2.70 (6H, m), 2.98-3.01 (2H, m), 3.30-3.34 (6H, m), 7.10 (1H, d), 7.24-7.26 (2H, m), 7.39 (1H, t), 7.52 (1H, d), 7.53-7.60 (2H, m), 7.73 (1H, br s). m/z 322 (M+H)$^+$; retention time=0.22.

Example 7

1-[3-(1H-Benzoimidazol-2-yl)-4-chloro-phenyl]-piperidin-4-ol

8-[3-(1H-Benzoimidazol-2-yl)-4-chloro-phenyl]-1,4-dioxa-8-aza-spiro[4.5]decane

The same procedure as that used in method A was used starting from 1,4-dioxa-8-azaspiro[4.5]decane hydrochloride.

1.25 g of the title compound were obtained (77%, last step).

$^1$H-NMR (400 MHz, DMSO): δ 1.70 (4H, br s), 3.31-3.34 (4H, m), 3.90 (4H, br s), 7.09-7.12 (1H, m), 7.19-7.21 (2H, m), 7.37-7.40 (2H, m), 7.60 (2H, br s), 12.62 (1H, s).

1-[3-(1H-Benzoimidazol-2-yl)-4-chloro-phenyl]-piperidin-4-one

Method G, H—Step a

To a suspension of 8-[3-(1H-benzoimidazol-2-yl)-4-chloro-phenyl]-1,4-dioxa-8-aza-spiro[4.5]decane (2.00 g, 5.42 mmol) in water (50 mL) was added H$_2$SO$_4$ (2.50 mL) dropwise and the resulting solution was stirred for 72 h at room temperature. The solution was neutralized with Na$_2$CO$_3$ and the oil obtained solidified on standing in water. The precipitate was filtered and dried to obtain 1.60 g (90%) of the title compound.

$^1$H-NMR (400 MHz, DMSO): δ 2.43 (4H, t), 3.68 (4H, t), 7.22-7.25 (1H, m), 7.33-7.36 (2H, m), 7.46-7.50 (2H, m), 7.69-7.71 (2H, m).

Example 18

1-[3-(1H-Benzoimidazol-2-yl)-4-chloro-phenyl]-piperidin-4-ol

1-[3-(1H-Benzoimidazol-2-yl)-4-chloro-phenyl]-piperidin-4-ol

Method G—Step b

To a suspension of 1-[3-(1H-benzoimidazol-2-yl)-4-chloro-phenyl]-piperidin-4-one (0.05 g, 0.17 mmol) in methanol (50 mL) was added sodium borohydride ($NaBH_4$) (0.01 g, 0.17 mmol) and the resulting mixture was stirred for 1 h at room temperature and then quenched with few drops of water. The solvent was removed under reduced pressure, the crude dissolved in EtOAc (5 mL) and filtered, then the organic phase was evaporated under reduced pressure to afford 0.02 g (36%) of the title compound.

$^1$H-NMR (400 MHz, DMSO): δ 1.43-1.45 (2H, m), 1.78-1.80 (2H, m), 2.89-2.94 (2H, m), 3.56-3.64 (3H, m), 4.68 (1H, d), 7.06-7.08 (1H, m), 7.18-7.21 (2H, m), 7.33-7.40 (2H, m), 7.52 (1H, d), 7.66 (1H, d), 12.59 (1H, s). m/z 328 (M+H)$^+$; retention time=1.55.

Example 19

2-[5-(4-Azepan-1-yl-piperidin-1-yl)-2-chloro-phenyl]-1H-benzoimidazole

2-[5-(4-Azepan-1-yl-piperidin-1-yl)-2-chloro-phenyl]-1H-benzoimidazole

Method H—Step c

To a suspension of 1-[3-(1H-benzoimidazol-2-yl)-4-chloro-phenyl]-piperidin-4-one (0.10 g, 0.31 mmol) in dichloromethane (2 mL) was added azepane (0.05 mL, 0.46 mmol). After 30 min stirring at room temperature a drop of acetic acid was added, and after 1 h a further aliquot of azepane (0.05 mL, 0.46 mmol) was added, followed by sodium triacetoxyborohydride ($NaB(OAc)_3H$) (0.10 g, 0.46 mmol). The reaction mixture was stirred at room temperature overnight, then the solvent was removed under reduced pressure, and the crude product dissolved in dichloromethane (10 mL). To the solution PS-isocyanate resin (PS-NCO) (Argonaut, loading 0.93 mmol/g) was added, then the mixture was shaken at room temperature overnight and filtered. The solvent was removed under reduced pressure to obtain a solid residue that was washed with EtOAc and $Et_2O$ then dried to give the desired product (0.07 g, 58%).

$^1$H-NMR (400 MHz, DMSO): δ 1.45-1.50 (9H, m), 1.74 (2H, d), 2.61-2.74 (6H, m), 3.31 (2H, s), 3.78 (2H, d), 7.06-7.08 (1H, m), 7.20-7.22 (2H, m), 7.33-7.38 (2H, m), 7.52 (1H, d), 7.66 (1H, d), 12.60 (1H, s). m/z 409 (M+H)$^+$; retention time=1.32.

Example 20

1-(4-{4-[3-(1-Difluoromethyl-1H-benzoimidazol-2-yl)-phenyl]-piperazine-1-carbonyl}-[1,4]diazepan-1-yl)-ethanone

2-(3-Bromo-phenyl)-1H-benzoimidazole

Method I, J, K—Step a

O-phenylenediamine (81.8 g, 756.6 mmol) and oxalic acid (3.40 g, 37.8 mmol) were completely dissolved in ethanol/water 1:1 (2 L) previously warmed at 80° C. Then 3-Bromobenzaldheyde (44.1 mL, 378.3 mmol) was added dropwise to the solution. The reaction mixture was stirred overnight at 70° C. to the open air fort two days. Solid was filtered off and triturated with methanol (150 mL) to afford the product as a pale yellow solid (27.50 g). 3.8 g of product were recovered from the mother liquors. Total yield 31.30 g (30%).

$^1$H-NMR (400 MHz DMSO): δ 7.24 (2H, m), 7.54 (2H, m), 7.70 (m, 2H), 8.19 (1H, m), 8.37 (1H, t), 13.2 (1H, s). m/z 273 (M+H)$^+$; retention time=8.60.

2-(3-Bromo-phenyl)-1-difluoromethyl-1H-benzoimidazole

Method I, J, K—Step b

In autoclave 2-(3-Bromo-phenyl)-1H-benzoimidazole (14.10 g, 51.6 mmol) 50% acq NaOH (8.3 mL, 154.8 mmol), TEBAC (0.58 g, 2.5 mmol) and THF (120 mL) were placed. The mixture was stirred at room temperature for 2 h, then chlorodifluoromethane was bubbled until complete conversion of the starting material (2 bar, ca. 3 h). The mixture was diluted with DCM (100 mL), the organic phase was decanted and dried over $Na_2SO_4$. The solvent was evaporated under reduced pressure to afford a dark red oil that was purified by flash chromatography on silica versaflash (1 g product/30 g silica) (eluent: cyclohexane:AcOEt gradient from cyclohexane 95:AcOEt 5 to cyclohexane 7:AcOEt 3) to afford 14.30 g of the title compound (86%).

$^1$H-NMR (400 MHz DMSO): δ 7.45 (2H, m), 7.59 (1H, t); 7.75 (1H, m), 7.83 (2H, m), 7.95 (1H, m), 8.09 (1H, s). m/z 323 (M+H)$^+$; retention time=8.60.

1-(4-{4-[3-(1-Difluoromethyl-1H-benzoimidazol-2-yl)-phenyl]-piperazine-1-carbonyl}-[1,4]diazepan-1-yl)-ethanone Method J—Step c 2-(3-Bromo-phenyl)-1-difluoromethyl-1H-benzoimidazole (0.10 g, 0.31 mmol), cesium carbonate (0.14 g, 0.43 mmol), rac-2,2' bis(diphenylphosphino)-1,1'-binaphtyl (BINAP) (0.007 g, 0.01 mmol) and tris-(dibenzilideneacetone)-dipalladium(0) (0.004 g) were placed into a 7 mL sealed vial and purged by repeated nitrogen/vacuum cycles for ten minutes. Dry toluene (0.6 mL) and N-acetylhomopiperazine (0.05 mL, 0.37 mmol) were added and reaction mixture was heated at 85° C. for 24 hours with stirring.

Reaction was cooled to room temperature and filtered through SCX cartridge (2 g), (eluent: DCM/methanol 1:1). The organic layer was concentrated under reduced pressure and purified by preparative HPLC to afford 58 mg of the title compound (48%).

$^1$H-NMR (400 MHz, $CD_3OD$): δ 1.95-2.08 (5H, m), 3.48-3.55 (2H, m), 3.65-3.77 (4H, m), 3.80-3.84 (2H, m), 6.93-6.95 (1H, m), 7.04-7.11 (2H, m), 7.41-7.67 (4H, m), 7.73-7.82 (2H, m). m/z 385 (M+H)$^+$; retention time=3.30.

Example 21

1-Difluoromethyl-2-(3-piperazin-1-yl-phenyl)-1H-benzoimidazole hydrochloride

4-[3-(1-Difluoromethyl-1H-benzoimidazol-2-yl-)-phenyl]-piperazine-1-carboxylic acid tert-butyl ester Method K—Step d 2-(3-bromo-phenyl)-1-difluoromethyl-1H-benzoimidazole (1.00 g, 3.10 mmol), piperazine-1-carboxylic acid tert-butyl ester (0.75 g, 4.02 mmol) and cesium carbonate (5.04 g, 15.48 mmol) were placed into a dry 250 mL round bottom flask and purged by repeated nitrogen/vacuum cycles for 30 minutes and dry toluene (50 mL) was added. At the same time palladium acetate (139 mg, 0.62 mmol), and rac-2,2' bis (diphenylphosphino)-1,1'-binaphtyl (BINAP) (0.58 g, 0.30 mmol) were placed into a dry 100 mL round bottom flask and purged by repeated nitrogen/vacuum cycles for 30 minutes.

Dry toluene (50 mL) was added and this suspension was stirred 10 minutes before being added to the first round bottom flask. The reaction mixture was refluxed overnight under nitrogen and cooled to room temperature. The mixture was filtered and the insoluble material was washed with EtOAC (3×20 mL) The organic solution was concentrated under reduced pressure and crude was purified by flash chromatography (eluent: cyclohexane:AcOEt gradient from 100% of cyclohexane to cyclohexane 5:AcOEt 1) to afford 1.10 g of the title compound (83%).

$^1$H-NMR (400 MHz, DMSO): δ 1.41 (9H, s), 3.19-3.22 (4H, m), 3.46-3.48 (4H, m), 7.08-7.10 (1H, m), 7.20-7.23 (2H, m), 7.37-7.46 (3H, m), 7.71-7.80 (3H, m).

m/z 429 (M+H)$^+$; retention time=4.53.

1-Difluoromethyl-2-(3-piperazin-1-yl-phenyl)-1H-benzoimidazole

Method K—Step e

To a solution of 4-[3-(1-Difluoromethyl-1H-benzoimidazol-2-yl-)-phenyl]-piperazine-1-carboxylic acid tert-butyl ester (1.10 g, 2.57 mmol) in DCM (2 mL) were added 2M HCl in Et2O (11 mL) and the resulting suspension was stirred at room temperature overnight. The precipitate was filtered and the resulting salt was tritured with Et2O (3×20 mL) to obtain 1.02 g (100%) of the title compound as hydrochloride salt.

$^1$H-NMR (400 MHz, DMSO): δ 3.21 (4H, bs), 3.47-3.50 (4H, m), 7.11-7.20 (1H, m), 7.25-7.30 (2H, m), 7.41-7.51 (3H, m), 7.74-8.02 (3H, m), 9.35 (2H, bs). m/z 329 (M+H)$^+$; retention time=1.77.

Example 22

1-{4-[3-(1-Difluoromethyl-1H-benzoimidazol-2-yl)-phenyl]-piperazin-1-yl}-2-methyl-propan-1-one 1-{4-[3-(1-Difluoromethyl-1H-benzoimidazol-2-yl)-phenyl]-piperazin-1-yl}-2-methyl-propan-1-one Method K—Step f CDI (0.05 g, 0.32 mmol) was added to a solution of isobutyric acid (0.029 g, 0.32 mmol) in acetonitrile (2.50 mL). The resulting solution was stirred at room temperature for 5 h.

1-Difluoromethyl-2-(3-piperazin-1-yl-phenyl)-1H-benzoimidazole (0.10 g, 0.27 mmol) and N,N-diisopropylethylamine (DIPEA) (0.05 mL, 0.27 mmol) were added and reaction was heated at 65° C. overnight. The reaction was cooled to room temperature, the solvent was removed and DCM (3 mL) was added. Organic solution was washed with water (2×2 mL) and with saturated Na$_2$CO$_3$ solution (2×2 mL) The organic layer concentrated under educed pressure and crude was purified by flash chromatography (eluent: cyclohexane: AcOEt gradient from 100% of cyclohexane to cyclohexane 3:AcOEt 1) to afford 0.067 g of the title compound (61%).

$^1$H-NMR (400 MHz, CDCl$_3$): δ 1.09 (6H, d), 2.77 (1H, septuplet), 3.21-3.29 (4H, m), 3.64-3.75 (4H, m), 7.04-7.07 (2H, m), 7.10-7.41 (5H, m), 7.70-7.73 (1H, m), 7.77-7.81 (1H, m). m/z 399 (M+H)$^+$; retention time=3.68.

Example 23

4-{4-[3-(1-Difluoromethyl-1H-benzoimidazol-2-yl)-phenyl]-piperazine-1-carbonyl}-piperidine-1-carboxylic acid tert-butyl ester 4-{4-[3-(1-Difluoromethyl-1H-benzoimidazol-2-yl)-phenyl]-piperazine-1-carbonyl}-piperidine-1-carboxylic acid tert-butyl ester Method K—Step g CDI (0.053 mg, 0.32 mmol) was added to a solution of piperidine-1,4-dicarboxylic acid mono-tert-butyl ester (0.074 g, 0.32 mmol) in acetonitrile (2.50 mL). The resulting solution was stirred at room temperature five hours.

1-Difluoromethyl-2-(3-piperazin-1-yl-phenyl)-1H-benzoimidazole (0.10 g, 0.27 mmol) and N,N-diisopropylethylamine (DIPEA) (0.05 mL, 0.27 mmol) were added and reaction was heated at 65° C. overnight. The reaction was cooled to room temperature, the solvent was removed and DCM (3 mL) was added. Organic solution was washed with water (2×2 mL) and with saturated Na$_2$CO$_3$ solution (2×2 mL). The organic layer was concentrated under reduced pressure and crude was purified by flash chromatography (eluent: cyclohexane:AcOEt gradient from 100% of cyclohexane to cyclohexane 3:AcOEt 1) to afford 0.067 g of the title compound (70%).

$^1$H-NMR (400 MHz, CDCl$_3$): δ 1.39 (9H, s), 1.60-1.74 (4H, m), 2.57-2.77 (3H, m), 3.21-3.26 (4H, m), 3.64-3.74 (4H, m), 4.10 (2H, m), 7.04-7.07 (2H, m), 7.11-7.41 (5H, m), 7.71-7.73 (1H, m), 7.78-7.82 (1H, m). m/z 540 (M+H)$^+$; retention time=4.25.

Example 24

{4-[3-(1-Difluoromethyl-1H-benzoimidazol-2-yl)-phenyl]-piperazin-1-yl}-piperidin-4-yl-methanone {4-[3-(1-Difluoromethyl-1H-benzoimidazol-2-yl)-phenyl]-piperazin-1-yl}-piperidin-4-yl-methanone Method K—Step h To a solution of 4-{4-[3-(1-Difluoromethyl-1H-benzoimidazol-2-yl)-phenyl]-piperazine-1-carbonyl}-piperidine-1-carboxylic acid tert-butyl ester (0.075 g, 0.14 mmol) in DCM (0.5 mL), 2M HCl in Et2O (2.5 mL) was added and the resulting suspension was stirred at room temperature for 6 h. The precipitate was filtered and tritured with Et2O (3×20 mL) The solid was purified by preparative HPLC. HPLC fractions were neutralized with K$_2$CO$_3$ and concentrated. DCM (5 mL) and water (5 mL) were added, organic phase was separated and concentrated to give 44 mg of the title compound (72%).

$^1$H-NMR (400 MHz, CDCl$_3$): δ 1.82-2.15 (4H, m), 2.72-2.86 (1H, m), 3.09-3.34 (6H, m), 3.48-3.64 (2H, m), 3.63-3.83 (4H, m), 7.09-7.15 (2H, m), 7.29-7.30 (2H, m), 7.37-7.47 (3H, m), 7.75-7.78 (1H, m), 7.81-7.85 (1H, m). m/z 440 (M+H)$^+$; retention time=2.03.

Example 25

1-[3-(1-Difluoromethyl-1H-benzoimidazol-2-yl)-phenyl-]piperidine-4-carboxylic acid ethyl ester 1-[3-(1-Difluoromethyl-1H-benzoimidazol-2-yl)-phenyl-]piperidine-4-carboxylic acid ethyl ester Method I—Step i Same procedure described in Method K, step d but starting from piperidine-4-carboxylic acid ethyl ester instead of piperazine-1-carboxylic acid tert-butyl ester. Quantitative yield.

$^1$H-NMR (400 MHz, CD$_3$OD): δ 1.26 (3H, t), 1.77-1.87 (2H, m), 2.01-2.05 (2H, m), 2.50-2.57 (1H, m), 2.88-2.94 (2H, m), 3.76-3.81 (2H, m), 4.12-4.17 (2H, q), 7.09-7.11 (1H, m), 7.24-7.26 (1H, m), 7.29-7.30 (1H, m), 7.41-7.81 (6H, m). m/z 400 (M+H)$^+$; retention time=4.25.

Example 26

{1-[3-(1-Difluoromethyl-1H-benzoimidazol-2-yl)-phenyl]-piperidine-4-yl}-(4-methyl-piperazin-1-yl)-methanone 1-[3-(1-Difluoromethyl-1H-benzoimidazol-2-yl)-phenyl-]piperidine-4-carboxylic acid Method I—Step 1

NaOH powder (0.24 g, 6.02 mmol) was added to a solution of 1-[3-(1-Difluoromethyl-1H-benzoimidazol-2-yl)-phenyl-]piperidine-4-carboxylic acid ethyl ester (1.20 g, 3.01 mmol) in ethanol:water 3:1 and the reaction was heated at 80° C. overnight. Reaction was cooled to room temperature and the organic solvent concentrated by evaporation under reduced pressure. The resulting solution was neutralized by dropwise addition of 6N HCl. A pale brown precipitated and it was filtered off and dried to afford 0.80 g of the title compound (72%).
$^1$H-NMR (400 MHz, CD$_3$OD): δ 1.83-1.93 (2H, m), 2.06-2.11 (2H, m), 2.52-2.59 (1H, m), 3.14-3.17 (2H, m), 3.71-3.76 (2H, m), 7.33-7.35 (1H, m), 7.40-7.42 (2H, m), 7.44-7.78 (6H, m). m/z 372 (M+H)$^+$; retention time=3.25.

{1-[3-(1-Difluoromethyl-1H-benzoimidazol-2-yl)-phenyl]-piperidine-4-yl}-(4-methyl-piperazin-1-yl)-methanone Method I—Step m HATU (0.11 g, 0.30 mmol) and diisopropylethylamine (DIPEA) (0.09 mL, 0.54 mmol) were added to a suspension of 1-[3-(1-Difluoromethyl-1H-benzoimidazol-2-yl)-phenyl] piperidine-4-carboxylic acid (0.10 g, 0.27 mmol) in dichloromethane at room temperature. Reaction was heated at 35° C. overnight. Reaction was cooled to room temperature and washed with saturated Na$_2$CO$_3$ solution (2×4 mL) and with water (1×3 mL) The organic layer was concentrated under reduced pressure and crude was purified by flash chromatography (eluent: cyclohexane:AcOEt gradient from cyclohexane 1:AcOEt 1 to 100% AcOEt and finally with AcOEt: 2.0 N ammonia in methanol 5:1) to afford 0.025 g of the title compound (20%).
$^1$H-NMR (400 MHz, CD$_3$OD): δ 1.79-1.88 (4H, m), 2.31 (3H, s), 2.39-2.48 (4H, m), 2.80-2.92 (3H, m), 3.60-3.68 (4H, m), 3.85-3.88 (2H, m), 7.08-7.10 (1H, m), 7.20-7.25 (1H, m), 7.28-7.29 (1H, m), 7.40-7.81 (6H, m). m/z 454 (M+H)$^+$; retention time=2.00.

Example 27

{4-[4-Fluoro-3-(1-methyl-1H-benzoimidazol-2-yl)-phenyl]-piperazin-1-yl}-pyrrolidin-1-yl-methanone N-(2-Amino-phenyl)-5-bromo-2-fluoro-benzamide Method L, M—Step a 5-Bromo-2-fluoro-benzoic acid (4.96 g, 22.6 mmol), benzene-1,2-diamine (4.90 g, 45.3 mmol), 1-(3-dimethylaminopropyl)-3-ethylcarbodiimide hydrochloride (EDC) (5.21 g, 27.2 mmol), 1-hydroxybenzotriazole hydrate (1-HOBt) (3.67 g, 27.2 mmol) and dimethyl-pyridin-4-yl-amine (DMAP) (0.03 g, 0.2 mmol) were placed into a 100 mL round bottom flask. Dry DMF (60 mL) was added and the reaction was stirred at room temperature overnight. Solvent was removed under reduced pressure, then the crude diluted with DCM (15 mL) and 0.4 M Na$_2$CO$_3$ solution (15 mL) A white precipitate formed and it was filtered off and washed again with DCM (10 mL) and dried to afford 4.96 g of the title compound. Solutions were collected, the organic phase was separated from the aqueous one and concentrated under reduced pressure: other precipitate formed and it was filtered off, washed with DCM (3 mL) to afford other 0.68 g of desired compound. Total yield 81%.
$^1$H-NMR (400 MHz, DMSO): δ 4.84-5.14 (2H, m), 6.54-6.59 (1H, m), 6.73-6.76 (1H, m), 6.93-6.97 (1H, m), 7.21-7.24 (1H, m), 7.31-7.35 (1H, m), 7.72-7.76 (1H, m), 9.62-9.64 (1H, m). m/z 308/310 (M+H)$^+$; retention time=1.87.

2-(5-Bromo-2-fluoro-phenyl)-1H-benzoimidazole

Method L, M—Step b

A suspension of N-(2-amino-phenyl)-5-bromo-2-fluoro-benzamide (5.64 g, 18.3 mmol) in acetic acid (20 mL) was heated at 60° C. After 30 min, the suspension became a solution and it was left overnight. The solvent was removed under reduced pressure and residue was triturated with DCM (10 mL) and filtered off. The precipitate was washed with DCM (3×10 mL) and dried to afford 4.76 g of the title compound (89%).
$^1$H-NMR (400 MHz, DMSO): δ 7.24-7.27 (2H, m), 7.43-7.48 (1H, m), 7.63-7.66 (2H, m), 7.72-7.76 (1H, m), 8.33-8.35 (1H, m). m/z 290/292 (M+H)$^+$; retention time=1.85.

2-(5-Bromo-2-fluoro-phenyl)-1-methyl-1H-benzoimidazole

Method L—Step c

NaH 60% suspension in mineral oil (0.61 g, 25.5 mmol) was added to a solution of 2-(5-Bromo-2-fluoro-phenyl)-1H-benzoimidazole (3.70 g, 12.76 mmol) in dry THF (100 mL) and the reaction was stirred at room temperature 30 minutes before adding methyl iodide (1.19 mL, 19.1 mmol). Reaction was left stirring for 2 h, then quenched with water (20 mL) The solution was concentrated, then AcOEt (30 mL) was added. The organic solution was separated, washed with brine (10 mL), dried over Na$_2$SO$_4$ and concentrated under reduced pressure to afford 3.80 g of desired compound. (97%).
$^1$H-NMR (400 MHz, CD$_3$OD): δ 3.76 (3H, s), 7.31-7.42 (3H, m), 7.59-7.61 (1H, m), 7.70-7.72 (1H, m), 7.78-7.82 (1H, m), 7.85-7.87 (1H, m). m/z 304/306 (M+H)$^+$; retention time=1.80.

{4-[4-Fluoro-3-(1-methyl-1H-benzoimidazol-2-yl)-phenyl]-piperazin-1-yl}-pyrrolidin-1-yl-methanone Method L—Step d The same procedure described in step c method J was followed but starting from 2-(5-bromo-2-fluoro-phenyl)-1-methyl-1H-benzoimidazole and piperazin-1-yl-pyrrolidin-1-yl-methanone. The crude reaction mixture was purified by preparative HPLC to afford 0.06 g of the title compound (44%).
$^1$H-NMR (400 MHz, CD$_3$OD): δ 1.82-1.89 (4H, m), 3.20-3.23 (4H, m), 3.40-3.42 (4H, m), 3.44-3.47 (4H, m), 3.77-3.78 (3H, m), 7.20-7.22 (1H, m), 7.24-7.26 (2H, m), 7.31-7.40 (2H, m), 7.57-7.59 (1H, m), 7.69-7.71 (1H, m). m/z 408 (M+H)$^+$; retention time=2.32.

Example 28

4-[4-Fluoro-3-(1-methyl-1H-benzoimidazol-2-yl)-phenyl]-piperazine-1-carboxylic acid tert-butyl ester 4-[4-Fluoro-3-(1-methyl-1H-benzoimidazol-2-yl)-phenyl]-piperazine-1-carboxylic acid tert-butyl ester Method L—Step e 2-(5-Bromo-2-fluoro-phenyl)-1-methyl-1H-benzoimidazole (2.10 g, 6.9 mmol), piperazine-1-carboxylic acid tert-butyl ester (1.16 g, 8.3 mmol), cesium carbonate (3.14 g, 9.6 mmol) rac-2,2' bis(diphenylphosphino)-1,1'-binaphtyl (BINAP) (0.17 g, 0.28 mmol) and tris-(dibenzilideneacetone)dipalladium(0) (0.06 g, 0.07 mmol) were placed in a Schlenk tube and purged by repeated nitrogen/vacuum cycles for 10 minutes. Dry toluene (13 mL) was added and the reaction was stirred at 85° C. for 24 h. Reaction was cooled to room temperature, diluted with AcOEt (20 mL) and washed with water (10 mL). The organic layer was dried over $Na_2SO_4$ and concentrated under reduced pressure. The crude reaction mixture was purified by flash chromatography (eluent: cyclohexane:AcOEt gradient from 100% cyclohexane to cyclohexane 2:AcOEt 1) to afford 1.14 g of the starting material and 0.70 g of the title compound (54%).

$^1$H-NMR (400 MHz, $CD_3OD$): δ 1.47 (9H, s), 3.14-3.17 (4H, m), 3.57-3.59 (4H, m), 7.20-7.26 (3H, m), 7.30-7.39 (2H, m), 7.56-7.58 (1H, m), 7.68-7.71 (1H, m). m/z 411 $(M+H)^+$; retention time=1.90.

Example 29

2-Dimethylamino-1-{4-[4-fluoro-3-(1-methyl-1H-benzoimidazol-2-yl)-phenyl]-piperazin-1-yl}-ethanone 2-(2-Fluoro-5-piperazin-1-yl-phenyl)-1-methyl-1H-benzoimidazole Method L—Step f To a solution of 4-[4-Fluoro-3-(1-methyl-1H-benzoimidazol-2-yl)-phenyl]-piperazine-1-carboxylic acid tert-butyl ester (0.86 g, 1.71 mmol) in DCM (2.0 mL) 2.0 M HCl in $Et_2O$ (10 mL) was added and the resulting suspension was stirred at room temperature overnight. The precipitate was filtered off and tritured with $Et_2O$ (3×15 mL) to afford the title compound (quantitative yield).

$^1$H-NMR (400 MHz, DMSO): δ 3.22-3.25 (4H, m), 3.44-3.47 (4H, m), 3.94 (3H, s), 7.43-7.53 (3H, m), 7.60-7.67 (2H, m), 7.87-7.89 (1H, m), 8.01-8.03 (1H, m), 9.42 (2H, m). m/z 311 $(M+H)^+$; retention time=split peak.

2-Dimethylamino-1-{-4-[4-fluoro-3-(1-methyl-1H-benzoimidazol-2-yl)-phenyl]-piperazin-1-yl}-ethanone Method L—Step g Same procedure used in method L-step h.

$^1$H-NMR (400 MHz, $CD_3OD$): δ 2.30 (6H, s), 3.18-3.25 (6H, m), 3.74-3.78 (7H, m), 7.21-7.28 (3H, m), 7.31-7.40 (2H, m), 7.57-7.59 (1H, m), 7.69-7.71 (1H, m). m/z 396 $(M+H)^+$; retention time=split peak.

Example 30

(S)-2-{4-[4-fluoro-3-(1-methyl-1H-benzoimidazol-2-yl)-phenyl]-piperazine-1-carbonyl}-pyrrolidine-1-carboxylic acid tert-butyl ester (S)-2-{4-[4-fluoro-3-(1-methyl-1H-benzoimidazol-2-yl)-phenyl]-piperazine-1-carbonyl}-pyrrolidine-1-carboxylic acid tert-butyl ester Method L—Step h CDI (0.05 g, 0.31 mmol) was added to a solution of N-Boc-L-Proline (0.07 g, 0.31 mmol) in acetonitrile (2.50 mL). The resulting solution was stirred at room temperature 6 hours.

2-(2-Fluoro-5-piperazin-1-yl-phenyl)-1-methyl-1H-benzoimidazole (0.10 g, 0.26 mmol) and N,N-diisopropylethylamine (DIPEA) (0.09 mL, 0.52 mmol) were added and reaction was heated at 65° C. overnight. The reaction was cooled to room temperature, the solvent was removed under reduced pressure and DCM (3 mL) was added. Organic solution was washed with water (2×2 mL) and with saturated $Na_2CO_3$ solution (2×2 mL) The organic layer was concentrated under reduced pressure and crude was purified by flash chromatography (eluent: cyclohexane:AcOEt gradient from cyclohexane 2:AcOEt 1 to 100% AcOEt) to afford 0.067 g of the title compound (51%).

$^1$H-NMR (400 MHz, $CD_3OD$): δ 1.40-1.45 (9H, m), 1.82-1.97 (3H, m), 2.23-2.36 (1H, m), 3.15-3.29 (4H, m), 3.42-3.57 (2H, m), 3.69-3.85 (7H, m), 4.72-4.77 (1H, m), 7.22-7.29 (3H, m), 7.31-7.40 (2H, m), 7.57-7.59 (1H, m), 7.69-7.71 (1H, m). m/z 508 $(M+H)^+$; retention time=2.63.

Example 31

{4-[4-fluoro-3-(1-methyl-1H-benzoimidazol-2-yl)-phenyl]-piperazin-1-yl}-(S)-pyrrolidin-2-yl-methanone hydrochloride {4-[4-fluoro-3-(1-methyl-1H-benzoimidazol-2-yl)-phenyl]-piperazin-1-yl}-(S)-pyrrolidin-2-yl-methanone Method L—Step i To a solution of (S)-2-{-4-[4-fluoro-3-(1-methyl-1H-benzoimidazol-2-yl)-phenyl]-piperazine-1-carbonyl}-pyrrolidine-1-carboxylic acid tert-butyl ester (0.05 g, 0.10 mmol) in DCM (0.5 mL) 2M HCl in $Et_2O$ (2.0 mL) was added and the resulting suspension was stirred at room temperature overnight. The reaction was concentrated under reduced pressure then water (4.0 mL) was added and the mixture was concentrated again to afford 0.04 g of the title compound as chlorhydrate salt (86%).

$^1$H-NMR (400 MHz, $CD_3OD$): δ 1.85-2.04 (4H, m), 2.42-2.51 (1H, m), 3.60-3.81 (4H, m), 3.98-3.99 (3H, m), 3.23-3.36 (5H, m), 4.60-4.69 (1H, m), 7.32-7.44 (3H, m), 7.62-7.68 (2H, m), 7.77-7.80 (1H, m), 7.89-7.93 (1H, m). m/z 408 $(M+H)^+$; retention time=split peak.

Example 32

1-{4-[3-(1H-Benzoimidazol-2-yl)-4-fluoro-phenyl]-piperazin-1-yl}-2-dimethylamino-ethanone 2-(5-Bromo-2-fluoro-phenyl)-benzoimidazole-1-carboxylic acid tert-butyl ester Method M—Step l NaH 60% dispersion in mineral oil (0.70 g, 17.34 mmol) was added to a solution of 2-(5-Bromo-2-fluoro-phenyl)-1H-benzoimidazole (3.87 g, 13.3 mmol) in dry THF (140 mL)

under nitrogen at room temperature. After 10 minutes a solution of Di-tert-butyl dicarbonate (0.30 g, 13.3 mmol) in dry THF (50 mL) was added and reaction was left 30 h. Water (40 mL) was added and reaction was concentrated under reduced pressure. AcOEt (30 mL) was added and the organic layer was separated. The water solution was washed with AcOEt (2×10 mL) Organic layers were collected, dried over $Na_2SO_4$ and concentrated under reduced pressure. The crude reaction mixture was purified by flash chromatography (eluent: cyclohexane:AcOEt gradient from 100% cyclohexane to cyclohexane 10:AcOEt 1) to 4.7 g of the title compound (90%).

$^1$H-NMR (400 MHz, $CD_3OD$): δ 1.44 (9H, s), 7.23-7.27 (1H, m), 7.41-7.50 (2H, m), 7.73-7.77 (2H, m), 7.84-7.86 (1H, m), 8.10-8.12 (1H, m). m/z 392 (M+H)$^+$; retention time=2.88.

2-[5-(4-tert-butoxycarbonyl-piperazin-1-yl)-2-fluoro-phenyl]-benzoimidazole-1-carboxylic acid tert-butyl ester Method M—Step m
2-(5-Bromo-2-fluoro-phenyl)-benzoimidazole-1-carboxylic acid tert-butyl ester (2.52 g, 6.5 mmol), piperazine-1-carboxylic acid tert-butyl ester (1.56 g, 8.40 mmol) and cesium carbonate (10.50 g, 32.20 mmol) were placed into a dry 500 mL round bottom flask under nitrogen and dry toluene (140 mL) was added. At the same time palladium acetate (0.29 g, 1.30 mmol) and BINAP (1.20 g, 1.93 mmol) were placed into a dry 250 mL round bottom flask under nitrogen and dry toluene (140 mL) was added. After 10 minutes the suspension containing BINAP and Palladium acetate was added to the 500 mL round bottom flask. The reaction mixture was heated at 85° C. overnight under nitrogen and cooled to room temperature. The mixture was filtered and the insoluble material was washed with EtOAC (3×20 mL). The organic solution was concentrated under reduced pressure and crude was purified by flash chromatography (eluent: cyclohexane:AcOEt gradient from 100% of cyclohexane to cyclohexane 4:AcOEt 1) to afford 2.48 g of the title compound (76%).

$^1$H-NMR (400 MHz, DMSO): δ 1.36 (9H, s), 3.08-3.10 (4H, m), 3.43-3.46 (4H, m), 7.12-7.18 (1H, m), 7.20-7.25 (2H, m), 7.38-7.47 (2H, m), 7.76-7.78 (1H, m), 7.97-7.99 (1H, m). m/z 497 (M+H)$^+$; retention time=2.93.

2-(2-Fluoro-5-piperazin-1-yl-phenyl)-1H-benzoimidazole

Method M—Step n
To a solution of 2-[5-(4-tert-butoxycarbonyl-piperazin-1-yl)-2-fluoro-phenyl]-benzoimidazole-1-carboxylic acid tert-butyl ester (0.45 g, 0.91 mmol) in DCM (1.0 mL) 2M HCl in $Et_2O$ (8.0 mL) was added and the resulting suspension was stirred at room temperature overnight. 2M HCl in $Et_2O$ (5.0 mL) more were added and reaction was left stirring for 24 h. The precipitate was filtered off and tritured with $Et_2O$ (3×15 mL) to afford 0.21 g of the title compound (55%).

$^1$H-NMR (400 MHz, DMSO): δ 3.26 (4H, bs), 3.49-3.51 (4H, m), 7.36-7.40 (1H, m), 7.45-7.53 (3H, m), 7.80-7.84 (2H, m), 7.91-7.93 (1H, m), 9.28 (2H, bs). m/z 297 (M+H)$^+$; retention time=split peak.

1-{4-[3-(1H-Benzoimidazol-2-yl)-4-fluoro-phenyl]-piperazin-1-yl}-2-dimethylamino-ethanone Method M—Step o
CDI (0.052 g, 0.32 mmol) was added to a solution of N,N-dimethylglicine (0.033 g, 0.32 mmol) in acetonitrile (2.50 mL). The resulting solution was stirred at room temperature for 5 hours. Then 2-(2-Fluoro-5-piperazin-1-yl-phenyl)-1H-benzoimidazole (0.10 g, 0.27 mmol) and N,N-diisopropylethylamine (DIPEA) (0.11 mL, 0.6 mmol) were added and reaction was heated at 65° C. overnight. Reaction was cooled to room temperature and solvent was removed under reduced pressure. DCM (2 mL) was added to the crude, organic solution was washed with water (2×4 mL) and with saturated $Na_2CO_3$ solution (2×4 mL) and concentrated. The crude reaction mixture was purified by flash chromatography (eluent: MeOH:AcOEt gradient from 100% of AcOEt to MeOH 0.6:AcOEt 4) to afford 0.049 g of the title compound (43%).

$^1$H-NMR (400 MHz, $CD_3OD$): δ 2.33 (6H, s), 3.22-3.29 (4H, m), 3.29 (2H, s), 3.77-3.79 (4H, m), 7.16-7.24 (2H, m), 7.26-7.31 (2H, m), 7.59-7.70 (2H, bp), 7.75-7.77 (1H, m). m/z 382 (M+H)$^+$; retention time=split peak.

Example 33

4-{4-[3-(1H-Benzoimidazol-2-yl)-4-fluoro-phenyl]-piperazin-1-yl}-piperidin-4-yl-methanone 4-{-4-[3-(1H-Benzoimidazol-2-yl)-4-fluoro-phenyl]-piperazine-1-carbonyl}-piperidine-1-carboxylic acid tert-butyl ester Method M—Step p
CDI (0.047 g, 0.29 mmol) was added to a solution of piperidine-1,4-dicarboxylic acid mono-tert-butyl ester (0.07 g, 0.29 mmol) in acetonitrile (2.50 mL). The resulting solution was stirred at room temperature for 5 hours. 2-(2-Fluoro-5-piperazin-1-yl-phenyl)-1H-benzoimidazole (0.10 g, 0.27 mmol) and DIPEA (0.05 mL, 0.26 mmol) were added and reaction was heated at 65° C. overnight. Reaction was cooled to room temperature and solvent was removed under reduced pressure. DCM (2 mL) was added to the crude, organic solution was washed with water (2×4 mL) and with saturated $Na_2CO_3$ solution (2×4 mL) and concentrated. The crude reaction mixture was purified by flash chromatography (eluent: cyclohexane:AcOEt gradient from 100% of cyclohexane to 100% AcOEt) to afford 0.08 g of the title compound (60%).

$^1$H-NMR (400 MHz, $CD_3OD$): δ 1.45 (9H, s), 1.55-1.66 (2H, m), 1.72-1.76 (2H, m), 2.82-3.00 (3H, m), 3.21-3.31 (4H, m), 3.77-3.83 (4H, m), 4.07-4.17 (2H, m), 7.17-7.24 (2H, m), 7.26-7.31 (2H, m), 7.55-7.72 (2H, m), 7.75-7.78 (1H, m).

4-{4-[3-(1H-Benzoimidazol-2-yl)-4-fluoro-phenyl]-piperazin-1-yl}-piperidin-4-yl-methanone Method M—Step q
To a solution of 4-{4-[3-(1H-Benzoimidazol-2-yl)-4-fluoro-phenyl]-piperazine-1-carbonyl}-piperidine-1-carboxylic acid tert-butyl ester (0.08 g, 0.16 mmol) in DCM (1 mL) 2M HCl in $Et_2O$ (3.0 mL) was added and the resulting suspension was stirred at room temperature for 3 days. The reaction was concentrated under reduced pressure, water (8 mL) was added and the solution was concentrated under reduced pressure. The solid was purified by preparative HPLC. HPLC fractions were neutralized with $K_2CO_3$ and concentrated. DCM (5 mL) and water (5 mL) were added, organic phase was separated and concentrated to give 44 mg of the title compound (72%).

$^1$H-NMR (400 MHz, $CD_3OD$): δ 1.70-1.80 (4H, m), 2.73-2.80 (2H, m), 2.91-2.98 (1H, m), 3.13-3.17 (2H, m), 3.20-

3.28 (4H, m), 7.15-7.32 (2H, m), 7.26-7.31 (2H, m), 7.62-7.65 (2H, m), 7.75-7.77 (1H, m). m/z 408 (M+H)$^+$; retention time=split peak.

Example 34

2-Ethoxy-N-{1-[3-(1-methyl-1H-benzoimidazol-2-yl)-phenyl]-piperidin-4-yl}-acetamide 2-(3-bromophenyl)-1H-benzimidazole Method N—Step a O-phenylenediamine (81.8 g, 756.6 mmol) and oxalic acid (3.4 g, 37.8 mmol) were completely dissolved in EtOH—H$_2$O/1:1 (2 L) previously warmed at 80° C. 3-Bromobenzaldehyde (44.10 mL, 378.30 mmol) was then added dropwise to the solution. The reaction mixture was stirred overnight at 70° C. to the open air. The day after solid was filtered off and triturated with MeOH (150 mL) to give the product as a pale yellow solid (27.50 g). 3.8 g were recovered from the mother liquors. Total yield 31.30 g (30%).

$^1$H-NMR (400 MHz DMSO): δ 7.24 (2H, m), 7.54 (2H, m), 7.70 (m, 2H), 8.19 (1H, m), 8.37 (1H, t), 13.2 (1H, s). m/z 273 (M+H)$^+$; retention time=8.60.

2-(3-Bromo-phenyl)-1-methyl-1H-benzimidazole

Method N—Step b 2-(3-bromophenyl)-1H-benzimidazole (7.8 g, 28.6 mmol) was completely dissolved in dry THF (300 ml), then NaH 60% m/m (1.49 g, 37.2 mmol) was added portionwise to the clear yellow solution. The light brown suspension was stirred 1 h rt, then CH$_3$I (2.5 ml, 40.0 mmol) was added dropwise. The reaction mixture was stirred rt overnight. The reaction was quenched with H$_2$O (300 ml), and extracted with EtOAc (2×450 ml). The organic extracts were dried over MgSO$_4$, filtered and evaporated, to afford the compound as a brown-yellow solid (7.4 g, 70%).

$^1$H-NMR (400 MHz DMSO): δ 3.90 (3H, s), 7.30 (2H, m), 7.55 (1H, t), 7.64 (1H, d), 7.70 (1H, d), 7.77 (1H, m), 7.88 (1H, m), 8.05 (1H, m). m/z=287 [M+H]$^+$, retention time=7.70

{1-[3-(1-Methyl-1H-benzoimidazol-2-yl)-phenyl]-piperidin-4-yl}-carbamic acid tert-butyl ester Method N—Step c Into a four-necked round bottomed flask, dried under Ar atmosphere, BINAP (5.85 g, 9.4 mmol) and Pd(OAc)$_2$ (1.41 g, 6.3 mmol) were placed. The mixture was stirred 10 minutes under Ar flux, then 300 ml of anhydrous toluene were added. Meantime into another four-necked round bottomed flask, dried under Ar atmosphere, 2-(3-bromophenyl)-1-methyl-1H-benzimidazole previously dissolved in 300 ml of anhydrous toluene, (9.0 g, 31.3 mmol), 4-N—BOC-aminopiperidine (8.18 g, 40.7 mmol) and Cs$_2$CO$_3$ (50.99 g, 156.5 mmol) were placed. The mixture was stirred for ca. 10 minutes then the content of the first flask was added into the second one. The reaction was stirred overnight at reflux temperature. After cooling to room temperature, the suspension was filtered on a gouch with a celite pad. The clear solution was evaporated under reduced pressure and the residue was triturated by MTBE affording 7.1 g (55%) of pure product as an off white solid.

$^1$H-NMR (DMSO): 1.39 (s, 9H); 1.49 (m, 2H); 1.82 (m, 2H); 2.83 (m, 2H); 3.44 (bs, 1H); 3.75 (m, 2H); 3.87 (s, 3H); 6.86 (d, 1H); 7.11-7.67 (m, 8H). m/z=407 [M+H]$^+$; retention time=8.02

{1-[3-(1-Methyl-1H-benzoimidazol-2-yl)-phenyl]-piperidin-4-ylamine hydrochloride Method N—Step d To a mixture of {1-[3-(1-Methyl-1H-benzoimidazol-2-yl)-phenyl]-piperidin-4-yl}-carbamic acid tert-butyl ester (2.00 g, 4.93 mmol) in dichloromethane (2 mL) and methanol (1 mL), 2M HCl in Et$_2$O (25 mL) was added and the resulting mixture was stirred overnight at room temperature.

The solid was filtered off, dried under vacuum and was re-dissolved in water (50 mL) and washed with dichloromethane (3×10 mL). Water was removed under reduced to afford 1.48 g (89%) of the title compound as hydrochloride salt.

$^1$H-NMR (400 MHz, DMSO): δ 1.67-1.77 (2H, m), 2.01-2.04 (2H, m), 2.95-3.00 (2H, m), 3.19-3.26 (1H, m), 3.89-3.95 (2H, m), 4.05 (3H, s), 7.36-7.44 (2H, m), 7.55-7.68 (4H, m), 7.86-7.89 (1H, m), 8.04-8.07 (1H, m), 8.41 (3H, bs). m/z=307 [M+H]$^+$; retention time=0.17

2-Ethoxy-N-{1-[3-(1-methyl-1H-benzoimidazol-2-yl)-phenyl]-piperidin-4-yl}-acetamide Method N—Step e To a solution of ethoxyacetic acid (0.05 mL, 0.49 mmol) in acetonitrile (3 mL) was added CDI as a stock solution (0.80 g, 0.49 mmol) and the resulting suspension was stirred at room temperature for 3 h. {1-[3-(1-Methyl-1H-benzoimidazol-2-yl)-phenyl]-piperidin-4-ylamine hydrochloride (0.13 g, 0.41 mmol) and DIPEA (0.07 mL, 0.41 mmol) were added and the resulting solution heated at 70° C. overnight. The reaction was then cooled to room temperature, the solvent removed under reduced pressure. The crude product was redissolved in dichloromethane (4 mL) and washed with saturated Na$_2$CO$_3$ solution (2 mL) and water (2 mL). The organic layer was dried over Na$_2$SO$_4$, filtered and concentrated under reduced pressure. The residue was purified by flash chromatography (eluent: dichloromethane:MeOH, gradient from 100% dichloromethane to 95% dichloromethane:5% MeOH) to afford 0.70 g (44%) of the title compound.

$^1$H-NMR (400 MHz, CDCl$_3$): δ 1.17 (3H, t), 1.51-1.61 (2H, m), 1.96-2.00 (2H, m), 2.89-2.95 (2H, m), 3.50 (2H, q), 3.67-3.71 (2H, m), 3.81 (3H, s), 3.86 (2H, s), 3.91-4.01 (1H, m), 6.44-6.46 (1H, m), 6.99-7.01 (1H, m), 7.05-7.07 (1H, m), 7.23-7.35 (5H, m), 7.77-7.80 (1H, m). m/z=393 [M+H]$^+$; retention time=1.67

Example 35

4-Fluoro-1'-[3-(1-methyl-1H-benzoimidazol-2-yl)-phenyl]-[1,4]bipiperidinyl 2-(3-bromophenyl)-1-methyl-1H-benzimidazole Method O, Oa—Step a—

2-(3-bromophenyl)-1H-benzimidazole (as described in method N, step a) (7.8 g, 28.6 mmol) was completely dissolved in dry THF (300 mL), then NaH 60% m/m (1.49 g, 37.2 mmol) was added portionwise to the clear yellow solution. The light brown suspension was stirred at room temperature for 1 h, then CH$_3$I (2.5 mL, 40.0 mmol) was added dropwise. The reaction mixture was stirred rt overnight. The reaction was quenched with H$_2$O (300 mL), and extracted with EtOAc (2×450 mL). The organic extracts were dried over MgSO$_4$, filtered and evaporated, to afford 7.4 g of the title compound as a brown-yellow solid (70%).

¹H-NMR (400 MHz DMSO): δ 3.90 (3H, s), 7.30 (2H, m), 7.55 (1H, t), 7.64 (1H, d), 7.70 (1H, d), 7.77 (1H, m), 7.88 (1H, m), 8.05 (1H, m). m/z 287 (M+H)$^+$; retention time=7.70.

8-[3-(1-Methyl-1H-benzoimidazol-2-yl)-phenyl]-1,4-dioxa-8-aza-spiro[4,5]decane Method O, Oa—Step b In a 4 necked round bottom flask equipped with a magnetic stirrer and dried under argon atmosphere BINAP (3.7 g, 5.9 mmol, 0.3 eq) and Pd(OAc)$_2$ (0.9 g, 3.9 mmol, 0.2 eq) were placed and left under argon flux for 15 min. At the meantime into a 4 necked round bottom flask equipped with magnetic stirrer, a reflux condenser and dried under argon atmosphere, 2-(3-bromophenyl)-1-methyl-1H-benzimidazole (5.6 g, 19.5 mmol, 1 eq) was dissolved in dry toluene (300 mL), then 1,4-Dioxa-8-azaspiro[4.5]decane (3.3 mL, 25.4 mmol, 1.3 eq), Cs$_2$CO$_3$ (31.8 g, 97.5 mmol, 5 eq) and the catalyst suspension were added to the solution. The reaction mixture was stirred overnight at reflux temperature, checking the conversion by LC-MS. The suspension was allowed to cool to r.t. then filtered on a gooch with a celite pad. Solvent was evaporated to give 16.0 g of a red-brown oil which was purified by automatic flash chromatography on silica versaflash (1 product g/30 silica g) by eluting from Cy:MTBE=85:15 to Cy:MTBE=15:85, to give 2.3 g of the pure product as a yellow oil (34%).

¹H-NMR (400 MHz DMSO): δ 1.70-1.73 (4H, m), 3.34-3.37 (4H, m), 3.84 (3H, s), 3.90 (4H, m), 7.11-7.39 (6H, m), 7.57-7.58/1H, m), 7.64-7.65 (1H, m). m/z 350 (M+H)$^+$; retention time=6.73.

1-[3-(1-methyl-1H-benzo[d]imidazol-2-yl)phenyl] piperidin-4-one

Method O, Oa—Step c

8-[3-(1-Methyl-1H-benzoimidazol-2-yl)-phenyl]-1,4-dioxa-8-aza-spiro[4,5]decane (2.30 g, 6.60 mmol) was dissolved in 120 mL of THF. The solution was cooled at 0° C. with a NaCl-ice bath, then HCl 6M (18 mL, 108 mmol) was added. The reaction progress was monitored by HPLC/MS and it was stirred rt until complete conversion. The solution was concentrated under reduced pressure, then it was neutralized with NaOH 2M (80 mL) and finally extracted with EtOAc (3×150 mL). The organic extracts were pooled together, dried over MgSO$_4$, filtered and evaporated, to afford 2 g of clean product as a pale yellow solid (92%).

¹H-NMR (400 MHz DMSO): δ 2.46 (4H, t), 3.70 (4H, t), 3.88 (3H, s), 7.20-76 (8H, m). m/z 306 (M+H)$^+$; retention time=5.90.

2-(5-bromo-2-chlorophenyl)-1H-benzimidazole

Method O, Oa—Step d

Into a one necked round bottomed flask equipped with a magnetic stirrer, 5-bromo-2-chlorobenzoic acid (70.0 g, 297.3 mmol), o-phenylenediamine (64.3 g, 594.6 mmol) and methansulfonic acid (140 mL) were placed and heated to 170° C. in order to melt the solids. The system was stirred 5 h at this temperature, then left to come rt. The blue solid was treated with NaOH 35% (200 mL) obtaining a violet suspension (pH 5) that was filtered and washed with NaOH 0.5 M (2 L) and H$_2$O (2 L). The product was dried under vacuum (60° C.), to give 61.6 g of a pure violet solid. (67%).

m/z 307/309 (M+H)$^+$; retention time=8.73.

Tert-butyl 2-(5-bromo-2-chlorophenyl)-1H-benzimidazole-1-carboxylate

Method O, Oa—Step e

Into a three necked round bottomed flask equipped with a magnetic stirrer, 2-(5-bromo-2-chlorophenyl)-1H-benzimidazole (30.7 g, 99.8 mmol) was suspended in THF (1 L). 50% NaOH (72.0 g, 598 mmol) was then added. The suspension was left at r.t. for 1 h under stirring. (BOC)$_2$O (37.0 g, 169.7 mmol) was dissolved in THF (200 mL) and added to the reaction mixture. The reaction was left under stirring overnight. The solvent was evaporated under reduced pressure. The obtained residue was diluted with water (500 mL) filtered and dried under vacuum (60° C.), to give 39.8 g of a brown solid. (98%).

m/z 407/409 (M+H)$^+$; retention time=10.14.

2-[2-Chloro-5-(1,4-dioxa-8-aza-spiro[4,5]dec-8-yl)-phenyl]-benzoimidazole-1-carboxylic acid tert-butyl ester Method O, Oa—Step f In a 4 necked round bottom flask equipped with a magnetic stirrer and dried under argon atmosphere BINAP (13.8 g, 22.1 mmol) and Pd(OAc)$_2$ (3.3 g, 14.7 mmol) were placed and left under argon flux for 15 min. Meantime into a 4 necked round bottom flask equipped with magnetic stirrer, reflux condenser and dried under argon atmosphere Tert-butyl 2-(5-bromo-2-chlorophenyl)-1H-benzimidazole-1-carboxylate (30.0 g, 73.6 mmol) was dissolved in dry toluene (1 L), then 1,4-Dioxa-8-azaspiro[4.5]decane (12.3 mL, 95.7 mmol), Cs$_2$CO$_3$ (119.9 g, 368.0 mmol) and the catalyst suspension were added to the solution. The reaction mixture was stirred 30 h at 80° C., checking the conversion by LC-MS. The suspension was allowed to cool to r.t. then filtered on a gooch with a celite pad. Solvent was evaporated to give 64.5 g of a brown oil which was used in the next step without any further purification.

m/z 471/473 (M+H)$^+$; retention time=9.70.

1-[3-(1H-benzo[d]imidazol-2-yl)-4-chlorophenyl] piperidin-4-one

Method O, Oa—Step g

In 4 necked round bottom flask equipped with a magnetic stirrer 2-[2-Chloro-5-(1,4-dioxa-8-aza-spiro[4,5]dec-8-yl)-phenyl]-benzoimidazole-1-carboxylic acid tert-butyl ester (59.5 g, 93.9 mmol, 1 eq) was dissolved in THF (250 mL), then HCl 4M (1.2 L, 4695 mmol) was added. The system was left under stirring rt overnight. The brown suspension was filtered washing the solid with cold water (500 mL), this solid is the catalyst from the previous step. The mother liquors were concentrated under reduced pressure in order to precipitate other solid that was filtered off. The acid aqueous phase (1.7 L) was cooled to 0° C. with an ice-NaCl bath and made basic with NaOH 4M (1.8 L). The solid was filtered, washed with water (600 mL) and dried under vacuum (60° C.) to give the pure 22.8 g of product as a light grey solid (75%).

¹H-NMR (400 MHz DMSO): δ 2.45 (4H, t), 3.70 (4H, t), 7.17-7.64 (7H, m), 12.85 (1H, bs). m/z 426/428 (M+H)$^+$; retention time=6.97.

4-Fluoro-1'-[3(1-methyl-1H-benzoimidazol-2-yl)-phenyl]-[1,4']bipiperidinyl

Method O—Step h

Sodium triacethoxyborohydride (0.10 g, 0.49 mmol) was added to a mixture of 1-[3-(1-Methyl-1H-benzoimidazol-2-yl)-phenyl]-piperidin-4-one (0.1 g, 0.33 mmol) and 4-fluoropiperidine hydrochloride (0.07 g, 0.49 mmol) in dichloroethane (2.50 mL). Reaction was left at room temperature 18 h. Reaction was diluted with DCM (4 mL), and washed with $Na_2CO_3$ saturated solution (4 mL) Organic layer was concentrated and crude was filtered through SCX cartridge (2 g) (eluent: at first 10 mL of DCM:MeOH 1:1 then 10 mL of 2.0 N ammonia solution in MeOH). The ammonia solution was concentrated and crude was purified by flash chromatography (eluent: AcOEt: 2.0 N ammonia solution in MeOH gradient from 100% of AcOEt to AcOEt 10:2.0 N ammonia solution in MeOH 1) to afford 0.06 g of the title compound (48%).

$^1$H-NMR (400 MHz, $CD_3OD$): δ 1.67-1.73 (2H, m), 1.86-2.06 (6H, m), 2.61-2.71 (3H, m), 2.77-2.89 (4H, m), 3.89-3.93 (5H, m), 4.61-4.77 (1H, m), 7.17-7.19 (2H, m), 7.28-7.37, (3H, m), 7.41-7.45 (1H, m), 7.54-7.56 (1H, m), 7.66-7.68 (1H, m). m/z 393 (M+H)$^+$; retention time=split peak.

Example 36

1'[3-(1-Methyl-1H-benzoimidazol-2-yl)-phenyl]-[1,4]bipiperidinyl

1'[3-(1-Methyl-1H-benzoimidazol-2-yl)-phenyl]-[1,4]bipiperidinyl

Method Oa—Step i

1-[3-(1-methyl-1H-benzo[d]imidazol-2-yl)phenyl]piperidin-4-one (0.06 g, 0.2 mmol) and piperidine (0.034 g, 0.4 mmol) with triethylamine (27 µL, 0.2 mmol) and molecular sieves (0.5 g) were heated to 40° C. in methanol (5 ml) for 16 hours. Sodiumcyanoborohydride (0.025 g, 0.4 mmol) and zinc chloride (0.027 g, 0.2 mmol) were added and the reaction heated for a further 16 hours, the reaction mixture was evaporated and the residue partitioned between 1N sodium hydroxide (2 ml) and dichloromethane (4 ml). The organic layer was separated, evaporated and purified by preparative HPLC.

$^1$H-NMR (400 MHz, $CD_3OD$): δ 1.56 (1H, bs), 1.84-1.98 (7H, m), 2.20-2.23 (2H, m), 2.89-2.94 (2H, m), 3.04 (2H, bs), 3.36-3.43 (1H, m), 3.56 (2H, bs), 3.94 (3H, s), 4.02-4.05 (2H, m), 7.23-7.26 (2H, m), 7.37-7.45 (3H, m), 7.47-7.51 (1H, m), 7.64-7.66 (1H, m), 7.71-7-73 (1H, m).

m/z 375 (M+H)$^+$; retention time=split peak.

Example 37

2-[3-(3-Fluoro-4-morpholin-4-yl-piperidin-1-yl)-phenyl]-1-methyl-1H-benzoimidazole 4-Trimethylsilanyloxy-3,6-dihydro-2H-pyridine-1-carboxylic acid tert-butyl ester Method P—Step a Chlorotrimethylsilane (1.52 mL, 12.05 mmol) and dry triethylamine (3.42 mL, 24.6 mmol) were added to a stirred solution of 4-oxopiperidine-1-carboxylic acid tert-butyl ester (2.0 g, 10.04 mmol) in dry DMF (20 mL) The reaction was heated at 80° C. 16 h, then cooled to room temperature and diluted with n-hexane (120 mL) Organic solution was washed with cold $NaHCO_3$ saturated solution (60 mL), dried over $Na_2SO_4$ and concentrated under reduced pressure to afford 2.56 g of the title compound (94%).

$^1$H-NMR (400 MHz, DMSO): δ 0.00 (9H, s), 1.23 (9H, s), 1.83-1.87 (2H, m), 3.24-3.27 (2H, m), 3.60-3.61 (2H, m), 4.63 (1H, bs). m/z 272 (M+H)$^+$; retention time=2.78.

3-Fluoro-4-oxo-piperidine-1-carboxylic acid tert-butyl ester

Method P—Step b

Selectfluor (5.52 g, 15.59 mmol) was added to a stirred solution of 4-trimethylsilanyloxy-3,6-dihydro-2H-pyridine-1-carboxylic acid tert-butyl ester (3.84 g, 14.17 mmol) in dry acetonitrile (150 mL) at room temperature under nitrogen. After 75 minutes reaction was diluted with AcOEt (500 mL) and washed with a dilutes solution of NaCl (300 mL) and then with brine (300 mL). Organic layer was dried over $Na_2SO_4$ and concentrated under reduced pressure. The crude reaction mixture was purified by flash chromatography through neutral alumina (eluent: cyclohexane:AcOEt:MeOH gradient from cyclohexane:AcOEt 1:1 to cyclohexane: AcOEt 1:2 to 100% AcOEt and finally AcOEt:MeOH 95:5) to afford 2.12 g of the title compound.

3-Fluoro-4-morpholin-4-yl-piperidine-1-carboxylic acid tert-butyl ester

Method P—Step c

Morpholine (0.71 mL, 8.11 mmol) was added to a stirred solution of 3-Fluoro-4-oxo-piperidine-1-carboxylic acid tert-butyl ester (1.60 g, 7.37 mmol) in dichloroethane (2 mL) under nitrogen. After 10 minutes sodium triacethoxyborohydride (2.35 g, 11.13 mmol) was added portionwise and reaction was left 3 h. $Na_2CO_3$ saturated solution (20 mL) was added to the reaction. Organic phase was separated and the aqueous solution was extracted with DCM (3×10 mL). Organic layers were collected, dried over $Na_2SO_4$ and concentrated under reduced pressure. The crude reaction mixture was purified by flash chromatography (eluent: cyclohexane: AcOEt:2.0 N ammonia solution in MeOH gradient from cyclohexane:AcOEt 2:1 to 100% AcOEt and finally AcOEt: 2.0 N ammonia solution in MeOH 10:1) to afford 1.28 g of the title compound. (57%).

$^1$H-NMR (400 MHz $CD_3OD$): δ 1.45 (9H, s), 1.74-1.80 (2H, m), 2.38-2.51 (1H, m), 2.65-2.68 (4H, m), 2.71-3.04 (2H, m), 3.65-3.72 (4H, m), 4.18-4.21 (1H, m), 4.37-4.38 (1H, m), 4.91-5.03 (1H, m). m/z 289 (M+H)$^+$; retention time=split peak.

4-(3-Fluoro-piperidin-4-yl)-morpholine

Method P—Step d 2.0 N HCl in $Et_2O$ (15 mL) was added to a solution of 3-Fluoro-4-morpholin-4-yl-piperidine-1-carboxylic acid tert-butyl ester (1.28 g, 4.44 mmol) in DCM (2 mL) and the resulting suspension was stirred at room temperature 4 days. The precipitate was filtered off and tritured with $Et_2O$ (2×5 mL) $Na_2CO_3$ saturated solution (10 mL) was added and the resulting solution was concentrated under reduced pressure. EtOH (15 mL) was added and precipitate was filtered off.

The filtrate was concentrated under reduced pressure to afford 0.71 g of the title compound. (85%).

$^1$H-NMR (400 MHz $CD_3OD$): δ 1.84-1.94 (2H, m), 2.47-2.60 (1H, m), 2.66-2.68 (4H, m), 2.78-2.86 (1H, m), 2.88-3.02 (1H, m), 3.23-3.28 (1H, m), 3.36-3.44 (1H, m), 3.68-3.71 (4H, m), 5.01-5.14 (1H, m). m/z 189 (M+H)$^+$; retention time=0.17.

2-[3-(3-Fluoro-4-morpholin-4-yl-piperidin-1-yl)-phenyl]-1-methyl-1H-benzoimidazole Method P—Step e 4-(3-Fluoro-piperidin-4-yl)-morpholine (0.085 g, 0.45 mmol), 2-(3-Bromo-phenyl)-1-methyl-1H-benzoimidazole (described in method N, step a, b) (0.10 g, 0.35 mmol), and cesium carbonate (10.50 g, 32.2 mmol) were placed into a dry sealed 7 mL vial under nitrogen and dry toluene (0.4 mL) was added. At the same time Palladium acetate (0.016 g, 0.07 mmol), and BINAP (0.065 g, 0.10 mmol) were placed into another dry sealed 7 mL vial under nitrogen and diluted with dry toluene (0.8 mL) After about 20 minutes the resulting suspension was added to the vial containing the starting materials.

The reaction mixture was heated at 85° C. 24 h then cooled to room temperature and filtered through SCX (eluent: at first 10 mL of DCM:MeOH 1:1 then 10 mL of 2.0 N ammonia solution in MeOH). The ammonia solution was concentrated under reduced pressure and crude was purified by flash chromatography (eluent: MeOH:AcOEt gradient from 100% AcOEt to MeOH:AcOEt 1:4) to afford 0.08 g of the title compound. (58%).

$^1$H-NMR (400 MHz CD$_3$OD): δ 1.91-1.95 (1H, m), 2.01-2.11 (1H, m), 2.41-2.54 (1H, m), 2.67-2.75 (4H, m), 2.84-3.04 (2H, m), 3.68-3.76 (4H, m), 3.88 (3H, s), 3.92-3.98 (1H, m), 4.09-4.16 (1H, m), 5.06-5.19 (1H, m). m/z 395 (M+H)$^+$; retention time=0.27

Example 38

{4-[3-(1H-Benzoimidazol-2-yl)-4-chloro-phenyl]-[1,4]diazepan-1-yl}-(1-methyl-piperidin-3-yl-methanone 4-(4-Chloro-3-ethoxycarbonyl-phenyl)-[1,4]diazepane-1-carboxylic acid tert-butyl ester Method Q—Step a

[1,4]diazepane-1-carboxylic acid tert-butyl ester (11.5 g, 0.057 mmol), 5,bromo-2-chloro benzoic acid ethyl ester (12.5 g, 0.047 mmol), Pd(OAc)$_2$ (0.21 g, 1 mmol), rac-2,2' bis(diphenylphosphino)-1,1'-binaphtyl (BINAP) (0.88 g, 1.4 mmol) and cesium carbonate (21.5 g, 66 mmol) were suspended in toluene (200 mL). Reaction was refluxed 16 h then cooled to 20° C. The reaction mixture was poured into water (200 mL), and extracted with AcOEt (3×150 mL). The combined extracts were washed with brine, dried over MgSO$_4$ and concentrated under reduced pressure to give a brown oil that was purified by flash chromatography (eluent: n-hexane:AcOEt gradient from n-hexane:AcOEt 4:1 to n-hexane:AcOEt 1:1) to afford 17.2 g of the title compound. (96%).

$^1$H-NMR (400 MHz CDCl$_3$): δ 1.37-1.48 (12H, m), 1.96-2.02 (2H, m), 3.22-3.35 (2H, m), 3.50-3.64 (6H, m), 4.39 (2H, q), 6.76-6.78 (1H, m), 7.10-7.11 (1H, m), 7.23-7.26 (1H, m). m/z 383 (M+H)$^+$; retention time=7.70.

2-(2-Chloro-5-[1,4]diazepan-1-yl-phenyl)-1H-benzoimidazole

Method Q—Step b

To a solution of trimethylaluminium (2.0 M solution in toluene) (90 mL, 180 mmol) in toluene (300 mL) cooled to 0° C. under nitrogen was added benzene-1,2-diamine (6.5 g, 60 mmol) portionwise. The solution was stirred for 30 minutes at 0° C. then at 15-20° C. until evolution of methane ceased. 4-(4-chloro-3-ethoxycarbonyl-phenyl)-[1,4]diazepane-1-carboxylic acid tert-butyl ester (15.2 g, 40 mmol) was added in one portion to the resulting solution. The reaction was heated to reflux for 24 h then cooled to 0° C. Water (70 mL) was added carefully followed by MeOH (700 mL) The solid precipitated was filtered and the filtrate was concentrated under reduced pressure. The precipitate was washed with hot DCM:MeOH 1:1 (400 mL) followed by AcOEt (200 mL) The solution was concentrated under reduced pressure. Two extracts were combined and purified by flash chromatography (eluent: AcOEt:MeOH:NH3 gradient from 100% AcOEt to AcOEt:MeOH:NH3 73:25:2) to afford 9.3 g of a mixture of 2-(2-Chloro-5-[1,4]diazepan-1-yl-phenyl)-1H-benzoimidazole and N-(2-amino-phenyl)-2-chlorodiazepan-1-yl-benzamide.

m/z 345 (M+H)$^+$; retention time=3.07; m/z 327 (M+H)$^+$; retention time=4.1.

2-(2-Chloro-5-[1,4]diazepan-1-yl-phenyl)-1H-benzoimidazole

Method Q—Step c

A 3:1 mixture of 2-(2-chloro-5-[1,4]diazepan-1-yl-phenyl)-1H-benzoimidazole and N-(2-amino-phenyl)-2-chlorodiazepan-1-yl-benzamide (10.1 g) was dissolved in acetic acid (120 mL), and heated at 55° C. for 16 h. Reaction was cooled to 20° C. and concentrated under reduced pressure. The resulting brown oil was triturated with Et$_2$O and dried. The acetate salt was dissolved in 10% MeOH/DCM (100 mL) and with NaHCO$_3$ 0.1 M aqueous solution (200 mL). A precipitate formed and it was stirred for 2 h then filtered and dried at 60° C. to afford 7.92 g of the title compound. (61% over two steps).

$^1$H-NMR (400 MHz DMSO): δ 2.11-2.17 (2H, m), 3.07-3.08 (2H, m), 3.26 (2H, bs), 3.60-3.63 (2H, m), 3.82-3.84 (2H, m), 7.12-7.15, (1H, m), 7.40-7.41 (1H, m), 7.54-7.56 (1H, m), 7.60-7.64 (2H, m), 7.88-7.92 (2H, m), 9.40 (2H, bs). m/z 327 (M+H)$^+$; retention time=4.1.

3-{4-[3-(1H-Benzoimidazol-2-yl)-4-chloro-phenyl]-[1,4]diazepane-1-carbonyl}-piperidine-1-carboxylic acid tert-butyl ester Method Q—Step d 2-(2-Chloro-5-[1,4]diazepan-1-yl-phenyl)-1H-benzoimidazole (0.25 g, 0.76 mmol), HOBt (0.12 g, 0.86 mmol), NMM (0.5 mL, 3.9 mmol), piperidine-1,3-dicarboxylic acid 1-tert-butyl ester (0.17 g, 0.76 mmol), and EDC (0.22 g, 1.16 mmol) were dissolved in DCM (8.0 mL) and stirred at 20° C. for 16 h. Water (6.0 mL) was added. Organic layer was separated, concentrated under reduced pressure and crude was purified by flash chromatography (eluent: 100% of AcOEt) to afford 0.25 g of the title compound. (100%).

$^1$H-NMR (400 MHz DMSO): δ 1.28-1.51 (11H, m), 1.56-1.89 (3H, m), 2.01 (1H, m,), 2.60-2.71 (3H, m), 3.41-3.76 (7H, m), 3.91-4.03 (3H, m), 6.90-6.95 (1H, m), 7.20-7.30 (3H, m), 7.34-7.37 (1H, m), 7.63 (2H, bs). m/z 536 (M+H)$^+$; retention time=1.85.

{4-[3-(1H-Benzoimidazol-2-yl)-4-chloro-phenyl]-[1,4]diazepan-1-yl}-piperidin-3-yl-methanone Method Q—Step e 3-{4-[3-(1H-Benzoimidazol-2-yl)-4-chloro-phenyl]-[1,4]diazepane-1-carbonyl}-piperidine-1-carboxylic acid tert-butyl ester (0.21 g, 0.39 mmol) was dissolved in isopropanol (4 mL) and acetyl chloride (0.17 mL, 2.4 mmol) was added. Reaction was heated at 40° C. for 16 h then cooled to room temperature and concentrated under reduced pressure and dried at 60° C. to afford 0.19 g of the title compound as dichlorhydrate salt. (94%).

¹H-NMR (400 MHz CD₃OD): δ 1.56-2.07 (6H, m), 3.04-3.25 (5H, m), 3.42-3.54 (1H, m), 3.59-3.87 (6H, m), 3.91-4.08 (1H, m), 7.14-7.20 (1H, m), 7.25-7.31 (1H, m), 7.50-7.56 (1H, m), 7.66-7.71 (2H, m), 7.87-7.92 (2H, m).

m/z 438 (M+H)⁺; retention time=split peak.

{4-[3-(1H-Benzoimidazol-2-yl)-4-chloro-phenyl]-[1,4]diazepan-1-yl}-(1-methyl-piperidin-3-yl-methanone Method Q—Step f {4-[3-(1H-Benzoimidazol-2-yl)-4-chloro-phenyl]-[1,4]diazepan-1-yl}-piperidin-3-yl-methanone (0.18 g, 0.34 mmol), was suspended in DCM (8 mL). Triethylamine (0.5 mL 3.5 mmol) was added to give a solution, followed by AcOH (0.5 mL) and formaldehyde (37% aqueous solution) (0.1 mL). Sodium triacethoxyborohydride (0.14 g, 0.63 mmol) was added and the reaction was stirred at room temperature for 24 h and then at 40° C. for 4 days. Reaction mixture was concentrated to 4 mL then formaldehyde (0.1 mL), triethylamine (0.5 mL, 3.5 mmol), AcOH (0.5 mL), and sodium triacethoxyborohydride (0.14 g, 0.63 mmol) were added again and the reaction was heated in microwave at 100° C. for 20 minutes. The reaction was quenched with NaOH 2.0 N solution (4 mL), and stirred for 15 minutes. Organic layer was separated and concentrated to reduced pressure. The residue was purified by flash chromatography (eluent: n-hexane:AcOEt:MeOH:NH₃ gradient from n-hexane:AcOEt 1:1 to AcOEt:MeOH:NH₃ 80:18:2) to afford 0.07 g of the title compound that was further purified by preparative HPLC to obtain 0.02 g of the title compound. (13%).

¹H-NMR (400 MHz CD₃OD): δ 1.37-1.94 (4H, m), 1.98-2.10 (2H, m), 2.56-2.62 (3H, m), 2.68-2.80 (2H, m), 2.98-3.06 (2H, m), 3.44-4.04 (9H, m), 6.90-6.98 (1H, m), 7.14-7.21 (1H, m), 7.28-7.40 (3H, m), 7.63-7.67 (2H, m). m/z 452 (M+H)⁺; retention time=split peak.

Example 39

4-[3-(1H-Benzoimidazol-2-yl)-4-chloro-phenyl]-[1,4]diazepane-1-carboxylic acid phenylamide 4-[3-(1H-Benzoimidazol-2-yl)-4-chloro-phenyl]-[1,4]diazepane-1-carboxylic acid phenylamide Method R To a solution of 2-(2-chloro-5-[1,4]diazepam-1-yl-phenyl)-1H-benzoimidazole (method Q, step a, b, c) (0.10 g, 0.30 mmol) in dichloromethane (4 mL) was added phenyl isocyanate (0.03 mL, 0.30 mmol) and the resulting suspension was stirred at room temperature for 16 h. The precipitate was filtered, then purified by flash chromatography (eluent: EtOAc:hexane, 1:4) to afford 0.06 g (45%) of the title compound.

¹H-NMR (400 MHz, DMSO): δ 1.89-1.95 (2H, m), 3.39-3.42 (2H, m), 3.56-3.59 (2H, m), 3.64 (4H, bs), 6.88-6.93 (2H, m), 7.16-7.24 (5H, m), 7.33-7.35 (1H, m), 7.38-7.41 (2H, m), 7.52-7.54 (1H, m), 7.67-7.69 (1H, m), 12.56 (1H, s). m/z=446 [M+H]⁺; retention time=5.87

Example 40

4-[3-(1H-Benzoimidazol-2-yl)-4-chloro-phenyl]-[1,4]diazepane-1-carboxylic acid (2-dimethylamino-ethyl)-amide 4-[3-(1H-Benzoimidazol-2-yl)-4-chloro-phenyl]-[1,4]diazepane-1-carboxylic acid (2-dimethylamino-ethyl)-amide Method S To a solution of N,N-dimethyl-ethane-1,2-diamine (0.85 g, 0.96 mmol) and triethylamine (0.50 mL, 3.84 mmol) in dioxane was added dropwise isopropylchloroformate (0.10 mL, 0.96 mmol) and after 1 h stirring at room temperature, 2-(2-Chloro-5-[1,4]diazepam-1-yl-phenyl)-1H-benzoimidazole (method Q, step a, b, c) (0.21 g, 0.64 mmol) was added. The resulting mixture was heated for 1 h at 15° C. at the microwave. Solvent was then removed under reduced pressure, the crude partitioned between dichloromethane (8 mL) and water (2 mL), organic layer was separated and loaded onto Silica column for purification (eluent: EtOAc:MeOH:NH₃, gradient from 80:18:2 to 70:28:2) to afford 279 mg of the title compound with quantitative yield.

¹H-NMR (400 MHz, CD₃OD): δ 1.97-2.00 (2H, m), 2.85 (6H, s), 2.92-2.95 (1H, m), 3.12-3.15 (1H, m), 3.41-3.46 (4H, m), 3.65-3.74 (6H, m), 6.97-7.00 (1H, m), 7.21-7.22 (1H, m), 7.38-7.41 (3H, m), 7.69-7.72 (2H, m).

m/z=441 [M+H]⁺; retention time=4.12

Example 41

1-{4-[3-(1H-Benzoimidazol-2-yl)-4-chloro-phenyl]-[1,4]diazepam-1-yl}-2-dimethylamino-ethanone 1-{4-[3-(1H-Benzoimidazol-2-yl)-4-chloro-phenyl]-[1,4]diazepam-1-yl}-2-dimethylamino-ethanone Method T—Step a A solution of dimethylglycine (0.78 g, 0.76 mmol), N,N-diisopropylethylamine (0.20 mL, 1.14 mmol) and o-benzotriazole-N,N,N',N'-tetramethyl-uronium-hexafluoro-phosphate (HBTU) (0.32 g, 0.84 mmol) in dichloromethane (20 mL) was stirred at room temperature for 15 min, then 2-(2-chloro-5-[1,4]diazepam-1-yl-phenyl)-1H-benzoimidazole (method Q, step a, b, c) (0.25 g, 0.76 mmol) was added. After 16 h stirring at room temperature solvent was removed and the crude was purified by flash chromatography (eluent: gradient EtOAc: hexane/50:50 to EtOAc:hexane:NH3/80:18:2) to afford 0.16 g of the title compound (50%)

¹H-NMR (400 MHz, CD₃OD): δ 1.93-2.04 (2H, m), 2.15 (3H, s), 2.21 (3H, s), 3.07-3.21 (2H, m), 3.45-3.51 (1H, m), 3.54-3.57 (1H, m), 3.63-3.70 (3H, m), 3.76-3.84 (3H, m), 6.90-6.95 (1H, m), 7.20-7.31 (3H, m), 7.33-7.37 (1H, m), 7.64 (2H, bs). m/z=412 [M+H]⁺; retention time=4.24

Example 42

(2-{4-[3-(1H-Benzoimidazol-2-yl)-4-chloro-phenyl]-[1,4]diazepan-1-yl}-ethyl)-dimethyl-amine (2-{4-[3-(1H-Benzoimidazol-2-yl)-4-chloro-phenyl]-[1,4]diazepan-1-yl}-ethyl)-dimethyl-amine Method T—Step b To a solution of 1-{4-[3-(1H-benzoimidazol-2-yl)-4-chloro-phenyl]-[1,4]diazepam-1-yl}-2-dimethylamino-ethanone (0.13 g, 0.31 mmol) in tetrahydrofuran (4 mL), 1M LiAlH$_4$ (0.31 mL, 0.31 mmol) was added and the resulting mixtures was stirred at room temperature for 72 h, then quenched with water (20 mL) and 2N NaOH (20 mL). The reaction mixture was then poured through a short plug (Na$_2$SO$_4$), solvent removed under reduced pressure and the crude was purified by preparative HPLC to obtain 0.03 g (25%) of the title compound.

$^1$H-NMR (400 MHz, CD$_3$OD): δ 1.98-2.04 (2H, m), 2.29 (6H, s), 2.53-2.56 (2H, m), 2.66-2.70 (4H, m), 2.85-2.88 (2H, m), 3.55-3.58 (2H, m), 3.61-3.63 (2H, m), 6.86-6.89 (1H, m), 7.16-7.17 (1H, m), 7.26-7.30 (2H, m), 7.32-7.35 (1H, m), 7.63 (2H, bs).

m/z=398 [M+H]$^+$; retention time=4.53.

Example 43

N,N-Dimethyl-2-{4-[3-(1-methyl-1H-benzoimidazol-2-yl)-phenyl]-[1,4]diazepan-1-yl}-acetamide 4-[3-(1-Methyl-1H-benzoimidazol-2-yl)-phenyl-[1,4]diazepane-1-carboxylic acid tert-butyl ester Methods U, V, W, Ab—Step a Into a four-necked round bottomed flask, dried under Ar atmosphere, BINAP (5.85 g, 9.4 mmol) and Pd(OAc)$_2$ (1.41 g, 6.3 mmol) were placed. The mixture was stirred 10 minutes under Ar flux, then 300 ml of anhydrous toluene were added. Meantime into another four-necked round bottomed flask, dried under Ar atmosphere, 2-(3-bromophenyl)-1-methyl-1H-benzimidazole (described method O, Oa step a) previously dissolved in 300 ml of anhydrous toluene, (9.0 g, 31.3 mmol), 1-BOC-homopiperazine (8.0 ml, 40.7 mmol) and Cs$_2$CO$_3$ (50.99 g, 156.5 mmol) were placed. The mixture was stirred for ca. 10 minutes then the content of the first flask was added into the second one. The reaction was stirred overnight at reflux temperature. After cooling to room temperature, the suspension was filtered on a gouch with a celite pad. The clear solution was evaporated under reduced pressure and the residue (25.0 g) was purified by automatic flash chromatography on silica versaflash (1 product g/30 silica g) by eluting from Cy:EtOAc=9:1 to Cy:EtOAc=1:9, to give the pure product as a brown foam (5.2 g, 41%).

$^1$H-NMR (d6 DMSO): 1.26 (d, 9H); 1.84 (m, 2H); 3.25 (m, 2H); 3.61 (m, 4H); 3.86 (s, 3H); 6.91 (dd, 1H) 7.00 (t, 1H); 7.10 (s, 1H); 7.27 (m, 3H); 7.59 (d, 1H); 7.67 (d, 1H). m/z=407[M+H]$^+$; retention time=8.20 min.

2-(3-[1,4]-Diazepan-1-yl phenyl)-1-methyl-1H-benzoimidazole dihydrochloride salt Methods U, V, W, Ab—Step b To a mixture of 4-[3-(1-Methyl-1H-benzoimidazol-2-yl)-phenyl-[1,4]diazepane-1-carboxylic acid tert-butyl ester (2.20 g, 5.61 mmol) in methanol (3 mL), 2M HCl in Et$_2$O (10 mL) was added and the resulting mixture was stirred 6 h at room temperature. The solvent was then removed under reduced pressure, and the resulting salt triturated with Et$_2$O, filtered under reduced pressure and dried under vacuum to obtain 1.60 g (93%) of the title compound as chloride salt.

$^1$H-NMR (400 MHz, DMSO): δ 2.13-2.19 (2H, m), 3.07-3.08 (2H, m), 3.24 (2H, bs), 3.61-3.64 (2H, m), 3.84-3.87 (2H, m), 4.06 (3H, s), 7.14-7.22 (2H, m), 7.33 (1H, bs), 7.49-7.53 (1H, m), 7.62-7.68 (2H, m), 7.86-7.90 (1H, m), 8.04-8.08 (1H, m), 9.54 (2H, bs). m/z=307[M+H]$^+$; retention time=split peak.

N,N-Dimethyl-2-{4-[3-(1-methyl-1H-benzoimidazol-2-yl)-phenyl]-[1,4]diazepan-1-yl}-acetamide Method U—Step c A mixture of 2-(3-[1,4]Diazepan-1-ylphenyl)-1-methyl-1H-benzoimidazole (0.30 g, 0.79 mmol), 2-Chloro-N,N-dimethyl-acetamide (0.14 g, 1.18 mmol) and triethylamine (0.44 mL, 3.20 mmol) in dioxane (8 mL) was heated for 16 h at 80 C. The reaction was then cooled to room temperature, the precipitate was filtered off and the organic phase was evaporated under reduced pressure. The residue was purified by flash chromatography (eluent: from EtOAc 100% to EtOAc:MeOH:NH3 89:10:1) to afford 0.11 g (34%) of the title compound.

$^1$H-NMR (400 MHz, CD$_3$OD): δ 1.93-2.04 (2H, m), 2.15 (3H, s), 2.21 (3H, s), 3.07-3.21 (2H, m), 3.45-3.51 (1H, m), 3.54-3.57 (1H, m), 3.63-3.70 (3H, m), 3.76-3.84 (3H, m), 6.90-6.95 (1H, m), 7.20-7.31 (3H, m), 7.33-7.37 (1H, m), 7.64 (2H, bs). m/z=392 [M+H]$^+$; retention time=4.87 min.

Example 44

2-[3-(4-Methanesulfonyl-[1,4]diazepan-1-yl)-phenyl]-1-methyl-1H-benzoimidazole

2-[3-(4-Methanesulfonyl-[1,4]diazepan-1-yl)-phenyl]-1-methyl-1H-benzoimidazole

Method V—Step d

To a solution of 2-(3-[1,4]Diazepan-1-ylphenyl)-1-methyl-1H-benzoimidazole (0.18 g, 0.46 mmol) and triethylamine (0.32 mL, 2.30 mmol) in dichloromethane (4 mL), was added methanesulfonyl chloride (0.04 mL, 0.55 mmol). After 16 h stirring at room temperature water (1 mL) was added, the organic layer was dried over Na$_2$SO$_4$, filtered and evaporated under reduced pressure. The resulting crude was purified by flash chromatography (eluent:EtOAc) to obtain 0.10 g (54%) of the title compound.

$^1$H-NMR (400 MHz, DMSO): δ 1.87-1.91 (2H, m), 2.81 (3H, s), 3.19-3.22 (2H, m), 3.42-3.45 (2H, m), 3.63-3.66 (2H, m), 3.69-3.71 (2H, m), 3.84 (3H, s), 6.91-6.94 (1H, m), 7.00-7.02 (1H, m), 7.09-7.10 (1H, m), 7.20-7.29 (2H, m), 7.32-7.36 (1H, m), 7.57-7.59 (1H, m), 7.65-7.66 (1H, m). m/z=385 [M+H]$^+$; retention time=5.49 min.

Example 45

{4-[3-(1-Methyl-1H-benzoimidazol-2-yl)-phenyl]-[1,4]diazepan-1-yl}-(4-methyl-piperazin-1-yl)-methanone {4-[3-(1-Methyl-1H-benzoimidazol-2-yl)-phenyl]-[1,4]diazepan-1-yl}-(4-methyl-piperazin-1-yl)-methanone Method W—Step e To a solution of triphosgene (0.41 g, 0.13 mmol) in dichloromethane (2 mL), was added 2-(3-[1,4]Diazepan-1-ylphenyl)-1-methyl-1H-benzoimidazole dihydrochloride salt (0.14 g, 0.37 mmol) and DIPEA (0.11 mL, 0.66 mmol) in dichloromethane (2 mL). After 15 minutes stirring at room temperature was added a solution of N-methyl-piperazine (0.04 mL, 0.44 mmol) and DIPEA (0.04 mL, 0.22 mmol) in dichloromethane (1.5 mL). The resulting suspension was stirred at room temperature for 10 min. The mixture was poured onto a mixture of saturated NaHCO$_3$ solution (25 mL) and dichloromethane (25 mL), the organic layer was dried over Na$_2$SO$_4$, filtered, and concentrated under reduced pressure to afford a residue that was purified by Preparative HPLC, to obtain 20 mg (13%) of the title compound.

$^1$H-NMR (400 MHz, CD$_3$OD): δ 2.02-2.13 (2H, m), 2.89 (3H, s), 3.02-3.58 (10H, m), 3.67-3.72 (4H, m), 3.84-3.86 (2H, m), 4.10 (3H, s), 7.08-7.20 (3H, m), 7.51-7.55 (1H, m), 7.63-7.69 (2H, m), 7.82-7.93 (2H, m).

m/z=433 [M+H]$^+$; retention time=4.75 min.

Example 46

1-{4-[3-(1-Methyl-1H-benzoimidazol-2-yl)-phenyl]-[1,4]diazepam-1-yl}-2-piperidin-1-yl-ethanone 1-{-4-[3-(1-Methyl-1H-benzoimidazol-2-yl)-phenyl]-[1,4]diazepam-1-yl}-2-piperidin-1-yl-1-ethanone Method Ab—step f A solution of piperidin-1-yl-acetic acid (0.12 g, 0.86 mmol) and 1,1-carbonyldiimidazole (0.14 g, 0.86 mmol) in acetonitrile (3 mL) was stirred for 4 h at room temperature, then a solution of 2-(3-[1,4]Diazepan-1-yl phenyl)-1-methyl-1H-benzoimidazole dihydrochloride salt (0.26 g, 0.86 mmol) and triethylamine (0.24 mL, 1.71 mmol) in acetonitrile (2 mL) was added. The resulting suspension was heated overnight at 70 C, then cooled to room temperature and the solvent removed under reduced pressure. The resulting residue was diluted with dichlomethane (10 mL), washed with water (2×3 mL) and the organic layer dried over Na$_2$SO$_4$, filtered and evaporated under reduced pressure. The residue was purified by flash chromatography (eluent: dichloromethane:MeOH, gradient from 100% dichloromethane to 95% dichloromethane:5% MeOH) to afford 0.12 g (32%) of the title compound.

$^1$H-NMR (400 MHz, DMSO): δ 1.21-1.46 (7H, m), 1.83-1.97 (2H, m), 2.21-2.31 (4H, m), 2.95-3.02 (2H, m), 3.27-3.30 (2H, m), 3.48-3.70 (5H, m), 3.84-3.85 (3H, m), 6.88-7.01 (2H, m), 7.06-7.11 (1H, m), 7.20-7.35 (3H, m), 7.57-7.61 (1H, m), 7.63-7.66 (1H, m). m/z=432 [M+H]$^+$; retention time=4.64 min.

Example 47

{1-[3-(1-Methyl-1H-benzoimidazol-2-yl)-phenyl]-piperidin-3-yl}-(4-methyl-piperazin-1-yl)-methanone 1-[3-(1-Methyl-1H-benzoimidazol-2-yl)-phenyl]-piperidine-3-carboxylic acid ethyl ester Method X—Step a Ethyl nipecotate (0.55 g, 3.48 mmol), 2-(3-bromophenyl)-1-methyl-1H-benzimidazole (described in method O, Oa step a) (0.50 g, 1.74 mmol), Pd(OAc)$_2$ (0.008 g, 0.035 mmol), rac-2,2' bis(diphenylphosphino)-1,1'-binaphtyl (BINAP) (0.78 g, 0.052 mmol) and cesium carbonate (0.78 g, 2.08 mmol) were suspended in toluene (20 mL) and degassed with N$_2$. Reaction was heated in microwave at 150° C. 30 minutes. Reaction was poured into water (200 mL) and extracted with AcOEt (100 mL). Organic layers were collected and concentrated under reduced pressure. The crude reaction mixture was purified by flash chromatography (eluent: n-hexane:AcOEt gradient from 100% n-hexane to n-hexane:AcOEt 7:3) to afford 0.4 g of the title compound. (63%).

$^1$H-NMR (400 MHz CDCl$_3$): δ 1.28 (3H, s), 1.66-1.77 (2H, m), 1.81-1.89 (1H, m), 2.04-2.07 (1H, m), 2.66-2.73 (1H, m), 2.89-2.96 (1H, m), 3.10-3.16 (1H, m), 3.58-3.62 (1H, m), 3.80-3.84 (1H, m), 3.88 (3H, s), 4.15-4.21 (2H, m), 7.09-7.12 (2H, m), 7.31-7.42 (5H, m), 7.83-7.86 (1H, m).

1-[3-(1-Methyl-1H-benzoimidazol-2-yl)-phenyl]-piperidine-3-carboxylic acid

Method X—Step b

1-[3-(1-Methyl-1H-benzoimidazol-2-yl)-phenyl]-piperidine-3-carboxylic acid ethyl ester (2.0 g, 5.51 mmol) was dissolved in MeOH:water 5:2 (35 mL) NaOH (0.44 g, 11 mmol) was added and reaction was heated 3 h at 40° C. Reaction mixture was concentrated under reduced pressure, taken up in water (30 mL) and washed with AcOEt (30 mL). Water layer was acidiphied to pH 5.5 with concentrated HCl. The white solid was filtered off and tritured with water (20 mL) and with n-hexane (20 mL) to afford 1.60 g of the title compound. (87%).

$^1$H-NMR (400 MHz CD$_3$OD): δ 1.68-1.77 (2H, m), 1.83-1.88 (1H, m), 2.01-2.06 (1H, m), 2.64-2.71 (1H, m), 2.92-2.99 (1H, m), 3.12-3.17 (1H, m), 3.57-3.60 (1H, m), 3.77-3.81 (1H, m), 3.90 (3H, s), 7.18-7.21 (2H, m), 7.29-7.38 (3H, m), 7.42-7.46 (1H, m), 7.56-7.58 (1H, m), 7.67-7.69 (1H, m). m/z 336 (M+H)$^+$; retention time=3.65.

{1-[3-(1-Methyl-1H-benzoimidazol-2-yl)-phenyl]-piperidin-3-yl}-(4-methyl-piperazin-1-yl)-methanone Method X—Step c 1-[3-(1-Methyl-1H-benzoimidazol-2-yl)-phenyl]-piperidine-3-carboxylic acid (0.10 g, 0.30 mmol) was added to a stirred solution of diisopropylethylamine (DIPEA) (89 μL, 0.36 mmol), HBTU (0.12 g, 0.33 mmol), and N-methyl-piperazine (0.04 g, 0.36 mmol) in dichloromethane (4 mL) The reaction was stirred at 35° C. overnight and concentrated under reduced pressure. The crude reaction mixture was purified by flash chromatography through NH2 column (eluent: n-hexane:AcOEt gradient from 100% n-hexane 100% AcOEt) to afford 0.055 g of the title compound. (44%).

$^1$H-NMR (400 MHz CD$_3$OD): δ 1.59-1.69 (1H, m), 1.74-1.86 (2H, m), 1.93-1.96 (1H, m), 2.35 (3H, s), 2.40-2.61 (4H, m), 2.79-2.86 (1H, m), 2.94-3.06 (2H, m), 3.60-3.66 (4H, m), 3.80-3.85 (2H, m), 3.89 (s, 3H), 7.16-7.19 (2H, m), 7.28-7.36 (3H, m), 7.42-7.46 (1H, m), 7.54-7.57 (1H, m), 7.66-7.68 (1H, m). m/z 418 (M+H)$^+$; retention time=4.75.

Example 48

{1-[3-(1H-Benzoimidazol-2-yl)-4-chloro-phenyl]-piperidin-4-yl}-(4-methyl-piperazin-1-yl)-methanone 2-[2-Chloro-5-(4-ethoxycarbonyl-piperidin-1-yl)-phenyl]-benzoimidazole-1-carboxylic acid tert-butyl ester Method Y, Z—Step a Ethyl isonipecotate (1.54 g, 9.8 mmol), tert-butyl 2-(5-bromo-2-chlorophenyl)-1H-benzimidazole-1-carboxylate (described Method O, OA, step d, e) (2.0 g, 4.9 mmol), Pd(OAc)$_2$ (0.22 g, 0.98 mmol), rac-2,2' bis(diphenylphosphino)-1,1'-binaphtyl (BINAP) (0.90 g, 1.47 mmol) and cesium carbonate (8.0 g, 24.5 mmol) were suspended in toluene (40 mL) and degassed with N$_2$. Reaction was refluxed until complete consumption of starting material. The reaction mixture was filtered off, washed with water (200 mL). The organic layer was extracted with AcOEt (100 mL) and concentrated under reduced pressure. The crude reaction mixture was purified by flash chromatography (eluent: n-hexane:AcOEt gradient from 100% n-hexane to n-hexane:AcOEt 1:1) to afford 1.6 g of the title compound. (67%).

$^1$H-NMR (400 MHz CDCl$_3$): δ 1.28 (3H, t), 1.40 (9H, s), 1.83-1.94 (2H, m), 2.01-2.09 (2H, m), 2.42-2.49 (1H, m), 2.82-2.88 (2H, m), 3.63-3.68 (2H, m), 4.16 (2H, q), 7.00 (1H, bs), 7.11 (1H, bs), 7.29-7.33 (1H, m), 7.37-7.45 (2H, m), 7.80-7.82 (1H, m), 8.11-8.13 (1H, m). m/z 484 (M+H)$^+$; retention time=8.69.

1-[3-(1H-Benzoimidazol-2-yl)-4-chloro-phenyl]-piperidine-4-carboxylic acid ethyl ester Method Y, Z—Step b 2-[2-Chloro-5-(4-ethoxycarbonyl-piperidin-1-yl)-phenyl]-benzoimidazole-1-carboxylic acid tert-butyl ester (1.98 g, 4.1 mmol) was dissolved in isopropanol (50 mL) Acetyl chloride (2.1 g, 28.7 mmol) was added dropwise and the reaction mixture was heated at 40° C. until no starting material remained. The reaction was concentrated under reduced pressure to afford 2.0 g of the title compound. (100%).

$^1$H-NMR (400 MHz DMSO): δ 1.18 (3H, t), 1.60-1.70 (2H, m), 1.89-1.93 (2H, m), 2.53-2.63 (1H, m), 2.92-2.98 (2H, m), 3.79-3.82 (2H, m), 4.07 (2H, q), 7.29-7.32 (1H, m), 7.53-7.64 (4H, m), 7.86-7.91 (2H, m). m/z 384 (M+H)$^+$; retention time=6.59.

1-[3-(1H-Benzoimidazol-2-yl)-4-chloro-phenyl]-piperidine-4-carboxylic acid

Method Y, Z—Step c

1-[3-(1H-Benzoimidazol-2-yl)-4-chloro-phenyl]-piperidine-4-carboxylic acid ethyl ester (2.0 g, 5.2 mmol), was dissolved in MeOH:water 3:2 (50 mL) and NaOH was added (0.41 g, 10.3 mmol). The reaction was stirred at 40° C. until complete consumption of starting material. The reaction mixture was concentrated under reduced pressure, taken up in water (30 mL) and washed with AcOEt (30 mL) The aqueous layer was neutralized with concentrated HCl, the white solid was filtered off and washed with water (20 mL) and Et2O (20 mL) to afford 1.2 g of the title compound. (82%).

$^1$H-NMR (400 MHz DMSO): δ 1.59-1.69 (2H, m), 1.88-1.92 (2H, m), 2.36-2.43 (1H, m), 2.81-2.87 (2H, m), 3.69-3.72 (2H, m), 7.07-7.10 (1H, m), 7.19-7.23 (2H, m), 7.37-7.40 (2H, m), 7.61 (2H, bs). m/z 356 (M+H)$^+$; retention time=3.66.

{1-[3-(1H-Benzoimidazol-2-yl)-4-chloro-phenyl]-piperidin-4-yl}-(4-methyl-piperazin-1-yl)-methanone Method Y—Step d Synthesized as described in Method X-Step c starting from 1-[3-(1H-Benzoimidazol-2-yl)-4-chloro-phenyl]-piperidine-4-carboxylic acid (0.1 g, 0.28 mmol) and 1-methyl-piperazine (37 µL, 0.34 mmol). Obtained 30 mg (24%).

$^1$H-NMR (400 MHz CD$_3$OD): δ 1.78-1.90 (4H, m), 2.32 (3H, s), 2.41-2.50 (4H, m), 2.82-2.89 (3H, m), 3.61-3.66 (4H, m), 3.82-3.85 (2H, m), 7.09-7.12 (1H, m), 7.26-7.30 (2H, m), 7.39-7.41 (2H, m), 7.62-7.64 (2H, m).

m/z 438 (M+H)$^+$; retention time=4.74.

Example 49

{1-[3-(1H-Benzoimidazol-2-yl)-4-chloro-phenyl]-piperidin-4-yl}-piperazin-1-yl-methanone hydrochloride 4-{1-[3-(1H-Benzoimidazol-2-yl)-4-chloro-phenyl]-piperidine-4-carbonyl}-piperazine-1-carboxylic acid tert-butyl ester Method Z—Step e Synthesised as described in Method X-Step c starting from 1-[3-(1H-Benzoimidazol-2-yl)-4-chloro-phenyl]-piperidine-4-carboxylic acid (0.1 g, 0.28 mmol) and piperazine-1-carboxylic acid tert-butyl ester (0.06 g, 0.34 mmol). (72%)

$^1$H-NMR (400 MHz CD$_3$OD): δ 1.47 (9H, s), 1.90-1.91 (4H, m), 2.84-2.90 (3H, m), 3.41-3.63 (8H, m), 3.83-3.88 (2H, m), 7.10-7.13 (1H, m), 7.26-7.31 (2H, m), 7.39-7.41 (2H, m), 7.63 (2H, bs). m/z 524 (M+H)$^+$; retention time=6.32.

{1-[3-(1H-Benzoimidazol-2-yl)-4-chloro-phenyl]-piperidin-4-yl}-piperazin-1-yl-methanone Method Z—Step f 4-{1-[3-(1H-Benzoimidazol-2-yl)-4-chloro-phenyl]-piperidine-4-carbonyl}-piperazine-1-carboxylic acid tert-butyl ester (0.05 g, 0.11 mmol) was suspended in isopropanol (4 mL). Acetyl chloride (55 µL, 0.77 mmol) was added dropwise and the reaction mixture was heated to 40° C. until no starting material remained. The reaction was concentrated under reduced pressure to afford 0.05 g of the title compound. (100%).

m/z 424 (M+H)$^+$; retention time=4.10

Table 1 shows a selection of the compounds synthesised, which were prepared according to the method indicated in the third column of the table and above discussed in detail with the synthesis of examples 1-49

| Example | Structure | Method | M + H | Retention Time |
|---|---|---|---|---|
| 50 | 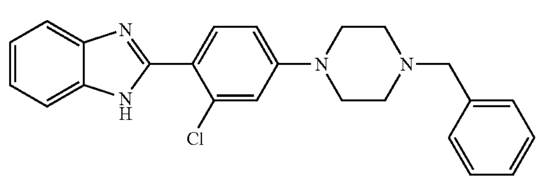 [SMILES: Clc1cc(N2CCN(Cc3ccccc3)CC2)ccc1-c1nc2ccccc2[nH]1] | A | 403 | 1.30 |

-continued

| Example | Structure | Method | M + H | Retention Time |
|---|---|---|---|---|
| 51 | 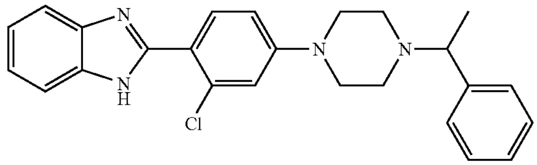 [SMILES: CC(c1ccccc1)N1CCN(c2ccc(-c3nc4ccccc4[nH]3)c(Cl)c2)CC1] | A | 417 | 1.38 |
| 52 | 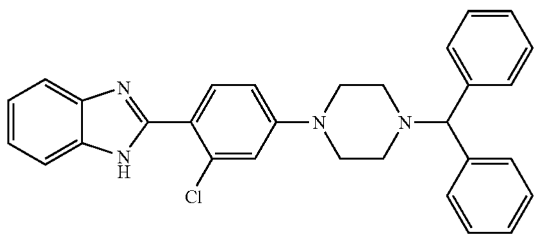 [SMILES: Clc1cc(N2CCN(C(c3ccccc3)c3ccccc3)CC2)ccc1-c1nc2ccccc2[nH]1] | A | 479 | 2.28 |
| 53 | 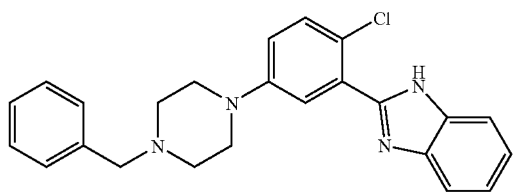 [SMILES: Clc1ccc(N2CCN(Cc3ccccc3)CC2)cc1-c1nc2ccccc2[nH]1] | A | 403 | 1.44 |
| 54 | 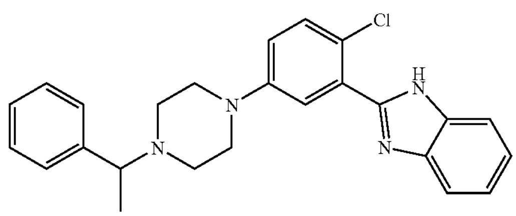 [SMILES: CC(c1ccccc1)N1CCN(c2ccc(Cl)c(-c3nc4ccccc4[nH]3)c2)CC1] | A | 417 | 1.58 |
| 55 | 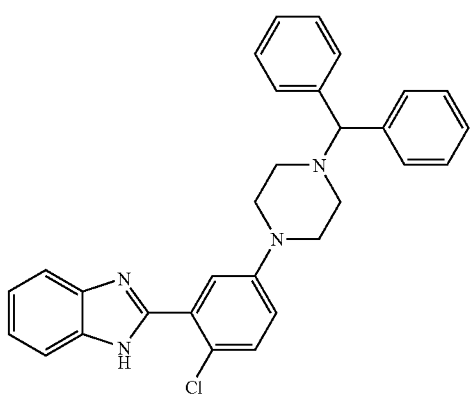 [SMILES: Clc1ccc(N2CCN(C(c3ccccc3)c3ccccc3)CC2)cc1-c1nc2ccccc2[nH]1] | A | 479 | 2.59 |
| 56 | 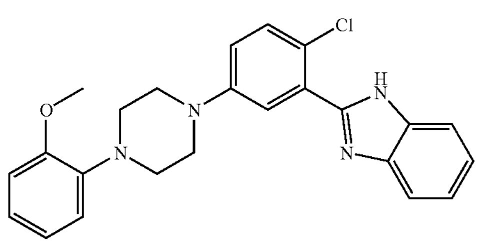 [SMILES: COc1ccccc1N1CCN(c2ccc(Cl)c(-c3nc4ccccc4[nH]3)c2)CC1] | A | 419 | 2.66 |

-continued

| Example | Structure | Method | M + H | Retention Time |
|---|---|---|---|---|
| 57 | 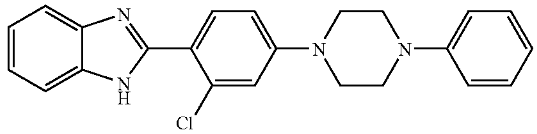 | A | 389 | 2.61 |
| 58 | 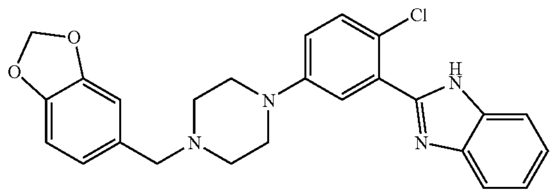 [SMILES: Clc1ccc(N2CCN(Cc3ccc4c(c3)OCO4)CC2)cc1-c1nc2ccccc2[nH]1] | A | 447 | 1.56 |
| 59 | 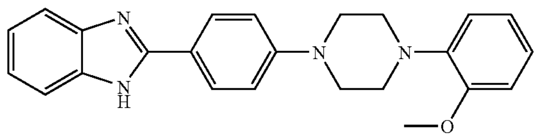 | A | 384 | 2.12 |
| 60 | 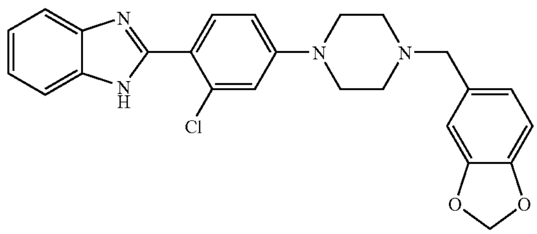 [SMILES: Clc1cc(N2CCN(Cc3ccc4c(c3)OCO4)CC2)ccc1-c1nc2ccccc2[nH]1] | A | 447 | 1.38 |
| 61 | 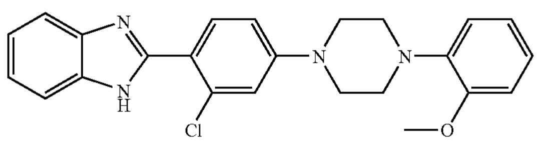 | A | 419 | 2.44 |
| 62 | 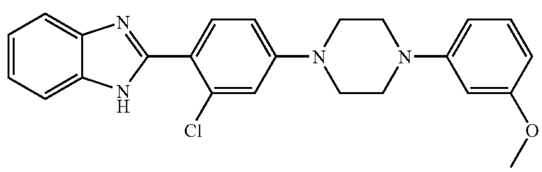 | A | 419 | 2.62 |
| 63 | 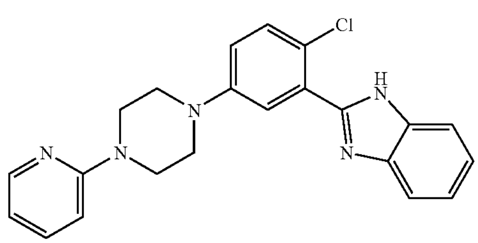 [SMILES: Clc1ccc(N2CCN(c3ccccn3)CC2)cc1-c1nc2ccccc2[nH]1] | A | 390 | 1.44 |
| 64 | 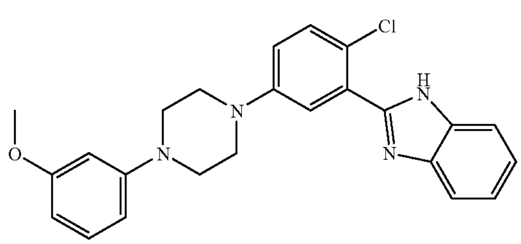 [SMILES: COc1cccc(N2CCN(c3ccc(Cl)c(-c4nc5ccccc5[nH]4)c3)CC2)c1] | A | 419 | 3.03 |

-continued

| Example | Structure | Method | M + H | Retention Time |
|---|---|---|---|---|
| 65 | 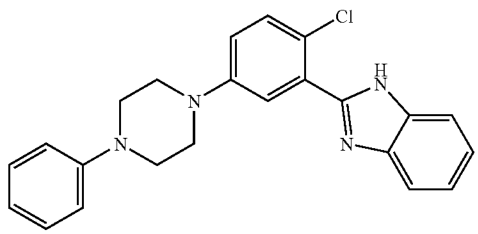 [SMILES: Clc1ccc(N2CCN(c3ccccc3)CC2)cc1-c1nc2ccccc2[nH]1] | A | 389 | 2.93 |
| 66 | 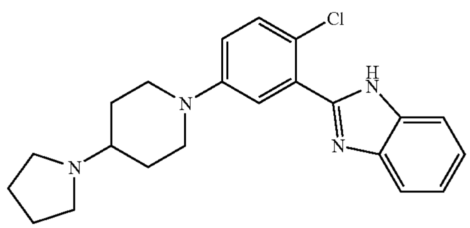 [SMILES: Clc1ccc(N2CCC(N3CCCC3)CC2)cc1-c1nc2ccccc2[nH]1] | A | 381 | 1.07 |
| 67 | 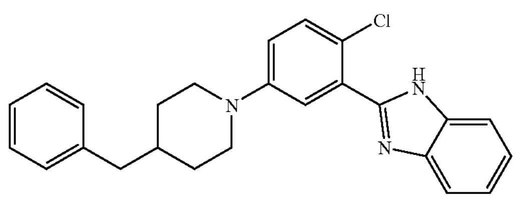 [SMILES: Clc1ccc(N2CCC(Cc3ccccc3)CC2)cc1-c1nc2ccccc2[nH]1] | A | 402 | 3.52 |
| 68 | 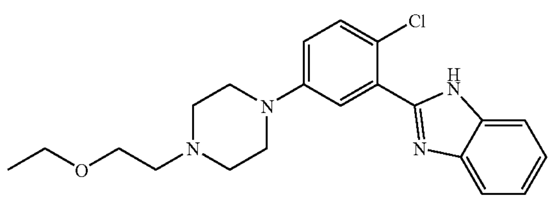 [SMILES: CCOCCN1CCN(c2ccc(Cl)c(-c3nc4ccccc4[nH]3)c2)CC1] | A | 385 | 1.17 |
| 69 | 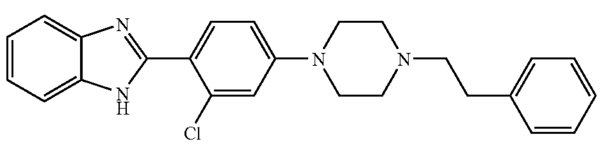 | A | 417 | 1.47 |
| 70 | 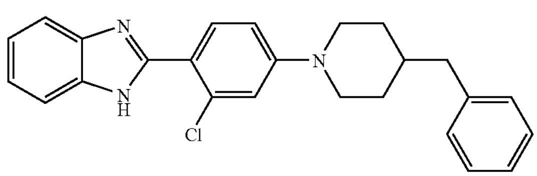 [SMILES: Clc1cc(N2CCC(Cc3ccccc3)CC2)ccc1-c1nc2ccccc2[nH]1] | A | 402 | 3.13 |
| 71 | 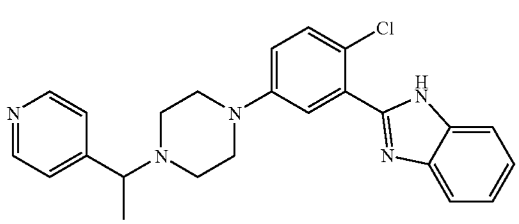 [SMILES: CC(c1ccncc1)N1CCN(c2ccc(Cl)c(-c3nc4ccccc4[nH]3)c2)CC1] | A | 418 | 1.02 |

-continued
| Example | Structure | Method | M + H | Retention Time |
|---|---|---|---|---|
| 72 | 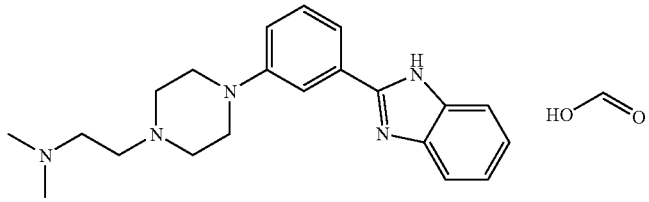 [SMILES: CN(C)CCN1CCN(c2cccc(-c3nc4ccccc4[nH]3)c2)CC1 ; O=CO] | A | 350 | solvent front |
| 73 | 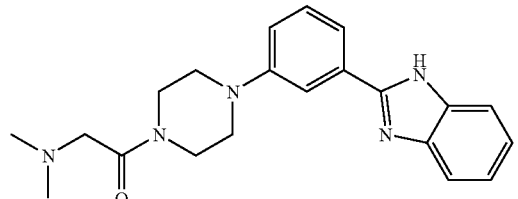 | B | 364 | 0.79 split peak |
| 74 | 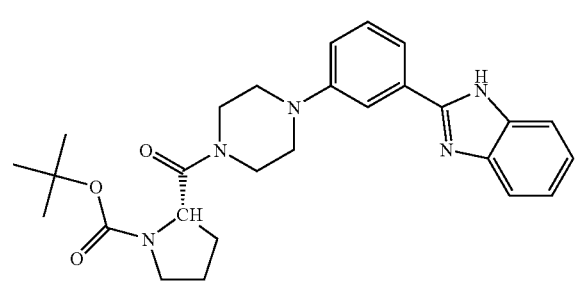 | B | 476 | 2.36 |
| 75 | 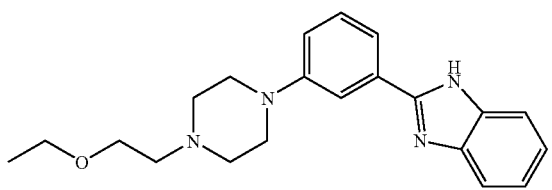 [SMILES: CCOCCN1CCN(c2cccc(-c3nc4ccccc4[nH]3)c2)CC1] | B | 351 | 1.04 split peak. |
| 76 | 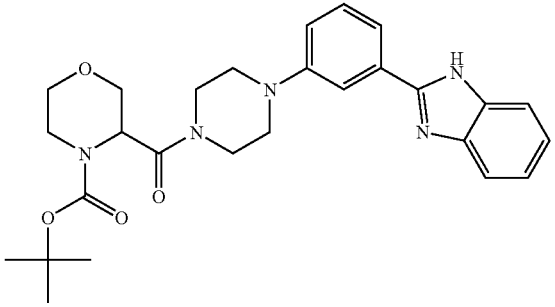 [SMILES: CC(C)(C)OC(=O)N1CCOCC1C(=O)N1CCN(c2cccc(-c3nc4ccccc4[nH]3)c2)CC1] | B | 492 | 2.33 |
| 77 | 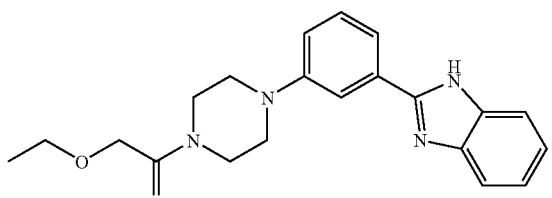 | B | 365 | 1.79 |

-continued
| Example | Structure | Method | M + H | Retention Time |
|---|---|---|---|---|
| 78 | 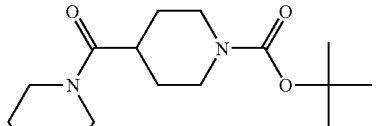 | B | 490 | 2.53 |
| 79 | 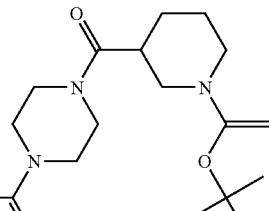 | B | 490 | 2.58 |
| 80 | 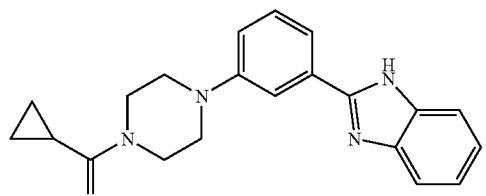 | B | 347 | 1.83 |
| 81 | 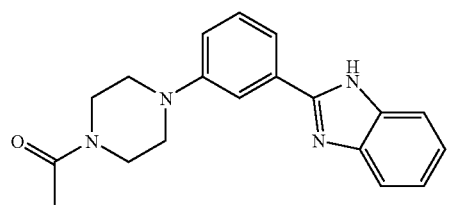 [SMILES: CC(=O)N1CCN(c2cccc(-c3nc4ccccc4[nH]3)c2)CC1] | B | 321 | 1.53 |
| 82 | 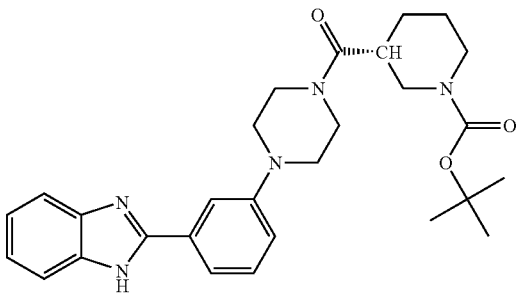 [SMILES: CC(C)(C)OC(=O)N1CCC[C@@H](C(=O)N2CCN(c3cccc(-c4nc5ccccc5[nH]4)c3)CC2)C1] | B | 490 | 2.60 |

-continued
| Example | Structure | Method | M + H | Retention Time |
|---|---|---|---|---|
| 83 | 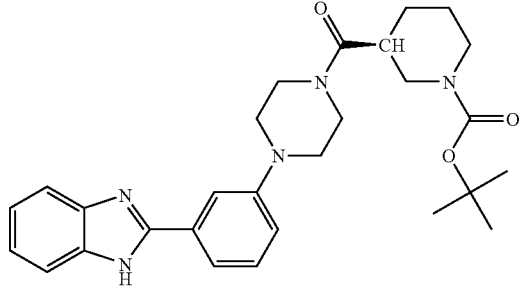 [SMILES: CC(C)(C)OC(=O)N1CCC[C@H](C(=O)N2CCN(c3cccc(-c4nc5ccccc5[nH]4)c3)CC2)C1] | B | 490 | 2.60 |
| 84 | 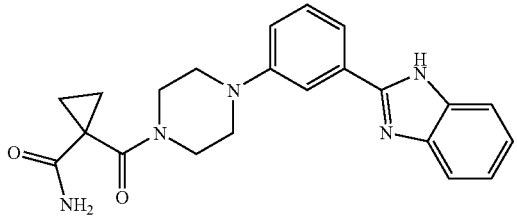 [SMILES: NC(=O)C1(C(=O)N2CCN(c3cccc(-c4nc5ccccc5[nH]4)c3)CC2)CC1] | B | 390 | 1.55 |
| 85 | 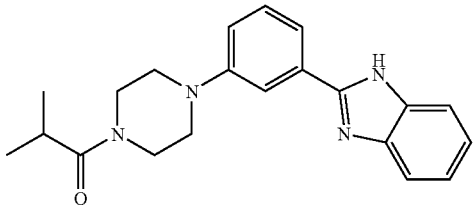 [SMILES: CC(C)C(=O)N1CCN(c2cccc(-c3nc4ccccc4[nH]3)c2)CC1] | B | 349 | 1.82 |
| 86 | 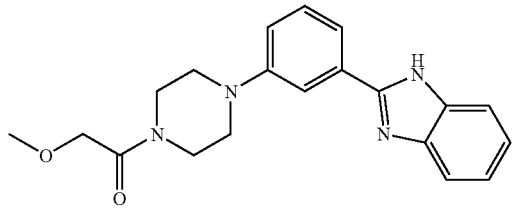 [SMILES: COCC(=O)N1CCN(c2cccc(-c3nc4ccccc4[nH]3)c2)CC1] | B | 351 | 1.62 |
| 87 | 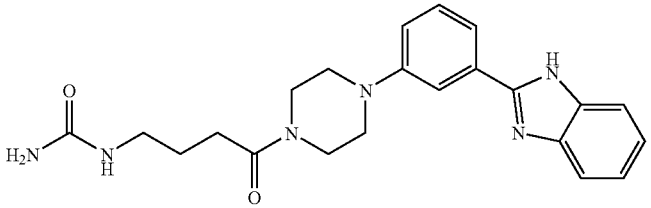 [SMILES: NC(=O)NCCCC(=O)N1CCN(c2cccc(-c3nc4ccccc4[nH]3)c2)CC1] | B | 407 | 1.45 split peak |
| 88 | 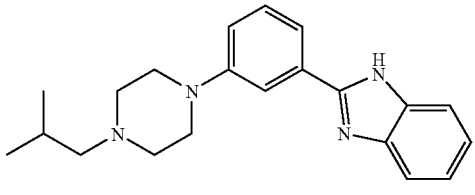 [SMILES: CC(C)CN1CCN(c2cccc(-c3nc4ccccc4[nH]3)c2)CC1] | B | 335 | 1.00 split peak |

-continued

| Example | Structure | Method | M + H | Retention Time |
|---|---|---|---|---|
| 89 | 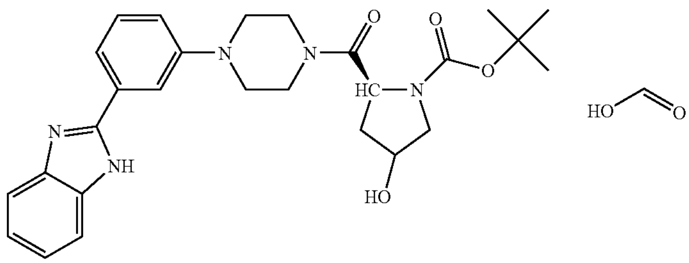 [SMILES: CC(C)(C)OC(=O)N1CC(O)C[C@H]1C(=O)N1CCN(c2cccc(-c3nc4ccccc4[nH]3)c2)CC1 ; O=CO] | B | 492 | 1.95 |
| 90 | 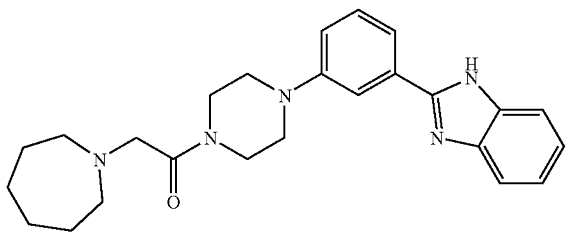 [SMILES: O=C(CN1CCCCCC1)N1CCN(c2cccc(-c3nc4ccccc4[nH]3)c2)CC1] | B | 418 | 1.28 split peak |
| 91 | 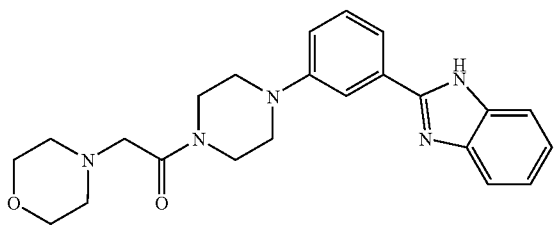 [SMILES: O=C(CN1CCOCC1)N1CCN(c2cccc(-c3nc4ccccc4[nH]3)c2)CC1] | B | 406 | 0.83 split peak |
| 92 | 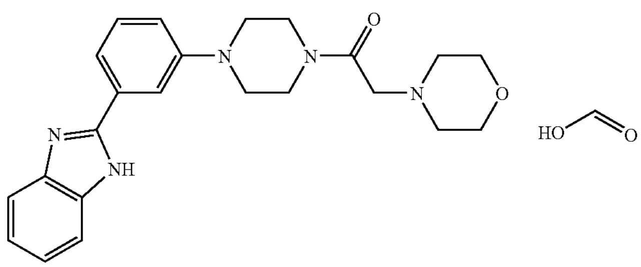 [SMILES: O=C(CN1CCOCC1)N1CCN(c2cccc(-c3nc4ccccc4[nH]3)c2)CC1 ; O=CO] | B | 406 | 0.88 split peak |
| 93 | 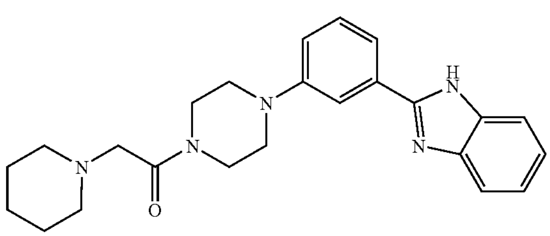 [SMILES: O=C(CN1CCCCC1)N1CCN(c2cccc(-c3nc4ccccc4[nH]3)c2)CC1] | B | 404 | 1.10 split peak |
| 94 | 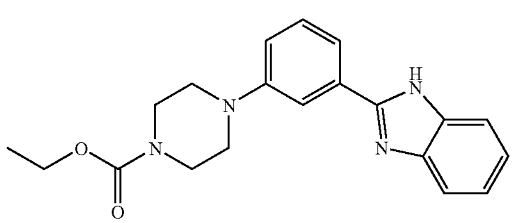 [SMILES: CCOC(=O)N1CCN(c2cccc(-c3nc4ccccc4[nH]3)c2)CC1] | B | 351 | 2.04 |

-continued
| Example | Structure | Method | M + H | Retention Time |
|---|---|---|---|---|
| 95 | 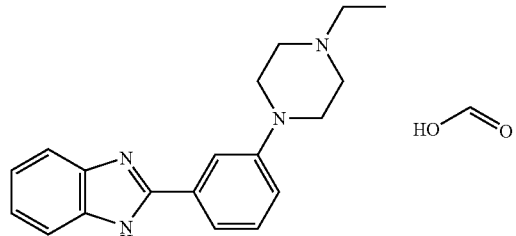 | B | 307 | 0.54 split peak |
| 96 | 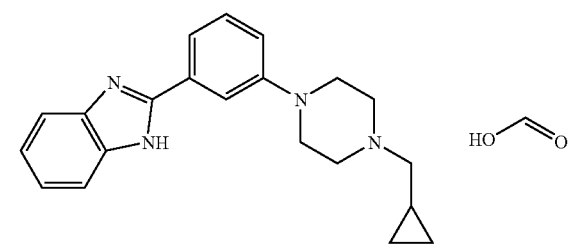 [SMILES: c1cc(-c2nc3ccccc3[nH]2)cc(N2CCN(CC3CC3)CC2)c1 ; O=CO] | B | 333 | 0.89 split peak |
| 97 | 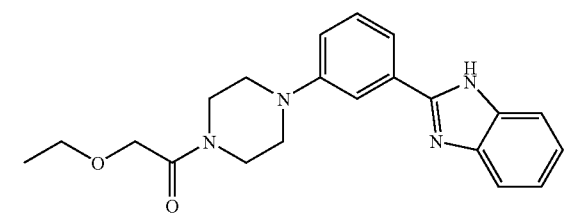 [SMILES: CCOCC(=O)N1CCN(c2cccc(-c3nc4ccccc4[nH]3)c2)CC1] | C | 379 | 1.71 |
| 98 | 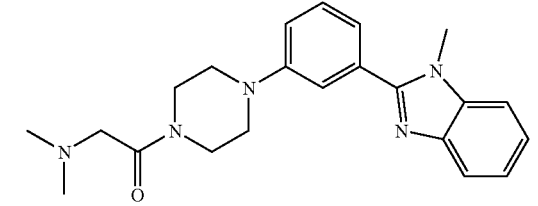 [SMILES: CN(C)CC(=O)N1CCN(c2cccc(-c3nc4ccccc4n3C)c2)CC1] | C | 378 | 0.64 split peak |
| 99 | 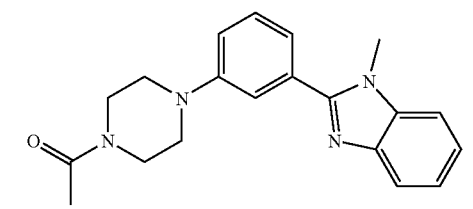 [SMILES: CC(=O)N1CCN(c2cccc(-c3nc4ccccc4n3C)c2)CC1] | C | 335 | 1.47 |
| 100 | 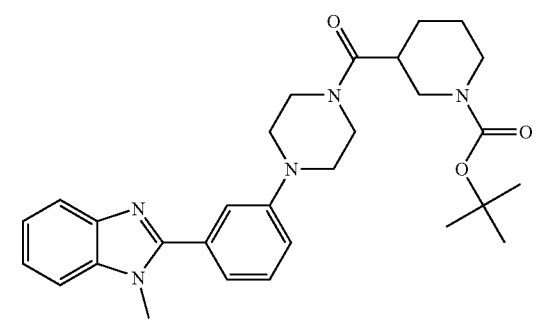 [SMILES: Cn1c(-c2cccc(N3CCN(C(=O)C4CCCN(C(=O)OC(C)(C)C)C4)CC3)c2)nc2ccccc21] | C | 504 | 2.55 |

-continued

| Example | Structure | Method | M + H | Retention Time |
|---|---|---|---|---|
| 101 | 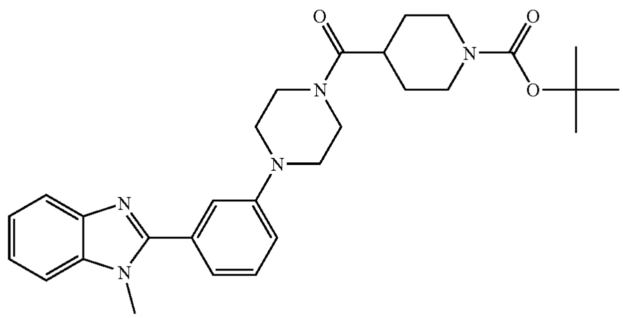 [SMILES: Cn1c(-c2cccc(N3CCN(C(=O)C4CCN(C(=O)OC(C)(C)C)CC4)CC3)c2)nc2ccccc21] | C | 504 | 2.50 |
| 102 | 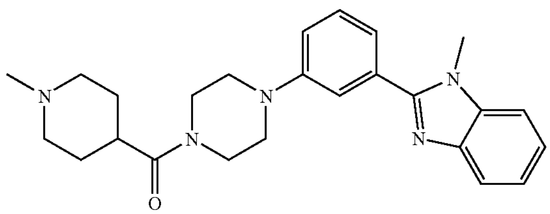 | C | 418 | 0.95 split peak |
| 103 | 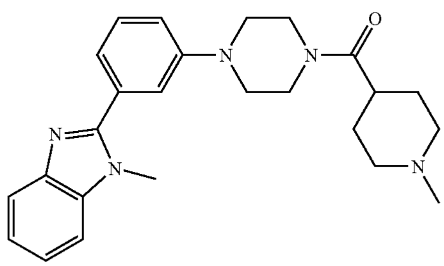 | C | 418 | 0.70 split peak |
| 104 | 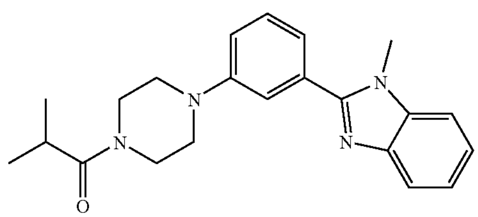 | C | 363 | 1.83 |
| 105 | 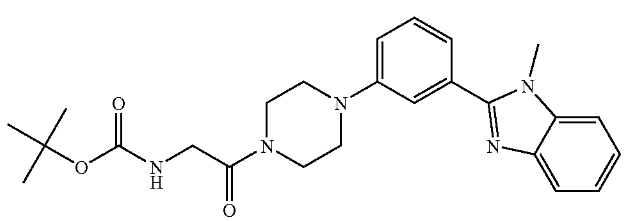 [SMILES: Cn1c(-c2cccc(N3CCN(C(=O)CNC(=O)OC(C)(C)C)CC3)c2)nc2ccccc21] | C | 450 | 2.10 |
| 106 | 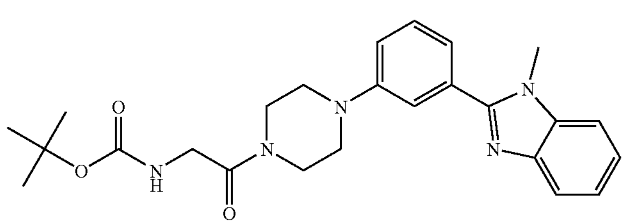 [SMILES: Cn1c(-c2cccc(N3CCN(C(=O)CNC(=O)OC(C)(C)C)CC3)c2)nc2ccccc21] | C | 450 | 2.10 |

-continued
| Example | Structure | Method | M + H | Retention Time |
|---|---|---|---|---|
| 107 | 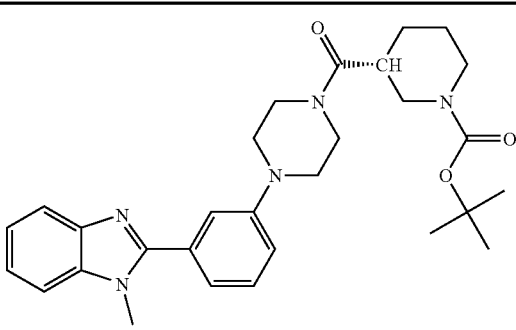 | C | 504 | 2.57 |
| 108 | 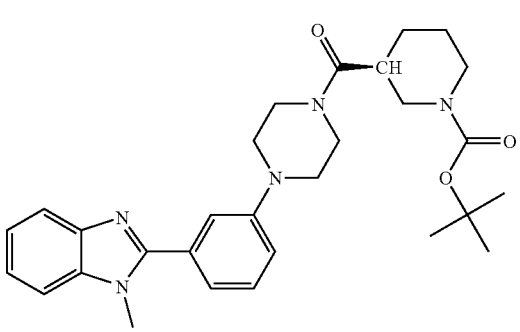 [SMILES: Cn1c(-c2cccc(N3CCN(C(=O)[C@H]4CCCN(C(=O)OC(C)(C)C)C4)CC3)c2)nc2ccccc21] | C | 504 | 2.57 |
| 109 | 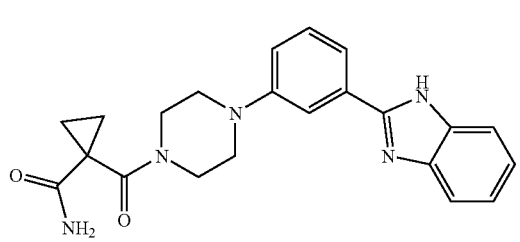 [SMILES: NC(=O)C1(C(=O)N2CCN(c3cccc(-c4nc5ccccc5[nH]4)c3)CC2)CC1] | C | 404 | 1.50 |
| 110 | 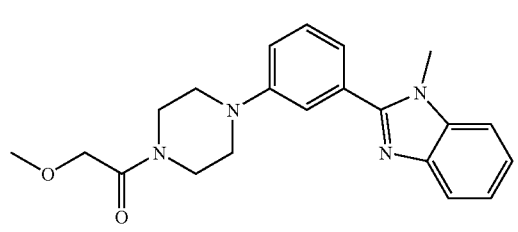 [SMILES: COCC(=O)N1CCN(c2cccc(-c3nc4ccccc4n3C)c2)CC1] | C | 365 | 1.50 |
| 111 | 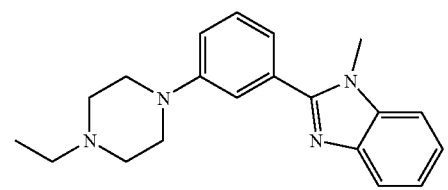 [SMILES: CCN1CCN(c2cccc(-c3nc4ccccc4n3C)c2)CC1] | C | 321 | solvent front |
| 112 | 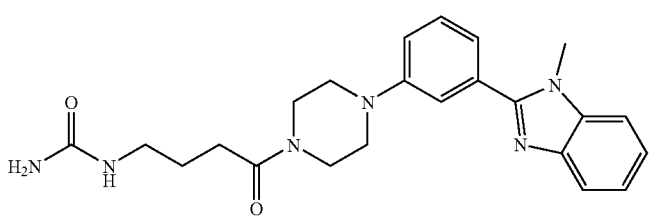 | C | 421 | 1.39 split peak |

-continued

| Example | Structure | Method | M + H | Retention Time |
|---|---|---|---|---|
| 113 | 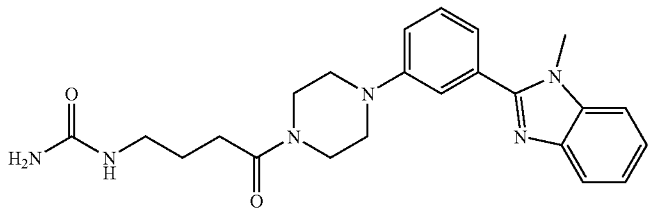 [SMILES: Cn1c(-c2cccc(N3CCN(C(=O)CCCNC(N)=O)CC3)c2)nc2ccccc21] | C | 421 | 1.39 split peak |
| 114 | 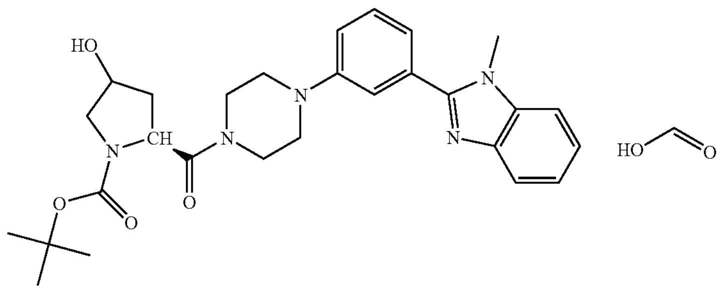 | C | 506 | 2.17 |
| 115 | 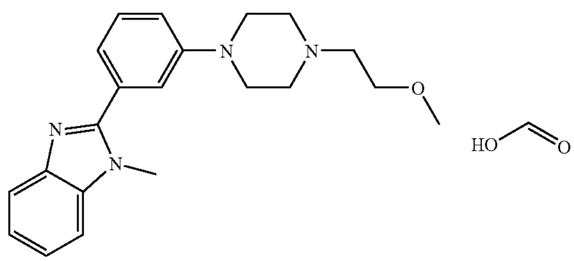 | C | 351 | 0.44 split peak |
| 116 | 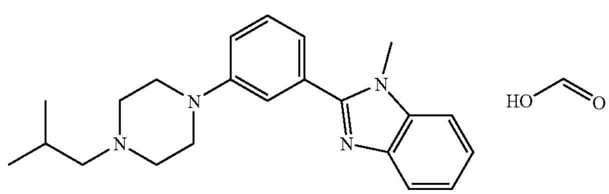 [SMILES: CC(C)CN1CCN(c2cccc(-c3nc4ccccc4n3C)c2)CC1 ; O=CO] | C | 349 | 0.84 split peak |
| 117 | 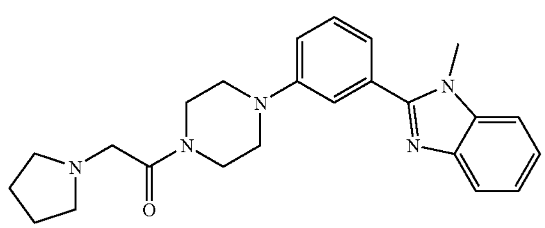 [SMILES: Cn1c(-c2cccc(N3CCN(C(=O)CN4CCCC4)CC3)c2)nc2ccccc21] | C | 404 | 0.93 split peak |
| 118 | 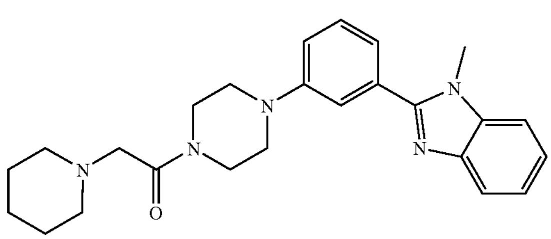 [SMILES: Cn1c(-c2cccc(N3CCN(C(=O)CN4CCCCC4)CC3)c2)nc2ccccc21] | C | 418 | 1.02 split peak |

-continued

| Example | Structure | Method | M + H | Retention Time |
|---|---|---|---|---|
| 119 | 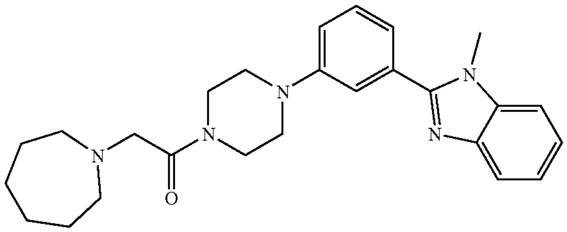 [SMILES: Cn1c(-c2cccc(N3CCN(C(=O)CN4CCCCCC4)CC3)c2)nc2ccccc21] | C | 432 | 1.17 split peak |
| 120 | 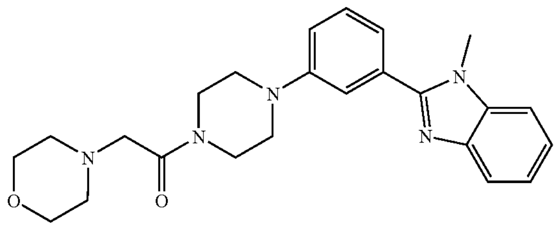 [SMILES: Cn1c(-c2cccc(N3CCN(C(=O)CN4CCOCC4)CC3)c2)nc2ccccc21] | C | 420 | 0.58 split peak |
| 121 | 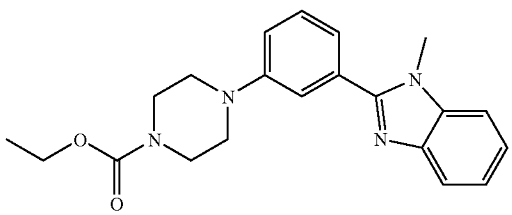 [SMILES: CCOC(=O)N1CCN(c2cccc(-c3nc4ccccc4n3C)c2)CC1] | C | 365 | 1.99 |
| 122 | 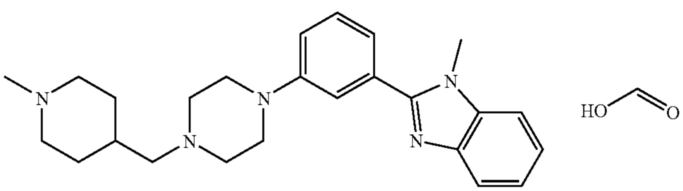 [SMILES: CN1CCC(CN2CCN(c3cccc(-c4nc5ccccc5n4C)c3)CC2)CC1 ; O=CO] | C | 404 | solvent front |
| 123 | 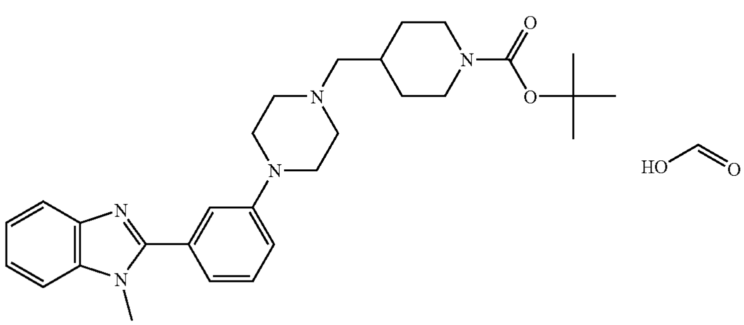 [SMILES: Cn1c(-c2cccc(N3CCN(CC4CCN(C(=O)OC(C)(C)C)CC4)CC3)c2)nc2ccccc21 ; O=CO] | C | 490 | 1.49 |
| 124 | 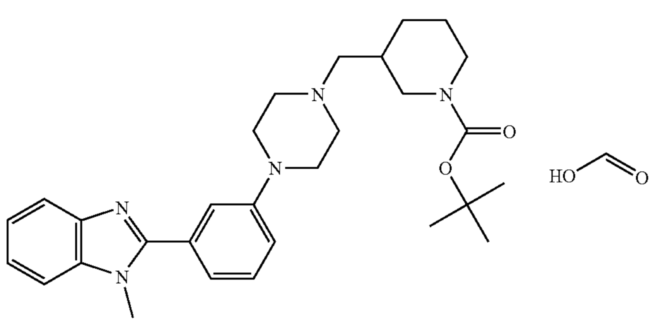 [SMILES: Cn1c(-c2cccc(N3CCN(CC4CCCN(C(=O)OC(C)(C)C)C4)CC3)c2)nc2ccccc21 ; O=CO] | C | 490 | 1.59 |

-continued

| Example | Structure | Method | M + H | Retention Time |
|---|---|---|---|---|
| 125 | 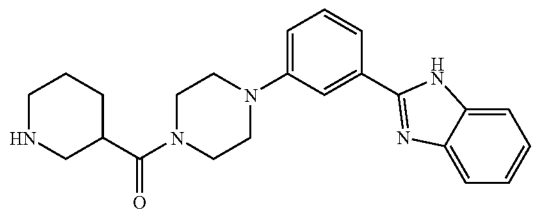 | D | 390 | 1.12 split peak |
| 126 | HCl | C | 390 | 1.07 split peak |
| 127 | HCl | D | 390 | 1.10 split peak |
| 128 | HCl | D | 390 | 1.12 split peak |
| 129 | 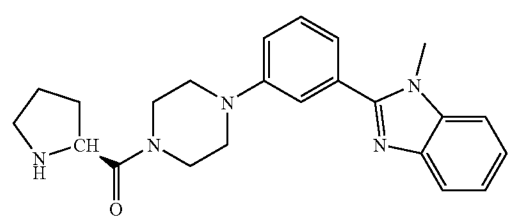 [SMILES: Cn1c(-c2cccc(N3CCN(C(=O)[C@@H]4CCCN4)CC3)c2)nc2ccccc21] | D | 390 | 0.80 split peak |
| 130 | 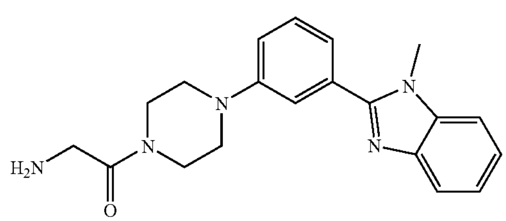 [SMILES: Cn1c(-c2cccc(N3CCN(C(=O)CN)CC3)c2)nc2ccccc21] | D | 350 | 0.37 split peak |

-continued

| Example | Structure | Method | M + H | Retention Time |
|---|---|---|---|---|
| 131 | 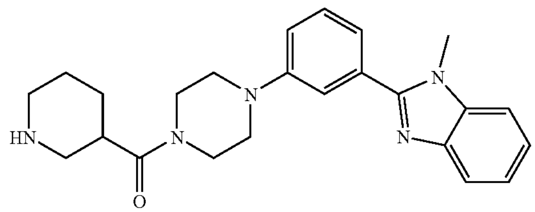 [SMILES: Cn1c(-c2cccc(N3CCN(C(=O)C4CCCNC4)CC3)c2)nc2ccccc21] | D | 404 | 0.87 split peak |
| 132 | 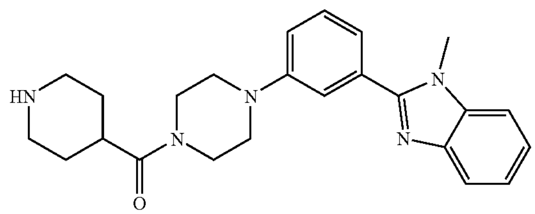 [SMILES: Cn1c(-c2cccc(N3CCN(C(=O)C4CCNCC4)CC3)c2)nc2ccccc21] | D | 404 | 0.79 split peak |
| 133 | 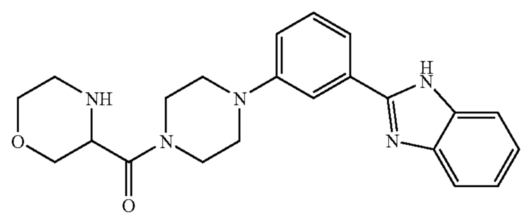 [SMILES: O=C(C1COCCN1)N1CCN(c2cccc(-c3nc4ccccc4[nH]3)c2)CC1] | D | 392 | 0.87 split peak |
| 134 | 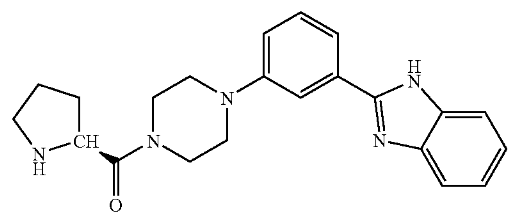 [SMILES: O=C([C@@H]1CCCN1)N1CCN(c2cccc(-c3nc4ccccc4[nH]3)c2)CC1] | D | 376 | 1.00 |
| 135 | 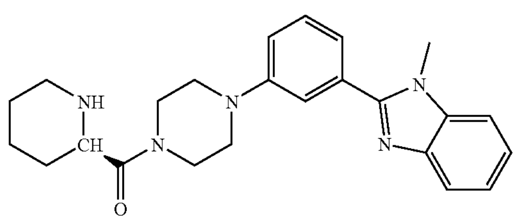 | D | 404 | 1.00 split peak |
| 136 | 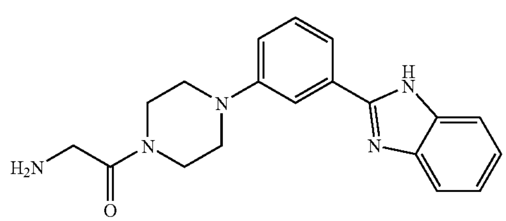 | D | 336 | 0.64 split peak |
| 137 | 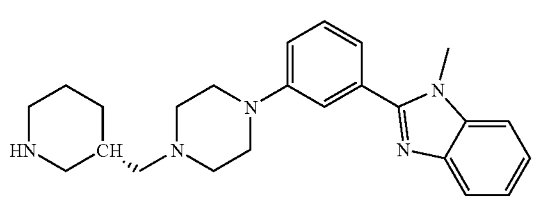 [SMILES: Cn1c(-c2cccc(N3CCN(C[C@H]4CCCNC4)CC3)c2)nc2ccccc21] | E | 390 | solvent front |

-continued

| Example | Structure | Method | M + H | Retention Time |
|---|---|---|---|---|
| 138 | 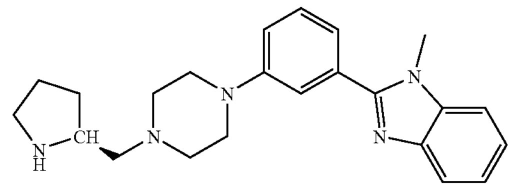 [SMILES: Cn1c(-c2cccc(N3CCN(C[C@@H]4CCCN4)CC3)c2)nc2ccccc21] | E | 376 | 0.49 split peak |
| 139 | 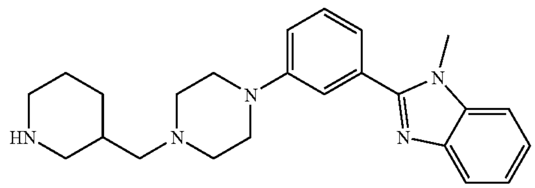 [SMILES: Cn1c(-c2cccc(N3CCN(CC4CCCNC4)CC3)c2)nc2ccccc21] | E | 390 | solvent front |
| 140 | 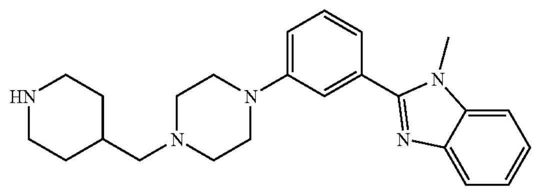 [SMILES: Cn1c(-c2cccc(N3CCN(CC4CCNCC4)CC3)c2)nc2ccccc21] | E | 390 | solvent front |
| 141 | 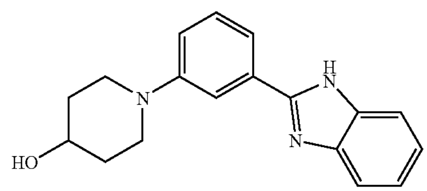 [SMILES: OC1CCN(c2cccc(-c3nc4ccccc4[nH]3)c2)CC1] | G | 294 | 1.29 split peak |
| 142 | 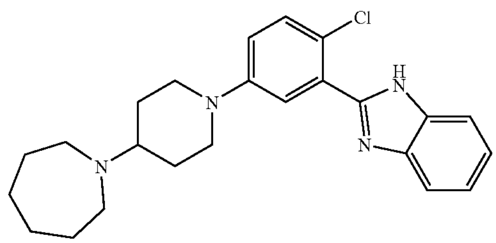 [SMILES: Clc1ccc(N2CCC(N3CCCCCC3)CC2)cc1-c1nc2ccccc2[nH]1] | H | 409 | 1.29 split peak |
| 143 | 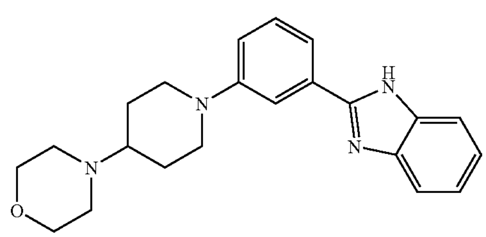 [SMILES: c1cc(-c2nc3ccccc3[nH]2)cc(N2CCC(N3CCOCC3)CC2)c1] | H | 363 | 0.72 split peak |
| 144 | 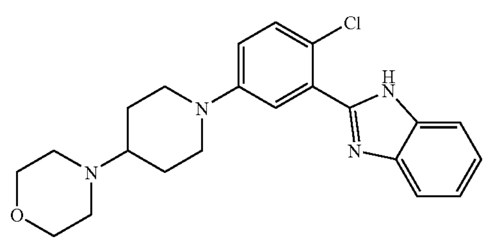 [SMILES: Clc1ccc(N2CCC(N3CCOCC3)CC2)cc1-c1nc2ccccc2[nH]1] | H | 397 | 0.94 split peak |

-continued

| Example | Structure | Method | M + H | Retention Time |
|---|---|---|---|---|
| 145 | 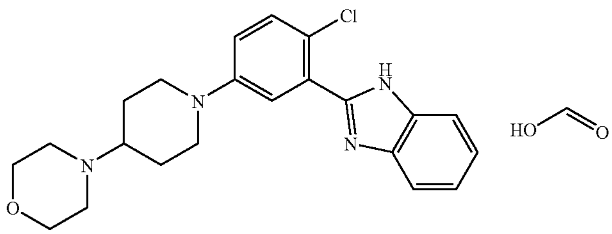 | H | 397 | 0.92 split peak |
| 146 | 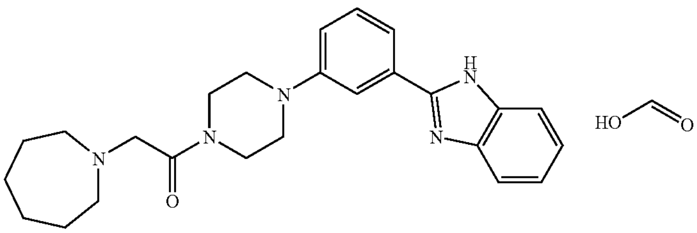 | B | 418 | 1.30 |
| 147 | 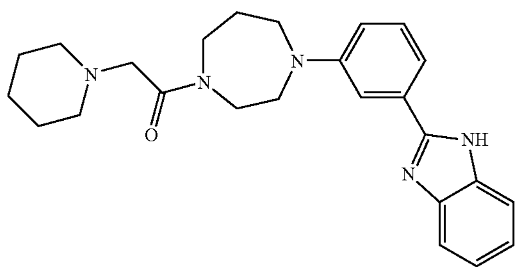 [SMILES: O=C(CN1CCCCC1)N1CCCN(c2cccc(-c3nc4ccccc4[nH]3)c2)CC1] | B | 418 | 4.49 |
| 148 | 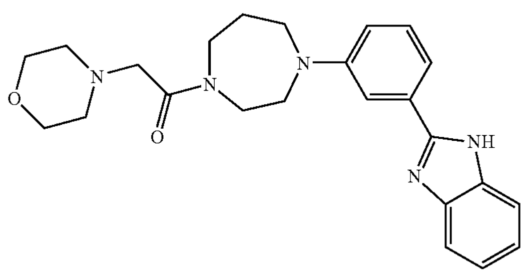 [SMILES: O=C(CN1CCOCC1)N1CCCN(c2cccc(-c3nc4ccccc4[nH]3)c2)CC1] | B | 420 | 4.2 |
| 149 | 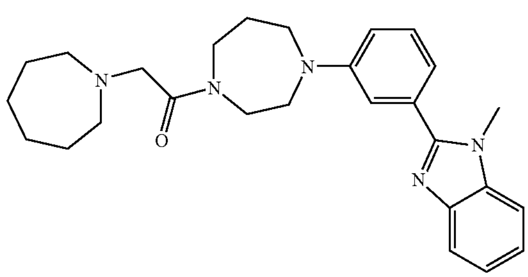 [SMILES: Cn1c(-c2cccc(N3CCCN(C(=O)CN4CCCCCC4)CC3)c2)nc2ccccc21] | Ab | 446 | 4.94 |
| 150 | 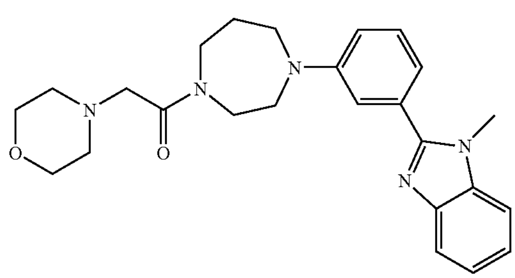 [SMILES: Cn1c(-c2cccc(N3CCCN(C(=O)CN4CCOCC4)CC3)c2)nc2ccccc21] | Ab | 434 | 4.34 |

-continued

| Example | Structure | Method | M + H | Retention Time |
|---|---|---|---|---|
| 151 | 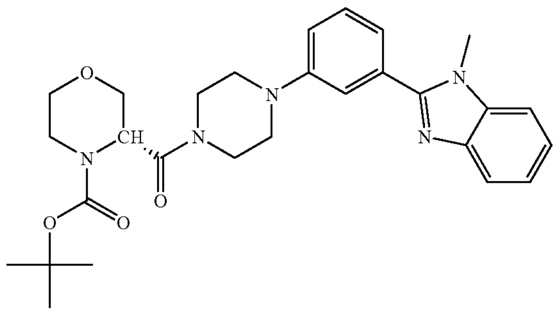 [SMILES: Cn1c(-c2cccc(N3CCN(C(=O)[C@H]4COCCN4C(=O)OC(C)(C)C)CC3)c2)nc2ccccc21] | D | 506 | 2.18 |
| 152 | 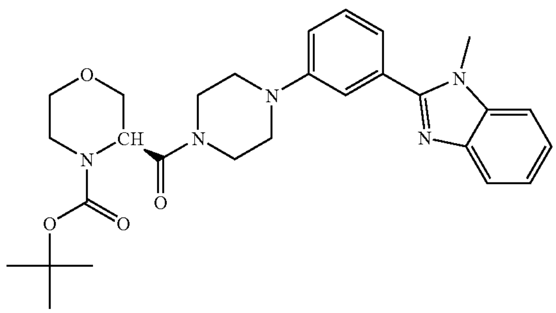 [SMILES: Cn1c(-c2cccc(N3CCN(C(=O)[C@@H]4COCCN4C(=O)OC(C)(C)C)CC3)c2)nc2ccccc21] | D | 506 | 2.17 |
| 153 | 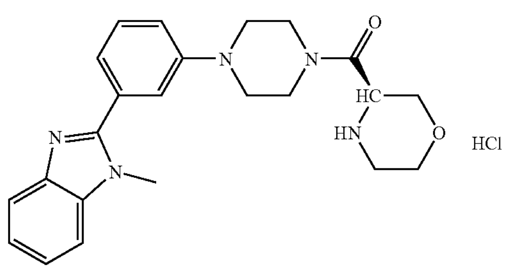 [SMILES: Cn1c(-c2cccc(N3CCN(C(=O)[C@H]4COCCN4)CC3)c2)nc2ccccc21 ; Cl] | D | 406 | 4.04 |
| 154 | 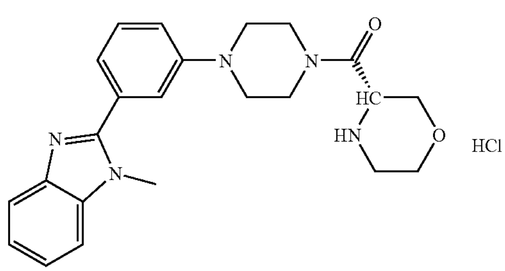 [SMILES: Cn1c(-c2cccc(N3CCN(C(=O)[C@@H]4COCCN4)CC3)c2)nc2ccccc21 ; Cl] | D | 406 | 4.04 |
| 155 | 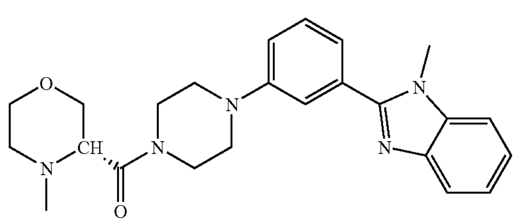 [SMILES: CN1CCOC[C@@H]1C(=O)N1CCN(c2cccc(-c3nc4ccccc4n3C)c2)CC1] | D | 420 | 4.14 |

-continued

| Example | Structure | Method | M + H | Retention Time |
|---|---|---|---|---|
| 156 | 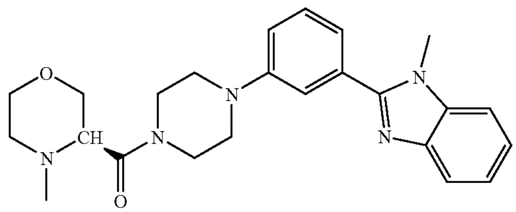 [SMILES: CN1CCOC[C@H]1C(=O)N1CCN(c2cccc(-c3nc4ccccc4n3C)c2)CC1] | D | 420 | 4.19 |
| 157 | 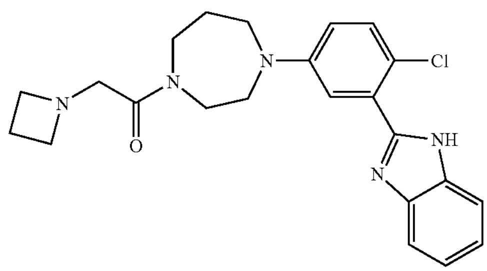 [SMILES: O=C(CN1CCC1)N1CCCN(c2ccc(Cl)c(-c3nc4ccccc4[nH]3)c2)CC1] | T | 424 | 4.2 |
| 158 | 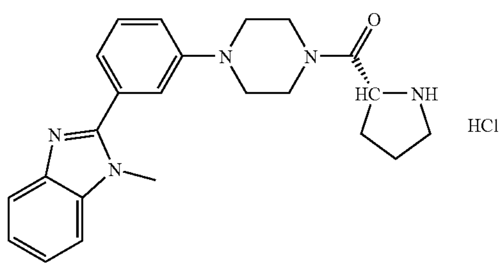 [SMILES: Cn1c(-c2cccc(N3CCN(C(=O)[C@H]4CCCN4)CC3)c2)nc2ccccc21 ; Cl] | D | 390 | 4.13 |
| 159 | 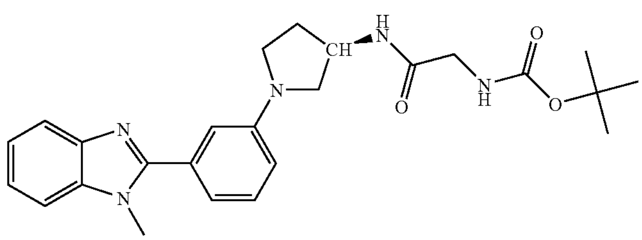 [SMILES: Cn1c(-c2cccc(N3CC[C@@H](NC(=O)CNC(=O)OC(C)(C)C)C3)c2)nc2ccccc21] | N | 450 | 2 |
| 160 | 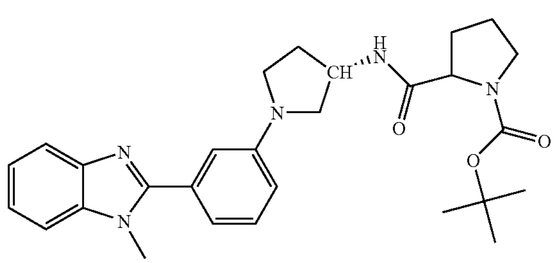 [SMILES: Cn1c(-c2cccc(N3CC[C@H](NC(=O)C4CCCN4C(=O)OC(C)(C)C)C3)c2)nc2ccccc21] | N | 490 | 2.18 |
| 161 | 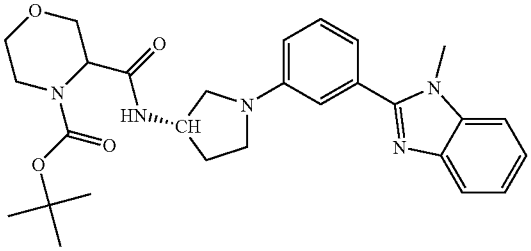 [SMILES: Cn1c(-c2cccc(N3CC[C@H](NC(=O)C4COCCN4C(=O)OC(C)(C)C)C3)c2)nc2ccccc21] | N | 506 | 2.2 |

-continued

| Example | Structure | Method | M + H | Retention Time |
|---|---|---|---|---|
| 162 | 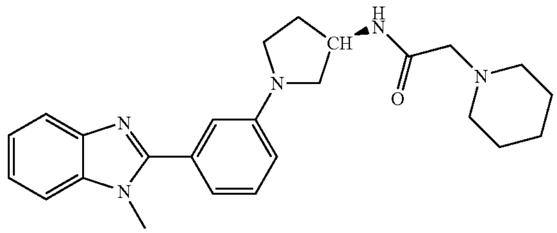 [SMILES: Cn1c(-c2cccc(N3CC[C@@H](NC(=O)CN4CCCCC4)C3)c2)nc2ccccc21] | N | 418 | 1.08 |
| 163 | 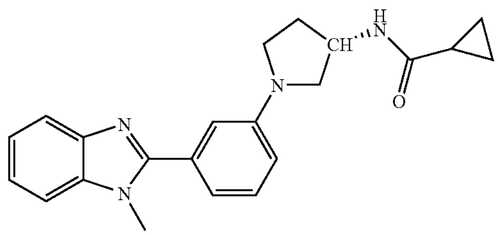 [SMILES: Cn1c(-c2cccc(N3CC[C@H](NC(=O)C4CC4)C3)c2)nc2ccccc21] | N | 361 | 1.72 |
| 164 | 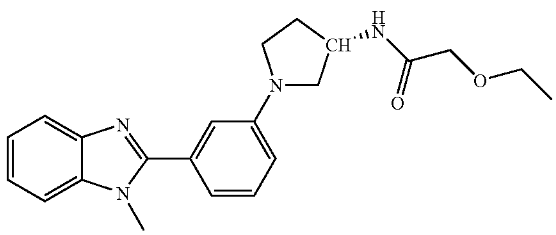 [SMILES: CCOCC(=O)N[C@H]1CCN(c2cccc(-c3nc4ccccc4n3C)c2)C1] | N | 379 | 1.77 |
| 165 | 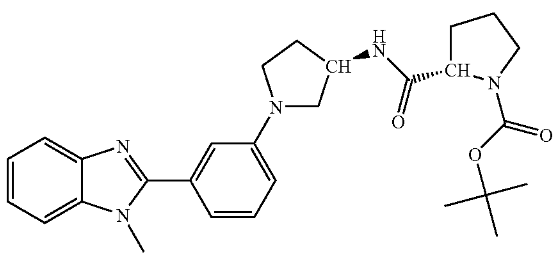 [SMILES: Cn1c(-c2cccc(N3CC[C@@H](NC(=O)[C@@H]4CCCN4C(=O)OC(C)(C)C)C3)c2)nc2ccccc21] | N | 490 | 2.18 |
| 166 | 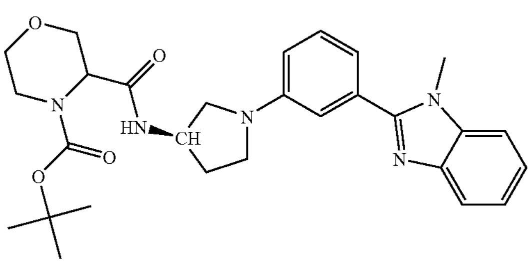 [SMILES: Cn1c(-c2cccc(N3CC[C@@H](NC(=O)C4COCCN4C(=O)OC(C)(C)C)C3)c2)nc2ccccc21] | N | 506 | 2.2 |
| 167 | 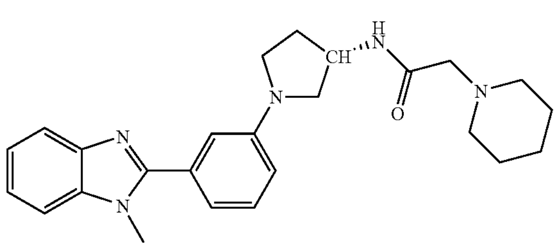 [SMILES: Cn1c(-c2cccc(N3CC[C@H](NC(=O)CN4CCCCC4)C3)c2)nc2ccccc21] | N | 418 | 1.12 |

-continued

| Example | Structure | Method | M + H | Retention Time |
|---|---|---|---|---|
| 168 | 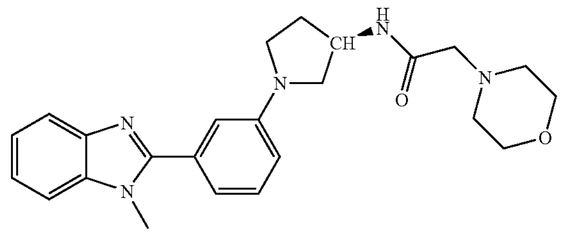 [SMILES: Cn1c(-c2cccc(N3CC[C@@H](NC(=O)CN4CCOCC4)C3)c2)nc2ccccc21] | N | 418 | 0.98 |
| 169 | 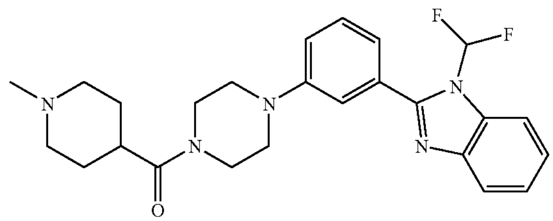 [SMILES: CN1CCC(C(=O)N2CCN(c3cccc(-c4nc5ccccc5n4C(F)F)c3)CC2)CC1] | K | 454 | 2.02 |
| 170 | 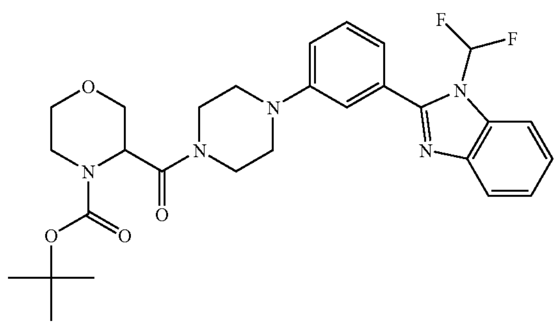 [SMILES: CC(C)(C)OC(=O)N1CCOCC1C(=O)N1CCN(c2cccc(-c3nc4ccccc4n3C(F)F)c2)CC1] | K | 542 | 3.98 |
| 171 | 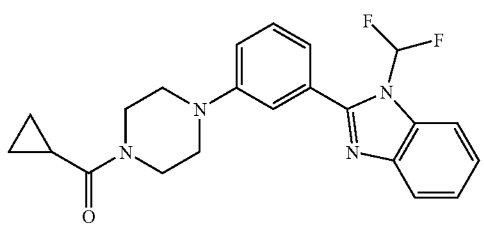 [SMILES: O=C(C1CC1)N1CCN(c2cccc(-c3nc4ccccc4n3C(F)F)c2)CC1] | K | 397 | 3.57 |
| 172 | 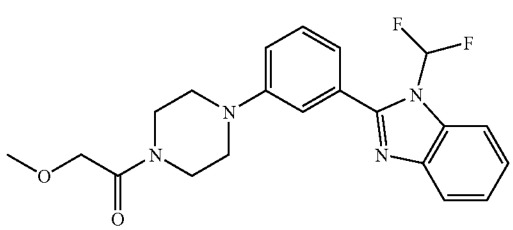 [SMILES: COCC(=O)N1CCN(c2cccc(-c3nc4ccccc4n3C(F)F)c2)CC1] | K | 401 | 3.18 |
| 173 | 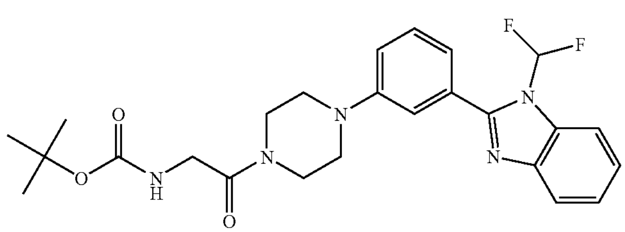 [SMILES: CC(C)(C)OC(=O)NCC(=O)N1CCN(c2cccc(-c3nc4ccccc4n3C(F)F)c2)CC1] | K | 486 | 3.85 |

-continued

| Example | Structure | Method | M + H | Retention Time |
|---|---|---|---|---|
| 174 | 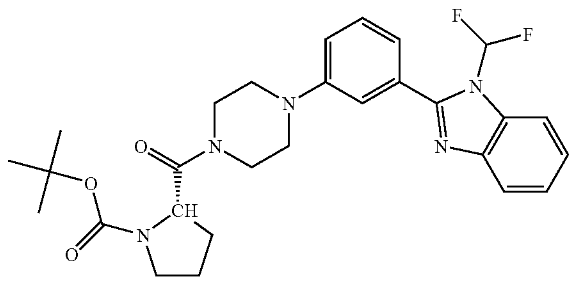 [SMILES: CC(C)(C)OC(=O)N1CCC[C@H]1C(=O)N1CCN(c2cccc(-c3nc4ccccc4n3C(F)F)c2)CC1] | K | 526 | 4 |
| 175 | 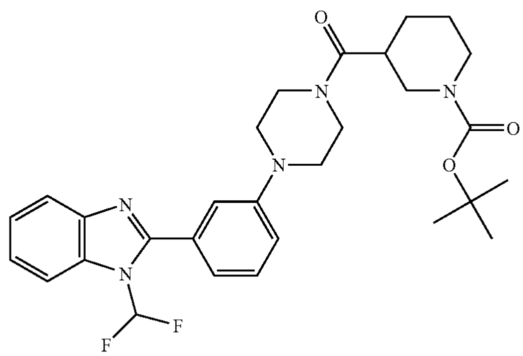 [SMILES: CC(C)(C)OC(=O)N1CCCC(C(=O)N2CCN(c3cccc(-c4nc5ccccc5n4C(F)F)c3)CC2)C1] | K | 540 | 4.32 |
| 176 | 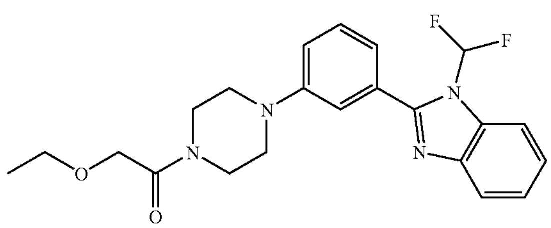 [SMILES: CCOCC(=O)N1CCN(c2cccc(-c3nc4ccccc4n3C(F)F)c2)CC1] | K | 415 | 3.42 |
| 177 | 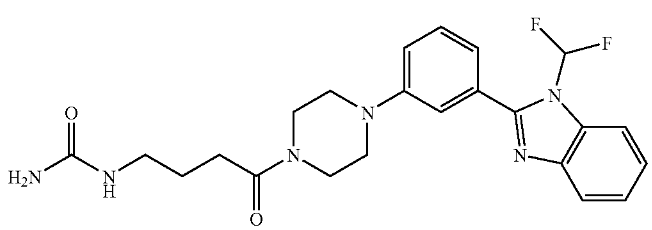 [SMILES: NC(=O)NCCCC(=O)N1CCN(c2cccc(-c3nc4ccccc4n3C(F)F)c2)CC1] | K | 457 | 2.88 |
| 178 | 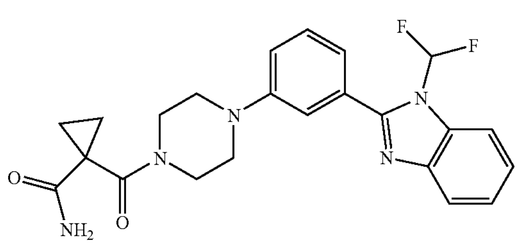 [SMILES: NC(=O)C1(C(=O)N2CCN(c3cccc(-c4nc5ccccc5n4C(F)F)c3)CC2)CC1] | K | 440 | 2.98 |

-continued

| Example | Structure | Method | M + H | Retention Time |
|---|---|---|---|---|
| 179 | 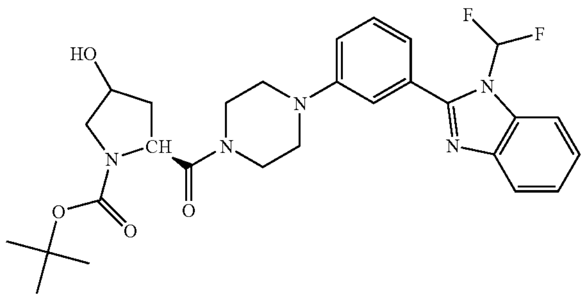 [SMILES: CC(C)(C)OC(=O)N1CC(O)C[C@H]1C(=O)N1CCN(c2cccc(-c3nc4ccccc4n3C(F)F)c2)CC1] | K | 542 | 3.47 |
| 180 | 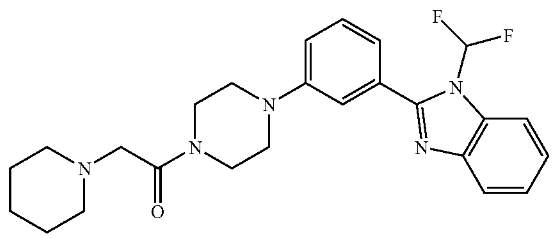 [SMILES: O=C(CN1CCCCC1)N1CCN(c2cccc(-c3nc4ccccc4n3C(F)F)c2)CC1] | K | 454 | 2.08 |
| 181 | 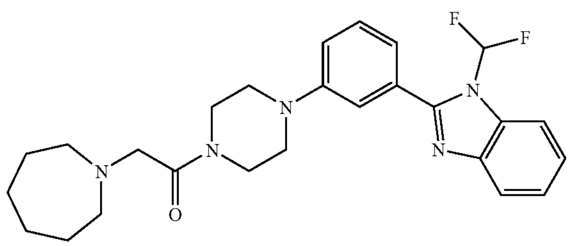 [SMILES: O=C(CN1CCCCCC1)N1CCN(c2cccc(-c3nc4ccccc4n3C(F)F)c2)CC1] | K | 468 | 2.12 |
| 182 | 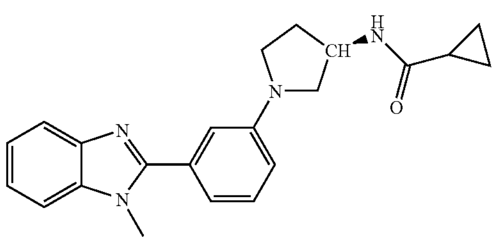 [SMILES: Cn1c(-c2cccc(N3CC[C@@H](NC(=O)C4CC4)C3)c2)nc2ccccc21] | N | 361 | 1.73 |
| 183 | 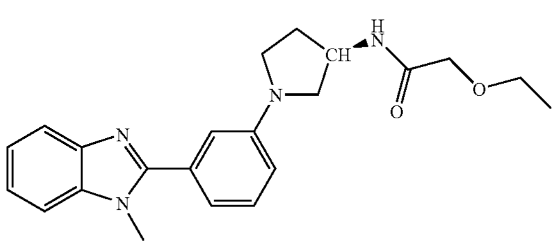 [SMILES: CCOCC(=O)N[C@@H]1CCN(c2cccc(-c3nc4ccccc4n3C)c2)C1] | N | 379 | 1.75 |
| 184 | 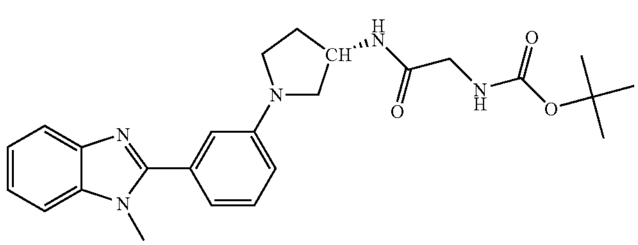 [SMILES: Cn1c(-c2cccc(N3CC[C@H](NC(=O)CNC(=O)OC(C)(C)C)C3)c2)nc2ccccc21] | N | 450 | 2 |

-continued

| Example | Structure | Method | M + H | Retention Time |
|---|---|---|---|---|
| 185 | 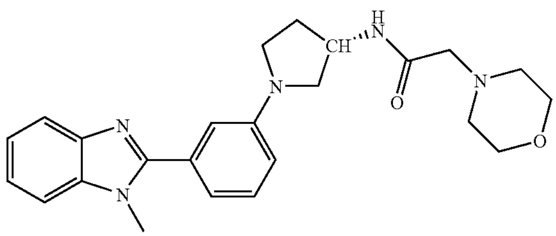 [SMILES: Cn1c(-c2cccc(N3CC[C@H](NC(=O)CN4CCOCC4)C3)c2)nc2ccccc21] | N | 420 | 0.98 |
| 186 | 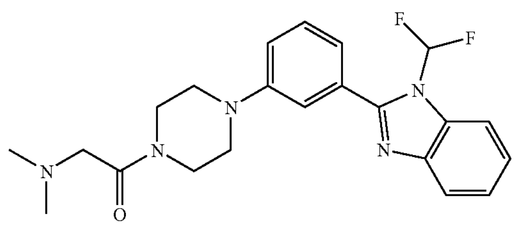 [SMILES: CN(C)CC(=O)N1CCN(c2cccc(-c3nc4ccccc4n3C(F)F)c2)CC1] | K | 414 | 1.97 |
| 187 | 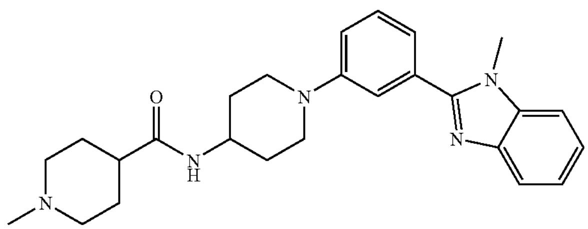 [SMILES: CN1CCC(C(=O)NC2CCN(c3cccc(-c4nc5ccccc5n4C)c3)CC2)CC1] | N | 432 | 4.42 |
| 188 | 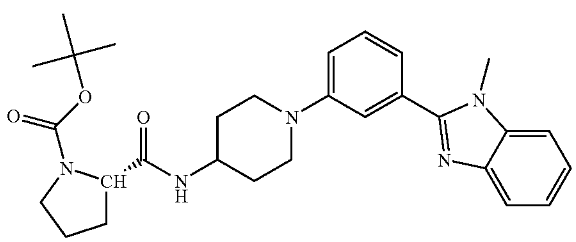 [SMILES: Cn1c(-c2cccc(N3CCC(NC(=O)[C@@H]4CCCN4C(=O)OC(C)(C)C)CC3)c2)nc2ccccc21] | N | 504 | 2.17 |
| 189 | 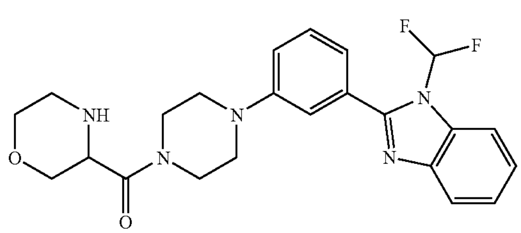 [SMILES: O=C(C1COCCN1)N1CCN(c2cccc(-c3nc4ccccc4n3C(F)F)c2)CC1] | K | 442 | 1.97 |
| 190 | 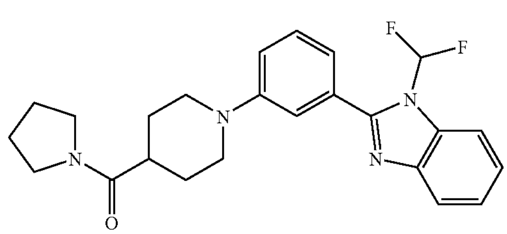 [SMILES: O=C(C1CCN(c2cccc(-c3nc4ccccc4n3C(F)F)c2)CC1)N1CCCC1] | J | 425 | 3.37 |

-continued

| Example | Structure | Method | M + H | Retention Time |
|---|---|---|---|---|
| 191 | 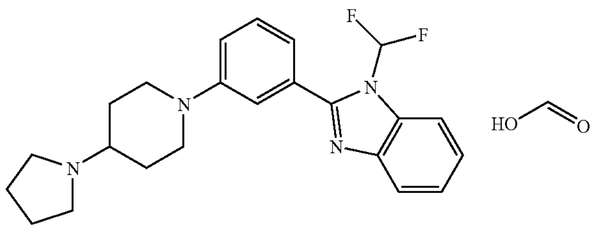 | J | 397 | 1.98 |
| 192 | 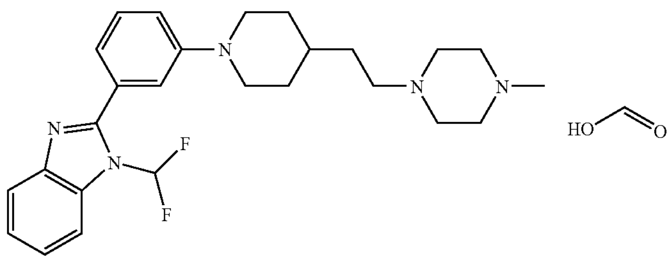 [SMILES: CN1CCN(CCC2CCN(c3cccc(-c4nc5ccccc5n4C(F)F)c3)CC2)CC1 ; O=CO] | J | 454 | 1.57 |
| 193 | 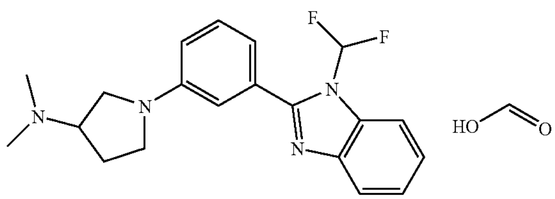 | J | 357 | 1.9 |
| 194 | 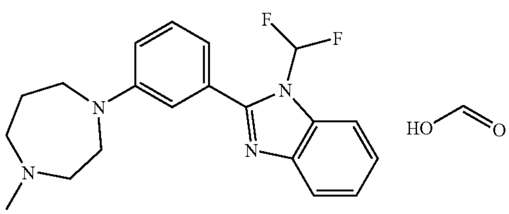 | J | 357 | 1.92 |
| 195 | 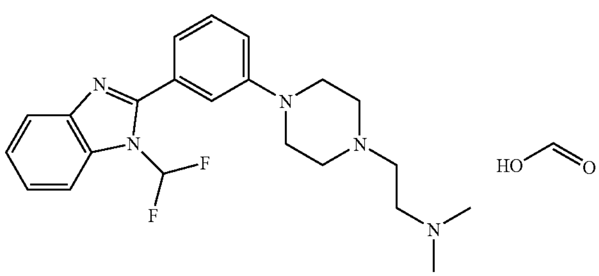 [SMILES: CN(C)CCN1CCN(c2cccc(-c3nc4ccccc4n3C(F)F)c2)CC1 ; O=CO] | J | 400 | 1.55 |
| 196 | 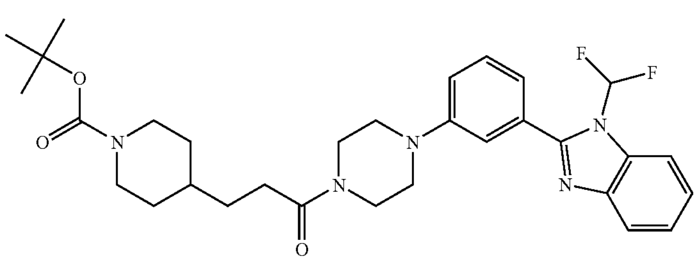 [SMILES: CC(C)(C)OC(=O)N1CCC(CCC(=O)N2CCN(c3cccc(-c4nc5ccccc5n4C(F)F)c3)CC2)CC1] | K | 568 | 4.52 |

-continued

| Example | Structure | Method | M + H | Retention Time |
|---|---|---|---|---|
| 197 | 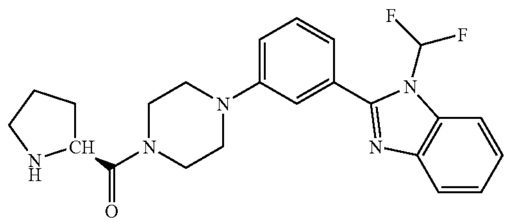 [SMILES: O=C([C@@H]1CCCN1)N1CCN(c2cccc(-c3nc4ccccc4n3C(F)F)c2)CC1] | K | 426 | 2.12 |
| 198 | 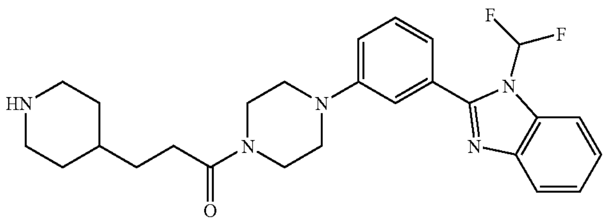 [SMILES: O=C(CCC1CCNCC1)N1CCN(c2cccc(-c3nc4ccccc4n3C(F)F)c2)CC1] | K | 468 | 2.2 |
| 199 | 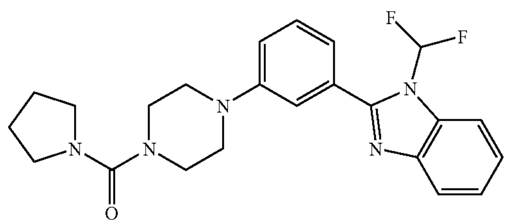 | J | 426 | 3.75 |
| 200 | 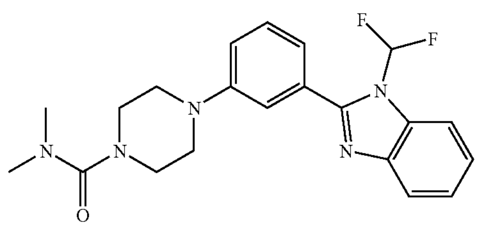 [SMILES: CN(C)C(=O)N1CCN(c2cccc(-c3nc4ccccc4n3C(F)F)c2)CC1] | J | 400 | 3.45 |
| 201 | 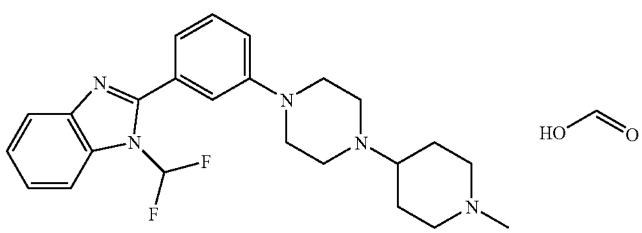 [SMILES: CN1CCC(N2CCN(c3cccc(-c4nc5ccccc5n4C(F)F)c3)CC2)CC1 ; O=CO] | J | 426 | 1.45 |
| 202 | 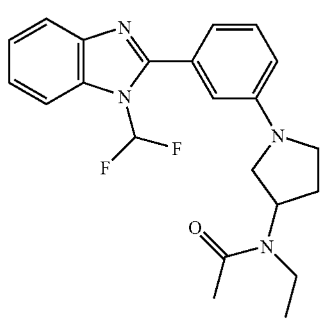 [SMILES: CCN(C(C)=O)C1CCN(c2cccc(-c3nc4ccccc4n3C(F)F)c2)C1] | J | 399 | 3.72 |

-continued

| Example | Structure | Method | M + H | Retention Time |
|---|---|---|---|---|
| 203 | 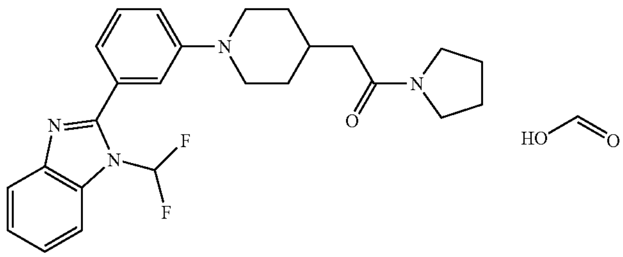 [SMILES: O=C(CC1CCN(c2cccc(-c3nc4ccccc4n3C(F)F)c2)CC1)N1CCCC1 ; O=CO] | J | 440 | 2.08 |
| 204 | 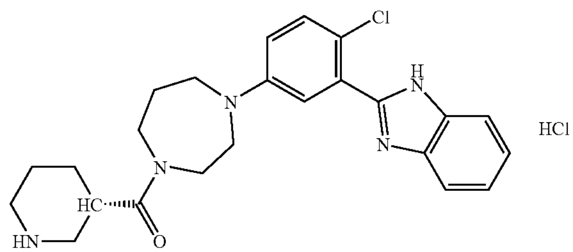 [SMILES: O=C([C@H]1CCCNC1)N1CCCN(c2ccc(Cl)c(-c3nc4ccccc4[nH]3)c2)CC1 ; Cl] | Q | 438 | 1.32 |
| 205 | 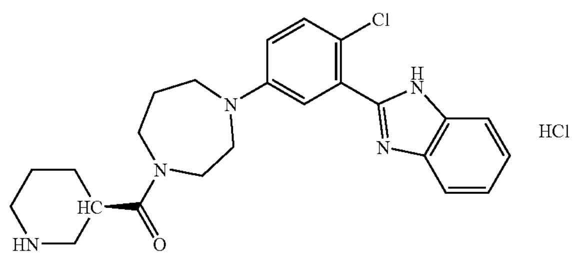 [SMILES: O=C([C@@H]1CCCNC1)N1CCCN(c2ccc(Cl)c(-c3nc4ccccc4[nH]3)c2)CC1 ; Cl] | Q | 438 | 1.27 |
| 206 | 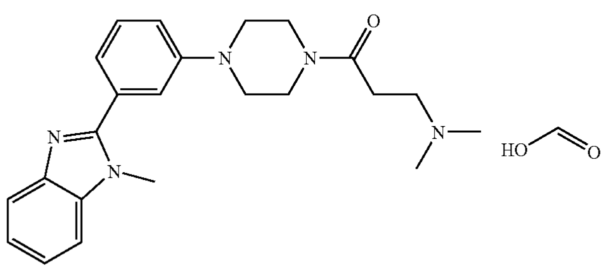 | C | 399 | 0.73 |
| 207 | 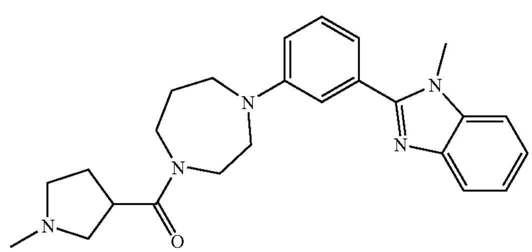 [SMILES: CN1CCC(C(=O)N2CCCN(c3cccc(-c4nc5ccccc5n4C)c3)CC2)C1] | Q | 418 | 4.17 |
| 208 | 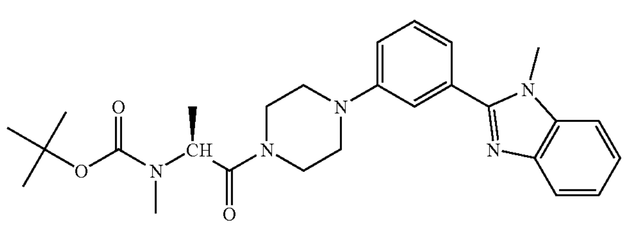 [SMILES: C[C@@H](C(=O)N1CCN(c2cccc(-c3nc4ccccc4n3C)c2)CC1)N(C)C(=O)OC(C)(C)C] | D | 478 | 2.48 |

-continued

| Example | Structure | Method | M + H | Retention Time |
|---|---|---|---|---|
| 209 | 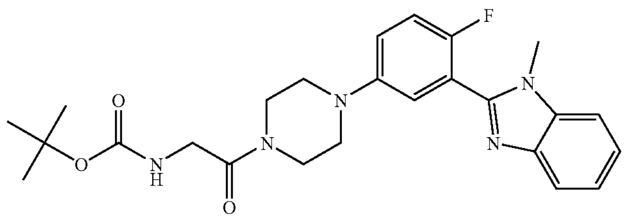 [SMILES: Cn1c(-c2cc(N3CCN(C(=O)CNC(=O)OC(C)(C)C)CC3)ccc2F)nc2ccccc21] | L | 468 | 2.47 |
| 210 | 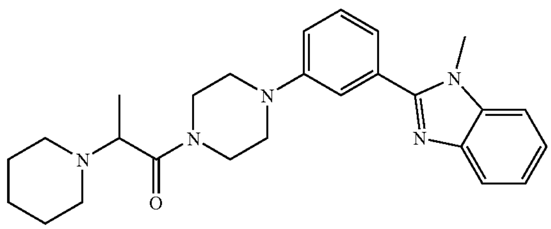 [SMILES: CC(C(=O)N1CCN(c2cccc(-c3nc4ccccc4n3C)c2)CC1)N1CCCCC1] | C | 432 | 1.03 |
| 211 | 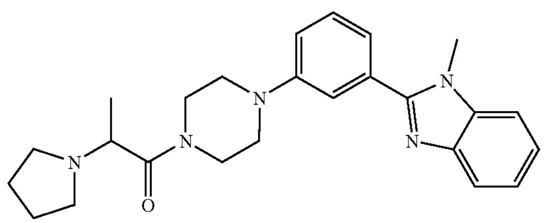 [SMILES: CC(C(=O)N1CCN(c2cccc(-c3nc4ccccc4n3C)c2)CC1)N1CCCC1] | C | 418 | 0.95 |
| 212 | 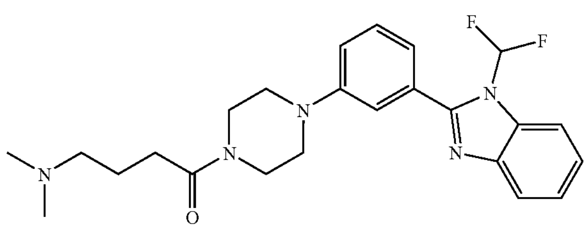 [SMILES: CN(C)CCCC(=O)N1CCN(c2cccc(-c3nc4ccccc4n3C(F)F)c2)CC1] | K | 442 | 2.03 |
| 213 | 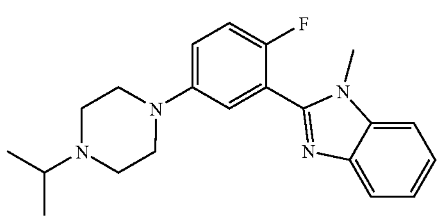 [SMILES: CC(C)N1CCN(c2ccc(F)c(-c3nc4ccccc4n3C)c2)CC1] | L | 353 | 0.87 |
| 214 | 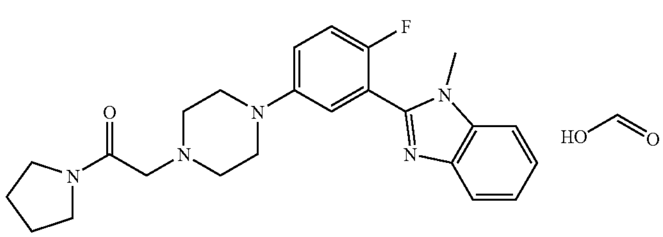 | L | 422 | 1.1 |

-continued

| Example | Structure | Method | M + H | Retention Time |
|---|---|---|---|---|
| 215 | 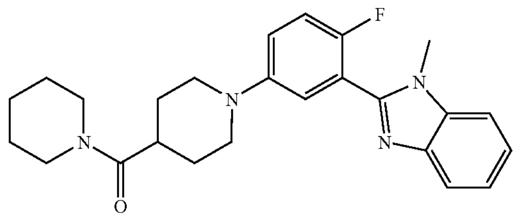 [SMILES: Cn1c(-c2cc(N3CCC(C(=O)N4CCCCC4)CC3)ccc2F)nc2ccccc21] | L | 421 | 2.4 |
| 216 | 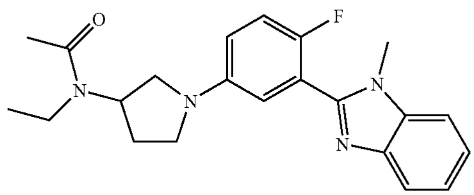 [SMILES: CCN(C(C)=O)C1CCN(c2ccc(F)c(-c3nc4ccccc4n3C)c2)C1] | L | 381 | 2.17 |
| 217 | 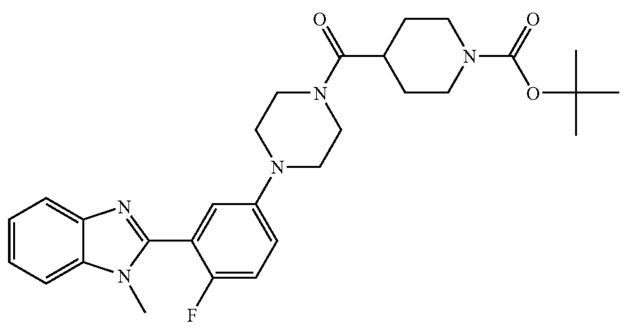 [SMILES: Cn1c(-c2cc(N3CCN(C(=O)C4CCN(C(=O)OC(C)(C)C)CC4)CC3)ccc2F)nc2ccccc21] | L | 522 | 2.9 |
| 218 | 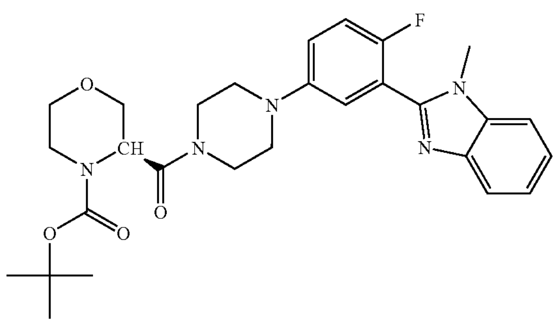 [SMILES: Cn1c(-c2cc(N3CCN(C(=O)[C@@H]4COCCN4C(=O)OC(C)(C)C)CC3)ccc2F)nc2ccccc21] | L | 524 | 2.62 |
| 219 | 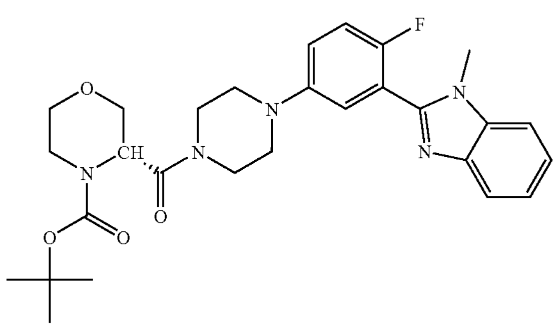 [SMILES: Cn1c(-c2cc(N3CCN(C(=O)[C@H]4COCCN4C(=O)OC(C)(C)C)CC3)ccc2F)nc2ccccc21] | L | 524 | 2.62 |

-continued

| Example | Structure | Method | M + H | Retention Time |
|---|---|---|---|---|
| 220 | 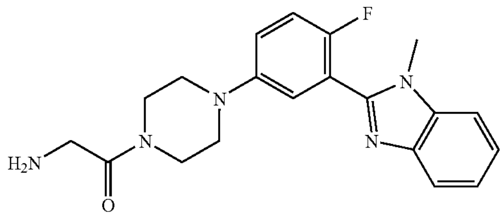 | L | 368 | 0.95 |
| 221 | 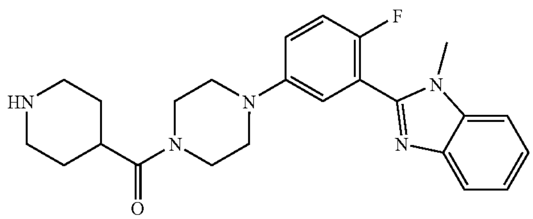 | L | 422 | 1.2 |
| 222 | 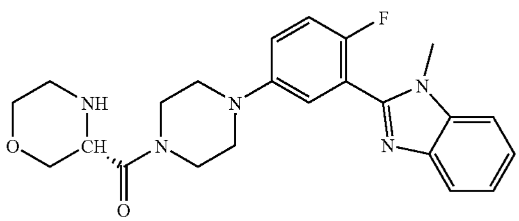 | L | 424 | 1.13 |
| 223 | 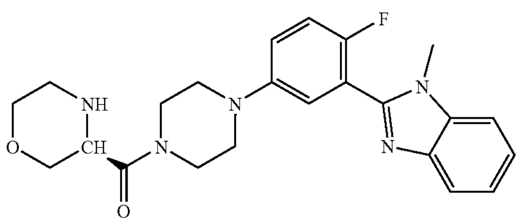 | L | 424 | 1.13 |
| 224 | 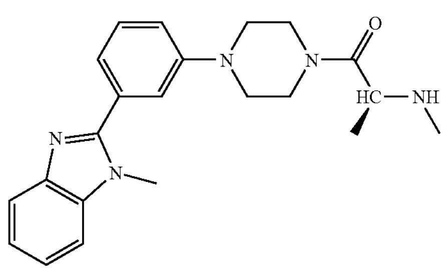 | L | 424 | 1.13 |
| 225 | 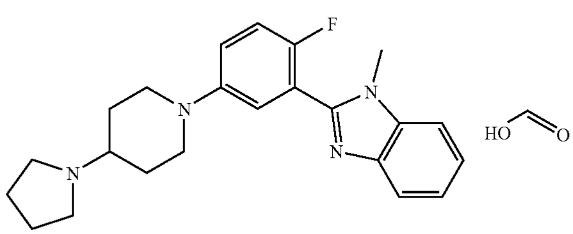 | L | 379 | 1.12 |

-continued

| Example | Structure | Method | M + H | Retention Time |
|---|---|---|---|---|
| 226 | 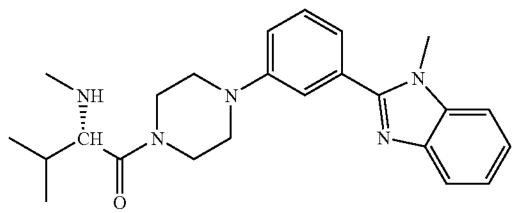 [SMILES: CN[C@H](C(=O)N1CCN(c2cccc(-c3nc4ccccc4n3C)c2)CC1)C(C)C] | D | 406 | 1.2 |
| 227 | 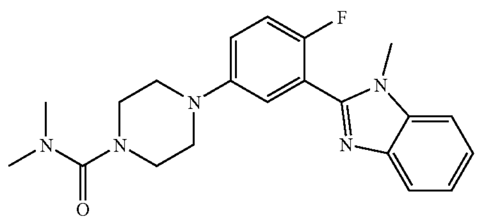 [SMILES: CN(C)C(=O)N1CCN(c2ccc(F)c(-c3nc4ccccc4n3C)c2)CC1] | L | 382 | 2 |
| 228 | 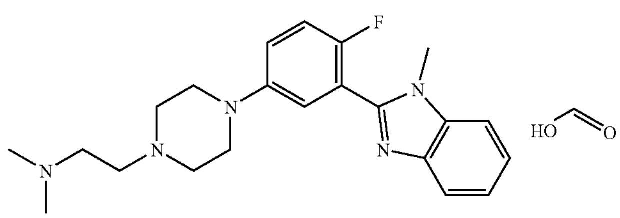 | L | 382 | 0.62 |
| 229 | 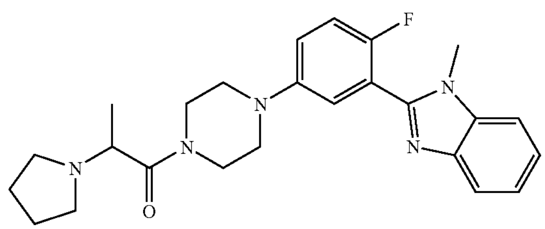 [SMILES: CC(C(=O)N1CCN(c2ccc(F)c(-c3nc4ccccc4n3C)c2)CC1)N1CCCC1] | L | 436 | 1.27 |
| 230 | 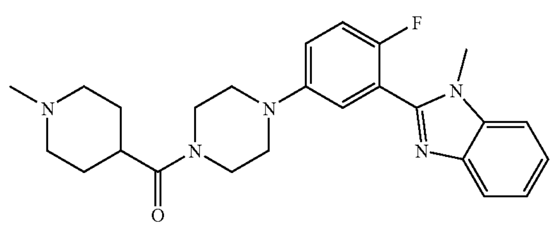 [SMILES: CN1CCC(C(=O)N2CCN(c3ccc(F)c(-c4nc5ccccc5n4C)c3)CC2)CC1] | L | 436 | 1.27 |
| 231 | 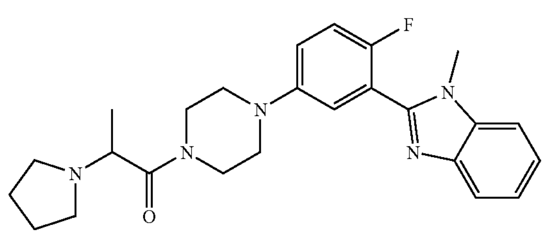 [SMILES: CC(C(=O)N1CCN(c2ccc(F)c(-c3nc4ccccc4n3C)c2)CC1)N1CCCC1] | M | 422 | 1.22 |
| 232 | 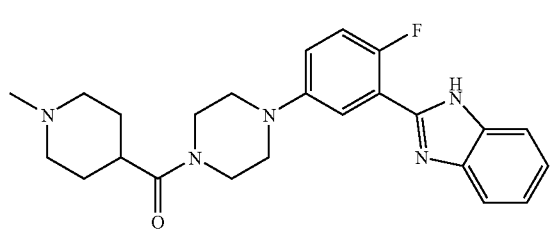 [SMILES: CN1CCC(C(=O)N2CCN(c3ccc(F)c(-c4nc5ccccc5[nH]4)c3)CC2)CC1] | M | 422 | 1.18 |

-continued

| Example | Structure | Method | M + H | Retention Time |
|---|---|---|---|---|
| 233 | 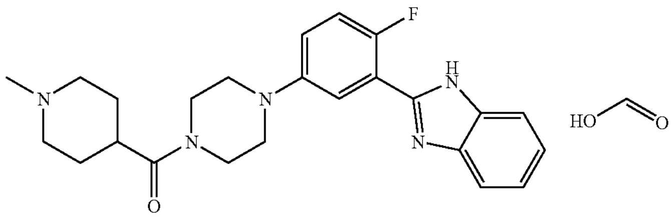 | M | 422 | 1.13 |
| 234 | 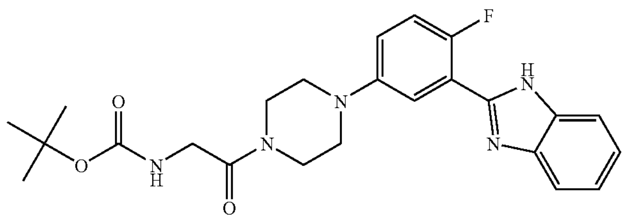 [SMILES: CC(C)(C)OC(=O)NCC(=O)N1CCN(c2ccc(F)c(-c3nc4ccccc4[nH]3)c2)CC1] | M | 454 | 2.38 |
| 235 | 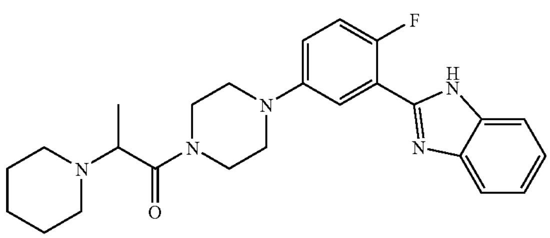 [SMILES: CC(C(=O)N1CCN(c2ccc(F)c(-c3nc4ccccc4[nH]3)c2)CC1)N1CCCCC1] | M | 436 | 1.33 |
| 236 | 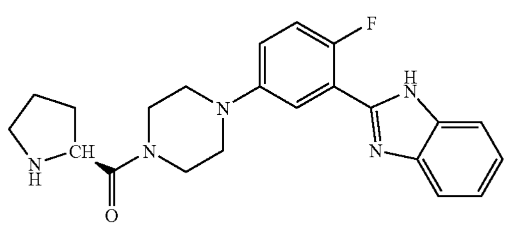 [SMILES: O=C([C@@H]1CCCN1)N1CCN(c2ccc(F)c(-c3nc4ccccc4[nH]3)c2)CC1] | M | 394 | 1.17 |
| 237 | 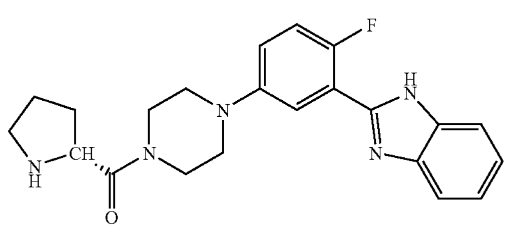 [SMILES: O=C([C@H]1CCCN1)N1CCN(c2ccc(F)c(-c3nc4ccccc4[nH]3)c2)CC1] | M | 394 | 1.2 |
| 238 | 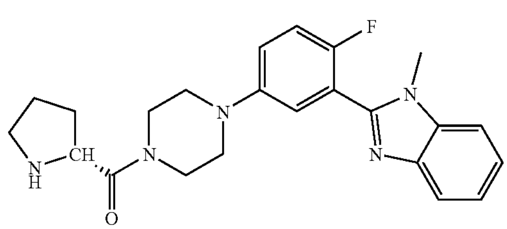 [SMILES: Cn1c(-c2cc(N3CCN(C(=O)[C@H]4CCCN4)CC3)ccc2F)nc2ccccc21] | L | 408 | 1.22 |

-continued

| Example | Structure | Method | M + H | Retention Time |
|---|---|---|---|---|
| 239 | 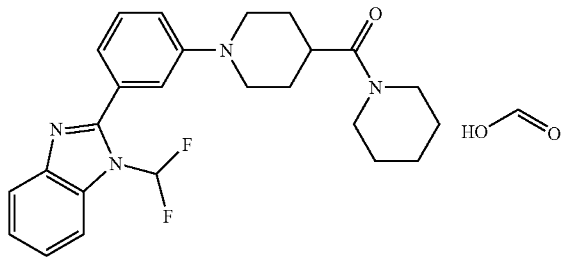 | I | 439 | 3.85 |
| 240 | 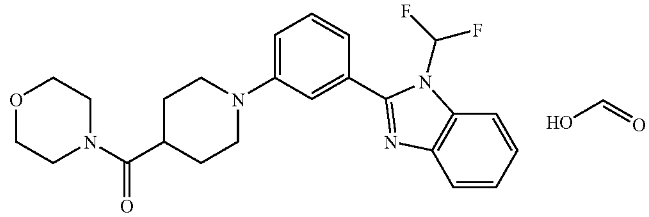 | I | 441 | 3.22 |
| 241 | 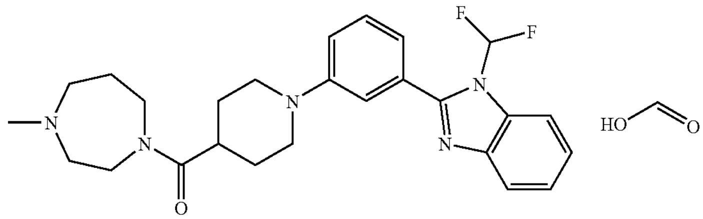 | I | 468 | 2.02 |
| 242 | 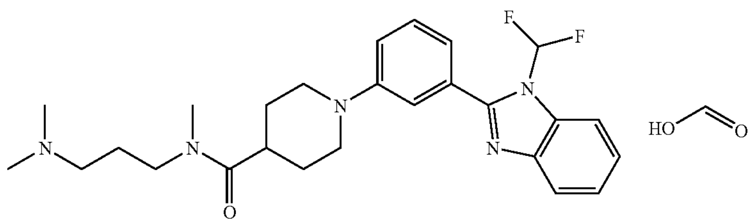 | I | 470 | 2.1 |
| 243 | 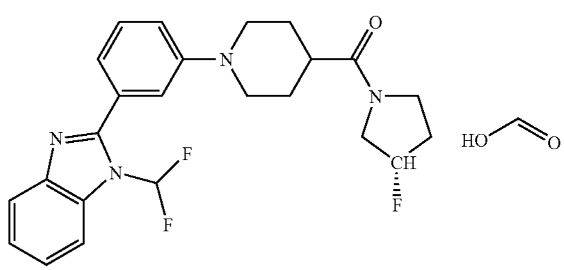 | I | 443 | 3.4 |
| 244 | 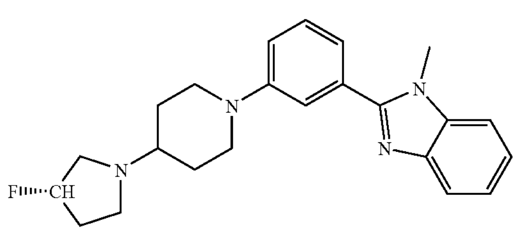 [SMILES: Cn1c(-c2cccc(N3CCC(N4CC[C@H](F)C4)CC3)c2)nc2ccccc21] | O | 379 | 0.62 |

-continued

| Example | Structure | Method | M + H | Retention Time |
|---|---|---|---|---|
| 245 | 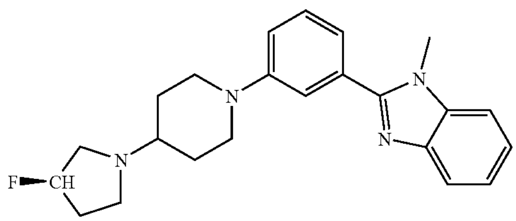 [SMILES: Cn1c(-c2cccc(N3CCC(N4CC[C@@H](F)C4)CC3)c2)nc2ccccc21] | O | 379 | 0.65 |
| 246 | 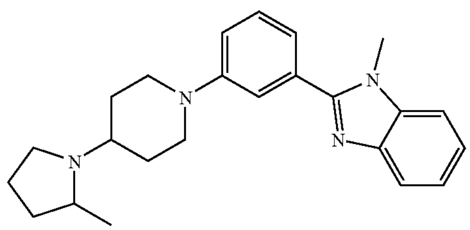 [SMILES: CC1CCCN1C1CCN(c2cccc(-c3nc4ccccc4n3C)c2)CC1] | O | 375 | 0.85 |
| 247 | 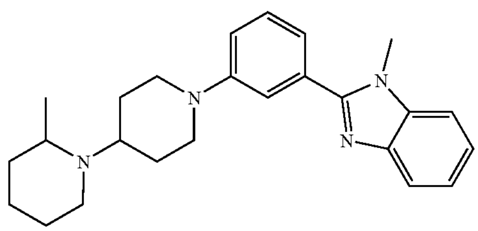 [SMILES: CC1CCCCN1C1CCN(c2cccc(-c3nc4ccccc4n3C)c2)CC1] | O | 389 | 1.07 |
| 248 | 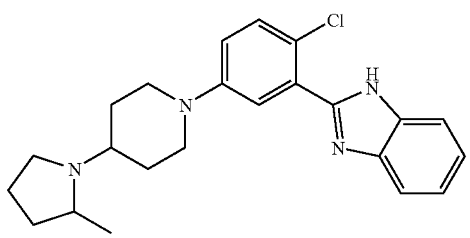 [SMILES: CC1CCCN1C1CCN(c2ccc(Cl)c(-c3nc4ccccc4[nH]3)c2)CC1] | O | 395 | 1.22 |
| 249 | 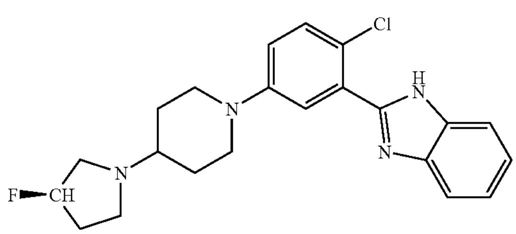 [SMILES: F[C@@H]1CCN(C2CCN(c3ccc(Cl)c(-c4nc5ccccc5[nH]4)c3)CC2)C1] | O | 399 | 1.13 |
| 250 | 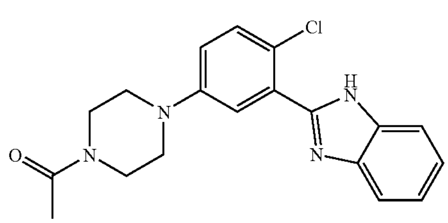 [SMILES: CC(=O)N1CCN(c2ccc(Cl)c(-c3nc4ccccc4[nH]3)c2)CC1] | B | 355 | 4.78 |

-continued

| Example | Structure | Method | M + H | Retention Time |
|---|---|---|---|---|
| 251 | 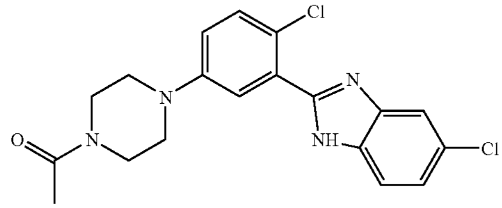 [SMILES: CC(=O)N1CCN(c2ccc(Cl)c(-c3nc4cc(Cl)ccc4[nH]3)c2)CC1] | T | 389 | 5.36 |
| 252 | 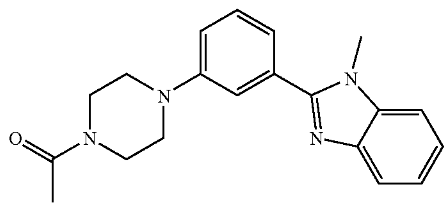 [SMILES: CC(=O)N1CCN(c2cccc(-c3nc4ccccc4n3C)c2)CC1] | C | 335 | 4.73 |
| 253 | 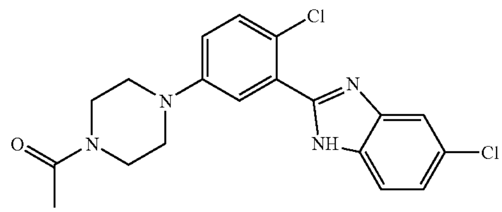 [SMILES: CC(=O)N1CCN(c2ccc(Cl)c(-c3nc4cc(Cl)ccc4[nH]3)c2)CC1] | T | 389 | 5.36 |
| 254 | 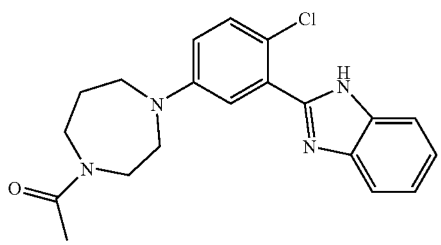 [SMILES: CC(=O)N1CCCN(c2ccc(Cl)c(-c3nc4ccccc4[nH]3)c2)CC1] | T | 369 | 4.92 |
| 255 | 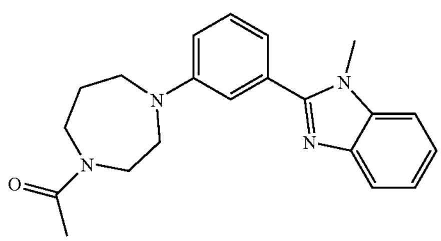 [SMILES: CC(=O)N1CCCN(c2cccc(-c3nc4ccccc4n3C)c2)CC1] | T | 349 | 4.87 |
| 256 | 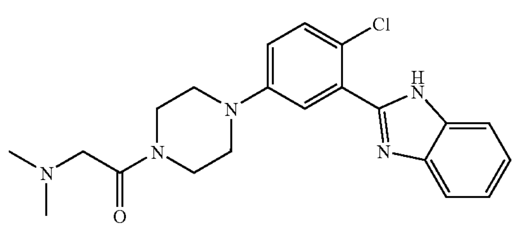 [SMILES: CN(C)CC(=O)N1CCN(c2ccc(Cl)c(-c3nc4ccccc4[nH]3)c2)CC1] | B | 398 | 4.39 |
| 257 | 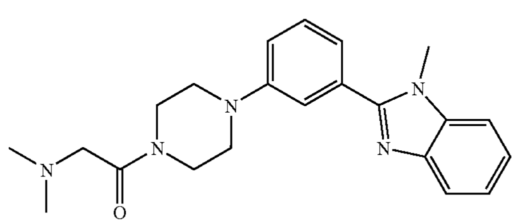 [SMILES: CN(C)CC(=O)N1CCN(c2cccc(-c3nc4ccccc4n3C)c2)CC1] | C | 378 | 4.07 |

-continued

| Example | Structure | Method | M + H | Retention Time |
|---|---|---|---|---|
| 258 | 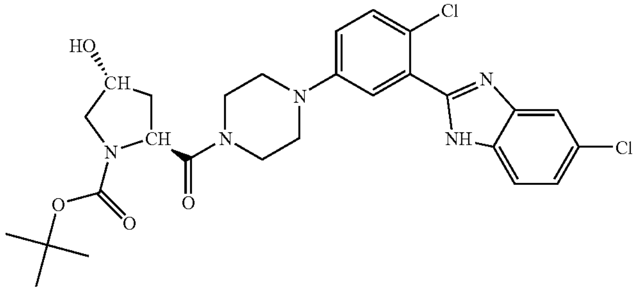 [SMILES: CC(C)(C)OC(=O)N1C[C@H](O)C[C@H]1C(=O)N1CCN(c2ccc(Cl)c(-c3nc4cc(Cl)ccc4[nH]3)c2)CC1] | Q | 560 | 5.51 |
| 259 | 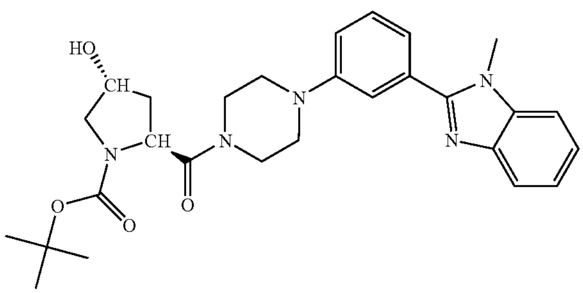 [SMILES: Cn1c(-c2cccc(N3CCN(C(=O)[C@@H]4C[C@@H](O)CN4C(=O)OC(C)(C)C)CC3)c2)nc2ccccc21] | D | 506 | 5.02 |
| 260 | 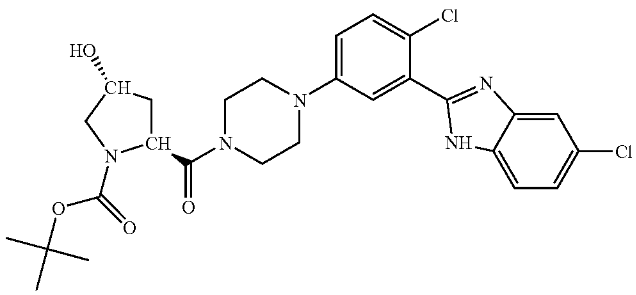 [SMILES: CC(C)(C)OC(=O)N1C[C@H](O)C[C@H]1C(=O)N1CCN(c2ccc(Cl)c(-c3nc4cc(Cl)ccc4[nH]3)c2)CC1] | Q | 560 | 5.51 |
| 261 | 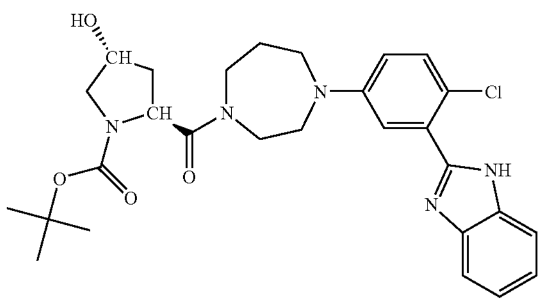 [SMILES: CC(C)(C)OC(=O)N1C[C@H](O)C[C@H]1C(=O)N1CCCN(c2ccc(Cl)c(-c3nc4ccccc4[nH]3)c2)CC1] | Q | 540 | 5.15 |
| 262 | 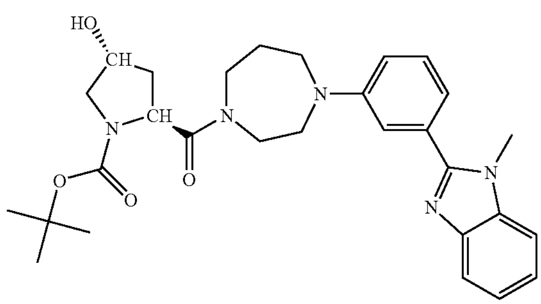 [SMILES: Cn1c(-c2cccc(N3CCCN(C(=O)[C@@H]4C[C@@H](O)CN4C(=O)OC(C)(C)C)CC3)c2)nc2ccccc21] | Q | 520 | 5.21 |

-continued

| Example | Structure | Method | M + H | Retention Time |
|---|---|---|---|---|
| 263 | 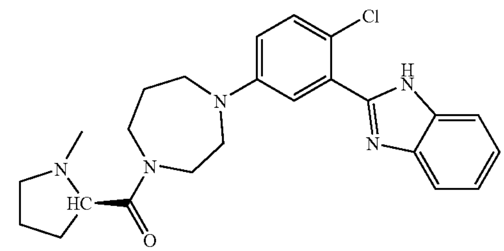 [SMILES: CN1CCC[C@@H]1C(=O)N1CCCN(c2ccc(Cl)c(-c3nc4ccccc4[nH]3)c2)CC1] | Q | 438 | 4.19 |
| 264 | 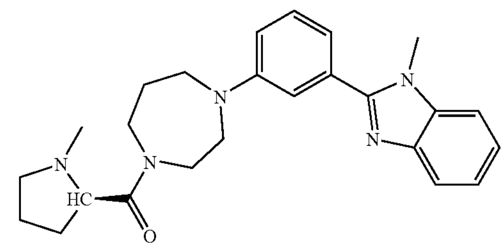 [SMILES: CN1CCC[C@@H]1C(=O)N1CCCN(c2cccc(-c3nc4ccccc4n3C)c2)CC1] | Q | 418 | 4.25 |
| 265 | 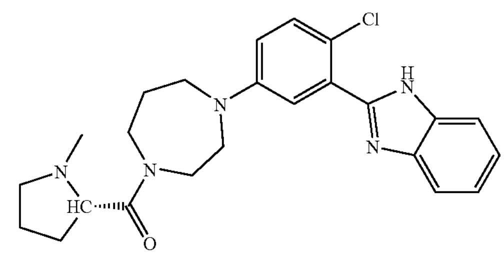 [SMILES: CN1CCC[C@H]1C(=O)N1CCCN(c2ccc(Cl)c(-c3nc4ccccc4[nH]3)c2)CC1] | Q | 438 | 4.2 |
| 266 | 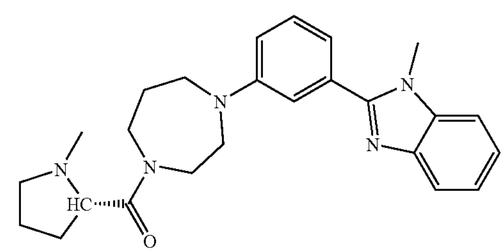 [SMILES: CN1CCC[C@H]1C(=O)N1CCCN(c2cccc(-c3nc4ccccc4n3C)c2)CC1] | Q | 418 | 4.25 |
| 267 | 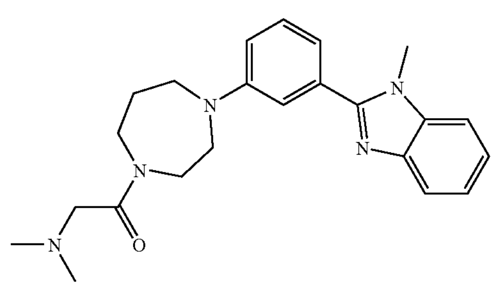 [SMILES: CN(C)CC(=O)N1CCCN(c2cccc(-c3nc4ccccc4n3C)c2)CC1] | T | 392 | 4.25 |
| 268 | 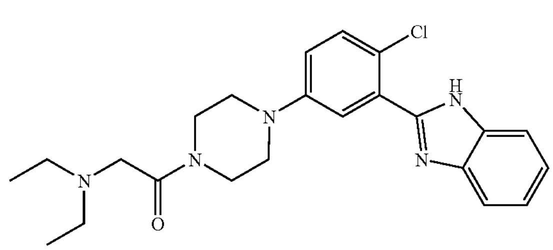 [SMILES: CCN(CC)CC(=O)N1CCN(c2ccc(Cl)c(-c3nc4ccccc4[nH]3)c2)CC1] | B | 426 | 4.66 |

-continued

| Example | Structure | Method | M + H | Retention Time |
|---|---|---|---|---|
| 269 | 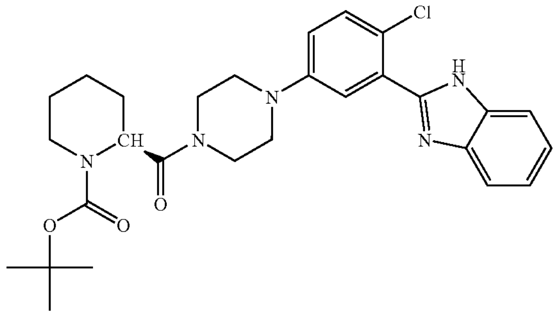 | D | 524 | 6.68 |
| 270 | 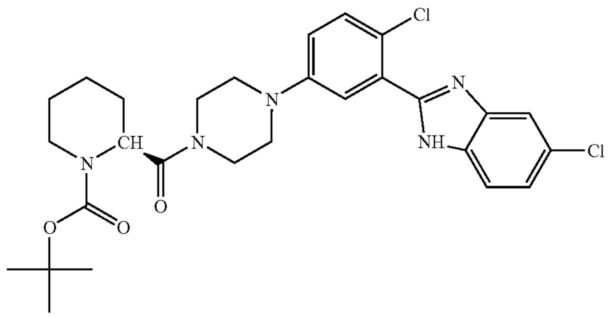 [SMILES: CC(C)(C)OC(=O)N1CCCC[C@H]1C(=O)N1CCN(c2ccc(Cl)c(-c3nc4cc(Cl)ccc4[nH]3)c2)CC1] | Q | 558 | 7.43 |
| 271 | 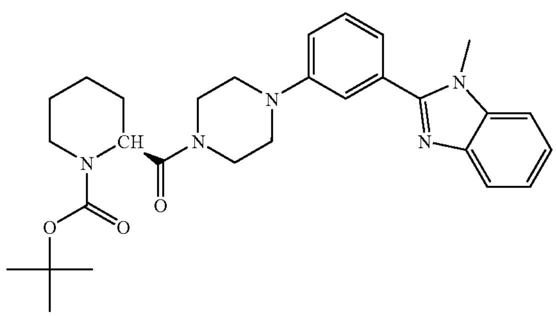 [SMILES: Cn1c(-c2cccc(N3CCN(C(=O)[C@@H]4CCCCN4C(=O)OC(C)(C)C)CC3)c2)nc2ccccc21] | D | 504 | 6.72 |
| 272 | 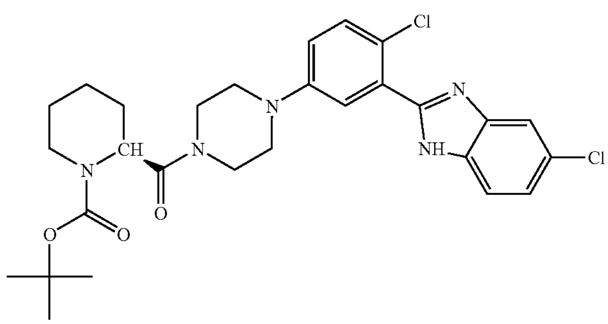 [SMILES: CC(C)(C)OC(=O)N1CCCC[C@H]1C(=O)N1CCN(c2ccc(Cl)c(-c3nc4cc(Cl)ccc4[nH]3)c2)CC1] | Q | 558 | 7.43 |
| 273 | 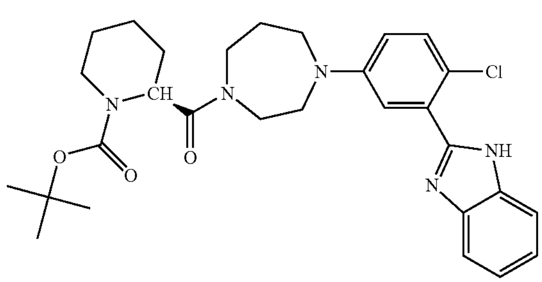 [SMILES: CC(C)(C)OC(=O)N1CCCC[C@H]1C(=O)N1CCCN(c2ccc(Cl)c(-c3nc4ccccc4[nH]3)c2)CC1] | Q | 538 | 6.97 |

-continued

| Example | Structure | Method | M + H | Retention Time |
|---|---|---|---|---|
| 274 | 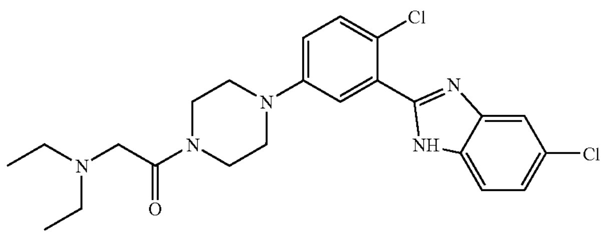 [SMILES: CCN(CC)CC(=O)N1CCN(c2ccc(Cl)c(-c3nc4cc(Cl)ccc4[nH]3)c2)CC1] | T | 460 | 5.22 |
| 275 | 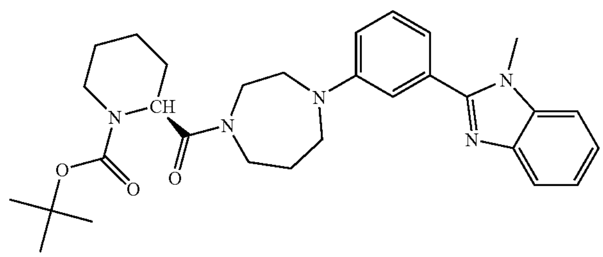 [SMILES: Cn1c(-c2cccc(N3CCCN(C(=O)[C@@H]4CCCCN4C(=O)OC(C)(C)C)CC3)c2)nc2ccccc21] | Q | 518 | 7.03 |
| 276 | HCl | D | 424 | 4.04 |
| 277 | HCl | Q | 458 | 4.65 |
| 278 | 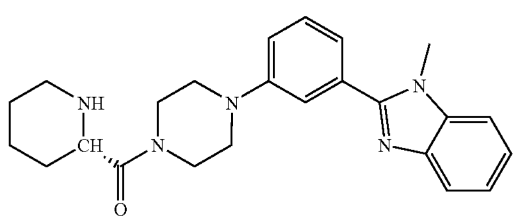 [SMILES: Cn1c(-c2cccc(N3CCN(C(=O)[C@@H]4CCCCN4)CC3)c2)nc2ccccc21] | D | 404 | 1.00 |
| 279 | HCl | Q | 458 | 4.65 |

-continued

| Example | Structure | Method | M + H | Retention Time |
|---|---|---|---|---|
| 280 | 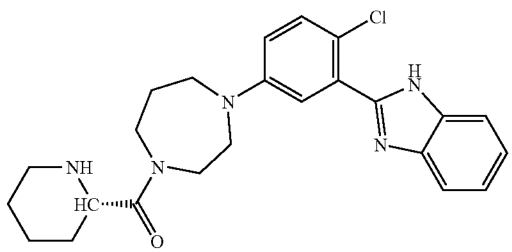 | Q | 438 | 4.24 |
| 281 | 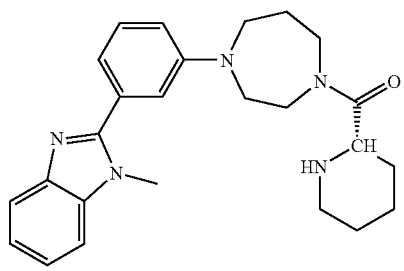 | Q | 418 | 4.3 |
| 282 | 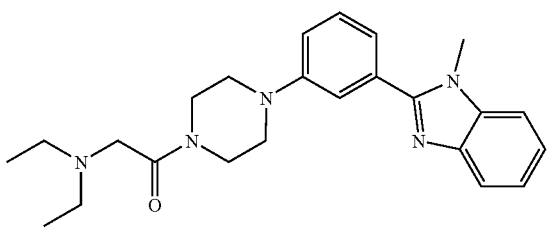 [SMILES: CCN(CC)CC(=O)N1CCN(c2cccc(-c3nc4ccccc4n3C)c2)CC1] | C | 406 | 4.31 |
| 283 | 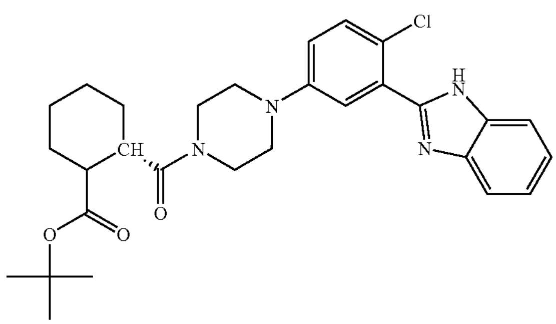 [SMILES: CC(C)(C)OC(=O)C1CCCC[C@@H]1C(=O)N1CCN(c2ccc(Cl)c(-c3nc4ccccc4[nH]3)c2)CC1] | D | 524 | 6.68 |
| 284 | 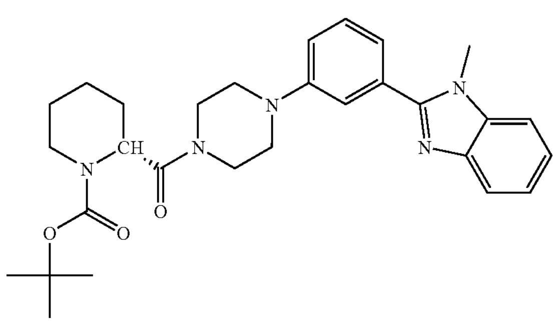 [SMILES: Cn1c(-c2cccc(N3CCN(C(=O)[C@H]4CCCCN4C(=O)OC(C)(C)C)CC3)c2)nc2ccccc21] | D | 504 | 6.73 |

-continued

| Example | Structure | Method | M + H | Retention Time |
|---|---|---|---|---|
| 285 | 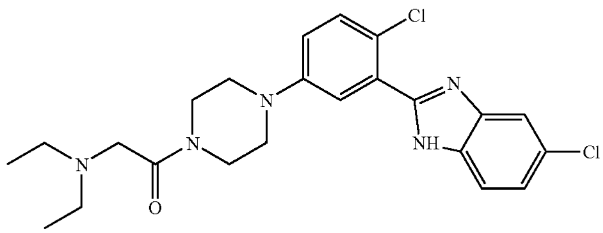 [SMILES: CCN(CC)CC(=O)N1CCN(c2ccc(Cl)c(-c3nc4cc(Cl)ccc4[nH]3)c2)CC1] | T | 460 | 5.22 |
| 286 | 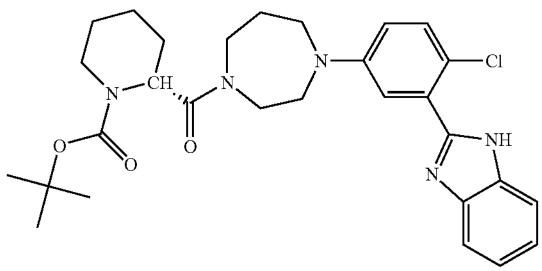 [SMILES: CC(C)(C)OC(=O)N1CCCC[C@@H]1C(=O)N1CCCN(c2ccc(Cl)c(-c3nc4ccccc4[nH]3)c2)CC1] | Q | 538 | 7.02 |
| 287 | 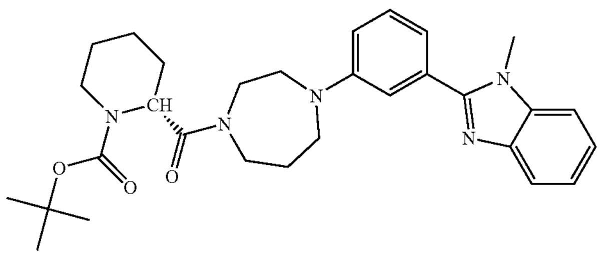 [SMILES: Cn1c(-c2cccc(N3CCCN(C(=O)[C@H]4CCCCN4C(=O)OC(C)(C)C)CC3)c2)nc2ccccc21] | Q | 518 | 7.04 |
| 288 | 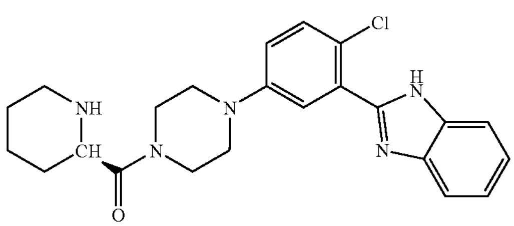 | D | 424 | 4.06 |
| 289 | 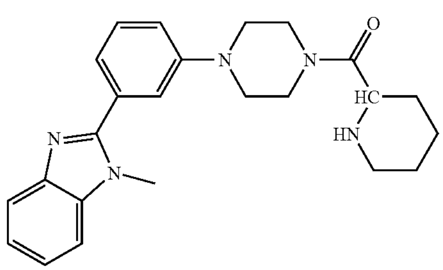 | D | 404 | 4.15 |
| 290 | 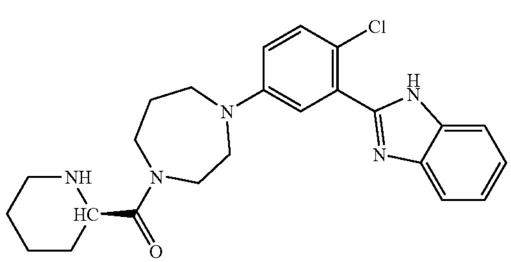 | Q | 438 | 4.27 |

-continued
| Example | Structure | Method | M + H | Retention Time |
|---|---|---|---|---|
| 291 | 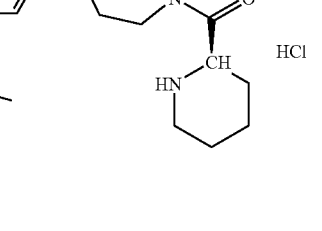 | Q | 418 | 4.3 |
| 292 | 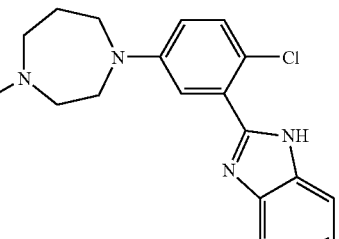 | T | 440 | 4.35 |
| 293 | 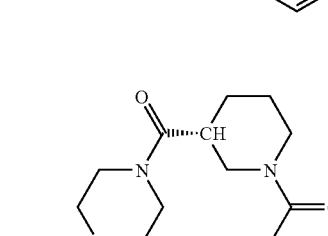 | D | 504 | 2.57 |
| 294 | 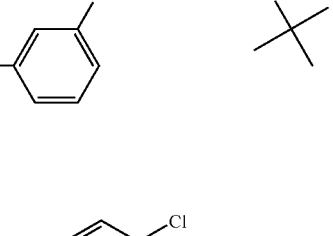 | Q | 438 | 1.32 |
| 295 | 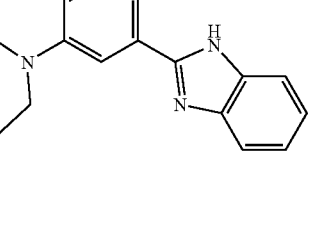 | B | 424 | 4.34 |

-continued

| Example | Structure | Method | M + H | Retention Time |
|---|---|---|---|---|
| 296 | 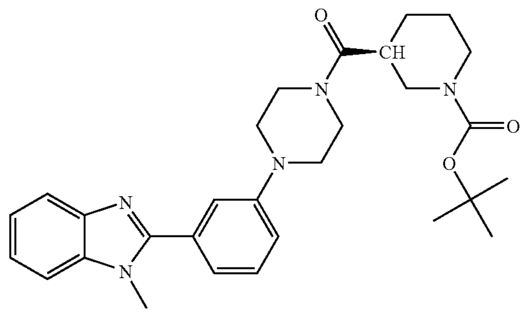 [SMILES: Cn1c(-c2cccc(N3CCN(C(=O)[C@H]4CCCN(C(=O)OC(C)(C)C)C4)CC3)c2)nc2ccccc21] | D | 504 | 2.57 |
| 297 | 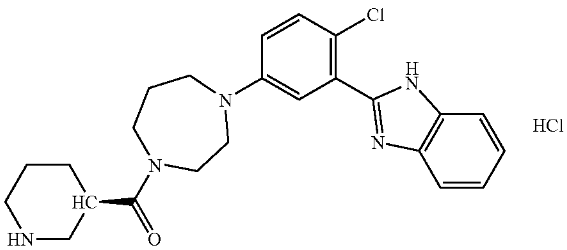 [SMILES: O=C([C@@H]1CCCNC1)N1CCCN(c2ccc(Cl)c(-c3nc4ccccc4[nH]3)c2)CC1 ; Cl] | Q | 438 | 1.27 |
| 298 | 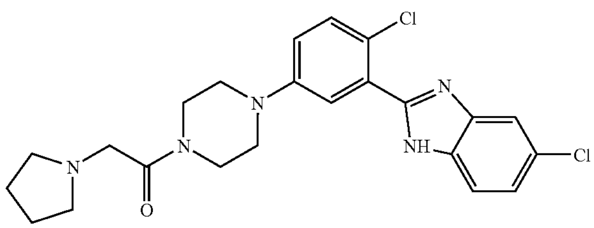 [SMILES: O=C(CN1CCCC1)N1CCN(c2ccc(Cl)c(-c3nc4cc(Cl)ccc4[nH]3)c2)CC1] | T | 458 | 5.05 |
| 299 | 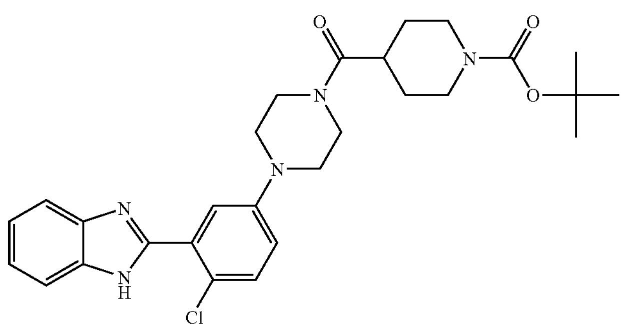 [SMILES: CC(C)(C)OC(=O)N1CCC(C(=O)N2CCN(c3ccc(Cl)c(-c4nc5ccccc5[nH]4)c3)CC2)CC1] | D | 524 | 6.17 |
| 300 | 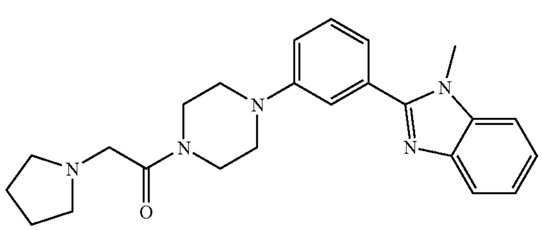 [SMILES: Cn1c(-c2cccc(N3CCN(C(=O)CN4CCCC4)CC3)c2)nc2ccccc21] | C | 404 | 4.18 |

-continued
| Example | Structure | Method | M + H | Retention Time |
|---|---|---|---|---|
| 301 | 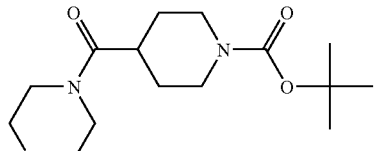 | Q | 558 | 6.79 |
| 302 | 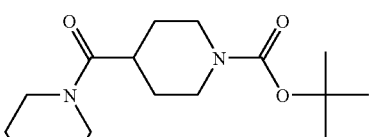 | C | 504 | 6.18 |
| 303 | 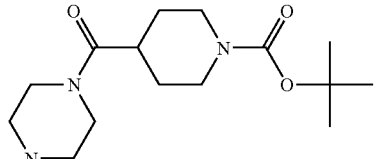 | Q | 558 | 6.79 |
| 304 | 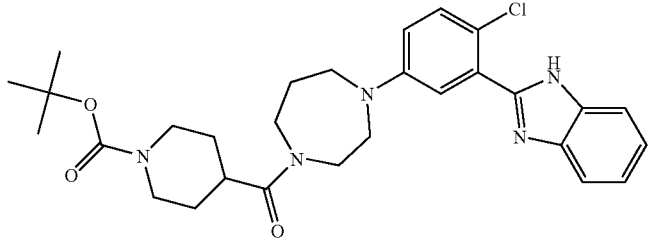 [SMILES: CC(C)(C)OC(=O)N1CCC(C(=O)N2CCCN(c3ccc(Cl)c(-c4nc5ccccc5[nH]4)c3)CC2)CC1] | Q | 538 | 6.22 |
| 305 | 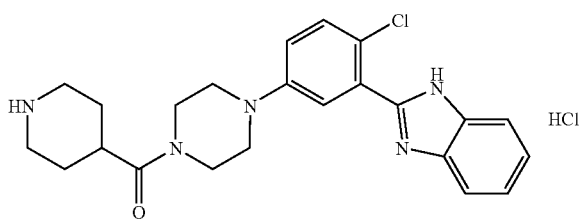 [SMILES: O=C(C1CCNCC1)N1CCN(c2ccc(Cl)c(-c3nc4ccccc4[nH]3)c2)CC1 ; Cl] | D | 424 | 3.92 |

-continued
| Example | Structure | Method | M + H | Retention Time |
|---|---|---|---|---|
| 306 | 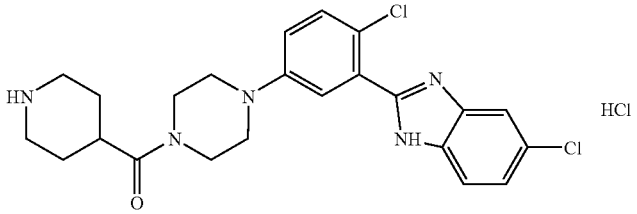 [SMILES: O=C(C1CCNCC1)N1CCN(c2ccc(Cl)c(-c3nc4cc(Cl)ccc4[nH]3)c2)CC1 ; Cl] HCl | Q | 458 | 4.44 |
| 307 | 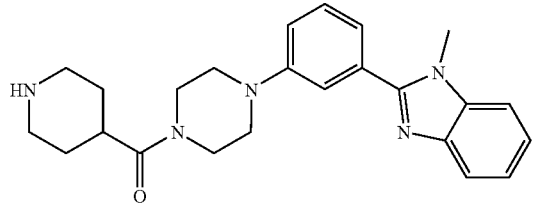 [SMILES: Cn1c(-c2cccc(N3CCN(C(=O)C4CCNCC4)CC3)c2)nc2ccccc21] | D | 404 | 0.79 |
| 308 | 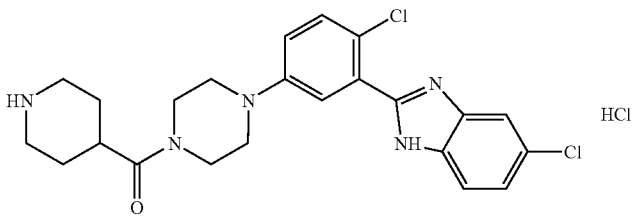 [SMILES: O=C(C1CCNCC1)N1CCN(c2ccc(Cl)c(-c3nc4cc(Cl)ccc4[nH]3)c2)CC1 ; Cl] HCl | Q | 458 | 4.44 |
| 309 | 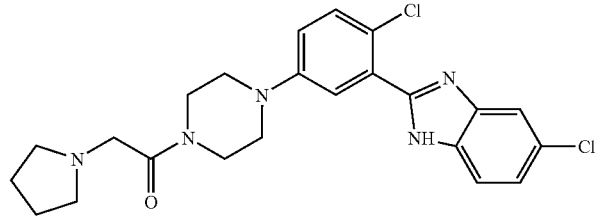 [SMILES: O=C(CN1CCCC1)N1CCN(c2ccc(Cl)c(-c3nc4cc(Cl)ccc4[nH]3)c2)CC1] | T | 458 | 5.05 |
| 310 | 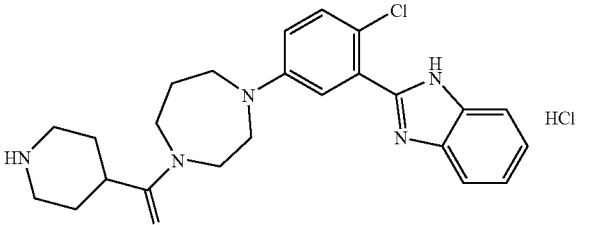 HCl | Q | 438 | 4.03 |
| 311 | 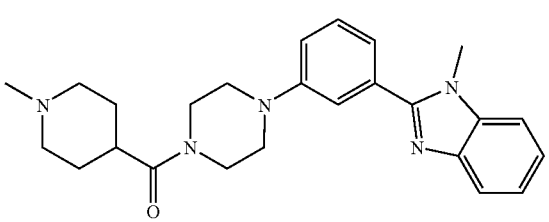 | C | 418 | 4.18 |

-continued

| Example | Structure | Method | M + H | Retention Time |
|---|---|---|---|---|
| 312 | 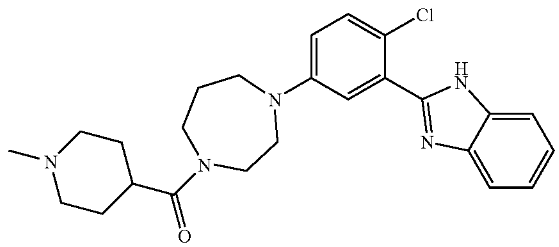 [SMILES: CN1CCC(C(=O)N2CCCN(c3ccc(Cl)c(-c4nc5ccccc5[nH]4)c3)CC2)CC1] | T | 452 | 4.19 |
| 313 | 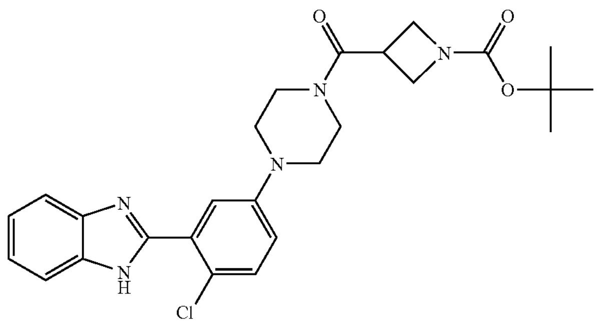 [SMILES: CC(C)(C)OC(=O)N1CC(C(=O)N2CCN(c3ccc(Cl)c(-c4nc5ccccc5[nH]4)c3)CC2)C1] | D | 496 | 5.94 |
| 314 | 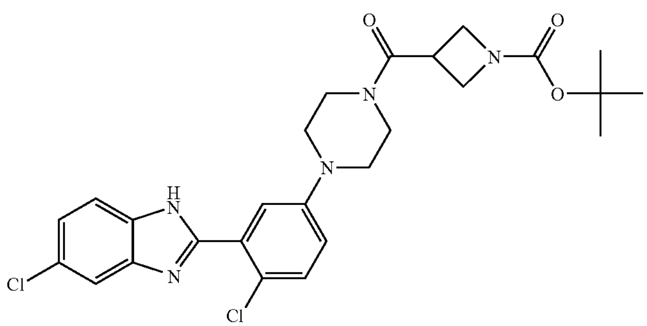 [SMILES: CC(C)(C)OC(=O)N1CC(C(=O)N2CCN(c3ccc(Cl)c(-c4nc5cc(Cl)ccc5[nH]4)c3)CC2)C1] | Q | 530 | 6.53 |
| 315 | 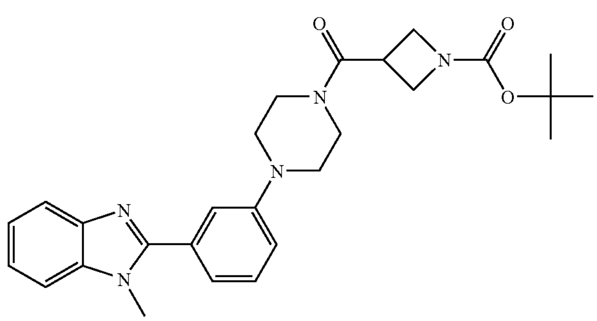 [SMILES: Cn1c(-c2cccc(N3CCN(C(=O)C4CN(C(=O)OC(C)(C)C)C4)CC3)c2)nc2ccccc21] | C | 476 | 5.92 |
| 316 | 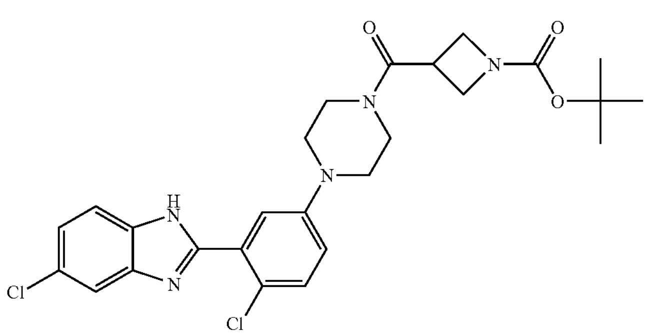 [SMILES: CC(C)(C)OC(=O)N1CC(C(=O)N2CCN(c3ccc(Cl)c(-c4nc5cc(Cl)ccc5[nH]4)c3)CC2)C1] | Q | 530 | 6.53 |

-continued

| Example | Structure | Method | M + H | Retention Time |
|---|---|---|---|---|
| 317 | 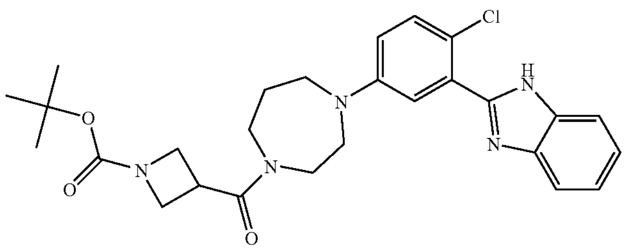 [SMILES: CC(C)(C)OC(=O)N1CC(C(=O)N2CCCN(c3ccc(Cl)c(-c4nc5ccccc5[nH]4)c3)CC2)C1] | Q | 510 | 5.95 |
| 318 | 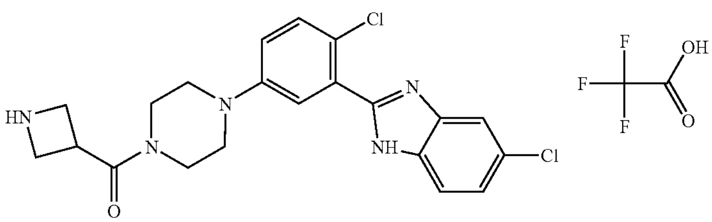 [SMILES: O=C(C1CNC1)N1CCN(c2ccc(Cl)c(-c3nc4cc(Cl)ccc4[nH]3)c2)CC1 ; O=C(O)C(F)(F)F] | Q | 430 | 4.45 |
| 319 | 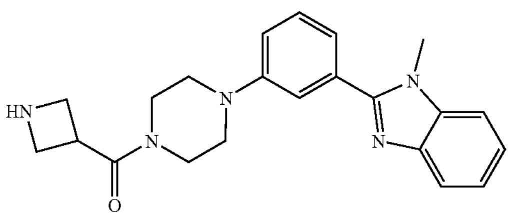 [SMILES: Cn1c(-c2cccc(N3CCN(C(=O)C4CNC4)CC3)c2)nc2ccccc21] | D | 376 | 3.97 |
| 320 | 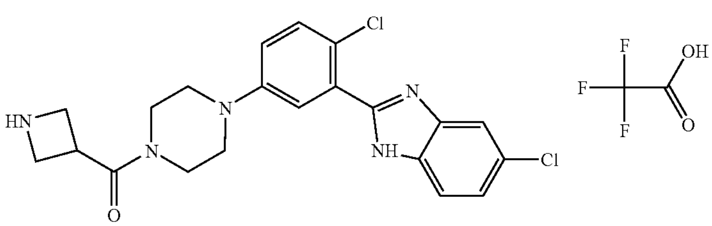 [SMILES: O=C(C1CNC1)N1CCN(c2ccc(Cl)c(-c3nc4cc(Cl)ccc4[nH]3)c2)CC1 ; O=C(O)C(F)(F)F] | Q | 430 | 4.45 |
| 321 | 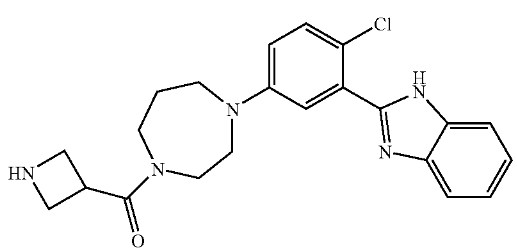 [SMILES: O=C(C1CNC1)N1CCCN(c2ccc(Cl)c(-c3nc4ccccc4[nH]3)c2)CC1] | Q | 410 | 4.07 |
| 322 | 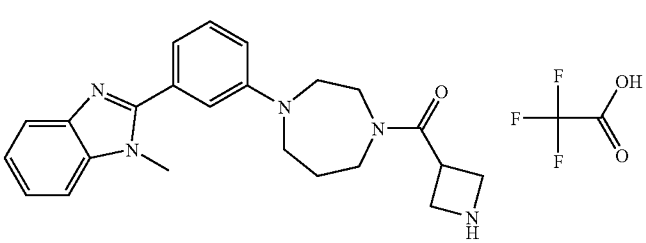 [SMILES: Cn1c(-c2cccc(N3CCCN(C(=O)C4CNC4)CC3)c2)nc2ccccc21 ; O=C(O)C(F)(F)F] | Q | 390 | 4.03 |

-continued
| Example | Structure | Method | M + H | Retention Time |
|---|---|---|---|---|
| 323 | 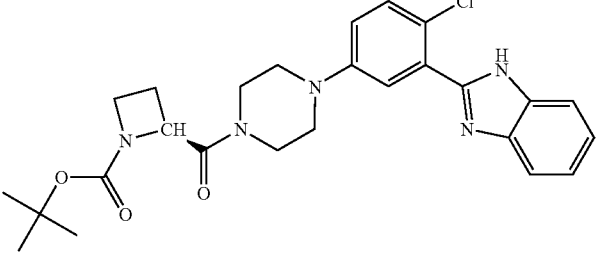 | D | 496 | 5.73 |
| 324 | 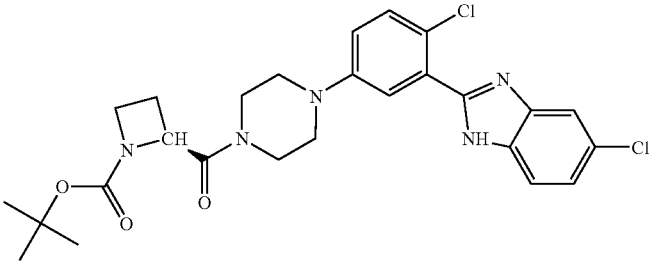 [SMILES: CC(C)(C)OC(=O)N1CC[C@H]1C(=O)N1CCN(c2ccc(Cl)c(-c3nc4cc(Cl)ccc4[nH]3)c2)CC1] | Q | 530 | 6.29 |
| 325 | 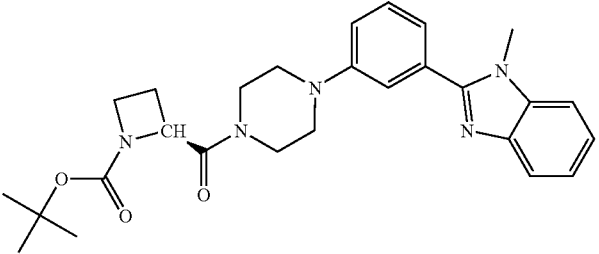 [SMILES: Cn1c(-c2cccc(N3CCN(C(=O)[C@@H]4CCN4C(=O)OC(C)(C)C)CC3)c2)nc2ccccc21] | D | 476 | 5.67 |
| 326 | 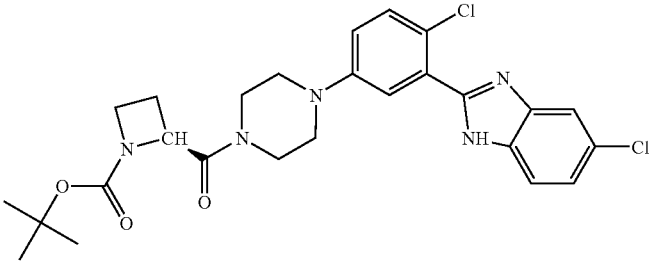 [SMILES: CC(C)(C)OC(=O)N1CC[C@H]1C(=O)N1CCN(c2ccc(Cl)c(-c3nc4cc(Cl)ccc4[nH]3)c2)CC1] | Q | 530 | 6.29 |
| 327 | 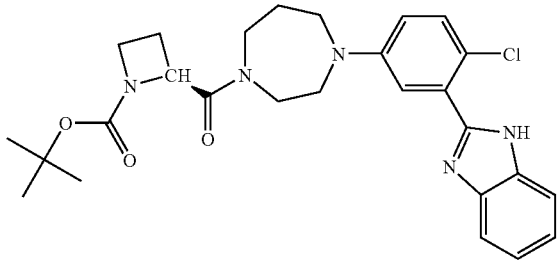 [SMILES: CC(C)(C)OC(=O)N1CC[C@H]1C(=O)N1CCCN(c2ccc(Cl)c(-c3nc4ccccc4[nH]3)c2)CC1] | Q | 510 | 5.9 |
| 328 | 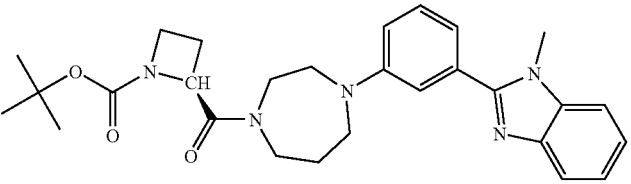 [SMILES: Cn1c(-c2cccc(N3CCCN(C(=O)[C@@H]4CCN4C(=O)OC(C)(C)C)CC3)c2)nc2ccccc21] | Q | 490 | 5.96 |

-continued

| Example | Structure | Method | M + H | Retention Time |
|---|---|---|---|---|
| 329 | 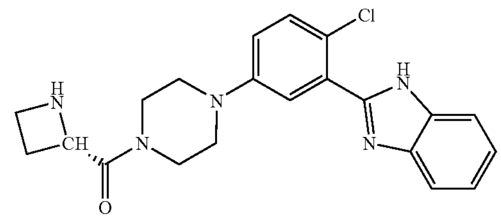 [SMILES: O=C([C@@H]1CCN1)N1CCN(c2ccc(Cl)c(-c3nc4ccccc4[nH]3)c2)CC1] | D | 396 | 3.97 |
| 330 | 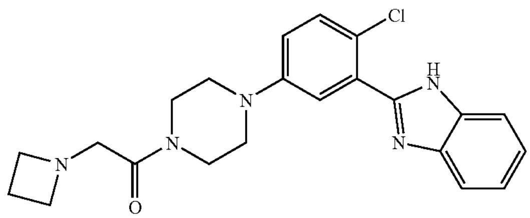 [SMILES: O=C(CN1CCC1)N1CCN(c2ccc(Cl)c(-c3nc4ccccc4[nH]3)c2)CC1] | B | 410 | 4.41 |
| 331 | 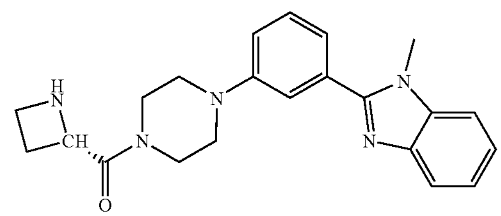 [SMILES: Cn1c(-c2cccc(N3CCN(C(=O)[C@@H]4CCN4)CC3)c2)nc2ccccc21] | D | 376 | 3.97 |
| 332 | 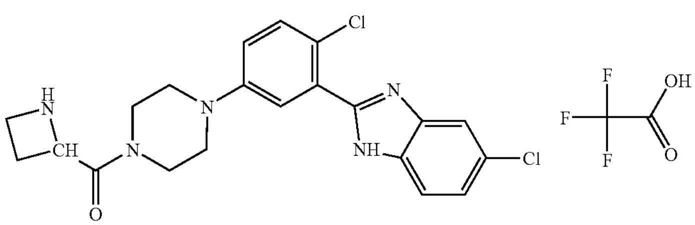 | Q | 430 | 4.59 |
| 333 | 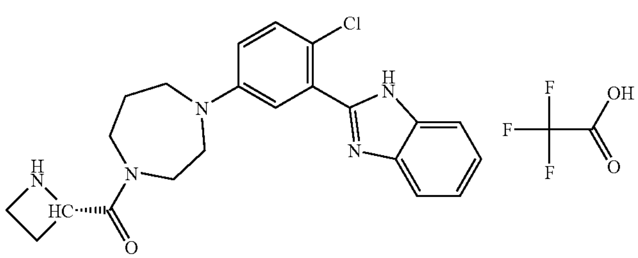 | Q | 410 | 4.16 |
| 334 | 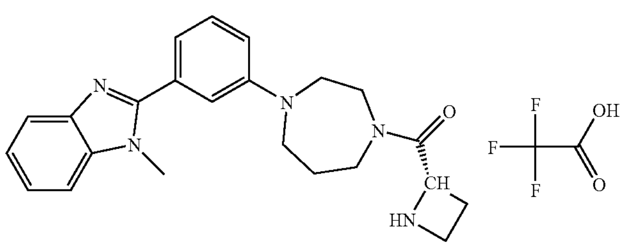 | Q | 390 | 4.17 |

-continued

| Example | Structure | Method | M + H | Retention Time |
|---|---|---|---|---|
| 335 | 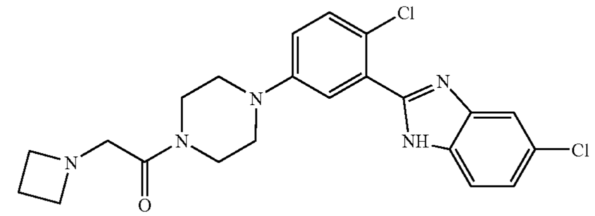 [SMILES: O=C(CN1CCC1)N1CCN(c2ccc(Cl)c(-c3nc4cc(Cl)ccc4[nH]3)c2)CC1] | T | 460 | 4.82 |
| 336 | 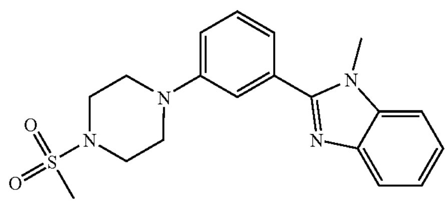 [SMILES: Cn1c(-c2cccc(N3CCN(S(C)(=O)=O)CC3)c2)nc2ccccc21] | V | 371 | 5.34 |
| 337 | 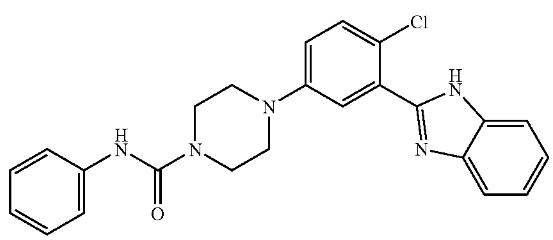 [SMILES: O=C(Nc1ccccc1)N1CCN(c2ccc(Cl)c(-c3nc4ccccc4[nH]3)c2)CC1] | R | 432 | 5.99 |
| 338 | 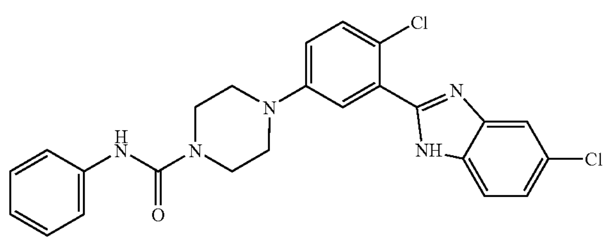 [SMILES: O=C(Nc1ccccc1)N1CCN(c2ccc(Cl)c(-c3nc4cc(Cl)ccc4[nH]3)c2)CC1] | R | 466 | 6.56 |
| 339 | 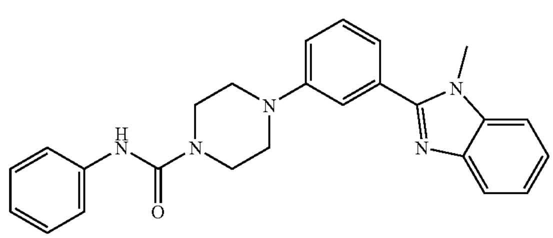 [SMILES: Cn1c(-c2cccc(N3CCN(C(=O)Nc4ccccc4)CC3)c2)nc2ccccc21] | R | 412 | 5.82 |
| 340 | 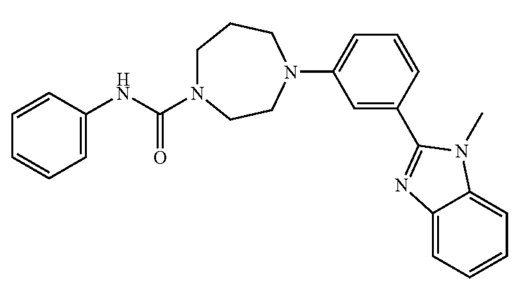 [SMILES: Cn1c(-c2cccc(N3CCCN(C(=O)Nc4ccccc4)CC3)c2)nc2ccccc21] | R | 426 | 5.92 |

-continued
| Example | Structure | Method | M + H | Retention Time |
|---|---|---|---|---|
| 341 | 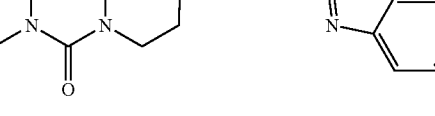 | W | 419 | 4.36 |
| 342 | 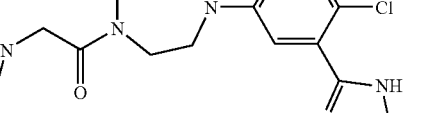 | T | 424 | 4.2 |
| 343 | 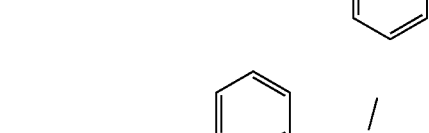 | C | 391 | 4.03 |
| 344 | 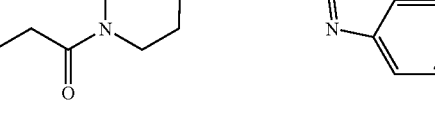 | U | 398 | 4.81 |
| 345 | 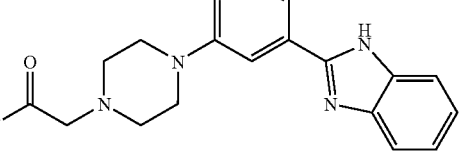 | U | 432 | 5.33 |
| 346 | 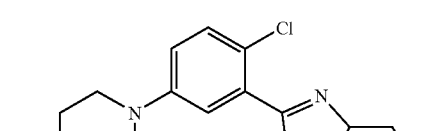 | U | 378 | 4.7 |
| 347 | 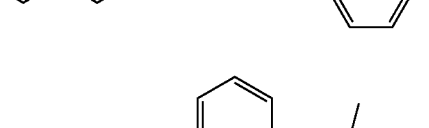 | U | 432 | 5.33 |

-continued
| Example | Structure | Method | M + H | Retention Time |
|---|---|---|---|---|
| 348 | 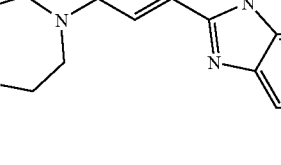 | U | 412 | 4.89 |
| 349 | 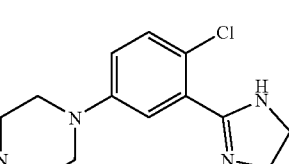 | U | 384 | 4.79 |
| 350 | 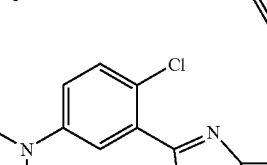 | U | 418 | 5.26 |
| 351 | 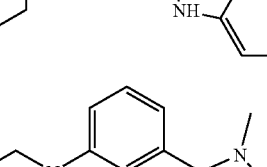 | U | 364 | 4.64 |
| 352 | 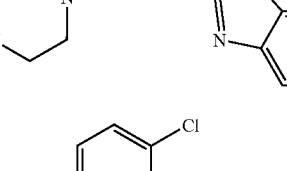 | U | 418 | 5.26 |
| 353 | 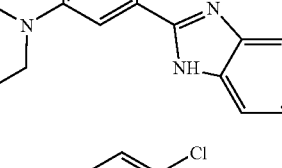 | U | 398 | 5.08 |
| 354 | 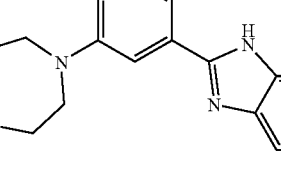 | U | 378 | 5.07 |

-continued

| Example | Structure | Method | M + H | Retention Time |
|---|---|---|---|---|
| 355 | 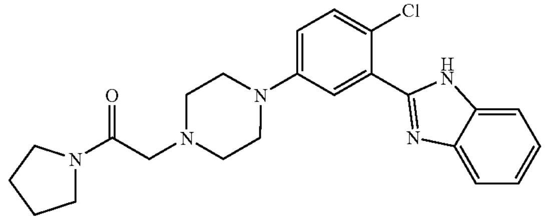 [SMILES: O=C(CN1CCN(c2ccc(Cl)c(-c3nc4ccccc4[nH]3)c2)CC1)N1CCCC1] | U | 424 | 5.11 |
| 356 | 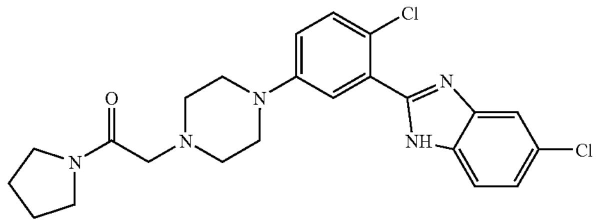 [SMILES: O=C(CN1CCN(c2ccc(Cl)c(-c3nc4cc(Cl)ccc4[nH]3)c2)CC1)N1CCCC1] | U | 458 | 5.57 |
| 357 | 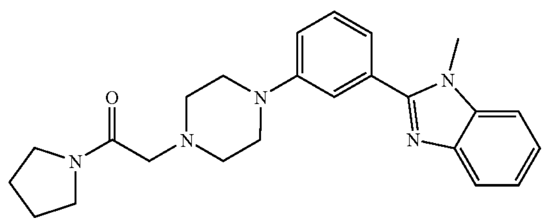 [SMILES: Cn1c(-c2cccc(N3CCN(CC(=O)N4CCCC4)CC3)c2)nc2ccccc21] | U | 404 | 4.96 |
| 358 | 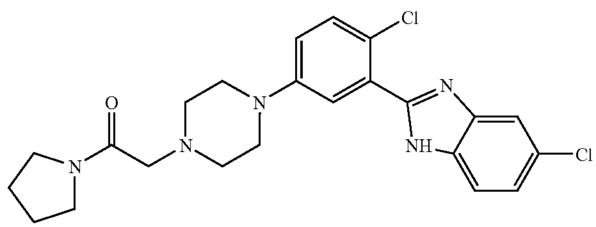 [SMILES: O=C(CN1CCN(c2ccc(Cl)c(-c3nc4cc(Cl)ccc4[nH]3)c2)CC1)N1CCCC1] | U | 458 | 5.57 |
| 359 | 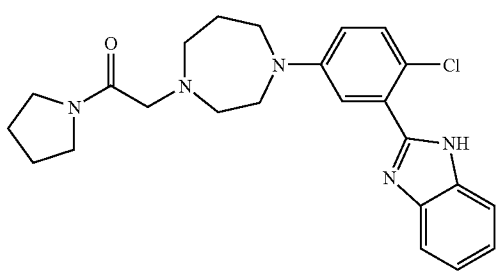 [SMILES: O=C(CN1CCCN(c2ccc(Cl)c(-c3nc4ccccc4[nH]3)c2)CC1)N1CCCC1] | U | 438 | 5.22 |
| 360 | 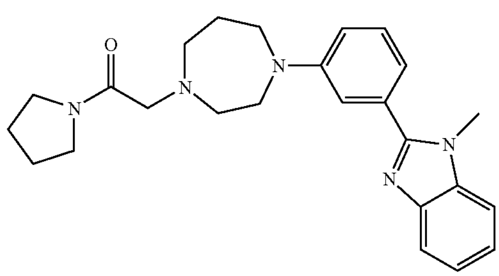 [SMILES: Cn1c(-c2cccc(N3CCCN(CC(=O)N4CCCC4)CC3)c2)nc2ccccc21] | U | 418 | 5.21 |

-continued

| Example | Structure | Method | M + H | Retention Time |
|---|---|---|---|---|
| 361 | 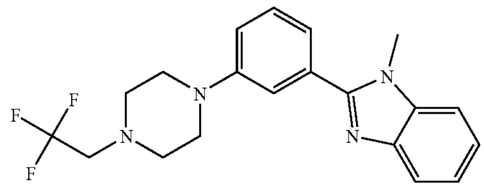 [SMILES: Cn1c(-c2cccc(N3CCN(CC(F)(F)F)CC3)c2)nc2ccccc21] | C | 375 | 6.51 |
| 362 | 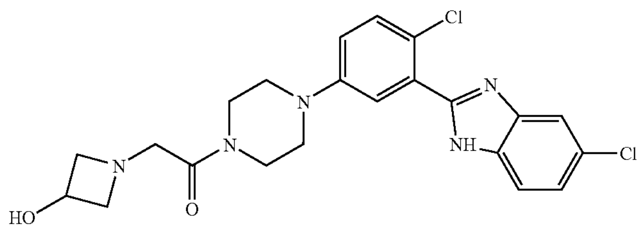 [SMILES: O=C(CN1CC(O)C1)N1CCN(c2ccc(Cl)c(-c3nc4cc(Cl)ccc4[nH]3)c2)CC1] | T | 460 | 4.80 |
| 363 | 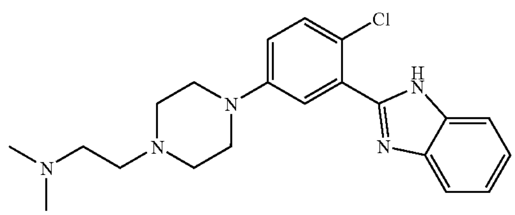 [SMILES: CN(C)CCN1CCN(c2ccc(Cl)c(-c3nc4ccccc4[nH]3)c2)CC1] | A | 384 | 4.12 |
| 364 | 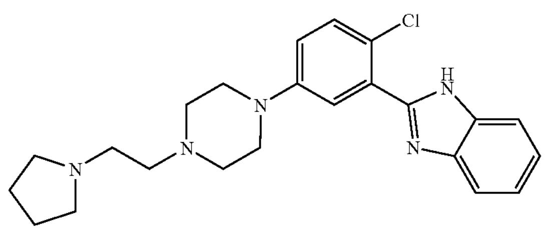 [SMILES: Clc1ccc(N2CCN(CCN3CCCC3)CC2)cc1-c1nc2ccccc2[nH]1] | T | 410 | 4.30 |
| 365 | 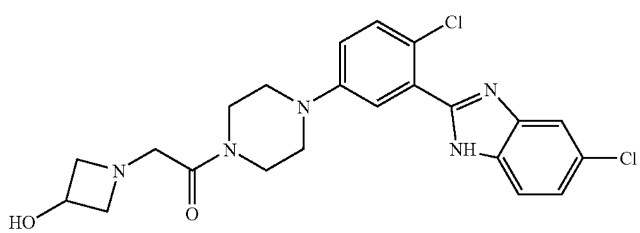 [SMILES: O=C(CN1CC(O)C1)N1CCN(c2ccc(Cl)c(-c3nc4cc(Cl)ccc4[nH]3)c2)CC1] | T | 460 | 4.80 |
| 366 | 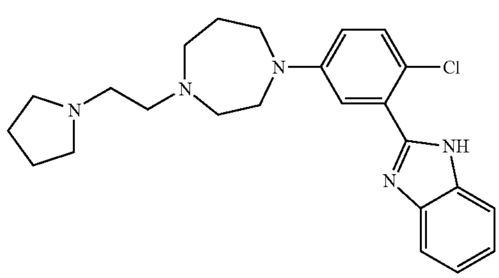 [SMILES: Clc1ccc(N2CCCN(CCN3CCCC3)CC2)cc1-c1nc2ccccc2[nH]1] | T | 424 | 4.63 |

-continued

| Example | Structure | Method | M + H | Retention Time |
|---|---|---|---|---|
| 367 | 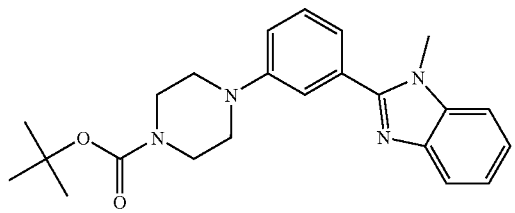 [SMILES: Cn1c(-c2cccc(N3CCN(C(=O)OC(C)(C)C)CC3)c2)nc2ccccc21] | C | 393 | 6.77 |
| 368 | 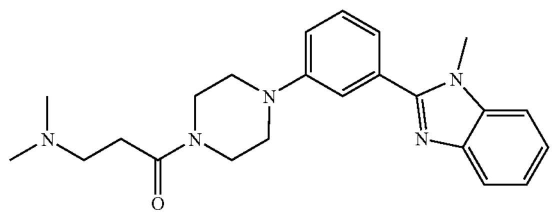 [SMILES: CN(C)CCC(=O)N1CCN(c2cccc(-c3nc4ccccc4n3C)c2)CC1] | C | 391 | 4.03 |
| 369 | 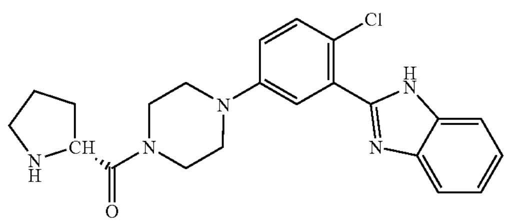 | B | 410 | 4.07 |
| 370 | 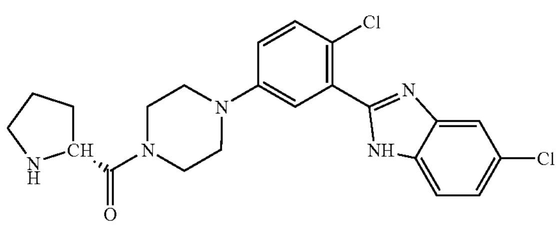 | Q | 444 | 4.54 |
| 371 | 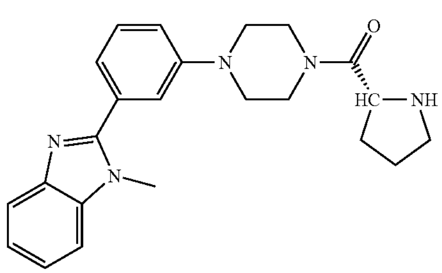 | D | 390 | 4.13 |
| 372 | 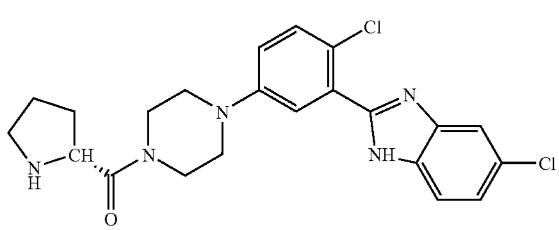 | Q | 444 | 4.54 |

-continued
| Example | Structure | Method | M + H | Retention Time |
|---|---|---|---|---|
| 373 | 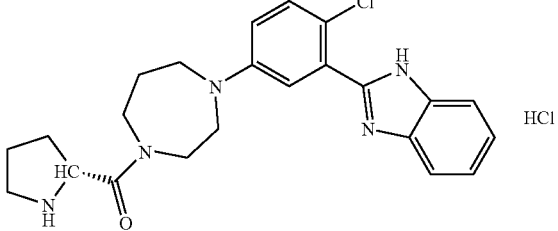 | Q | 424 | 4.24 |
| 374 | 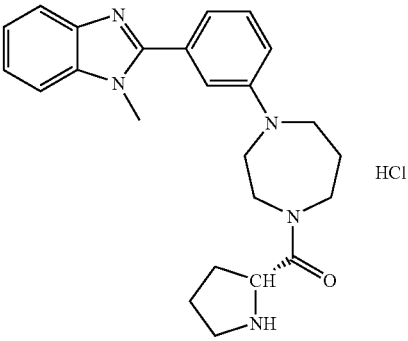 [SMILES: Cn1c(-c2cccc(N3CCCN(C(=O)[C@H]4CCCN4)CC3)c2)nc2ccccc21 ; Cl] | Q | 404 | 4.24 |
| 375 | 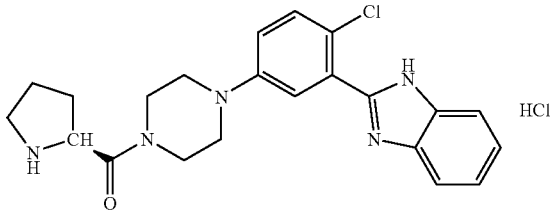 [SMILES: O=C([C@@H]1CCCN1)N1CCN(c2ccc(Cl)c(-c3nc4ccccc4[nH]3)c2)CC1 ; Cl] | D | 410 | 4.01 |
| 376 | 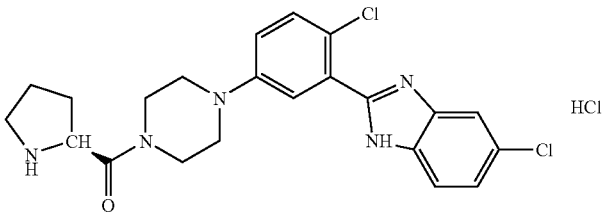 [SMILES: O=C([C@@H]1CCCN1)N1CCN(c2ccc(Cl)c(-c3nc4cc(Cl)ccc4[nH]3)c2)CC1 ; Cl] | Q | 444 | 4.61 |
| 377 | 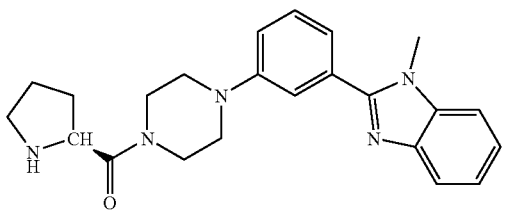 | D | 390 | 1.02 |
| 378 | 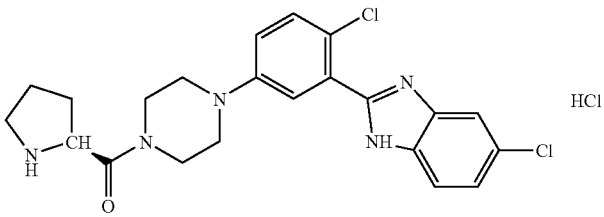 [SMILES: O=C([C@@H]1CCCN1)N1CCN(c2ccc(Cl)c(-c3nc4cc(Cl)ccc4[nH]3)c2)CC1 ; Cl] | Q | 444 | 4.61 |

-continued

| Example | Structure | Method | M + H | Retention Time |
|---|---|---|---|---|
| 379 | 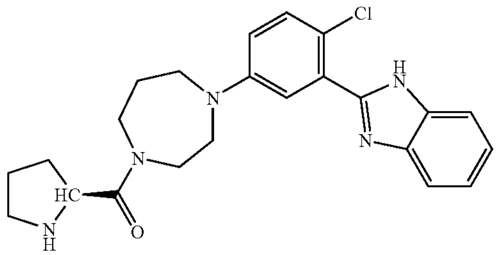 | Q | 424 | 4.19 |
| 380 | 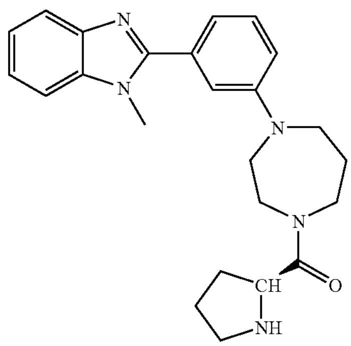 | Q | 404 | 4.25 |
| 381 | 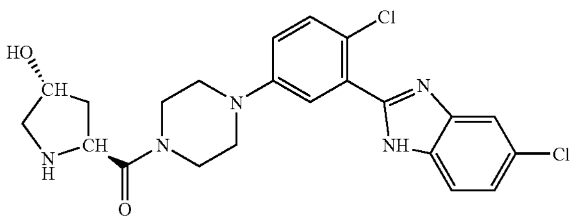 | Q | 460 | 4.45 |
| 382 | 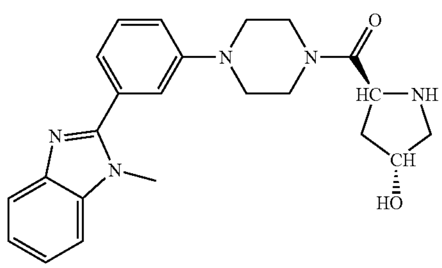 | D | 406 | 3.96 |
| 383 | 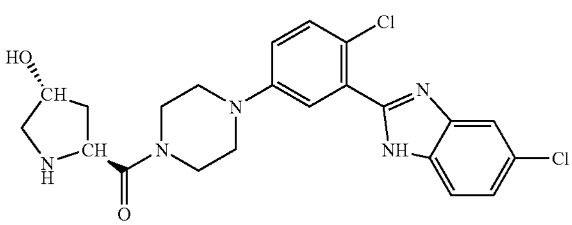 | Q | 460 | 4.45 |
| 384 | 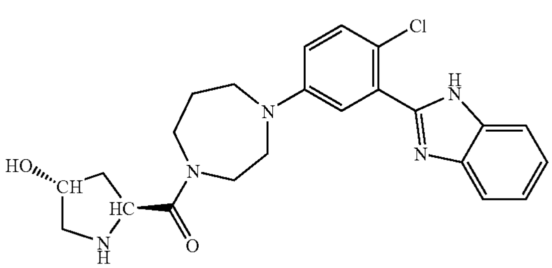 | Q | 440 | 4.07 |

| Example | Structure | Method | M + H | Retention Time |
|---|---|---|---|---|
| 385 | 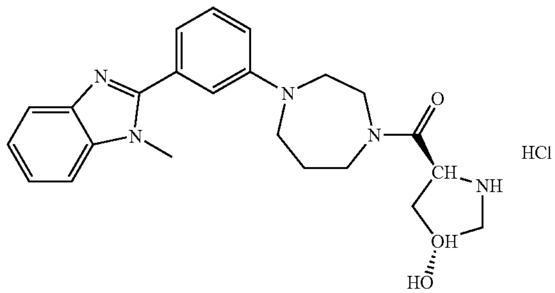 | Q | 420 | 4.06 |
| 386 | 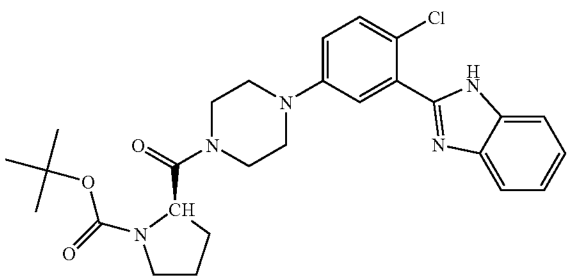 [SMILES: CC(C)(C)OC(=O)N1CCC[C@@H]1C(=O)N1CCN(c2ccc(Cl)c(-c3nc4ccccc4[nH]3)c2)CC1] | D | 510 | 5.88 |
| 387 | 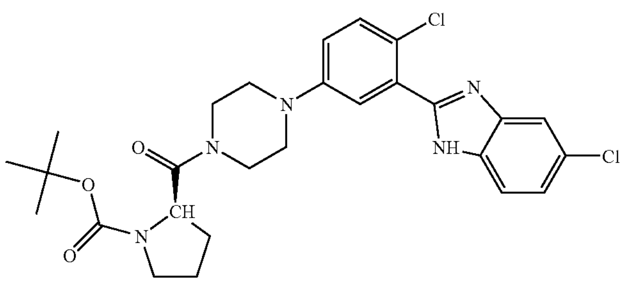 [SMILES: CC(C)(C)OC(=O)N1CCC[C@@H]1C(=O)N1CCN(c2ccc(Cl)c(-c3nc4cc(Cl)ccc4[nH]3)c2)CC1] | Q | 544 | 6.45 |
| 388 | 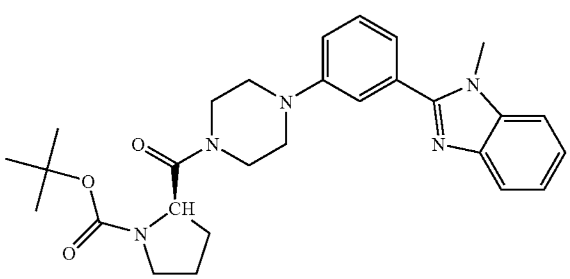 [SMILES: Cn1c(-c2cccc(N3CCN(C(=O)[C@H]4CCCN4C(=O)OC(C)(C)C)CC3)c2)nc2ccccc21] | D | 490 | 5.85 |
| 389 | 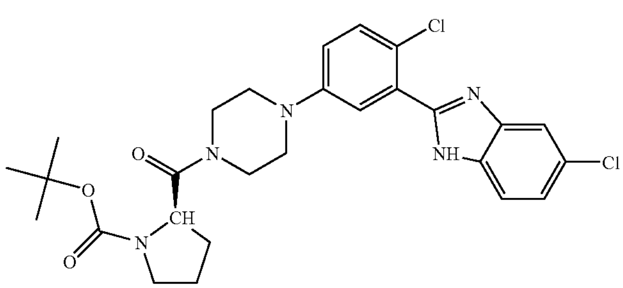 [SMILES: CC(C)(C)OC(=O)N1CCC[C@@H]1C(=O)N1CCN(c2ccc(Cl)c(-c3nc4cc(Cl)ccc4[nH]3)c2)CC1] | Q | 544 | 6.45 |

-continued

| Example | Structure | Method | M + H | Retention Time |
|---|---|---|---|---|
| 390 | 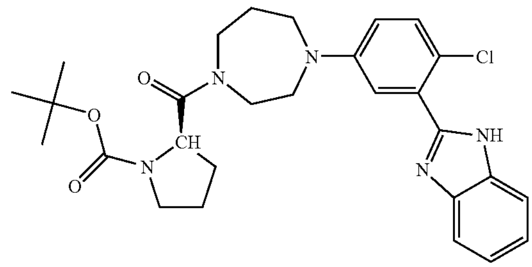 [SMILES: CC(C)(C)OC(=O)N1CCC[C@@H]1C(=O)N1CCCN(c2ccc(Cl)c(-c3nc4ccccc4[nH]3)c2)CC1] | Q | 524 | 6.04 |
| 391 | 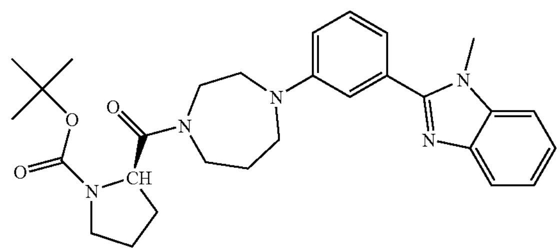 | Q | 504 | 6.04 |
| 392 | 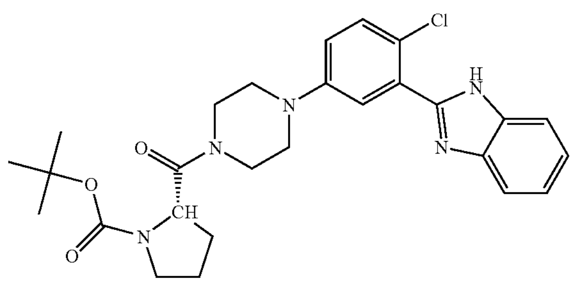 [SMILES: CC(C)(C)OC(=O)N1CCC[C@H]1C(=O)N1CCN(c2ccc(Cl)c(-c3nc4ccccc4[nH]3)c2)CC1] | D | 510 | 5.86 |
| 393 | 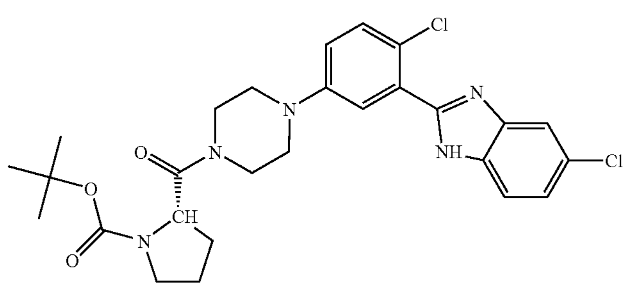 [SMILES: CC(C)(C)OC(=O)N1CCC[C@H]1C(=O)N1CCN(c2ccc(Cl)c(-c3nc4cc(Cl)ccc4[nH]3)c2)CC1] | Q | 544 | 6.46 |
| 394 | 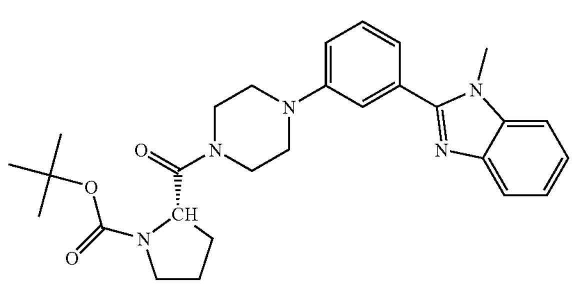 [SMILES: Cn1c(-c2cccc(N3CCN(C(=O)[C@@H]4CCCN4C(=O)OC(C)(C)C)CC3)c2)nc2ccccc21] | D | 490 | 5.84 |

| Example | Structure | Method | M + H | Retention Time |
|---|---|---|---|---|
| 395 | 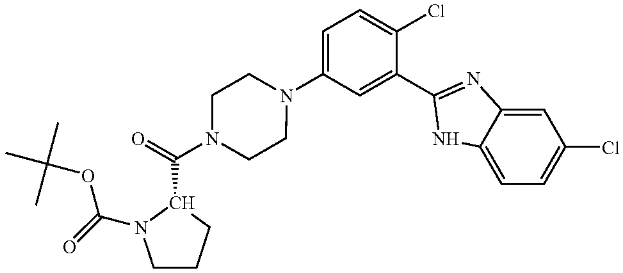 [SMILES: CC(C)(C)OC(=O)N1CCC[C@H]1C(=O)N1CCN(c2ccc(Cl)c(-c3nc4cc(Cl)ccc4[nH]3)c2)CC1] | Q | 544 | 6.46 |
| 396 | 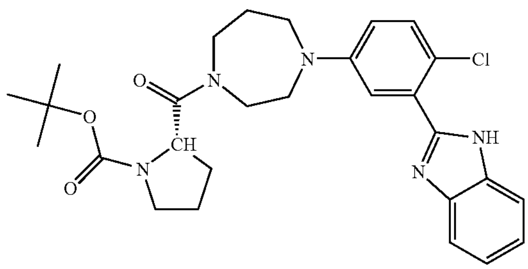 [SMILES: CC(C)(C)OC(=O)N1CCC[C@H]1C(=O)N1CCCN(c2ccc(Cl)c(-c3nc4ccccc4[nH]3)c2)CC1] | Q | 524 | 6.03 |
| 397 | 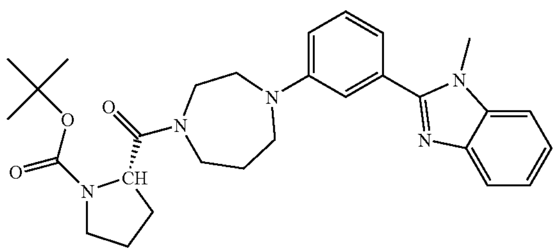 [SMILES: Cn1c(-c2cccc(N3CCCN(C(=O)[C@@H]4CCCN4C(=O)OC(C)(C)C)CC3)c2)nc2ccccc21] | Q | 504 | 6.04 |
| 398 | 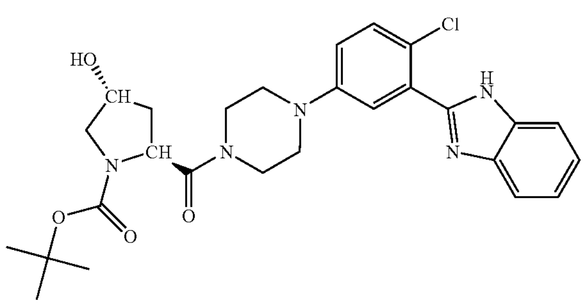 [SMILES: CC(C)(C)OC(=O)N1C[C@H](O)C[C@H]1C(=O)N1CCN(c2ccc(Cl)c(-c3nc4ccccc4[nH]3)c2)CC1] | D | 526 | 4.95 |
| 399 | 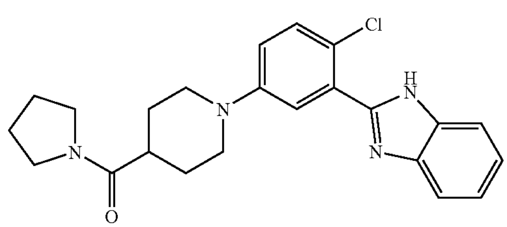 [SMILES: O=C(C1CCN(c2ccc(Cl)c(-c3nc4ccccc4[nH]3)c2)CC1)N1CCCC1] | Y | 409 | 5.50 |
| 400 | 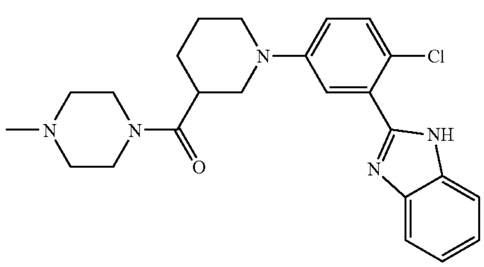 [SMILES: CN1CCN(C(=O)C2CCCN(c3ccc(Cl)c(-c4nc5ccccc5[nH]4)c3)C2)CC1] | Y | 438 | 4.89 |

-continued

| Example | Structure | Method | M + H | Retention Time |
|---|---|---|---|---|
| 401 | 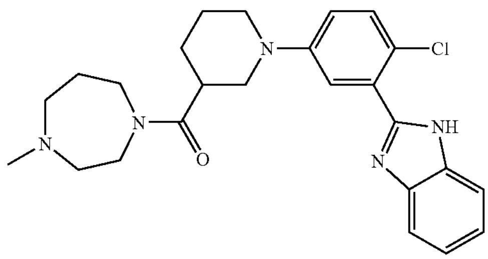 [SMILES: CN1CCCN(C(=O)C2CCCN(c3ccc(Cl)c(-c4nc5ccccc5[nH]4)c3)C2)CC1] | Y | 450 | 4.49 |
| 402 | 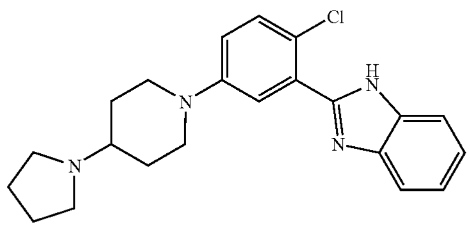 [SMILES: Clc1ccc(N2CCC(N3CCCC3)CC2)cc1-c1nc2ccccc2[nH]1] | A | 381 | 4.65 |
| 403 | 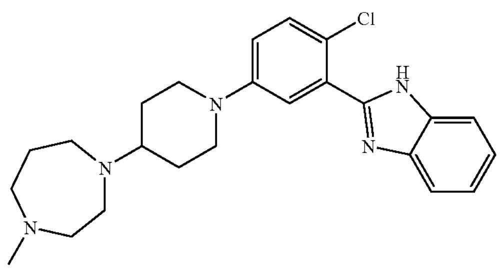 [SMILES: CN1CCCN(C2CCN(c3ccc(Cl)c(-c4nc5ccccc5[nH]4)c3)CC2)CC1] | OA | 424 | 4.38 |
| 404 | 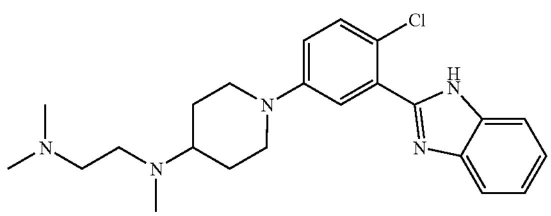 [SMILES: CN(C)CCN(C)C1CCN(c2ccc(Cl)c(-c3nc4ccccc4[nH]3)c2)CC1] | OA | 412 | 4.49 |
| 405 | 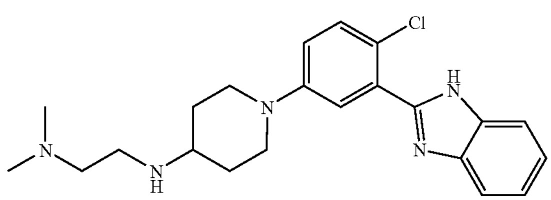 [SMILES: CN(C)CCNC1CCN(c2ccc(Cl)c(-c3nc4ccccc4[nH]3)c2)CC1] | OA | 398 | 4.38 |
| 406 | 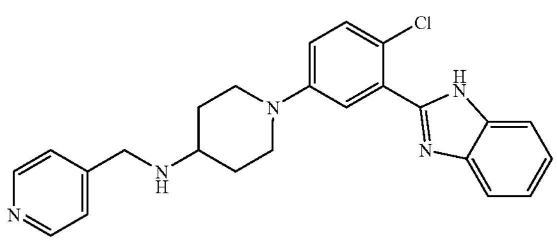 [SMILES: Clc1ccc(N2CCC(NCc3ccncc3)CC2)cc1-c1nc2ccccc2[nH]1] | OA | 418 | 4.69 |

-continued

| Example | Structure | Method | M + H | Retention Time |
|---|---|---|---|---|
| 407 | 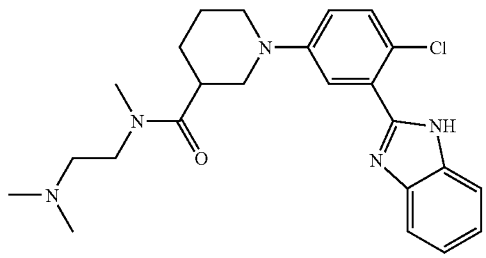 [SMILES: CN(C)CCN(C)C(=O)C1CCCN(c2ccc(Cl)c(-c3nc4ccccc4[nH]3)c2)C1] | Y | 440 | 4.49 |
| 408 | 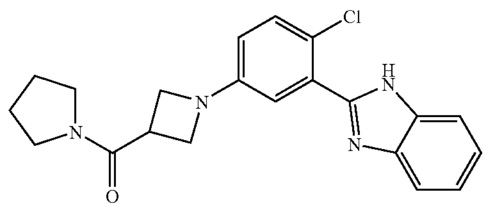 [SMILES: O=C(C1CN(c2ccc(Cl)c(-c3nc4ccccc4[nH]3)c2)C1)N1CCCC1] | Y | 381 | 5.14 |
| 409 | 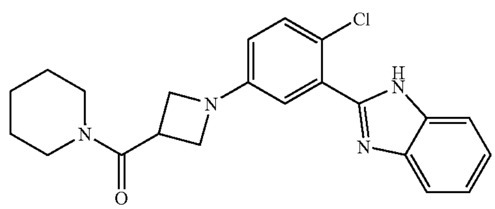 [SMILES: O=C(C1CN(c2ccc(Cl)c(-c3nc4ccccc4[nH]3)c2)C1)N1CCCCC1] | Y | 395 | 5.72 |
| 410 | 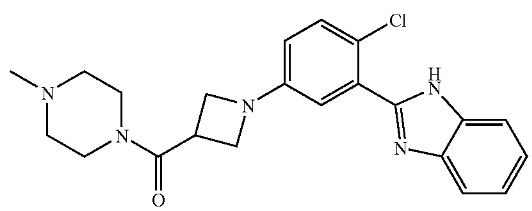 [SMILES: CN1CCN(C(=O)C2CN(c3ccc(Cl)c(-c4nc5ccccc5[nH]4)c3)C2)CC1] | Y | 410 | 4.40 |
| 411 | 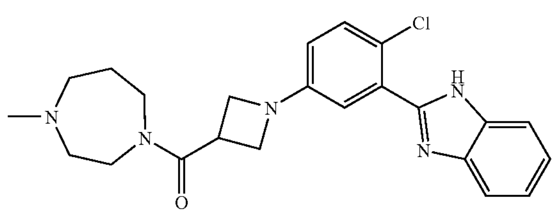 [SMILES: CN1CCCN(C(=O)C2CN(c3ccc(Cl)c(-c4nc5ccccc5[nH]4)c3)C2)CC1] | Y | 424 | 4.13 |
| 412 | 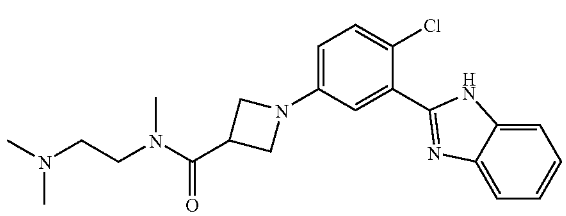 [SMILES: CN(C)CCN(C)C(=O)C1CN(c2ccc(Cl)c(-c3nc4ccccc4[nH]3)c2)C1] | Y | 412 | 4.10 |
| 413 | 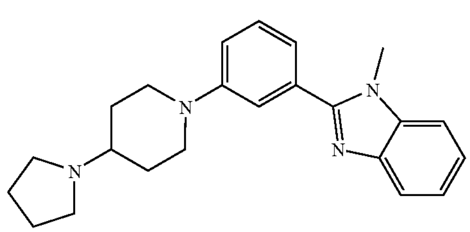 [SMILES: Cn1c(-c2cccc(N3CCC(N4CCCC4)CC3)c2)nc2ccccc21] | OA | 361 | 4.29 |

-continued

| Example | Structure | Method | M + H | Retention Time |
|---|---|---|---|---|
| 414 | 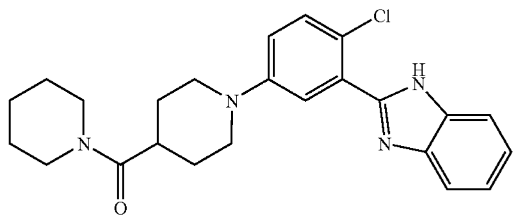 [SMILES: O=C(C1CCN(c2ccc(Cl)c(-c3nc4ccccc4[nH]3)c2)CC1)N1CCCCC1] | Y | 423 | 6.05 |
| 415 | 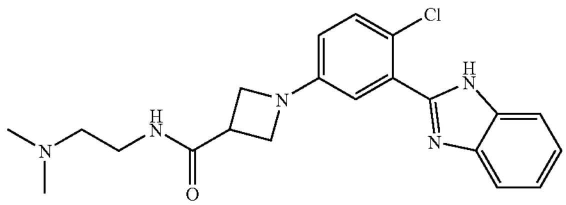 [SMILES: CN(C)CCNC(=O)C1CN(c2ccc(Cl)c(-c3nc4ccccc4[nH]3)c2)C1] | Y | 398 | 3.96 |
| 416 | 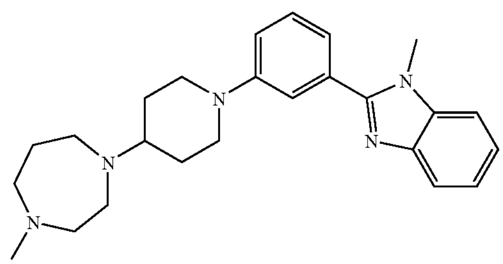 [SMILES: CN1CCCN(C2CCN(c3cccc(-c4nc5ccccc5n4C)c3)CC2)CC1] | OA | 404 | 4.25 |
| 417 | 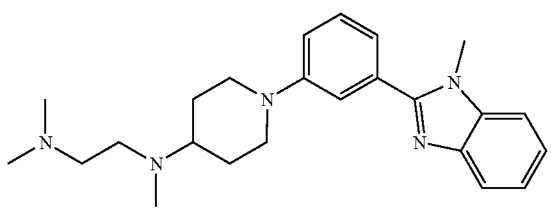 [SMILES: CN(C)CCN(C)C1CCN(c2cccc(-c3nc4ccccc4n3C)c2)CC1] | OA | 392 | 4.35 |
| 418 | 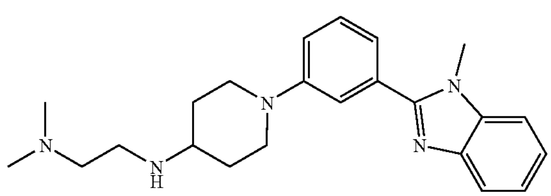 [SMILES: CN(C)CCNC1CCN(c2cccc(-c3nc4ccccc4n3C)c2)CC1] | OA | 378 | 4.12 |
| 419 | 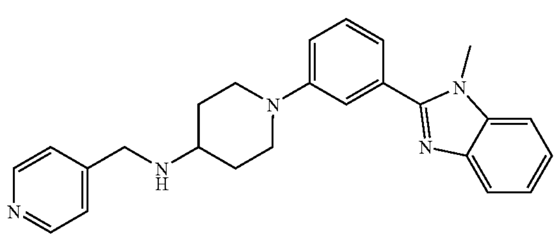 [SMILES: Cn1c(-c2cccc(N3CCC(NCc4ccncc4)CC3)c2)nc2ccccc21] | OA | 398 | 4.54 |
| 420 | 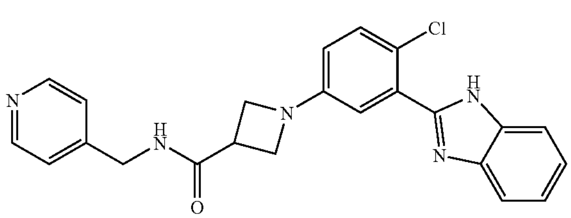 [SMILES: O=C(NCc1ccncc1)C1CN(c2ccc(Cl)c(-c3nc4ccccc4[nH]3)c2)C1] | Y | 418 | 4.53 |

-continued

| Example | Structure | Method | M + H | Retention Time |
|---|---|---|---|---|
| 421 | 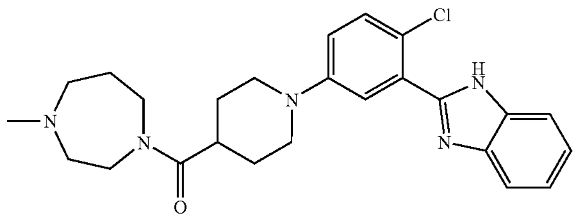 [SMILES: CN1CCCN(C(=O)C2CCN(c3ccc(Cl)c(-c4nc5ccccc5[nH]4)c3)CC2)CC1] | Y | 452 | 4.43 |
| 422 | 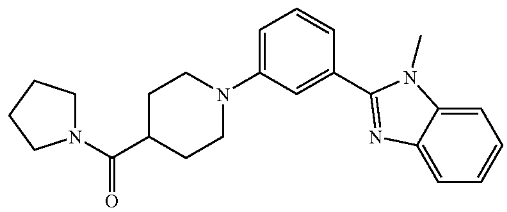 [SMILES: Cn1c(-c2cccc(N3CCC(C(=O)N4CCCC4)CC3)c2)nc2ccccc21] | X | 389 | 5.26 |
| 423 | 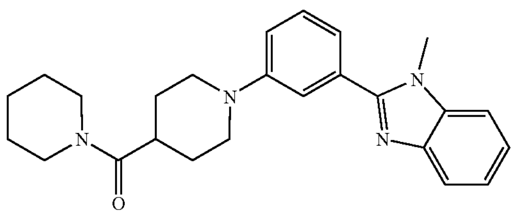 [SMILES: Cn1c(-c2cccc(N3CCC(C(=O)N4CCCCC4)CC3)c2)nc2ccccc21] | X | 403 | 5.85 |
| 424 | 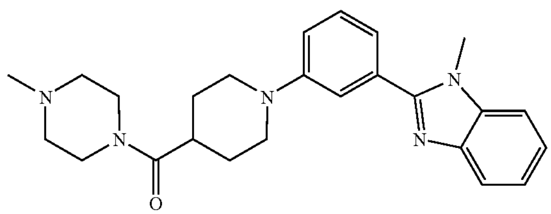 | X | 418 | 4.52 |
| 425 | 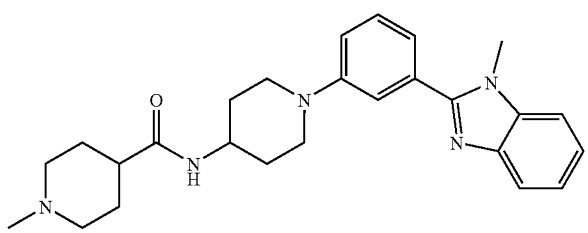 [SMILES: CN1CCC(C(=O)NC2CCN(c3cccc(-c4nc5ccccc5n4C)c3)CC2)CC1] | N | 432 | 4.42 |
| 426 | 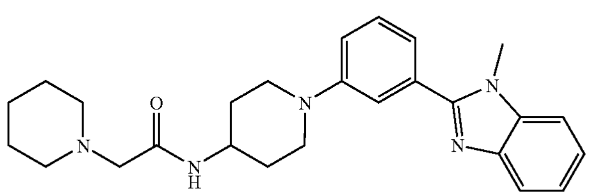 [SMILES: Cn1c(-c2cccc(N3CCC(NC(=O)CN4CCCCC4)CC3)c2)nc2ccccc21] | N | 432 | 4.44 |
| 427 | 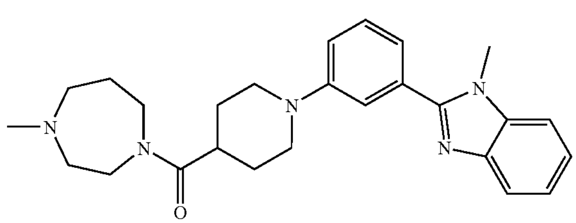 [SMILES: CN1CCCN(C(=O)C2CCN(c3cccc(-c4nc5ccccc5n4C)c3)CC2)CC1] | X | 432 | 4.26 |

-continued

| Example | Structure | Method | M + H | Retention Time |
|---|---|---|---|---|
| 428 | 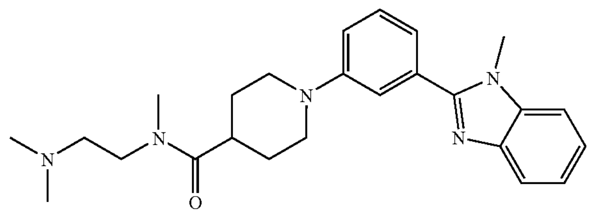 [SMILES: CN(C)CCN(C)C(=O)C1CCN(c2cccc(-c3nc4ccccc4n3C)c2)CC1] | X | 420 | 4.27 |
| 429 | 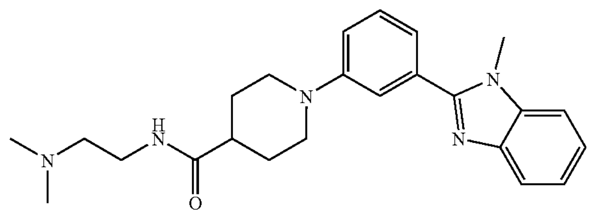 [SMILES: CN(C)CCNC(=O)C1CCN(c2cccc(-c3nc4ccccc4n3C)c2)CC1] | X | 406 | 4.08 |
| 430 | 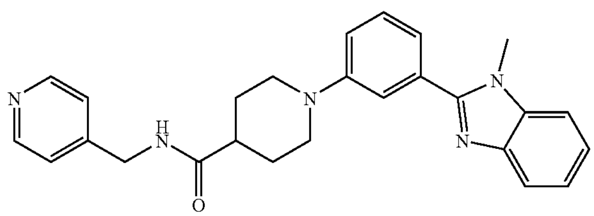 [SMILES: Cn1c(-c2cccc(N3CCC(C(=O)NCc4ccncc4)CC3)c2)nc2ccccc21] | X | 426 | 4.65 |
| 431 | 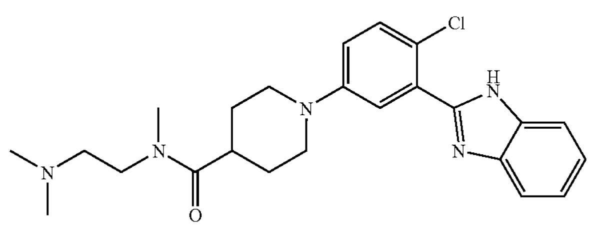 [SMILES: CN(C)CCN(C)C(=O)C1CCN(c2ccc(Cl)c(-c3nc4ccccc4[nH]3)c2)CC1] | Y | 440 | 4.50 |
| 432 | 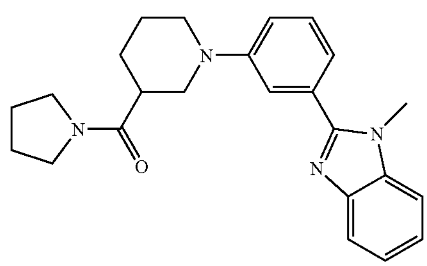 [SMILES: Cn1c(-c2cccc(N3CCCC(C(=O)N4CCCC4)C3)c2)nc2ccccc21] | X | 389 | 5.48 |
| 433 | 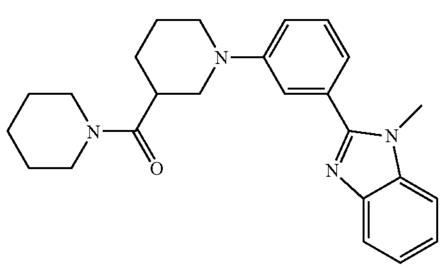 [SMILES: Cn1c(-c2cccc(N3CCCC(C(=O)N4CCCCC4)C3)c2)nc2ccccc21] | X | 403 | 6.09 |

-continued

| Example | Structure | Method | M + H | Retention Time |
|---|---|---|---|---|
| 434 | 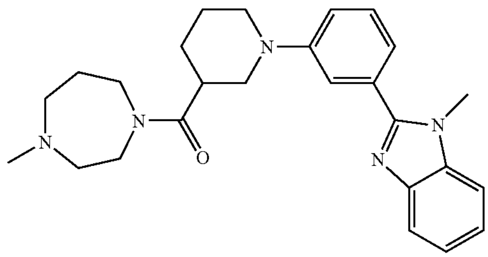 [SMILES: CN1CCCN(C(=O)C2CCCN(c3cccc(-c4nc5ccccc5n4C)c3)C2)CC1] | X | 432 | 4.83 |
| 435 | 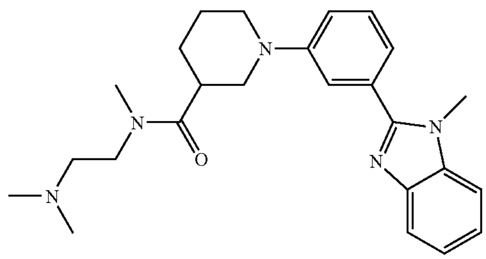 [SMILES: CN(C)CCN(C)C(=O)C1CCCN(c2cccc(-c3nc4ccccc4n3C)c2)C1] | X | 420 | 4.89 |
| 436 | 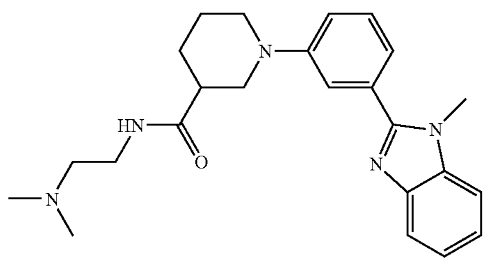 [SMILES: CN(C)CCNC(=O)C1CCCN(c2cccc(-c3nc4ccccc4n3C)c2)C1] | X | 406 | 4.75 |
| 437 | 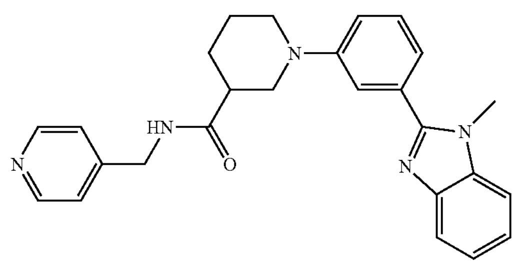 [SMILES: Cn1c(-c2cccc(N3CCCC(C(=O)NCc4ccncc4)C3)c2)nc2ccccc21] | X | 426 | 4.91 |
| 438 | 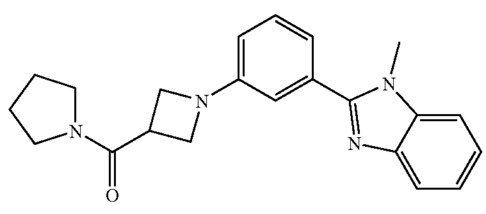 [SMILES: Cn1c(-c2cccc(N3CC(C(=O)N4CCCC4)C3)c2)nc2ccccc21] | X | 361 | 5.33 |
| 439 | 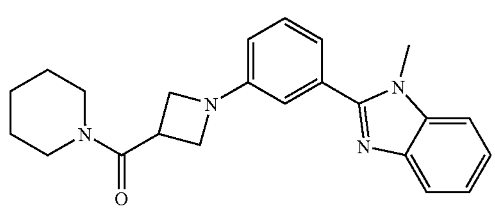 [SMILES: Cn1c(-c2cccc(N3CC(C(=O)N4CCCCC4)C3)c2)nc2ccccc21] | X | 375 | 5.84 |

-continued

| Example | Structure | Method | M + H | Retention Time |
|---|---|---|---|---|
| 440 | 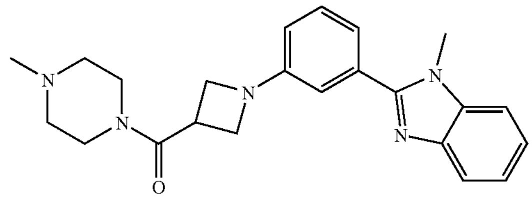 [SMILES: CN1CCN(C(=O)C2CN(c3cccc(-c4nc5ccccc5n4C)c3)C2)CC1] | X | 390 | 4.50 |
| 441 | 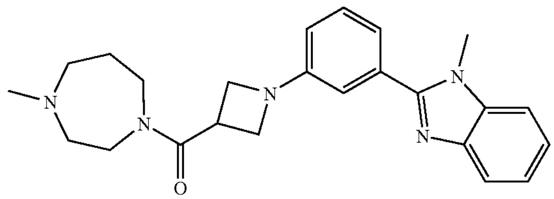 [SMILES: CN1CCCN(C(=O)C2CN(c3cccc(-c4nc5ccccc5n4C)c3)C2)CC1] | X | 404 | 4.27 |
| 442 | 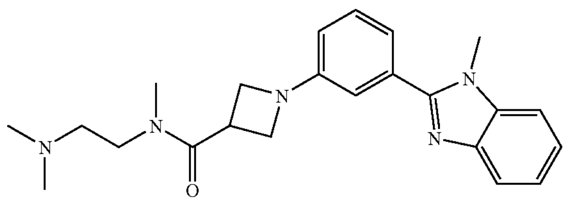 [SMILES: CN(C)CCN(C)C(=O)C1CN(c2cccc(-c3nc4ccccc4n3C)c2)C1] | X | 392 | 4.16 |
| 443 | 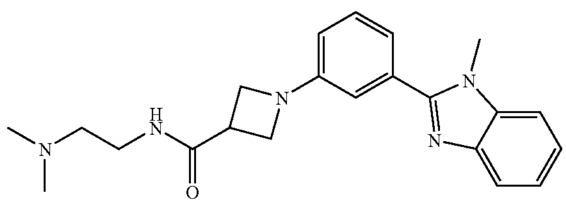 [SMILES: CN(C)CCNC(=O)C1CN(c2cccc(-c3nc4ccccc4n3C)c2)C1] | X | 378 | 3.96 |
| 444 | 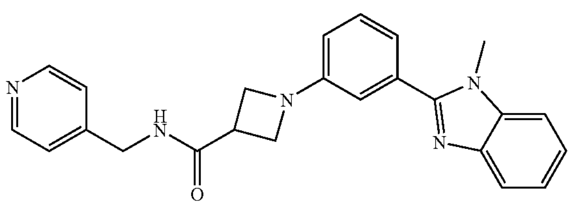 [SMILES: Cn1c(-c2cccc(N3CC(C(=O)NCc4ccncc4)C3)c2)nc2ccccc21] | X | 397 | 4.67 |
| 445 | 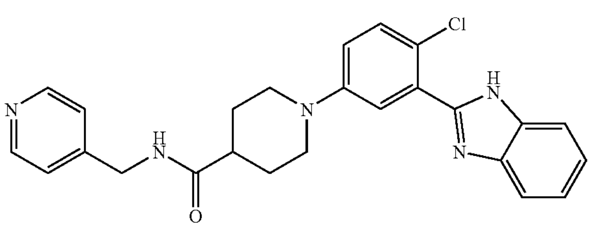 [SMILES: O=C(NCc1ccncc1)C1CCN(c2ccc(Cl)c(-c3nc4ccccc4[nH]3)c2)CC1] | Y | 446 | 5.13 |
| 446 | 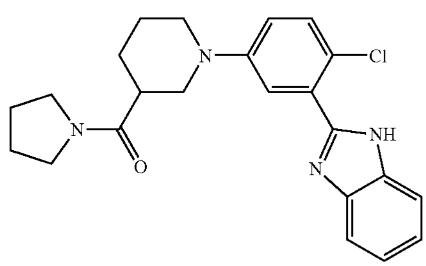 [SMILES: O=C(C1CCCN(c2ccc(Cl)c(-c3nc4ccccc4[nH]3)c2)C1)N1CCCC1] | Y | 409 | 5.67 |

| Example | Structure | Method | M + H | Retention Time |
|---|---|---|---|---|
| 447 | 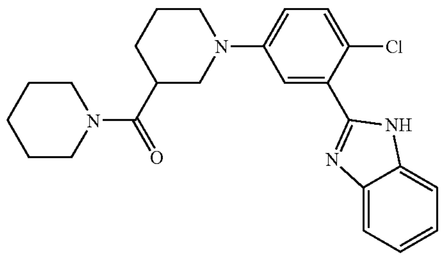 [SMILES: O=C(C1CCCN(c2ccc(Cl)c(-c3nc4ccccc4[nH]3)c2)C1)N1CCCCC1] | Y | 423 | 6.26 |
| 448 | 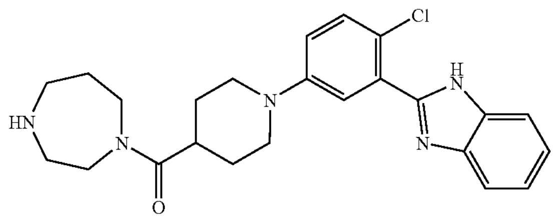 [SMILES: O=C(C1CCN(c2ccc(Cl)c(-c3nc4ccccc4[nH]3)c2)CC1)N1CCCNCC1] | S | 483 | 4.54 |
| 449 | 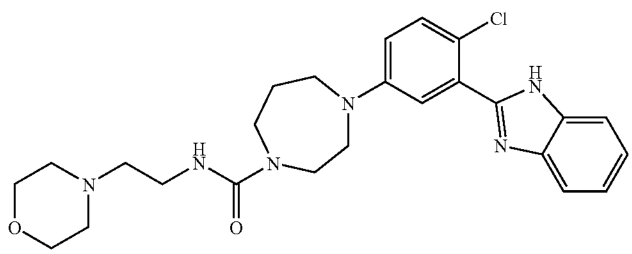 [SMILES: O=C(NCCN1CCOCC1)N1CCCN(c2ccc(Cl)c(-c3nc4ccccc4[nH]3)c2)CC1] | Z | 439 | 4.09 |

Biological Activity

Cloning of Smo and Generation of Stable Recombinant Smo Expressing Cell Lines

The human Smo coding sequence was amplified by PCR using standard conditions. The template was pCMV6-XL5-Smo from Origene (cat. TC122724). The primers were designed as follows:

Forward (5' GATCGGTACCGGGCTTTTGCTGAGTT 3') has a KpnI restriction site;

Reverse (5' GATCGCGGCCGCCTACTTATCGTCGT-CATCCTTG TAATCGAAGTCCGAGTCTGC 3') has a NotI restriction site, a stop codon and a FLAG-coding sequence at the 5' end.

The obtained amplicon was 2424 bp long and contained the complete Smo-coding sequence, a FLAG-tag and two restriction sites, one at each end. The amplicon was double-digested with KpnI and NotI restriction enzymes, as well as pcDNA5/FRT plasmid (Invitrogen) chosen for cloning. The ligation and cloning of the Smo-FLAG coding sequence into the pcDNA5/FRT plasmid produced a plasmid that was named pcDNA5/FRT Smo-FLAG and that was 7432 bp long.

The FlpIN technique (Invitrogen) was used to create the stable expressing Smo-FLAG cell line using the FlpIN293 cell line (Invitrogen, RT50-07). This is a line derived from HEK293 cells by stable transfection with pFRT/lacZeo plasmid to generate the zeocin-resistant FlpIN293 host cell line. FlpIN293 cells are suitable to create a stable mammalian cell line containing an integrated Flp Recombinant Target (FRT) site (Invitrogen).

Transfection with pcDNA5/FRT_Smo-FLAG plasmid (or, in the case of the mock transfected cells, transfection with the empty plasmid) was made together with transfection of pOG44 plasmid, carrying the Flp recombinase, that catalyzed a homologous recombination between the FRT site in the host cells and the pcDNA5/FRT_Smo-FLAG expression vector or the pcDNA5/FRT empty vector respectively. Smo-FLAG expressing cells as well as mock transfected cells possess hygromycin B resistance and are negative to β-gal staining. The expression of Smo and FLAG antigens was checked also by western blot. The two cell lines generated were named 293FlpIN/clone E-3 indicating the mock transfected and 293FlpIN/clone 3-5 indicating the Smo-FLAG transfected cell line.

Cell Cultures Conditions

Cells were maintained in DMEM containing 10% foetal bovine serum (both from Invitrogen), with addition of 0.25 mg/ml hygromycin B (Invitrogen). Cells were maintained at 37° C. in a 95% air-5% carbon dioxide fully humidified environment, and used up to 22-25 cycles after thawing.

Binding Assay Development

The interaction of compounds with the Smo receptor was tested by a displacement binding assay using fluorescent ligand for the Smo receptor (Bodipy-Cyclopamine, Toronto Research Chemical Inc, cat#B674800) as the labeled ligand to be displaced.

In order to determine the Kd (concentration of the ligand where 50% of the maximal binding is reached) and the Bmax (maximal amount of ligand which can bind specifically to the receptor in a biological preparation) of the fluorescent ligand, the Specific Binding (SB) was calculated by subtraction Non Specific Binding (NSB) from Total Binding (TB). The TB was determined by adding increasing concentration of Bodipy-Cyclopamine to the cells, while the NSB was determined by adding a mixture of increasing concentration of Bodipy-Cyclopamine with a saturating concentration of an well described antagonist (in this case, N-[3-(1H-benzimidazol-2-yl)-4-chlorophenyl]-3,5-dimethoxy-benzamide (Rubin et al. WO2003011219) at 10 µM was selected) to the cells. For each concentration of Bodipy-Cyclopamine, the SB was calculated by subtracting the value of NSB from TB. From the SB curve Bmax and Kd were calculated. In this case, the stable mock transfected cell line clone E-3 was found to have a Kd of 115 nM, while the stable Smo-FLAG transfected cell line clone 3-5 was found to have a Kd of 44.3 nM. The Ki is the concentration of non labeled ligand which inhibits 50% of the specific binding (SB) of the labeled ligand, and corrected for the effective used concentration of the labeled ligand. Ki was calculated following the Cheng-Prusoff equation, as $K_i = IC_{50}/[1+[bodipy-cyclopamine]/Kd)]$.

Testing Compounds with the Binding Assay

293FlpIN/clone E-3 and 293FlpIN/clone 3-5 cells were counted with a Burker chamber and 100000 cells/1000 DMEM 1% FBS were transferred in two 96 well plates (U bottom, Sigma Aldrich, cat#M8185-100EA). 293FlpIN/clone E-3 cells were used as internal control to check Smo over-expressing 293FlpIN/clone 3-5 cells fluorescence (FLU) variation in time.

Controls and compounds were prepared in DMEM 1% FBS and 100 µl were added to the cells. All the controls and compounds were incubated with a final concentration of 5 nM Bodipy-Cyclopamine.

Compounds were dissolved in DMSO (stock 10 mM), and were tested first at 10 µM (single concentration assay); each compound was repeated at least twice (in two different plates). When Bodipy-Cyclopamine was displaced above a 30% threshold the compound was re-tested with a concentration-response assay with a throughput of 8 compounds per plate and the concentration range was: 100, 10, 1, 0.5, 0.1, 0.01, 0.05, 0.001 and 0.0001 µM.

As negative control 293FlpIN/clone 3-5 cells were used in which DMSO was added diluted 1:1000 for single concentration assay and 1:100 for concentration response assay.

As positive control to completely displace Bodipy-Cyclopamine binding, N-[3-(1H-benzimidazol-2-yl)-4-chlorophenyl]-3,5-dimethoxy-benzamide (Rubin et al. WO2003011219) was used at a concentration of 10 µM.

The two plates were incubated 4 hours at room temperature protected from light on a rocking platform. After incubation plates were centrifuged for 5 min. at 1600 rpm and washed twice with PBS containing 2% FBS. Cells were finally re-suspended in 170 µl of washing buffer and fluorescent signals were acquired with FACScalibur HTS system (Becton Dickinson).

Instrument acquisition parameters were set at the beginning of the reading of each plate using untreated non-labeled 293FlpIN/clone E-3 cells. The HTS acquisition program used was BD™ Plate Manager (BD Bioscience) and data analysis was performed using BD CellQuest™ Pro software (BD Bioscience).

Quantification was made by overlaying the FL1-H histograms of the positive and negative controls and setting a marker at the intersection between the two curves. Only those events more fluorescent than the set marker were quantified. Values were then normalized according to the negative control (0% Bodipy-Cyclopamine displacement) and the positive control (100% Bodipy-Cyclopamine displacement).

Compounds from examples 1-449 when tested in the above conditions, all display a $K_i$ value ranging between 83 µM and 31 µM.

Testing Compounds with an Alkaline Phosphatase Assay

Shh has been demonstrated in vitro to induce alkaline phosphatase (AP), a marker of osteoblast differentiation, in the mouse mesenchymal cell line $C_3H_{10}T1/2$ (Katsuura et al., 1999; Kinto et al., 1997; Murone et al., 1999; Nakamura et al., 1997, Wu et al. 2004. Therefore and to analyse interference of small molecules with Hedgehog-Gli signaling a functional assay based on activation of AP in this mouse cell line was implemented. The substrate of the AttoPhos® kit (Cat S1000, Promega) was used to detect AP in solution. Briefly, the following procedure was applied.

Polylysine-coated clear, flat bottomed 96-well plates (Corning, Cat. 3667) were filled with 10.000 cells in 100 µl of cell culture solution per well. Cell culture medium consisted of DMEM (Cat 21969-035) with 1% Glutamax (Cat 35050-038), 1% Penicillin/Streptomycin (Cat 15140-122) and 1% Hepes (15630-056). All reagents were obtained from Invitrogen. The plates were incubated overnight at 37° C. with 5% carbon dioxide. Then medium was removed, and 100 µl of fresh medium containing either compound or reference antagonist (N-[3-(1H-benzimidazol-2-yl)-4-chlorophenyl]-3,5-dimethoxy-benzamide (Rubin et al. WO2003011219)) was added to the wells. All compound and reference solutions contained the agonist purmorphamine (Sinha et al. Nature Chem. Biol. 2, 29-30 (2005)) at a concentration of 2 µM. Compounds were tested at ten concentrations in triplicates in the range between 100 pM and 50 µM. The final DMSO concentration in each sample was adjusted to 1% in culture medium. Cells were incubated with compound solution for 72 hours at 37° C. in the presence of 5% carbon dioxide. Cell culture medium was removed from the plates, and 40 µl of a 1:5 diluted lysis solution (Cat E194A, Promega) was added to each well. Plates were then incubated in the dark for 20 minutes on a shaker. Finally, 40 µl of reconstituted AttoPhos substrate solution was added to the wells, followed by another incubation period of 15 minutes on a shaker. The AttoPhos substrate was reconstituted according to the instructions of the supplier but substrate solution was always stored at −80° C. The Safire 2 plate reader (Tecan) was used for measurement of changes in fluorescence intensity in the samples, with an excitation wavelength of 430 nm and an emission wavelength of 560 nm.

Compounds from examples 1-449 when tested in the above conditions, all display an $IC_{50}$ value ranging between 26 pM and 42 µM.

The invention claimed is:

1. Compounds of formula (Ia)

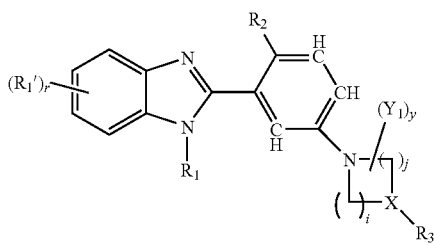

(Ia)

wherein X can be either N or CH:
when X is N, R$_3$ is

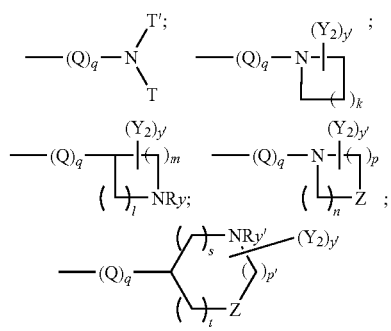

and
q is 1,
when x is CH, R$_3$ is a)

b)

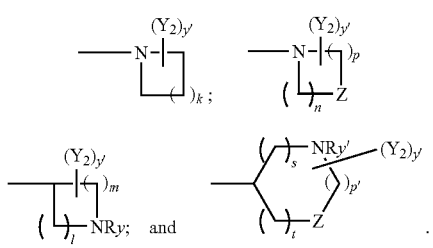

R$_1$ is H; linear, branched or cyclic (C$_1$-C$_4$) alkyl, group optionally substituted with one or more halogen, a branched or linear (C$_1$-C$_4$)alkoxy or a mono- or di-linear branched or cyclic (C$_1$-C$_6$)alkylamino group;

r equals 0, 1, 2 or 3;

R$_1$' represents, independently from one another when r>1, halogen; linear, branched or cyclic (C1-C4) alkoxy group; linear, branched or cyclic (C$_1$-C$_4$) alkyl optionally substituted with linear or branched (C$_1$-C$_4$)alkoxy, alkylamino, or dialkylamino group;

R$_2$ is H, Cl, F or Br;

i and j are 1, 2 or 3, the sum i+j cannot exceed 5, and when X is N then i and j cannot be 1

Q is such that no direct bond is formed between two nitrogen atoms or between a nitrogen atom and an oxygen atom and may be carbonyl; aminocarbonyl; carbonylamino, imine; SO$_2$; linear or branched (C$_1$-C$_6$) alkyl optionally substituted with one or more fluorines wherein one methylene group may be replaced by O, NRx, carbnonyl or SO$_2$ or wherein two subsequent methylene groups may be replaced with a carbonylamino, aminocarbonyl, sulphonylamino, aminosulphonyl group;

k is 1, 2, 3 or 4;

l, m, n, p, p' and s are independently be 1, 2 or 3;

t is 0, 1 or 2;

the sums l+m, n+p or p'+s+t cannot exceed 5;

T and T' represent, independently from one another, hydrogen; a linear, branched or cyclic (C$_1$-C$_6$) alkyl, azaalkyl, oxaalkyl, alkenyl, azaalkenyl, oxaalkenyl, chain optionally substituted with halogen, amino, cyano, hydroxy, oxo, linear, branched or cyclic (C$_1$-C$_3$)alkylcarbonyl, alkoxycarbonyl, alkylcarbonylamino, alkylaminocarbonyl, carbamoyl, guanidino, alkenylcarbonyl, oxaalkenylcarbonyl, alkenyloxycarbononyl, alkenylaminocarbonyl;

Z is O, S, SO$_2$, SO, or NRy';

Ry and Ry' independently represent H; linear, branched or cyclic (C$_1$-C6) alkyl, alkylcarbonyl, alkoxycarbonyl of alkylaminocarbonyl group optionally substituted with one or more fluorine atoms;

y and y' are independently 0, 1, 2 or 3;

Y$_1$ and Y$_2$ independently represent halogen; hydroxy; amino; cyano; nitro; oxo; linear, or branched (C$_1$-C$_6$) alkyl, dihalogen; azaalkyl, oxaalkyl, alkylcarbonyl, oxaalkylcarbonyl, alkoxycarbonyl, alkylaminocarbonyl, alkylcarbonylamino, alkenyl, oxaalkenyl, azaalkenyl, alkenylcarbonyl, oxaalkenylcarbonyl, alkenyloxycarbonyl, alkenylaminocarbonyl, alkylamino, mercaptoalkyl, alkoxy, alkylthio group optionally substituted with one or more fluorine atoms; wherein two $Y_2$ groups may form a 5- to 8-membered ring with spiro or fused junction.

2. The compounds of claim 1 wherein X is N q is 1 and Q is carbonyl; linear, branched or cyclic $(C_1-C_6)$alkyl, $(C_1-C_5)$ alkylcarbonyl or carbonyl$(C_1-C_5)$alkyl optionally substituted with one or more fluorine atoms.

3. A pharmaceutical composition containing a compound according to claim 1 with a pharmaceutically acceptable carrier or excipient.

4. A method of binding to the Smo receptor comprising administering to a subject in need thereof an effective amount of the compound according to claim 1, wherein diseases treatable by such administration are abnormally functioning Hedgehog pathway-associated cancers.

5. A method according to claim 4, wherein said effective amount ranges from about 0.01 to about 200 mg/kg daily.

\* \* \* \* \*

SEQUENCE LISTING

```
<160> NUMBER OF SEQ ID NOS: 2

<210> SEQ ID NO 1
<211> LENGTH: 26
<212> TYPE: DNA
<213> ORGANISM: Unknown
<220> FEATURE:
```

```
<223> OTHER INFORMATION: oligonucleotide primer

<400> SEQUENCE: 1
gatcggtacc gggcttttgc tgagtt                                    26

<210> SEQ ID NO 2
<211> LENGTH: 54
<212> TYPE: DNA
<213> ORGANISM: Unknown
<220> FEATURE:
<223> OTHER INFORMATION: oligonucleotide primer

<400> SEQUENCE: 2
gatcgcggcc gcctacttat cgtcgtcatc cttgtaatcg aagtccgagt ctgc     54
```